(12) United States Patent
Vegas et al.

(10) Patent No.: US 12,186,453 B2
(45) Date of Patent: Jan. 7, 2025

(54) MATERIALS WITH IMPROVED BIOCOMPATIBILITY

(71) Applicants: Massachusetts Institute of Technology, Cambridge, MA (US); The Children's Medical Center Corporation, Boston, MA (US)

(72) Inventors: Arturo J. Vegas, Belmont, MA (US); Joshua C. Doloff, Quincy, MA (US); Omid Veiseh, Cambridge, MA (US); Robert S. Langer, Newton, MA (US); Daniel G. Anderson, Framingham, MA (US)

(73) Assignees: MASSACHUSETTS INSTITUTE OF TECHNOLOGY, Cambridge, MA (US); THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/341,118

(22) Filed: Nov. 2, 2016

(65) Prior Publication Data
US 2018/0117216 A1    May 3, 2018
US 2019/0046690 A9   Feb. 14, 2019

Related U.S. Application Data

(63) Continuation of application No. PCT/US2016/059966, filed on Nov. 1, 2016.

(60) Provisional application No. 62/249,323, filed on Nov. 1, 2015.

(51) Int. Cl.
| | |
|---|---|
| A61L 27/38 | (2006.01) |
| A61K 9/00 | (2006.01) |
| A61K 35/36 | (2015.01) |
| A61K 38/02 | (2006.01) |
| A61L 27/04 | (2006.01) |
| A61L 27/10 | (2006.01) |
| A61L 27/16 | (2006.01) |
| A61L 27/18 | (2006.01) |
| A61L 27/20 | (2006.01) |
| A61L 27/34 | (2006.01) |
| A61L 27/54 | (2006.01) |
| A61L 27/56 | (2006.01) |
| A61L 29/14 | (2006.01) |
| C08J 7/12 | (2006.01) |
| A61K 35/12 | (2015.01) |
| A61K 35/39 | (2015.01) |

(52) U.S. Cl.
CPC ........ *A61L 27/3804* (2013.01); *A61K 9/0051* (2013.01); *A61K 35/36* (2013.01); *A61K 38/02* (2013.01); *A61L 27/04* (2013.01); *A61L 27/10* (2013.01); *A61L 27/16* (2013.01); *A61L 27/18* (2013.01); *A61L 27/20* (2013.01); *A61L 27/34* (2013.01); *A61L 27/3813* (2013.01); *A61L 27/3839* (2013.01); *A61L 27/54* (2013.01); *A61L 27/56* (2013.01); *A61L 29/14* (2013.01); *C08J 7/12* (2013.01); *A61K 35/12* (2013.01); *A61K 2035/128* (2013.01); *A61K 35/39* (2013.01); *A61L 2300/252* (2013.01); *A61L 2300/254* (2013.01); *A61L 2400/18* (2013.01)

(58) Field of Classification Search
None
See application file for complete search history.

(56) References Cited

U.S. PATENT DOCUMENTS

| | | | |
|---|---|---|---|
| 2,881,161 A | 4/1959 | Kohler | |
| 2,860,130 A | 11/1985 | McNeely | |
| 4,816,567 A | 3/1989 | Rock | |
| 4,868,121 A | 9/1989 | Scharp | |
| 5,273,904 A | 12/1993 | Langley | |
| 5,322,790 A | 6/1994 | Scharp | |
| 5,336,668 A | 8/1994 | dellaValle | |
| 5,443,505 A * | 8/1995 | Wong | A61K 9/0051 623/4.1 |
| 5,447,863 A | 9/1995 | Langley | |
| 5,622,718 A | 4/1997 | Al-Shamkhani | |
| 5,624,821 A | 4/1997 | Winter | |
| 5,821,121 A | 10/1998 | Brothers | |
| 5,876,452 A * | 3/1999 | Athanasiou | A61F 2/28 424/424 |

(Continued)

FOREIGN PATENT DOCUMENTS

| | | |
|---|---|---|
| CN | 101565469 | 10/2009 |
| DE | 102005049833 | 4/2007 |

(Continued)

OTHER PUBLICATIONS

Pedraza, E. "Engineering an optimal bioartificial pancreas for islet transplantation using bioactive scaffolds" Ph.D. dissertation, University of Miami, 2011. (Year: 2011).*

(Continued)

*Primary Examiner* — Erin E Hirt
(74) *Attorney, Agent, or Firm* — PABST PATENT GROUP LLP

(57) ABSTRACT

Products, such as devices, prostheses, and materials, whose surfaces have been modified in order to impart beneficial properties to these products are disclosed. The surface-modified products have improved biocompatibility compared to a corresponding product that lacks the modification. Following implantation in a subject, the surface-modified products induce a lower foreign-body response, compared to a corresponding unmodified product.

22 Claims, No Drawings
Specification includes a Sequence Listing.

(56) References Cited

U.S. PATENT DOCUMENTS

| | | | |
|---|---|---|---|
| 6,159,531 A | 12/2000 | Dang | |
| 6,194,551 B1 | 2/2001 | Idusogie | |
| 9,422,373 B2* | 8/2016 | Vegas | C08B 37/0084 |
| 10,898,443 B2* | 1/2021 | Vegas | A61P 3/10 |
| 11,090,413 B2* | 8/2021 | Vegas | A61K 9/0024 |
| 2003/0113478 A1 | 6/2003 | Dang | |
| 2004/0253532 A1 | 12/2004 | Wu | |
| 2008/0003250 A1 | 1/2008 | Margulies | |
| 2008/0044900 A1 | 2/2008 | Mooney | |
| 2008/0177021 A1* | 7/2008 | Berlin | A61L 27/50 528/10 |
| 2008/0242738 A1 | 10/2008 | Marks | |
| 2008/0268189 A1 | 10/2008 | Sun | |
| 2009/0148591 A1 | 6/2009 | Wang | |
| 2009/0197791 A1 | 8/2009 | Balastre | |
| 2011/0111004 A1 | 5/2011 | Barbieri | |
| 2011/0319569 A1 | 12/2011 | Emrick | |
| 2012/0009159 A1 | 1/2012 | Humayun | |
| 2012/0041546 A1 | 2/2012 | Belcheva | |
| 2012/0042456 A1 | 2/2012 | Jager Lezer | |
| 2012/0083767 A1 | 4/2012 | Gerstenblith | |
| 2012/0121657 A1 | 5/2012 | Zhou | |
| 2012/0282299 A1 | 11/2012 | Delamarre | |
| 2013/0149351 A1 | 6/2013 | Lee | |
| 2013/0224276 A1 | 8/2013 | Hunter | |
| 2015/0183939 A1 | 7/2015 | Lequeux | |
| 2015/0368713 A1 | 12/2015 | Bharti | |
| 2016/0030360 A1* | 2/2016 | Vegas | A61K 9/5036 424/493 |
| 2017/0014776 A1 | 1/2017 | Li | |
| 2017/0226232 A1* | 8/2017 | Vegas | C08B 37/0084 |
| 2017/0239397 A1* | 8/2017 | Vegas | A61L 29/085 |
| 2017/0246347 A1* | 8/2017 | Vegas | A61L 27/34 |
| 2022/0031913 A1* | 2/2022 | Vegas | A61K 47/36 |

FOREIGN PATENT DOCUMENTS

| | | | |
|---|---|---|---|
| EP | 1614696 | 1/2006 | |
| FR | 2699545 | 6/1994 | |
| GB | 676618 | 7/1952 | |
| GB | 768309 | 2/1957 | |
| WO | WO 99/00070 | 1/1999 | |
| WO | WO 99/58572 | 11/1999 | |
| WO | WO 2003/010354 | 2/2003 | |
| WO | 03085372 | 10/2003 | |
| WO | 2005058382 | 6/2005 | |
| WO | 2005063147 | 7/2005 | |
| WO | 2009032158 | 3/2009 | |
| WO | 2010090767 | 8/2010 | |
| WO | WO 2012/167223 | 12/2012 | |
| WO | WO-2012167223 A1 * | 12/2012 | C08B 37/0084 |
| WO | 2013121983 | 8/2013 | |
| WO | 2014044697 | 3/2014 | |
| WO | 2014052080 | 4/2014 | |
| WO | 2015054484 | 4/2015 | |
| WO | 2015187204 | 12/2015 | |
| WO | WO 2016/019391 | 2/2016 | |

OTHER PUBLICATIONS

Chen et al. World Journal of Gastroenterology, 2004, 10(20), 3016-3020. (Year: 2004).*
Kovach (J. of Biomedical Material Research Pt. A, 2014, 102A, 4195-4205) (Year: 2014).*
Pedraza, E. et al. "Preventing hypoxia-induced cell death . . . " Proceedings of the National Academy of Sciences (PNAS), 2012, 109(11), 4245-4250. (Year: 2012).*
Anderson, P.D. et al. "Conotoxins: Potential weapons from the sea" J. Bioterr. Biodef., 2012, 3:120 doi:10.4172/2157-2526.1000120. No pagination (4 pages). (Year: 2012).*
Chem Europe "Hexazine", https://www.chemeurope.com/en/encyclopedia/Hexazine.html, no pagination, no date available.*
Lee et al. (Langmuir, 2005, 21, 11957-11962) (Year: 2005).*
Pedraza et al. J. of Biomaterials Science—Polymer Edition, 2013, 9, 1041-1056, published online Oct. 2012.*
Anderson, et al., "Foreign body reaction to biomaterials", *Semin. Immunol.* 20:86-100 (2008).
Costa, et al., "Covalent immobilization of antimicrobial peptides (AMPs) onto biomaterial surfaces", *Acta Biomater.*, 7:1431-40 (2010).
Field, et al., "Improved islet isolation from rat pancreas using 35% bovine serum albumin in combination with Dextran gradient separation", *Transplantation* 61:1554-6 (1996).
Grainger, "All charged up about implanted biomaterials", *Nat. Biotechnol.* 31:507-9 (2013).
Gruber, et al., "Efficient tumor cell lysis mediated by a bispecific single chain antibody expressed in *Escherichia coli*", *J. Immunol.*, 152:5368 (1994).
Harding and Reynolds, "Combating medical device fouling", *Trends Biotechnol.* 32:140-6 (2014).
Hetrick, et al., "Reduced foreign body response at nitric oxide-releasing subcutaneous implants", *Biomaterials*, 28:4571-80 (2007).
Hollinger, et al., ""Diabodies": small bivalent and bispecific antibody fragments", *PNAS*, 90:6444-8 (1993).
Hudalla, et al., "Immobilization of peptides with distinct biological activities onto stem cell culture substrates using orthogonal chemistries", *Langmuir*, 26(9):6449-56 (2010).
Langer, "Perspectives and challenges in tissue engineering and regenerative medicine", *Adv. Mater.* 21:3235-3236 (2009).
Linetsky, et al., "Improved human islet isolation using a new enzyme blend, liberase", *Diabetes* 46:1120-3 (1997).
Poncin, et al., "Comparing and Optimizing Co—Cr Tubing for Stent Applications," Materials & Processes for Medical Devices Conference, ASM International, pp. 1-6, Aug. 2004.
Ratner, "Reducing capsular thickness and enhancing angiogenesis around implant drug release systems", *J. Controlled Release* 78:211-18 (2002).
Rodriguez, et al., "Quantitative in vivo cytokine analysis at synthetic biomaterial implant", *J. Biomed. Mater. Res. A*, 89:152-9 (2009).
Sussman, et al., "Porous Implants Modulate Healing and Induce Shifts in Local Macrophage Polarization in the Foreign Body Reaction", *Ann. Biomed. Eng*, 42(7):1508-16. (2013).
Thevenot, et al., "Surface chemistry influences implant biocompatibility", Curr Top Med Chem., 8(4):270-80 (2011).
Ward, "A review of the foreign-body response to subcutaneously-implanted devices: the role of macrophages and cytokines in biofouling and fibrosis", *J. Diabetes Sci. Technol.*, 2:768-77 (2008).
Wick, et al., "The immunology of fibrosis", *Annu. Rev. Immunol.* 31:107-35 (2013).
Williams, "On the mechanisms of biocompatibility", *Biomaterials* 29:2941-53 (2008).
Wynn and Ramalingam, "Mechanisms of fibrosis: therapeutic translation for fibrotic disease", *Nat. Med.* 18:1028-1040 (2012).
Zhang, et al., "Zwitterionic hydrogels implanted in mice resist the foreign-body reaction", *Nat. Biotechnol.* 31:553-6 (2013).
International Search Report for corresponding PCT application PCT/US2016/059966 mailed Mar. 4, 2017.
Wikstrom, "Alginate-based microencapsulation of retinal pigment epithelial cell line for cell therapy", *Biomaterial*, 29:869-76 (2008).
Vallee, et al., "Synthesis and rheological properties of hydrogels based on amphiphilic alginate-amide derivatives", Carbohydrate Res., 344:223-8 (2009).
Extended European Search Report issued for EP 18 16 2427 mailed Jun. 19, 2018.
Ahad, et al., "Surface modification of polymers for biocompatibility via exposure to extreme ultraviolet radiation", Society for Biomaterials, 3296-3310 (2013).
Chen, "Differentiation of rat marrow mesenchymal stem cells into pancreatic islet beta-cells", World Journal of Gastroenterology, 10(20): 3016-3020 (2004).
Chen, et al., "Multifunctional Biocompatible Membrane and Its Application to Fabricate A Miniaturized Glucose Sensor with Potential for Use in Vivo", Biomedical Microdevices, 1(2):155-166 (1998).

(56) References Cited

OTHER PUBLICATIONS

Chu, et al., "A soft and flexible biosensor using a phospholipid polymer for continuous glucose monitoring", Biomedical Microdevices, 11(4):837-842 (2009).
Cui, et al., "Electrochemical deposition and characterization of poly (3, 4-ethylenedioxythiophen) on neural microelectrode arrays", Sensors and Actuators B, 89:92-102 (2003).
Hersel, et al., "RGD modified polymers: biomaterials for stimulated cell adhesion and beyond", Biomaterials, 24(24):4385-4415 (2003).
Huh, et al., "From 3D cell culture to organs-on chips", Trends in Cell Biology, 21(12):745-754 (2011).
Lee, et al., "Development and characterization of an alginate-impregnated polyester vascular graft", Journal of Biomed. Mater. Research, 36(2):200-208 (1996).
Skousen, et al. "A strategy to passively reduce inflammation surrounding devices implanted chronically brain tissue by manipulating device surface permeability", Biomaterials, 36:33-43 (2015).
Sun, et al., "Functionalization of quantum dots with multidentate zwitterionic ligands: impact on cellular interactions and cytotoxicity", Journal of Materials Chemistry B, 1(44): 6137 (2013).
West, et al., "The biocompatibility of crosslinkable copolymer coatings containing sulfobetaines and phosphobetaines", Biomaterials, 25(7-8):1195-1204 (2004).
Yang, et al., "Zwitterionic poly(carboxybetaine) hydrogels for glucose biosensors in complex media", Biosensors and Bioelectronics, 26(5):2454-2459 (2011).

Ratner, "A pore way to heal and regenerate: 21st century thinking on biocompatibility", Regenerative Biomaterials, 107-110 (2016).
DeVos, et al., "Improved biocompatibility but limited graft survival after purification of alginate for microencapsulation of pancreatic islets", Diabetologia, 40(3):262-270 (1997).
Gattas-Asfura, "Chemoselective cross-linking and functionalization of alginate via Staudinger ligation", Biomacromolecules, 10:3122-3129 (2009).
Hall, et al., "Microencapsulation of islets within alginate/poly)ethylene glycol) gels cross-linked via Staudinger ligation", Acta Biomaterialia, 7:614-24 (2011).
Pedraza, et al., "Macroporous three-dimensional PDMS scaffolds for extrahepatic islet transplantation", Cell Transplantation, 22:1123-1135 (2013).
Tang, et al., "Reprogramming liver-stem WB fcells into functional insulin-prodcuing cells by persistent expression of Pdx1-and Pdx1-VP16 mediated by lentiviral vectors", Lab Invest 86(1)83-93 (2006).
Yang, et al., "Research progress on chemical modification of alginate: A review", Carbohydrate Polymers, 84(1):33-39 (2011b).
Yimin, et al., "Alginic Acid", 137-140.
Belikov, et al., Pharmaceutical Chemistry, Moscow, Higher School, 43-47 (1993).
Mørch, et al., "Effect of Ca2+, Ba2+, and Sr2+ on alginate microbeads", Biomacromolecules, 7(5): 1471-1480 (2006).
Sun, "Microencapsulation of pancreatic islet cells: a bioartificial endocrine pancreas", Methods in Enzymology, 137:575-580 (1988).

\* cited by examiner

MATERIALS WITH IMPROVED BIOCOMPATIBILITY

CROSS-REFERENCE TO RELATED APPLICATIONS

This application is a continuation of PCT Application No. PCT/US2016/059966, filed Nov. 1, 2016, which claims the benefit of and priority to U.S. Provisional Application No. 62/249,323, filed Nov. 1, 2015, the entire contents of which is incorporated by reference in its entirety.

STATEMENT REGARDING FEDERALLY SPONSORED RESEARCH

This invention was made with government support under Grants EB000244, EB000351, DE013023 and CA151884 awarded by the National Institutes of Health (NIH) and Grant W81XWH-13-1-0215 awarded by the Department of Defense (DOD). The government has certain rights in the invention.

REFERENCE TO SEQUENCE LISTING

The Sequence Listing submitted as a text file named "MIT_17502_ST25.txt," created on Nov. 1, 2016, and having a size of 4,941 bytes is hereby incorporated by reference pursuant to 37 C.F.R. § 1.52(e)(5).

FIELD OF THE INVENTION

This invention is in the field of materials with improved properties, e.g., biocompatibility, particularly implantable devices with reduced foreign body response and moieties that confer improved properties, e.g., biocompatibility.

BACKGROUND OF THE INVENTION

The foreign body response is an immune-mediated reaction that impacts the fidelity of implanted biomedical devices (Anderson et al., Semin. Immunol. 20:86-100 (2008); Langer, Adv. Mater. 21:3235-3236 (2009); Ward, J. Diabetes Sci. Technol. Online 2:768-777 (2008); Harding & Reynolds, Trends Biotechnol. 32:140-146 (2014)). Macrophage recognition of biomaterial surfaces in these devices initiate a cascade of inflammatory events that result in the fibrous and collagenous encapsulation of these foreign materials (Anderson et al. (2008); Ward (2008); Harding & Reynolds (2014); Grainger, Nat. Biotechnol. 31:507-509 (2013); Williams, Biomaterials 29:2941-2953 (2008)). This encapsulation, over time, often leads to device failure and can result in discomfort for the recipient (Anderson et al. (2008); Harding & Reynolds (2014); Williams (2008)). These adverse outcomes emphasize the critical need for biomaterials that do not elicit foreign body responses to overcome this key challenge to long-term biomedical device function.

The foreign body response to implanted biomaterials is the culmination of inflammatory events and wound-healing processes resulting in implant encapsulation (Anderson et al. (2008)). The final pathological product of this response is fibrosis, which is characterized by the accumulation of excessive extracellular matrix at sites of inflammation and is a key obstacle for implantable medical devices as the cellular and collagenous deposition isolate the device from the host (Anderson et al. (2008); Wick et al., Annu. Rev. Immunol. 31:107-135 (2013); Wynn & Ramalingam, Nat. Med. 18:1028-1040 (2012)). This device isolation can interfere with sensing of the host environment, lead to painful tissue distortion, cut off nourishment (for implants containing living, cellular components), and ultimately lead to device failure. Materials commonly used for medical device manufacture today elicit a foreign body response that results in fibrous encapsulation of the implanted material (Langer (2009); Ward (2008); Harding & Reynolds (2014); Williams (2008); Zhang et al., Nat. Biotechnol. 31:553-556 (2013)). Overcoming the foreign body response to implanted devices could pave the way for implementing new medical advances, making the development of materials with both anti-inflammatory and anti-fibrotic properties a critical medical need (Anderson et al. (2008); Langer (2009); Harding & Reynolds (2014)).

Macrophages are a key component of material recognition and actively adhere to the surface of foreign objects (Anderson et al. (2008); Ward (2008); Grainger, Nat. Biotechnol. 31:507-509 (2013); Sussman et al., Ann. Biomed. Eng. 1-9 (2013) (doi:10.1007/s10439-013-0933-0)). Objects too large for macrophage phagocytosis initiate processes that result in the fusion of macrophages into foreign-body giant cells. These multi-nucleated bodies amplify the immune response by secreting cytokines and chemokines that result in the recruitment of fibroblasts that actively deposit matrix to isolate the foreign material (Anderson et al. (2008); Ward (2008); Rodriguez et al., J. Biomed. Mater. Res. A 89:152-159 (2009); Hetrick et al., Biomaterials 28:4571-4580 (2007)). This response has been described for materials of both natural and synthetic origins that encompass a wide range of physicochemical properties, including alginate, chitosan, dextran, collagen, hyaluronan, poly(ethylene glycol) (PEG), poly(methyl methacrylate) (PMMA), poly(2-hydroxyethyl methacrylate) (PHEMA), polyurethane, polyethylene, silicone rubber, Teflon, gold, titanium, silica, and alumina (Ward (2008); Ratner, J. Controlled Release 78:211-218 (2002)).

The development of implantable devices that resist host foreign body responses for protracted periods of time is important for improving the performance and safety of such devices, and remains an unmet need. Accordingly, the search for materials of clinical relevance that address the foreign body response to implantable devices, i.e., ameliorate biocompatibility, remains an area of active research.

Therefore, it is an object of the invention to provide chemical compounds suitable for modifying the surface or a surface of a product to impart a beneficial effect to the product compared to a corresponding product that lacks the chemical modification.

It is also an object of the invention to provide chemical compounds suitable for modifying the surface or a surface of a product, where the chemically modified product has optimized biocompatibility, e.g., greater long term biocompatibility, following implantation of the product compared to a corresponding product that lacks the chemical modification.

It is also an object of the invention to provide chemical compounds suitable for modifying the surface or a surface of a product, where the chemically modified product elicits a lower foreign body response following implantation of the product compared to a corresponding product that lacks the chemical modification.

It is also an object of the invention to provide a chemically modified product with improved biocompatibility and tailored physico-chemical properties, including porosity, roughness, lubricity, hydrophilicity, and hydrophobicity, compared to a corresponding product that lacks the chemical modification.

It is also an object of the invention to provide a chemically modified product that elicits a lower foreign body response, compared to a corresponding product that lacks the chemical modification.

It is also an object of the invention to provide methods for chemically modifying the surface or a surface of a product using compounds, where the chemically modified product has improved biocompatibility compared to a corresponding product that lacks the chemical modification.

It is also an object of the invention to provide methods for chemically modifying the surface or a surface of a product using compounds, where the chemically modified product elicits a lower foreign body response compared to a corresponding product that lacks the chemical modification.

It is also an object of the invention to provide methods for treating a disorder or disease in a subject by transplanting or implanting a product modified with a compound, where the modified product has improved biocompatibility compared to a corresponding product that lacks the chemical modification.

It is also an object of the invention to provide methods for treating a disorder or disease in a subject by transplanting or implanting a product modified with a compound, where the modified product elicits a lower foreign body response compared to a corresponding product that lacks the chemical modification.

SUMMARY OF THE INVENTION

Products, such as devices, prostheses, and materials, having surfaces comprising moieties or compounds that impart beneficial properties to these products are disclosed. The surface-modified products have optimized properties, e.g., improved biocompatibility, compared to a corresponding product that lacks the moieties or compounds on its surface. Following implantation in a subject, the surface-modified products induce a lower foreign-body response, compared to a corresponding unmodified product.

In some embodiments, the surfaces of the products can be covalently modified using chemical compounds. In some embodiments, the chemical compounds contain hydrophobic groups. In preferred embodiments, the chemical compounds contain aryl/heteroaryl groups. In currently preferred embodiments for improving biocompatibility, the chemical compounds contain a triazole linked to a moiety or compound that can provide anti-fibrotic properties. In preferred embodiments, the moiety can be tetrahydropyran, thiomorpholine-1,1-dioxide, or aniline.

In one aspect, the products described herein can be implanted or administered to a subject comprising a human or an animal including, but not limited to, a mouse, dog, cat, horse, bovine or ovine and the like, that is in need thereof, e.g., in need of alleviation or amelioration from a disorder, e.g., a recognized medical condition.

Disclosed are products, such as devices, prostheses, and materials, where the surface or a surface of the product includes one or more of the moieties or compounds described herein. In some embodiments, the product can be formed from a starting material or intermediate which includes the moiety or compound. In some embodiments, the product can be formed by covalently modifying a starting material or the surface of a starting material, intermediate, or an otherwise finished object. For example, the surface or a surface of the product can be chemically modified after formation of the product with one or more compounds. The compounds are preferably compounds that confer a beneficial effect, such as lower foreign body response and improved biocompatibility, on the product. In some embodiments, the modifying compounds can provide anti-fibrotic properties. Also disclosed are methods of chemically modifying products and methods of using the chemically modified products, such as by implantation into a subject.

In some embodiments, the compound can have a structure —X—$R_1$, where

X is oxygen, sulfur, $NR_2$, or another group compatible with attachment or coupling of the compound to a product or surface;

$R_1$ is hydrogen, or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_1$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_2+Q_3$); and $R_2$ is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_3$).

In some embodiments, $R_1$ is, independently in one or more sites of chemical modification,

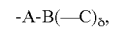 Formula XII wherein

A is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_3$);

B, and C are, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_3$); and δ is an integer from, as valency permits, 0 to 30.

In some embodiments, $R_1$ is, independently in one or more sites of chemical modification,

 Formula II wherein $R_3$ is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_3$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_3$); and $R^b$ is absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R^b$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_3$).

Independently in some embodiments of A and $R_3$, and independently in combination with any embodiments of any other relevant substituent classes, A and $R_3$ can be, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_3$).

Independently in some embodiments of B, C, and $R^b$, and independently in combination with any embodiments of any other relevant substituent classes, B, C, and $R^b$ can be, independently, absent, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_3$).

Independently in some embodiments of A and $R_3$, and independently in combination with any embodiments of any other relevant substituent classes, A and $R_3$ can be, independently, hydrogen, amino, hydroxyl, thiol, oxo, phosphate, or $J_1$.

Independently in some embodiments of A and $R_3$, and independently in combination with any embodiments of any other relevant substituent classes, A and $R_3$ can be, independently, hydrogen, amino, hydroxyl, thiol, oxo, phosphate, or $J_2$.

Independently in some embodiments of B, C, and $R^b$, and independently in combination with any embodiments of any other relevant substituent classes, B, C, and $R^b$ can be, independently, absent, hydrogen, amino, hydroxyl, thiol, oxo, phosphate, or $J_1$.

Independently in some embodiments of B, C, and $R^b$, and independently in combination with any embodiments of any other relevant substituent classes, B, C, and $R^b$ can be, independently, absent, hydrogen, amino, hydroxyl, thiol, oxo, phosphate, or $J_2$.

Independently in some embodiments of A and $R_3$, and independently in combination with any embodiments of any other relevant substituent classes, A and $R_3$ can be, independently,

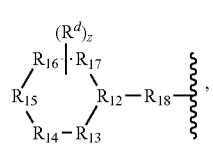

Formula VI

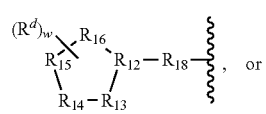

Formula IX

-continued

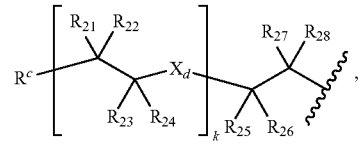

Formula VIII wherein z is an integer from 0-11; wherein w is an integer from 0-9; wherein k is an integer from 0 to 20;

wherein $R^d$ are independently B, C, $-B(-C)_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_3$); or together with the carbon atom to which they are attached, form a 3- to 8-membered unsubstituted or substituted carbocyclic or heterocyclic ring;

wherein $X_d$ are independently absent, O, or S;

wherein $R^c$ is B, C, $-B(-C)_\delta$, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_3$);

wherein $R_{12}$, $R_{13}$, $R_{14}$, $R_{15}$, $R_{16}$, and $R_{17}$ are independently C, O, N, S, S(O), or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently B, C, absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently B, C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of B, and independently in combination with any embodiments of any other relevant substituent classes, B can be

Formula VI

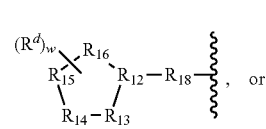

Formula IX

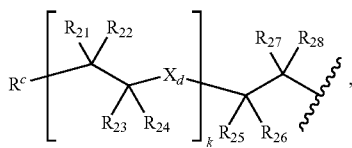

Formula VIII wherein z is an integer from 0-11; wherein w is an integer from 0-9; wherein k is an integer from 0 to 20;

wherein $R^d$ are independently C, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $X_d$ are independently absent, O, or S;

wherein $R^c$ is C, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$);

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently C, $R^b$, absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R^b$, and independently in combination with any embodiments of any other relevant substituent classes, $R^b$ can be

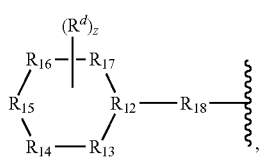

Formula VI

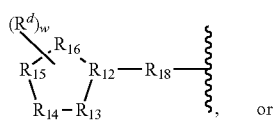

Formula IX

, or

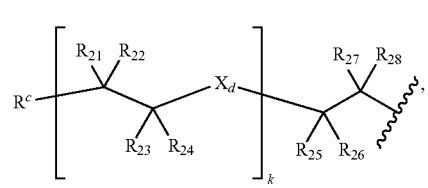

Formula VIII wherein z is an integer from 0-11; wherein w is an integer from 0-9; wherein k is an integer from 0 to 20;

wherein $R^d$ are independently C, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $X_d$ are independently absent, O, or S;

wherein $R^c$ is C, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$);

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently C, absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of C, and independently in combination with any embodiments of any other relevant substituent classes C can be

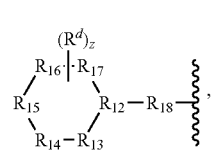

Formula VI

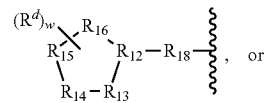

Formula IX

, or

-continued

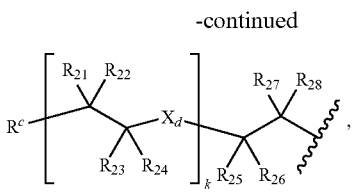

Formula VIII wherein z is an integer from 0-11; wherein w is an integer from 0-9; wherein k is an integer from 0 to 20;

wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $X_d$ are independently absent, O, or S;

wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$);

wherein $R_{12}$, $R_{13}$, $R_{14}$, $R_{15}$, $R_{16}$, and $R_{17}$ are independently C, O, N, S, S(O), or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —$S(O)_2$—, or $NR_{20}$, wherein each $R_{19}$ is, as valency permits, independently absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of A and $R_3$, and independently in combination with any embodiments of any other relevant substituent classes, A and $R_3$ can be, independently,

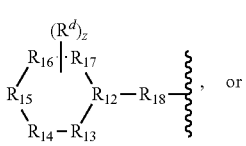

Formula VI

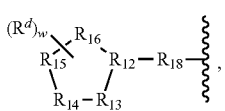

Formula IX wherein z is an integer from 0-11; wherein w is an integer from 0-9;

wherein $R^d$ are independently B, C, —B(—C)$_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —$S(O)_2$—, or $NR_{20}$, wherein each $R_{19}$ is, as valency permits, independently B, C, absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of B, and independently in combination with any embodiments of any other relevant substituent classes, B can be

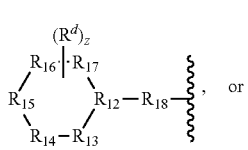

Formula VI

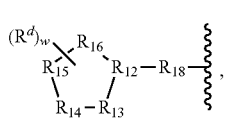

Formula IX wherein z is an integer from 0-11; wherein w is an integer from 0-9;

wherein $R^d$ are independently C, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —$S(O)_2$—, or $NR_{20}$, wherein each $R_{19}$ is, as valency permits, independently C, $R^b$, absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of $R^b$, and independently in combination with any embodiments of any other relevant substituent classes, $R^b$ can be

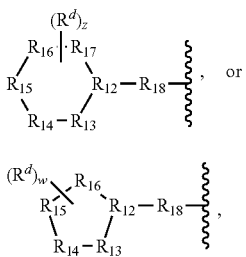

Formula VI

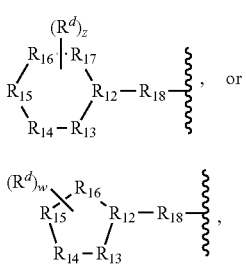

Formula IX wherein z is an integer from 0-11; wherein w is an integer from 0-9;
wherein $R^d$ are independently C, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and
wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently C, absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of C, and independently in combination with any embodiments of any other relevant substituent classes, C can be

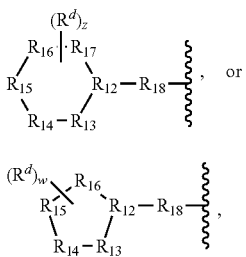

Formula VI

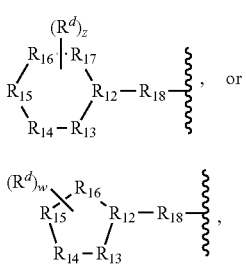

Formula IX wherein z is an integer from 0-11; wherein w is an integer from 0-9;
wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and
wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of A and $R_3$, and independently in combination with any embodiments of any other relevant substituent classes, A and $R_3$ can be, independently,

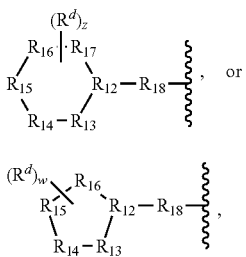

Formula VI wherein z is an integer from 0-11;
wherein $R^d$ are independently B, C, —B(—C)$_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and
wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently B, C, absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of B, and independently in combination with any embodiments of any other relevant substituent classes, B can be

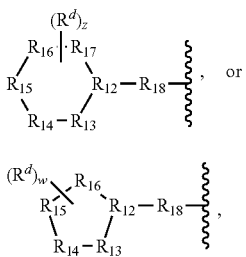

Formula VI wherein z is an integer from 0-11;
wherein $R^d$ are independently C, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein X$_b$ is absent, —O—, —S—, —S(O)—, —S(O)$_2$—, or NR$_{20}$, wherein each $R_{19}$ is, as valency permits, independently C, R$^b$, absent, hydrogen, =O, =S, —OH, —SH, or —NR$_{20}$, wherein $R_{20}$ is U$_1$, U$_1$+Q$_1$, U$_1$+Q$_2$, U$_1$+Q$_3$, U$_1$+Q$_1$+Q$_2$, U$_1$+Q$_1$+Q$_3$, U$_1$+Q$_2$+Q$_3$, or U$_1$+Q$_1$+Q$_2$+Q$_3$ (preferably, in these embodiments, U$_1$+Q$_1$+Q$_3$).

Independently in some embodiments of R$^b$, and independently in combination with any embodiments of any other relevant substituent classes, R$^b$ can be

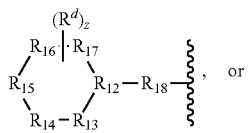

Formula VI wherein z is an integer from 0-11;

wherein R$^d$ are independently C, U$_2$, U$_2$+Q$_1$, U$_2$+Q$_2$, U$_2$+Q$_3$, U$_2$+Q$_1$+Q$_2$, U$_2$+Q$_1$+Q$_3$, U$_2$+Q$_2$+Q$_3$, U$_2$+Q$_1$+Q$_2$+Q$_3$, U$_3$, U$_3$+Q$_1$, U$_3$+Q$_2$, U$_3$+Q$_3$, U$_3$+Q$_1$+Q$_2$, U$_3$+Q$_1$+Q$_3$, U$_3$+Q$_2$+Q$_3$, or U$_3$+Q$_1$+Q$_2$+Q$_3$ (preferably, in these embodiments, U$_3$+Q$_1$+Q$_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein X$_b$ is absent, —O—, —S—, —S(O)—, —S(O)$_2$—, or NR$_{20}$, wherein each $R_{19}$ is, as valency permits, independently C, absent, hydrogen, =O, =S, —OH, —SH, or —NR$_{20}$, wherein $R_{20}$ is U$_1$, U$_1$+Q$_1$, U$_1$+Q$_2$, U$_1$+Q$_3$, U$_1$+Q$_1$+Q$_2$, U$_1$+Q$_1$+Q$_3$, U$_1$+Q$_2$+Q$_3$, or U$_1$+Q$_1$+Q$_2$+Q$_3$ (preferably, in these embodiments, U$_1$+Q$_1$+Q$_3$).

Independently in some embodiments of C, and independently in combination with any embodiments of any other relevant substituent classes, C can be

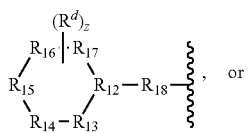

Formula VI wherein z is an integer from 0-11;

wherein R$^d$ are independently U$_2$, U$_2$+Q$_1$, U$_2$+Q$_2$, U$_2$+Q$_3$, U$_2$+Q$_1$+Q$_2$, U$_2$+Q$_1$+Q$_3$, U$_2$+Q$_2$+Q$_3$, U$_2$+Q$_1$+Q$_2$+Q$_3$, U$_3$, U$_3$+Q$_1$, U$_3$+Q$_2$, U$_3$+Q$_3$, U$_3$+Q$_1$+Q$_2$, U$_3$+Q$_1$+Q$_3$, U$_3$+Q$_2$+Q$_3$, or U$_3$+Q$_1$+Q$_2$+Q$_3$ (preferably, in these embodiments, U$_3$+Q$_1$+Q$_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein X$_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is U$_1$, U$_1$+Q$_1$, U$_1$+Q$_2$, U$_1$+Q$_3$, U$_1$+Q$_1$+Q$_2$, U$_1$+Q$_1$+Q$_3$, U$_1$+Q$_2$+Q$_3$, or U$_1$+Q$_1$+Q$_2$+Q$_3$ (preferably, in these embodiments, U$_1$+Q$_1$+Q$_3$).

Independently in some embodiments of A and $R_3$, and independently in combination with any embodiments of any other relevant substituent classes, A and $R_3$ can be, independently,

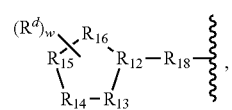

Formula IX wherein w is an integer from 0-9;

wherein R$^d$ are independently B, C, —B(—C)$_\delta$, R$^b$, U$_2$, U$_2$+Q$_1$, U$_2$+Q$_2$, U$_2$+Q$_3$, U$_2$+Q$_1$+Q$_2$, U$_2$+Q$_1$+Q$_3$, U$_2$+Q$_2$+Q$_3$, U$_2$+Q$_1$+Q$_2$+Q$_3$, U$_3$, U$_3$+Q$_1$, U$_3$+Q$_2$, U$_3$+Q$_3$, U$_3$+Q$_1$+Q$_2$, U$_3$+Q$_1$+Q$_3$, U$_3$+Q$_2$+Q$_3$, or U$_3$+Q$_1$+Q$_2$+Q$_3$ (preferably, in these embodiments, U$_3$+Q$_1$+Q$_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C, O, N, S, S(O), or S(O)$_2$, wherein the bonds between adjacent $R_{12}$ to $R_{16}$ are double or single according to valency, and wherein $R_{12}$ to $R_{16}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein X$_b$ is absent, —O—, —S—, —S(O)—, —S(O)$_2$—, or NR$_{20}$, wherein each $R_{19}$ is, as valency permits, independently B, C, absent, hydrogen, =O, =S, —OH, —SH, or —NR$_{20}$, wherein $R_{20}$ is U$_1$, U$_1$+Q$_1$, U$_1$+Q$_2$, U$_1$+Q$_3$, U$_1$+Q$_1$+Q$_2$, U$_1$+Q$_1$+Q$_3$, U$_1$+Q$_2$+Q$_3$, or U$_1$+Q$_1$+Q$_2$+Q$_3$ (preferably, in these embodiments, U$_1$+Q$_1$+Q$_3$).

Independently in some embodiments of B, and independently in combination with any embodiments of any other relevant substituent classes, B can be Formula IX

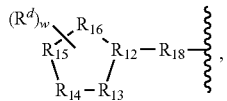

wherein w is an integer from 0-9;
wherein $R^d$ are independently C, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, and $R_{16}$ are independently C, O, N, S, S(O), or $S(O)_2$, wherein the bonds between adjacent $R_{12}$ to $R_{16}$ are double or single according to valency, and wherein $R_{12}$ to $R_{16}$ are bound to none, one, or two hydrogens according to valency; and
wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently C, $R^b$, absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of $R^b$, and independently in combination with any embodiments of any other relevant substituent classes, $R^b$ can be Formula IX

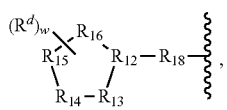

wherein w is an integer from 0-9;
wherein $R^d$ are independently C, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, and $R_{16}$ are independently C, O, N, S, S(O), or $S(O)_2$, wherein the bonds between adjacent $R_{12}$ to $R_{16}$ are double or single according to valency, and wherein $R_{12}$ to $R_{16}$ are bound to none, one, or two hydrogens according to valency; and
wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of C, and independently in combination with any embodiments of any other relevant substituent classes, C can be Formula IX

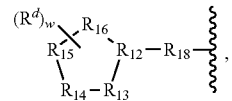

wherein w is an integer from 0-9;
wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, and $R_{16}$ are independently C, O, N, S, S(O), or $S(O)_2$, wherein the bonds between adjacent $R_{12}$ to $R_{16}$ are double or single according to valency, and wherein $R_{12}$ to $R_{16}$ are bound to none, one, or two hydrogens according to valency; and
wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of A and $R_3$, and independently in combination with any embodiments of any other relevant substituent classes, A and $R_3$ can be, independently, Formula IX

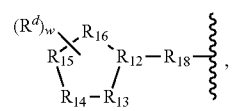

wherein w is an integer from 0-9;
wherein $R^d$ are independently B, C, $-B(-C)_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and
wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently B, C, absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of B, and independently in combination with any embodiments of any other relevant substituent classes, B can be

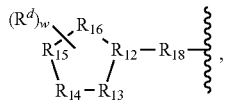

Formula IX wherein w is an integer from 0-9;

wherein $R^d$ are independently C, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —S(O)$_2$—, or $NR_{20}$, wherein each $R_{19}$ is, as valency permits, independently C, $R^b$, absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of $R^b$, and independently in combination with any embodiments of any other relevant substituent classes, $R^b$ can be

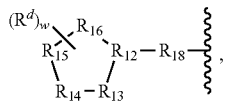

Formula IX wherein w is an integer from 0-9;

wherein $R^d$ are independently C, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —S(O)$_2$—, or $NR_{20}$, wherein each $R_{19}$ is, as valency permits, independently C, absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of C, and independently in combination with any embodiments of any other relevant substituent classes, C can be

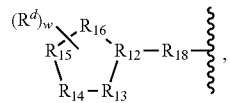

Formula IX wherein w is an integer from 0-9;

wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —S(O)$_2$—, or $NR_{20}$, wherein each $R_{19}$ is, as valency permits, independently absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of A and $R_3$, and independently in combination with any embodiments of any other relevant substituent classes, A and $R_3$ can be, independently,

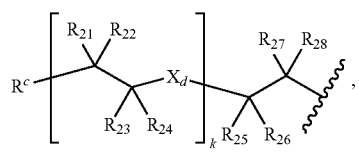

Formula VIII wherein k is an integer from 0 to 20;
wherein $X_d$ are independently absent, O, or S;
wherein $R^c$ is B, C, —B(—C)$_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently B, C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of B, and independently in combination with any embodiments of any other relevant substituent classes, B can be

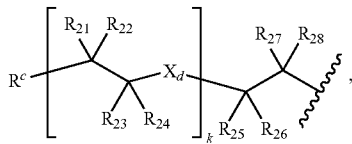

Formula VIII wherein k is an integer from 0 to 20;
wherein $X_d$ are independently absent, O, or S;
wherein $R^c$ is C, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R^b$, and independently in combination with any embodiments of any other relevant substituent classes, $R^b$ can be

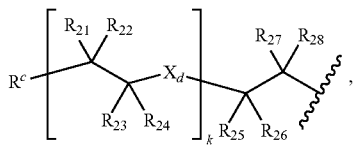

Formula VIII wherein k is an integer from 0 to 20;
wherein $X_d$ are independently absent, O, or S;
wherein $R^c$ is C, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of C, and independently in combination with any embodiments of any other relevant substituent classes, C can be

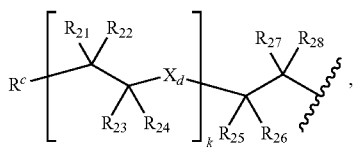

Formula VIII wherein k is an integer from 0 to 20;
wherein $X_d$ are independently absent, O, or S;
wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of A and $R_3$, and independently in combination with any embodiments of any other relevant substituent classes, A and $R_3$ can be, independently,

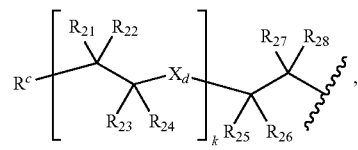

Formula VIII wherein k is an integer from 0 to 20;
wherein $X_d$ are independently O or S;
wherein $R^c$ is B, C, —B(—C)$_\delta$, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently B, C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of B, and independently in combination with any embodiments of any other relevant substituent classes, B can be Formula VIII wherein k is an integer from 0 to 20;
wherein $X_d$ are independently O or S;
wherein $R^c$ is C, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R^b$, and independently in combination with any embodiments of any other relevant substituent classes, $R^b$ can be

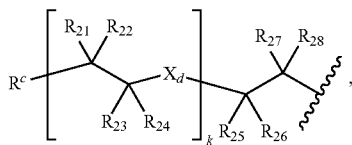

wherein k is an integer from 0 to 20;
wherein $X_d$ are independently O or S;
wherein $R^c$ is C, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of C, and independently in combination with any embodiments of any other relevant substituent classes, C can be

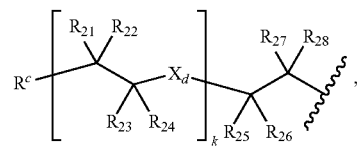

wherein k is an integer from 0 to 20;
wherein $X_d$ are independently O or S;
wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of A and $R_3$, and independently in combination with any embodiments of any other relevant substituent classes, A and $R_3$ can be, independently,

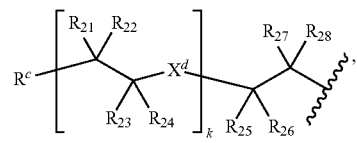

wherein k is an integer from 1 to 20;
wherein $X_d$ are O;
wherein $R^c$ is B, C, —B(—C)$_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently B, C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of B, and independently in combination with any embodiments of any other relevant substituent classes, B can be

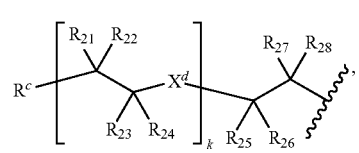

wherein k is an integer from 1 to 20;
wherein $X_d$ are O;
wherein $R^c$ is C, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R^b$, and independently in combination with any embodiments of any other relevant substituent classes, $R^b$ can be

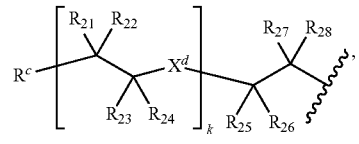

wherein k is an integer from 1 to 20;
wherein $X_d$ are O;
wherein $R^c$ is C, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of C, and independently in combination with any embodiments of any other relevant substituent classes, C can be

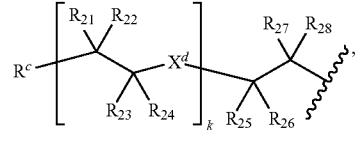

wherein k is an integer from 1 to 20;
wherein $X_d$ are O;

wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, $R_1$ is, independently in one or more sites of chemical modification,

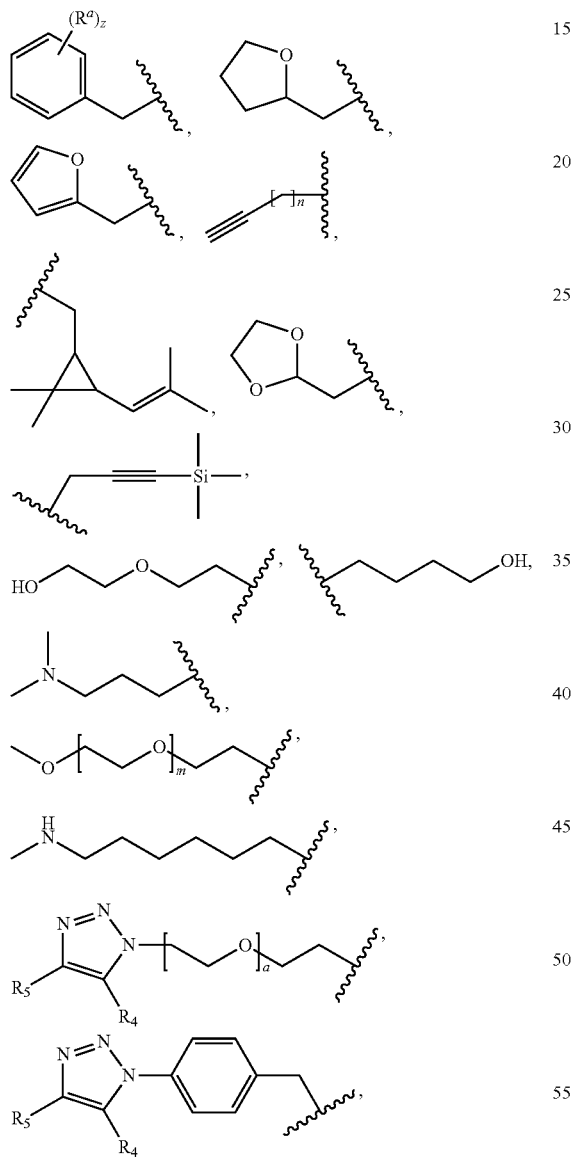

where a is an integer from 1 to 30, z is an integer from 0-5, n is an integer from 1 to 12, m is an integer from 3 to 16, and $R^a$ and $R^b$ are independently selected from $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_2+Q_3$), and $R^b$ is

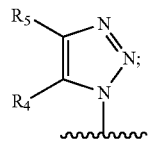

and $R_3$, $R_4$, and $R_5$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, the compound can have a structure —X—$R_1$, where

X is oxygen, sulfur, $NR_2$, or another group compatible with attachment or coupling of the compound to a product or surface;

$R_1$ is, independently in one or more sites of chemical modification, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$);

$R_2$ is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In some embodiments, $R_1$ is, independently in one or more sites of chemical modification,

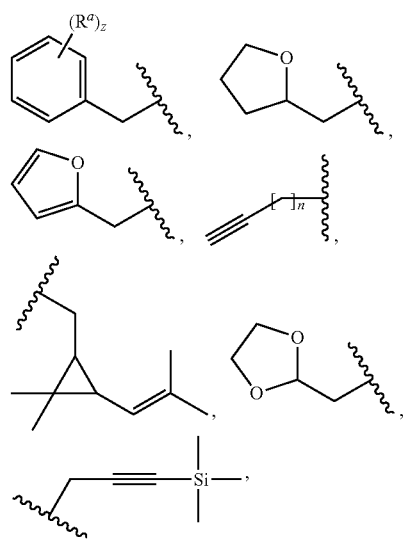

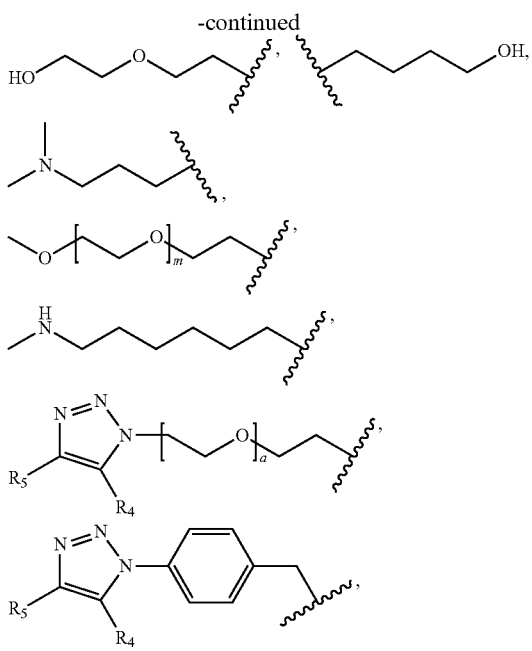

or —$R_3$—$R^b$, where a is an integer from 1 to 30, z is an integer from 0-5, n is an integer from 1 to 12, m is an integer from 3 to 16, $R^a$ is independently selected from $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_2+Q_3$), and $R^b$ is

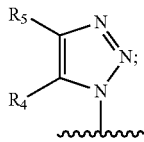

and $R_3$, $R_4$, and $R_5$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_3$, $R_4$, and $R_5$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of a, and independently in combination with any embodiments of any other relevant substituent classes, a can be an integer from 1 to 30, 2 to 30, 3 to 30, 4 to 30, 5 to 30, 6 to 30, 7 to 30, 8 to 30, 9 to 30, 10 to 30, 11 to 30, 12 to 30, 13 to 30, 14 to 30, 15 to 30, 16 to 30, 17 to 30, 18 to 30, 19 to 30, 20 to 30, 21 to 30, 22 to 30, 23 to 30, 24 to 30, 25 to 30, 26 to 30, 27 to 30, 28 to 30, 29 to 30, 1 to 29, 2 to 29, 3 to 29, 4 to 29, 5 to 29, 6 to 29, 7 to 29, 8 to 29, 9 to 29, 10 to 29, 11 to 29, 12 to 29, 13 to 29, 14 to 29, 15 to 29, 16 to 29, 17 to 29, 18 to 29, 19 to 29, 20 to 29, 21 to 29, 22 to 29, 23 to 29, 24 to 29, 25 to 29, 26 to 29, 27 to 29, 28 to 29, 1 to 28, 2 to 28, 3 to 28, 4 to 28, 5 to 28, 6 to 28, 7 to 28, 8 to 28, 9 to 28, 10 to 28, 11 to 28, 12 to 28, 13 to 28, 14 to 28, 15 to 28, 16 to 28, 17 to 28, 18 to 28, 19 to 28, 20 to 28, 21 to 28, 22 to 28, 23 to 28, 24 to 28, 25 to 28, 26 to 28, 27 to 28, 1 to 27, 2 to 27, 3 to 27, 4 to 27, 5 to 27, 6 to 27, 7 to 27, 8 to 27, 9 to 27, 10 to 27, 11 to 27, 12 to 27, 13 to 27, 14 to 27, 15 to 27, 16 to 27, 17 to 27, 18 to 27, 19 to 27, 20 to 27, 21 to 27, 22 to 27, 23 to 27, 24 to 27, 25 to 27, 26 to 27, 1 to 26, 2 to 26, 3 to 26, 4 to 26, 5 to 26, 6 to 26, 7 to 26, 8 to 26, 9 to 26, 10 to 26, 11 to 26, 12 to 26, 13 to 26, 14 to 26, 15 to 26, 16 to 26, 17 to 26, 18 to 26, 19 to 26, 20 to 26, 21 to 26, 22 to 26, 23 to 26, 24 to 26, 25 to 26, 1 to 25, 2 to 25, 3 to 25, 4 to 25, 5 to 25, 6 to 25, 7 to 25, 8 to 25, 9 to 25, 10 to 25, 11 to 25, 12 to 25, 13 to 25, 14 to 25, 15 to 25, 16 to 25, 17 to 25, 18 to 25, 19 to 25, 20 to 25, 21 to 25, 22 to 25, 23 to 25, 24 to 25, 1 to 24, 2 to 24, 3 to 24, 4 to 24, 5 to 24, 6 to 24, 7 to 24, 8 to 24, 9 to 24, 10 to 24, 11 to 24, 12 to 24, 13 to 24, 14 to 24, 15 to 24, 16 to 24, 17 to 24, 18 to 24, 19 to 24, 20 to 24, 21 to 24, 22 to 24, 23 to 24, 1 to 23, 2 to 23, 3 to 23, 4 to 23, 5 to 23, 6 to 23, 7 to 23, 8 to 23, 9 to 23, 10 to 23, 11 to 23, 12 to 23, 13 to 23, 14 to 23, 15 to 23, 16 to 23, 17 to 23, 18 to 23, 19 to 23, 20 to 23, 21 to 23, 22 to 23, 1 to 22, 2 to 22, 3 to 22, 4 to 22, 5 to 22, 6 to 22, 7 to 22, 8 to 22, 9 to 22, 10 to 22, 11 to 22, 12 to 22, 13 to 22, 14 to 22, 15 to 22, 16 to 22, 17 to 22, 18 to 22, 19 to 22, 20 to 22, 21 to 22, 1 to 21, 2 to 21, 3 to 21, 4 to 21, 5 to 21, 6 to 21, 7 to 21, 8 to 21, 9 to 21, 10 to 21, 11 to 21, 12 to 21, 13 to 21, 14 to 21, 15 to 21, 16 to 21, 17 to 21, 18 to 21, 19 to 21, 20 to 21, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 1 to 17, 2 to 17, 3 to 17, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 3 to 11, 4 to 11, 5 to 11, 6 to 11, 7 to 11, 8 to 11, 9 to, 0 to 11, 0 to 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, a is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

Independently in some embodiments of a, and independently in combination with any embodiments of any other relevant substituent classes, a can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of a, and independently in combination with any embodiments of any other relevant substituent classes, a can be 1, 2, 3, 4, 5, 6, 7, 8, 9, or 10.

Independently in some embodiments of a, and independently in combination with any embodiments of any other relevant substituent classes, a can be an integer from 1 to 5, 2 to 5, 3 to 5, 4 to 5, 1 to 4, 2 to 4, 3 to 4, 1 to 3, 2 to 3, or 1 to 2. In preferred embodiments, a is 1, 2, 3, 4, or 5.

Independently in some embodiments of m, and independently in combination with any embodiments of any other relevant substituent classes, m can be an integer from 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 3 to 15, 4 to 15, 5 to 15, 6 to 15, 7 to 15, 8 to 15, 9 to 15, 10 to 15, 11 to 15, 12 to 15, 13 to 15, 14 to 15, 3 to 14, 4 to 14, 5 to 14, 6 to 14, 7 to 14, 8 to 14, 9 to 14, 10 to 14, 11 to 14, 12 to 14, 13 to 14, 3 to 13, 4 to 13, 5 to 13, 6 to 13, 7 to 13, 8 to 13, 9 to 13, 10 to 13, 11 to 13, 12 to 13, 3 to 12, 4 to 12, 5 to 12, 6 to 12, 7 to 12, 8 to 12, 9 to 12, 10 to 12, 11 to 12, 3 to 11, 4 to 11, 5 to 11, 6 to 11, 7 to 11, 8 to 11, 9 to 11, 10 to 11, 3 to 10, 4 to 10, 5 to 10, 6 to 10, 7 to 10, 8 to 10, 9 to 10, 3 to 9, 4 to 9, 5 to 9, 6 to 9, 7 to 9, 8 to 9, 3 to 8, 4 to 8, 5 to 8, 6 to 8, 7 to 8, 3 to 7, 4 to 7, 5 to 7, 6 to 7, 3 to 6, 4 to 6, 5 to 6, 3 to 5, 4 to 5, and 3 to 4. In some embodiments, m is 3, 4, 5, 6, 7, 8, 9, 10, 11, 12, 13, 14, 15, or 16.

Independently in some embodiments of m, and independently in combination with any embodiments of any other relevant substituent classes, m can be an integer from 3 to 10, 4 to 10, 5 to 10, 6 to 10, 7 to 10, 8 to 10, 9 to 10, 3 to 9, 4 to 9, 5 to 9, 6 to 9, 7 to 9, 8 to 9, 3 to 8, 4 to 8, 5 to 8, 6 to 8, 7 to 8, 3 to 7, 4 to 7, 5 to 7, 6 to 7, 3 to 6, 4 to 6, 5 to 6, 3 to 5, 4 to 5, and 3 to 4. Independently in some embodiments of m, and independently in combination with any embodiments of any other relevant substituent classes, m can be 3, 4, 5, 6, 7, 8, 9, or 10.

Independently in some embodiments of m, and independently in combination with any embodiments of any other relevant substituent classes, m can be an integer from 3 to 5, 4 to 5, or 3 to 4. In preferred embodiments, m is 3, 4, or 5.

Independently in some embodiments of n, and independently in combination with any embodiments of any other relevant substituent classes, n can be an integer from 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, n is 1, 2, 3, 4, 5, 6, 7, 8, 9, 10, 11, 12, 13, 14, 15, 16, 17, 18, 19, or 20.

Independently in some embodiments of n, and independently in combination with any embodiments of any other relevant substituent classes, n can be an integer from 1 to 5, 2 to 5, 3 to 5, 4 to 5, 1 to 4, 2 to 4, 3 to 4, 1 to 3, 2 to 3, or 1 to 2. In preferred embodiments, n is 1, 2, 3, 4, or 5.

In some embodiments, $R_3$ is —$CH_2$—Ar— or —$CH_2$—$CH_2$—(O—$CH_2$—$CH_2$)$_3$—; $R_2$ is hydrogen; $R_4$ is hydrogen, methyl, —COOH, —$CH_2$—O—$CH_2$—$CH_2$—OH, or —$CH_2$—OH; and $R_5$ is methyl, —$COCH_3$, —$CH_2$—N($CH_2$—$CH_3$)$_2$, —N($CH_2$—$CH_3$)$_2$, —$CH_2$—O—$CH_3$, —($CH_2$)$_6$—$CH_3$, —$CH_2$—O—$CH_2$—$CH_2$—OH, —$CH_2$—CH(COOH)—($CH_2$)$_5$—$CH_3$,

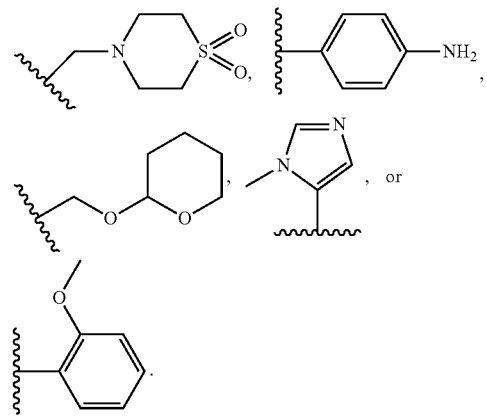

In some embodiments, $R_4$ is hydrogen; and $R_5$ is

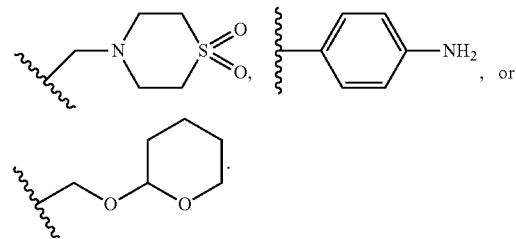

In some embodiments, $R_4$ is hydrogen; and $R_5$ is

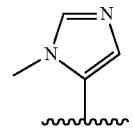

In some embodiments, $R_5$ is methyl, —$COCH_3$, or —$CH_2$—N($CH_2$—$CH_3$)$_2$.

In some embodiments, X is oxygen or $NR_2$, wherein $R_2$ is hydrogen, methyl, or —$CH_2$—$CH_3$; and $R_1$ is —$CH_2$—$CH_2$—$CH_2$—$CH_2$—OH, —$CH_2$—$CH_2$—(O—$CH_2$—$CH_2$)$_n$—O—$CH_3$, where n is an integer from 3 to 16, —$CH_2$—$CH_2$—O—$CH_2$—$CH_2$—OH, —($CH_2$—$CH_2$)$_3$—NH—$CH_3$,

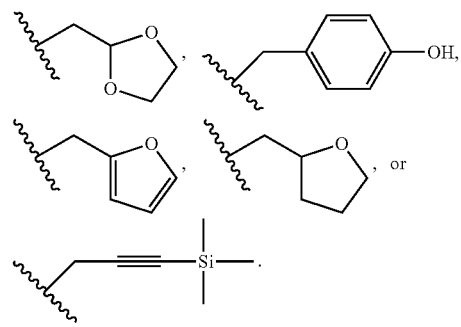

Independently in some embodiments of Formula I, X is oxygen, sulfur, or $NR_2$, wherein $R_2$ is hydrogen, alkyl, or substituted alkyl, wherein $R_1$ is $$-A-B(-C)_\delta, \qquad \text{Formula XII}$$

wherein A is

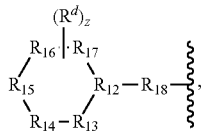

Formula VI $R^{18}$ in A is $-(CR_{19}R_{19})_p-$; p is an integer from 0 to 5; each $R_{19}$ is hydrogen; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; z is an integer from 0 to 11; $R_{12}$, $R_{13}$, $R_{14}$, $R_{15}$, $R_{16}$, and $R_{17}$ are independently C or N, wherein the bonds between adjacent $R_{12}$ to $R_{17}$ are double or single according to valency, and wherein $R_{12}$ to $R_{17}$ are bound to none, one, or two hydrogens according to valency;

wherein B is

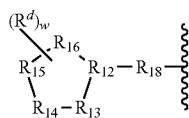

Formula IX $R^{18}$ in B is $-(CR_{19}R_{19})_p-$; p is an integer from 0 to 5; each $R_{19}$ is hydrogen; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; w is an integer from 0 to 4; each $R_{12}$, $R_{13}$, $R_{14}$, $R_{15}$, and $R_{16}$, are independently C or N, wherein the bonds between adjacent $R_{12}$ to $R_{16}$ are double or single according to valency, and wherein $R_{12}$ to $R_{16}$ are bound to none, one, or two hydrogens according to valency;

wherein C is

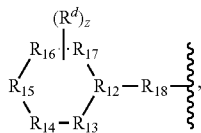

Formula VI $R^{18}$ in C is $-(CR_{19}R_{19})_p-$ or $-(CR_{19}R_{19})_p-X_b-(CR_{19}R_{19})_q-$, wherein p and q are independently integers from 0 to 5; $X_b$ is absent, $-O-$, $-S-$, $-S(O)-$, $-S(O)_2-$, or $NR_{20}$; each $R_{19}$ is hydrogen; $R_{20}$ is alkyl or substituted alkyl; $R^d$ are independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; z is an integer from 0 to 11; each $R_{12}$, $R_{13}$, $R_{14}$, $R_{15}$, $R_{16}$, and $R_{17}$ are independently C, O, N, or S, wherein the bonds between adjacent $R_{12}$ to $R_{17}$ are double or single according to valency, and wherein $R_{12}$ to $R_{17}$ are bound to none, one, or two hydrogens according to valency; and wherein $\delta$ is 1.

Independently in some embodiments of Formula I, X is oxygen, sulfur, or $NR_2$, wherein $R_2$ is hydrogen, alkyl, or substituted alkyl, wherein $R_1$ is $$-A-B(-C)_\delta, \qquad \text{Formula XII}$$

wherein A is

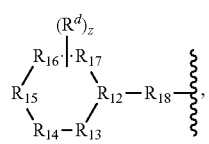

Formula VI $R^{18}$ in A is $-(CH_2)_p-$; p is an integer from 0 to 5; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; z is an integer from 0 to 11; $R_{12}$, $R_{13}$, $R_{14}$, $R_{15}$, $R_{16}$, and $R_{17}$ are independently C or N, wherein the bonds between adjacent $R_{12}$ to $R_{17}$ are double or single according to valency, wherein $R_{12}$ to $R_{17}$ are bound to none, one, or two hydrogens according to valency; and $R^{15}$ is bound to B;

wherein B is

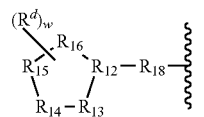

Formula IX $R^{18}$ in B is $-(CH_2)_p-$; p is an integer from 0 to 5; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; w is an integer from 0 to 4; each $R_{12}$, $R_{13}$, $R_{14}$, $R_{15}$, and $R_{16}$, are independently C or N, wherein the bonds between adjacent $R_{12}$ to $R_{16}$ are double or single according to valency, and wherein $R_{12}$ to $R_{16}$ are bound to none, one, or two hydrogens according to valency, and $R^{14}$ is bound to C;

wherein C is

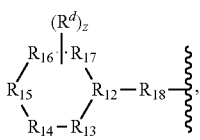
Formula VI $R^{18}$ in C is —$(CR_{19}R_{19})_p$—$X_b$—$(CR_{19}R_{19})_q$—, p is 1 and q is 0; $X_b$ is —O—; each $R_{19}$ is hydrogen; $R^d$ are independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; z is an integer from 0 to 11; each $R_{12}$, $R_{13}$, $R_{14}$, $R_{15}$, $R_{16}$, and $R_{17}$ are independently C, O, N, or S, wherein the bonds between adjacent $R_{12}$ to $R_{17}$ are double or single according to valency, and wherein $R_{12}$ to $R_{17}$ are bound to none, one, or two hydrogens according to valency; and wherein δ is 1.

Independently in some embodiments of Formula I, X is oxygen, sulfur, or $NR_2$, wherein $R_2$ is hydrogen, alkyl, or substituted alkyl, wherein $R_1$ is

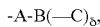 Formula XII wherein A is

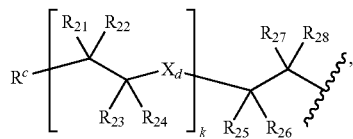
Formula VI $R_{21}$, $R_{22}$, $R_{23}$, $R_{24}$, $R_{25}$, $R_{26}$, $R_{27}$, and $R_{28}$ in A are independently hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, arylalkyl, substituted arylalkyl, alkoxy, substituted alkoxy, aroxy, substituted aroxy, carbonyl, substituted carbonyl, carboxyl, substituted carboxyl, amino, substituted amino, amido, substituted amido, $C_3$-$C_{20}$ cyclic, substituted $C_3$-$C_{20}$ cyclic, heterocyclic, substituted heterocyclic, poly(ethylene glycol), or poly(lactic-co-glycolic acid); k is an integer from 0 to 20; each $X_d$ is independently absent, O, or S; and $R^c$ is B;

wherein B is

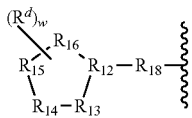
Formula IX $R^{18}$ in B is —$(CR_{19}R_{19})_p$—; p is an integer from 0 to 5; each $R_{19}$ is hydrogen; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; w is an integer from 0 to 4; each $R_{12}$, $R_{13}$, $R_{14}$, $R_{15}$, and $R_{16}$, are independently C or N, wherein the bonds between adjacent $R_{12}$ to $R_{16}$ are double or single according to valency, and wherein $R_{12}$ to $R_{16}$ are bound to none, one, or two hydrogens according to valency;

wherein C is

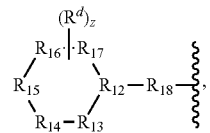
Formula VI $R^{18}$ in C is —$(CR_{19}R_{19})_p$— or —$(CR_{19}R_{19})_p$—$X_b$—$(CR_{19}R_{19})_q$—, wherein p and q are independently integers from 0 to 5; $X_b$ is absent, —O—, —S—, —S(O)—, —S(O)$_2$—, or $NR_{20}$; each $R_{19}$ is hydrogen; $R_{20}$ is alkyl or substituted alkyl; $R^d$ are independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; z is an integer from 0 to 11; wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein δ is 1.

Independently in some embodiments of Formula I, X is oxygen, sulfur, or $NR_2$, wherein $R_2$ is hydrogen, alkyl, or substituted alkyl, wherein $R_1$ is

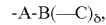 Formula XII wherein A is

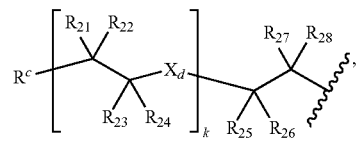
Formula VI $R_{21}$, $R_{22}$, $R_{23}$, $R_{24}$, $R_{25}$, $R_{26}$, $R_{27}$, and $R_{28}$ in A are independently hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, arylalkyl, substituted arylalkyl, alkoxy, substituted alkoxy, aroxy, substituted aroxy, carbonyl, substituted carbonyl, carboxyl, substituted carboxyl, amino, substituted amino, amido, substituted amido, $C_3$-$C_{20}$ cyclic, substituted $C_3$-$C_{20}$ cyclic, heterocyclic, substituted heterocyclic, poly(ethylene glycol), or poly(lactic-co-glycolic acid); k is an integer from 0 to 20; each $X_d$ is independently absent, O, or S; and $R^c$ is B;

wherein B is

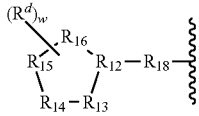

Formula IX $R^{18}$ in B is $-(CR_{19}R_{19})_p-$; p is an integer from 0 to 5; each $R_{19}$ is hydrogen; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; w is an integer from 0 to 4; each $R_{12}$, $R_{13}$, $R_{14}$, $R_{15}$, and $R_{16}$, are independently C or N, wherein the bonds between adjacent $R_{12}$ to $R_{16}$ are double or single according to valency, and wherein $R_{12}$ to $R_{16}$ are bound to none, one, or two hydrogens according to valency, and $R^{14}$ is bound to C;

wherein C is

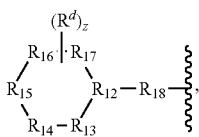

Formula VI $R^{18}$ in C is $-(CR_{19}R_{19})_p-$; p is an integer from 0 to 5; each $R_{19}$ is hydrogen; $R^d$ are independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; z is an integer from 0 to 11; wherein $R_{12}$, $R_{13}$, $R_{14}$, $R_{15}$, $R_{16}$, and $R_{17}$ are independently C, N, or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein δ is 1.

In some embodiments, the compound is

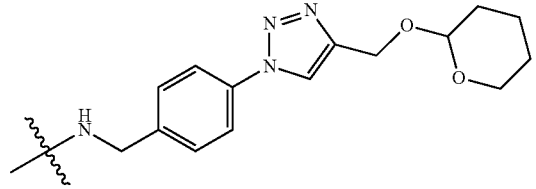

Z2-Y12

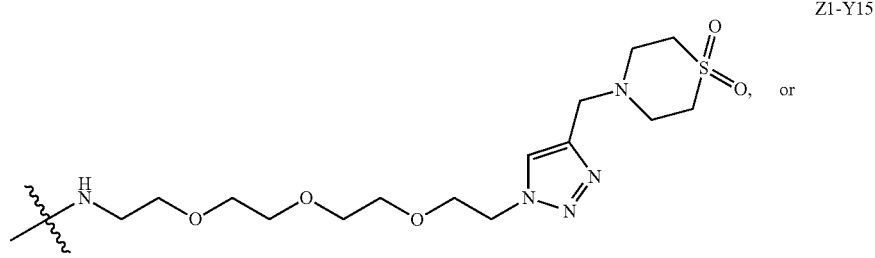

Z1-Y15 or

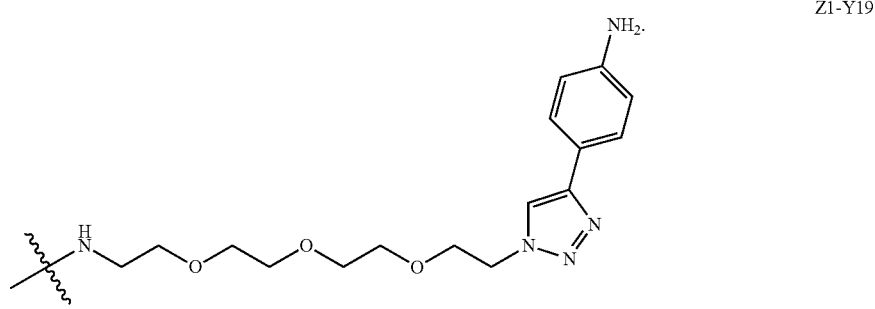

Z1-Y19

In some embodiments, the product includes a cargo or payload, such as a biological material. For example, the biological material can be cells or tissue. In some embodiments, the cargo is disposed within an outer member (e.g. a coating or encapsulating layer) that includes compounds as described herein on its surface.

In some embodiments, the product can be a cardiac pacemaker, a catheter, a needle injection catheter, a blood clot filter, a vascular transplant, a balloon, a stent transplant, a biliary stent, an intestinal stent, a bronchial stent, an esophageal stent, a ureteral stent, an aneurysm-filling coil or other coil device, a surgical repair mesh, a transmyocardial revascularization device, a percutaneous myocardial revascularization device, a prosthesis, an organ, a vessel, an aorta, a heart valve, a tube, an organ replacement part, an implant, a fiber, a hollow fiber, a membrane, a textile, banked blood, a blood container, a titer plate, an adsorber media, a dialyzer, a connecting piece, a sensor, a valve, an endoscope, a filter, a pump chamber, or another medical device intended to have hemocompatible properties.

In some embodiments, the product includes cells or tissues encapsulated or coated with a polymer, where the surface or a surface of the polymeric product includes compounds as described herein. In some embodiments of such products:

(a) the polymer comprises polydimethylsiloxane (PDMS);

(b) the compound comprises the formula -A-B(—C)$_\delta$ (Formula XIII), where A is Formula VIII or Formula VI, B is Formula IX, δ is 1, C is Formula VI;

(c) the product is spherical or spheroidal in shape;

(d)) the product has an average diameter of 1.5 mm;

(e) the cell is a cell producing a recombinant product; and, optionally, (f) the product has a pore size of 0.1 to 1 μm.

In some embodiments, the product is provided as a preparation of products and the products in the preparation have one or more of the following characteristics:

(1) at least 50% of the products in the preparation have a surface with a concentration of 1 to 5% surface modifications as measured by X-ray photoelectron spectroscopy (XPS);

(2) at least 50% of the products in the preparation have the shape specified in (c); (3) at least 50% of the products in the preparation have a the diameter specified in (d); and (4) at least 50% of the products in the preparation have the pore size of (f).

In some embodiments, the product has properties (1) and (2).

In some embodiments, the product has properties (1) and (3).

In some embodiments, the product has properties (1) and (4).

In some embodiments, the product has properties (2) and (3).

In some embodiments, the product has properties (2) and (4).

In some embodiments, the product has properties (3) and (4).

In some embodiments, the product has properties (1), (2), and (3).

In some embodiments, the product has properties (1), (2), (3). and (4).

In some embodiments, when implanted into the subject, at least 5% of the cells are alive after 30 days.

In some embodiments, when implanted into the subject, the cells respond to an increase in blood glucose by secreting insulin.

In some embodiments, the product is singularly modified with the compound of (b).

In some embodiments, the product is encapsulated or coated with a polymer, wherein the polymer comprises a compound with a structure-X—R$_1$, wherein X is oxygen, sulfur, NR$_2$, or another group compatible with attachment or coupling of the compound to a product or surface; R$_2$ is hydrogen, alkyl, or substituted alkyl; and R$_1$ is -A-B(—C)$_\delta$,   Formula XII wherein A is

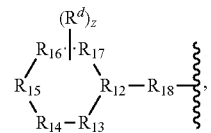

Formula VI $R^{18}$ in A is —(CH$_2$)$_p$—; p is an integer from 0 to 5; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, C$_3$-C$_{20}$ cyclic, substituted C$_3$-C$_{20}$ cyclic, heterocyclic, or substituted heterocyclic; z is an integer from 0 to 11; R$_{12}$, R$_{13}$, R$_{14}$, R$_{15}$, R$_{16}$, and R$_{17}$ are independently C or N, wherein the bonds between adjacent R$_{12}$ to R$_{17}$ are double or single according to valency, wherein R$_{12}$ to R$_{17}$ are bound to none, one, or two hydrogens according to valency; and R$^{15}$ is bound to B;

wherein B is

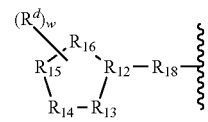

Formula IX $R^{18}$ in B is —(CH$_2$)$_p$—; p is an integer from 0 to 5; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, C$_3$-C$_{20}$ cyclic, substituted C$_3$-C$_{20}$ cyclic, heterocyclic, or substituted heterocyclic; w is an integer from 0 to 4; each R$_{12}$, R$_{13}$, R$_{14}$, R$_{15}$, and R$_{16}$, are independently C or N, wherein the bonds between adjacent R$_{12}$ to R$_{16}$ are double or single according to valency, and wherein R$_{12}$ to R$_{16}$ are bound to none, one, or two hydrogens according to valency, and R$^{14}$ is bound to C.

wherein C is

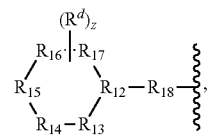

Formula VI $R^{18}$ in C is —(CR$_{19}$R$_{19}$)$_p$—X$_b$—(CR$_{19}$R$_{19}$)$_q$—, p is 1 and q is 0; X$_b$ is —O—; each R$_{19}$ is hydrogen; $R^d$ are independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, C$_3$-C$_{20}$ cyclic, substituted C$_3$-C$_{20}$ cyclic, heterocyclic, or substituted heterocyclic; z is an integer from 0 to 11; each R$_{12}$, R$_{13}$, R$_{14}$, R$_{15}$, R$_{16}$, and R$_{17}$ are independently C, O, N, or S, wherein the bonds between adjacent R$_{12}$ to $R_{17}$ are double or single according to valency, and wherein $R_{12}$ to $R_{17}$ are bound to none, one, or two hydrogens according to valency;

wherein δ is 1; and wherein the product has one or more characteristics selected from:
(a) a spherical or spheroidal shape;
(b) a mean diameter between 1 mm and 4 mm;
(c) a mean pore size ranging from 0.1 μm to 10 μm;
(d) a density of chemical derivatizations between 100 and 1000 per μm² on the surface or a surface of the products, in the interior of the products, or both; and
(e) a concentration of between 10 and 100 percent surface modifications.

In some embodiments, the product is encapsulated or coated with a polymer, wherein the polymer comprises a compound with a structure-X—$R_1$, wherein X is oxygen, sulfur, $NR_2$, or another group compatible with attachment or coupling of the compound to a product or surface; $R_2$ is hydrogen, alkyl, or substituted alkyl; and $R_1$ is -A-B(—C)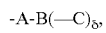,      Formula XII wherein A is

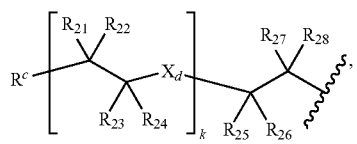      Formula VI $R_{21}$, $R_{22}$, $R_{23}$, $R_{24}$, $R_{25}$, $R_{26}$, $R_{27}$, and $R_{28}$ in A are independently hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, arylalkyl, substituted arylalkyl, alkoxy, substituted alkoxy, aroxy, substituted aroxy, carbonyl, substituted carbonyl, carboxyl, substituted carboxyl, amino, substituted amino, amido, substituted amido, $C_3$-$C_{20}$ cyclic, substituted $C_3$-$C_{20}$ cyclic, heterocyclic, substituted heterocyclic, poly(ethylene glycol), or poly(lactic-co-glycolic acid); k is an integer from 0 to 20; each $X_d$ is independently absent, O, or S; and $R^c$ is B;

wherein B is

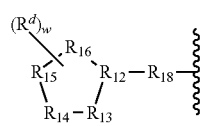      Formula IX $R^{18}$ in B is —$(CR_{19}R_{19})_p$—; p is an integer from 0 to 5; each $R_{19}$ is hydrogen; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; w is an integer from 0 to 4; each $R_{12}$, $R_{13}$, $R_{14}$, $R_{15}$, and $R_{16}$ are independently C or N, wherein the bonds between adjacent $R_{12}$ to $R_{16}$ are double or single according to valency, and wherein $R_{12}$ to $R_{16}$ are bound to none, one, or two hydrogens according to valency, and $R^{14}$ is bound to C;

wherein C is

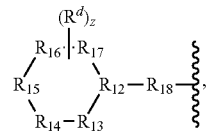      Formula VI $R^{18}$ in C is —$(CR_{19}R_{19})_p$—; p is an integer from 0 to 5; each $R_{19}$ is hydrogen; $R^d$ are independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; z is an integer from 0 to 11; wherein $R_{12}$, $R_{13}$, $R_{14}$, $R_{15}$, $R_{16}$, and $R_{17}$ are independently C, N, or $S(O)_2$, wherein the bonds between adjacent $R_{12}$ to $R_{17}$ are double or single according to valency, and wherein $R_{12}$ to $R_{17}$ are bound to none, one, or two hydrogens according to valency;

wherein δ is 1; and wherein the product has one or more characteristics selected from:
(a) a spherical or spheroidal shape;
(b) a mean diameter between 1 mm and 4 mm;
(c) a mean pore size ranging from 0.1 μm to 10 μm;
(d) a density of chemical derivatizations between 100 and 1000 per μm² on the surface or a surface of the products, in the interior of the products, or both; and
(e) a concentration of between 10 and 100 percent surface modifications.

In some embodiments, the product is multiply modified with the compound of (b) and another compound of different structure (for example, another compound as disclosed herein).

In some embodiments, the product is purified after chemical modification to remove any unreacted or partially reacted contaminants present with the chemically modified product, wherein the purified chemically modified product induces a lower foreign body response than a similar product that has not been chemically modified.

DETAILED DESCRIPTION OF THE INVENTION

It has been discovered that certain classes of chemical compounds confer beneficial effects, such as lower foreign body response, when used to chemically modify products for implantation into the body of a subject. In tests of a range of product materials, the disclosed chemical modifications improve the in vivo performance of implantable biomedical devices through chemical surface modification of commonly and widely used materials for device manufacture.

I. Definitions

"Biocompatible," as used herein, refers to a substance or object that performs its desired function when introduced into an organism without inducing significant inflammatory response, immunogenicity, or cytotoxicity to native cells, tissues, or organs. For example, a biocompatible product is a product that performs its desired function when introduced into an organism without inducing significant inflammatory response, immunogenicity, or cytotoxicity to native cells, tissues, or organs. Biocompatibility, as used herein, can be quantified using the in vivo biocompatibility assay described below.

In this assay, a material or product as disclosed can be considered biocompatible if it produces, in a test of biocompatibility related to immune system reaction less than 50%, 45%, 40%, 35%, 30%, 25%, 20%, 15%, 10%, 8%, 6%, 5%, 4%, 3%, 2%, or 1% of the reaction, in the same test of biocompatibility, produced by a material or product the same as the test material or product except for a lack of the surface modification on the test material or product. Examples of useful biocompatibility tests include measuring and assessing cytotoxicity in cell culture, inflammatory response after implantation (such as by fluorescence detection of cathepsin activity), and immune system cells recruited to implant (for example, macrophages and neutrophils).

"Foreign body response" as used herein, refers to the immunological response of biological tissue to the presence of any foreign material in the tissue which can include protein adsorption, macrophages, multinucleated foreign body giant cells, fibroblasts, and angiogenesis.

"Contacting" as used herein in the context of coating refers to any way for coating a product, using one or more of the compounds disclosed herein, on a substrate such as a product. Contacting can include, but is not limited to, intraoperative dip-coating, spraying, wetting, immersing, dipping, painting, bonding or adhering, stepwise surface derivatization, or otherwise providing a substrate or surface with a compound. The compound can be covalently attached, non-covalently attached, or both, to the substrate or surface.

"Coating" as used herein, refers to any temporary, semi-permanent or permanent layer, covering or surface. A coating can be applied as a gas, vapor, liquid, paste, semi-solid, or solid. In addition a coating can be applied as a liquid and solidified into a hard coating. Elasticity can be engineered into coatings to accommodate pliability, e.g. swelling or shrinkage, of the substrate or surface to be coated.

"Chemical modification" and related terms, as used herein in the context of the disclosed products, refers to chemical modification of the product. Generally, such chemical modification is by direct attachment, coupling, or adherence of a compound to the surface material of the product. Preferably, the chemical modification involves modification with one or more of the disclosed compounds. Chemical modification, as defined herein in the context of the disclosed products, can be accomplished at any time and in any manner, including, for example, synthesis or production of the modified form of the product or material when the product or material is formed, addition of the chemical modification after the final product or material is formed, or at any time in between. The terms "replaced," "replace," "modified," "singularly modified," "singular modification," "multiply modified," "multiple modifications," "chemically modified," "surface modified," "modification," "chemical modification," "surface modification," "substituted," "substitution," "derived from," "based on," or "derivatized," and similar terms, as used herein to describe a structure, do not limit the structure to one made from a specific starting material or by a particular synthetic route. Except where specifically and expressly provided to the contrary, the terms refer to a structural property, regardless of how the structure was formed, and the structure is not limited to a structure made by any specific method.

In some embodiments, where explicitly indicated, addition or application of a material, compound, or composition to a starting material or intermediate before it is made into or incorporated into the final product can be specifically excluded. Thus, for example, chemical modification of alginate or another polymer prior to the polymer being incorporated into a capsule or other structure can be, in some embodiments, specifically excluded as the manner of producing a chemical modification of the capsule or structure. As another example, coating a device, prosthesis, or other product with a material that was chemically modified prior to being applied as a coating can be, in some embodiments, specifically excluded as the manner of producing a chemical modification of the device, prosthesis, or product. However, for such embodiments where such specific exclusions are used, so long as the product was itself chemically modified, coating of or addition to the product of another material that has chemical modifications does not alter the fact that the product was chemically modified according to the meaning of the term used herein.

"Surface modification" and related terms, as used herein in the context of a product, e.g., the disclosed products, refers to chemical modification of the surface or a surface of the product. Generally, such surface modification is by direct attachment, coupling, or adherence of a compound to the surface material of the product. Preferably, the surface modification involves modification with one or more of the disclosed compounds. Surface modification, as defined herein in the context of the disclosed products, can be accomplished at any time and in any manner, including, for example, synthesis or production of the modified form of the product or material when the product or material is formed, addition of the chemical modification after the final product or material is formed, or at any time in between. Except where specifically and expressly provided to the contrary, the term "surface modification" refers to a structural property, regardless of how the structure was formed, and the structure is not limited to a structure made by any specific method.

In some embodiments, where explicitly indicated, addition or application of a material, compound, or composition to a starting material or intermediate before it is made into or incorporated into the final product can be specifically excluded. Thus, for example, chemical or surface modification of alginate or another polymer prior to the polymer being incorporated into a capsule or other structure can be, in some embodiments, specifically excluded as the manner of producing a surface modification of the capsule or structure. As another example, coating a device, prosthesis, or other product with a material that was chemically modified prior to being applied as a coating can be, in some embodiments, specifically excluded as the manner of producing a surface modification of the device, prosthesis, or product. However, for such embodiments where such specific exclusions are used, so long as the product was itself surface modified, coating of or addition to the product of another material that has chemical modifications does not alter the fact that the product was surface modified according to the meaning of the term used herein.

In some embodiments, the moieties or compounds modifying the product can be present on the surface or a surface of the product, and are not present, or are not present in a significant amount, elsewhere in the product, e.g., on internal or interior surfaces. In some embodiments, at least 50, 60, 70, 80, 90, 95, or 99% of the moieties or compounds are present on the surface or a surface of the product. In some embodiments, the moieties or compounds are present on the exterior face of the surface or a surface of the product, and are not present, or not present in a significant amount, elsewhere in the product, e.g., on internal or interior surfaces. In some embodiments, at least 50, 60, 70, 80, 90, 95, or 99% of the moieties or compounds are present on the external face of the surface or a surface of the product.

In some embodiments, the moieties or compounds modifying the product can be present on a portion or component of the product, and are not present, or are not present in a significant amount, elsewhere in the product. Such differences can be referred to as asymmetry of the modification or coating. In some embodiments, at least 50, 60, 70, 80, 90, 95, or 99% of the moieties or compounds are present on the portion or component of the product. In some embodiments, the moieties or compounds are present on the exterior face of the portion or component of the product, and are not present, or not present in a significant amount, elsewhere in the product. In some embodiments, at least 50, 60, 70, 80, 90, 95, or 99% of the moieties or compounds are present on the external face of the portion or component of the product.

"Surface," as used herein in the context of the disclosed products, refers to the exterior or outer boundary of a product. Generally, the surface or a surface of a product corresponds to the idealized surface of a three dimensional solid that is topological homeomorphic with the product. The surface or a surface of the product can be an exterior surface or an interior surface of the product. An exterior surface forms the outermost layer of a product or device. An interior surface surrounds an inner cavity of a product or device, such as the inner cavity of a tube. As an example, both the outside surface of a tube and the inside surface of a tube are part of the surface or a surface of the tube. However, internal surfaces of the product that are not in topological communication with the exterior surface, such as a tube with closed ends, can be excluded as the surface or a surface of a product. Preferred surfaces to be chemically modified are the outside surface and surfaces that can contact immune system components. Where the product is porous or has holes in its mean (idealized or surface, the internal faces of passages and holes would not be considered part of the surface or a surface of the product if its opening on the mean surface of the product is less than 5 nm.

"Corresponding product" and "similar product," as used herein, refers a product that has, as far as is practical or possible, the same composition, structure, and construction as a reference product. The terms "corresponding" and "similar" can be used for the same meaning with any particular or subgroup of products or other materials described herein. For example, a "similar surface modification" refers a surface modification that has, as far as is practical or possible, the same composition, structure, and construction as a reference surface modification.

"Control corresponding product" and "control similar product," as used herein, refers a product that has, as far as is practical or possible, the same composition, structure, and construction as a reference product except for one or more specified parameters. For example, a control corresponding product that lacks the chemical modification in reference to a chemically modified product refers to a product that has, as far as is practical or possible, the same composition, structure, and construction as a reference product except for the chemical modification. Generally, a product prior to chemical modification constitutes a control corresponding product to the chemically modified form of the product. The terms "control corresponding" and "control similar" can be used for the same meaning with any particular or subgroup of products or other materials described herein. For example, a "control similar surface modification" refers a surface modification that has, as far as is practical or possible, the same composition, structure, and construction as a reference surface modification except for one or more specified parameters. Components that are "control corresponding" or "control similar" relative to a reference component are useful as controls in assays assessing the effect of independent variables.

"Preparation," as used herein in reference to products, compounds, and other objects and components themselves (as opposed to their production or preparation), refers to a plurality of the product, compound, or other object or component, each such product, compound, or other object or component having a set of common properties and structure but also having some differences in properties or structure. For example, a preparation of capsules with capsules having the same composition, structure, and functional properties, can include, for example, capsules having a variance in shape, size, pore size, generally around a desired mean. It is not necessary that such variance be intended or purposely designed, although that is contemplated. Rather, such variance generally is a consequence of the variability in production or preparation of the products, compounds, and other objects and components (as is exemplified by production of capsules).

"Implanting," as used herein, refers to the insertion or grafting into the body of a subject a product or material.

"Administering," as used herein, refers to contacting a substance or product to the body of a subject. For example, administering a substance or a product includes contacting the skin of a subject and injecting or implanting a substance or product into the subject.

"Chemical compound," as used herein, refers to an organic compound. The disclosed compounds for chemically modifying products are examples of chemical compounds.

"High," "higher," "increases," "elevates," and "elevation," as used herein, refer to increases above a reference level, e.g., a basal level, e.g., as compared to a control. "Low," "lower," "reduces," and "reduction," as used herein, refer to decreases below a reference level, e.g., a basal level, e.g., as compared to a control. "Improved," as used herein, refers to a change that is desirable, which may be a higher or lower value of some measure.

"Long term," as used herein, refers to a state or situation that extends for longer than days or weeks. Preferred long term effects last several months or years.

"Monitoring" as used herein refers to any method in the art by which an activity can be measured.

"Providing," as used herein, refers to any method, device, or means of adding a compound or molecule to something, e.g., a method or device known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

"Preventing," as used herein, refers to administering or applying a treatment or therapy prior to the onset of clinical symptoms of a disease or conditions so as to prevent a physical manifestation of aberrations associated with the disease or condition.

"In need of treatment," as used herein, refers to a subject that would benefit from the treatment. In some embodiments, it comprises a judgment made by a caregiver (e.g. physician, nurse, nurse practitioner, or individual in the case of humans; veterinarian in the case of animals, including non-human mammals) that a subject requires or will benefit from treatment. This judgment can be made based on a variety of factors that are in the realm of a care giver's expertise, but that includes the knowledge that the subject is ill, or will be ill, as the result of a condition that is treatable by the compounds of the invention.

"Subject," as used herein, includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

"Treatment" and "treating," as used herein, refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

"Beneficial effect," as used herein, refers to any effect that is desired. In the context of the disclosed chemically modified products, beneficial effects include lower foreign body response, improved biocompatibility, and reduced immune response or reaction.

"Independently" as used herein in the context of chemical formulae (and unless the context clearly indicates otherwise), means that each instance of the group referred to is chosen independently of the other instances of that group. For example, each instance of the group could be different from every other instance, some other instances, or no other instances of the group. Where multiple groups are referred to, "independently" means that each instance of each given group is chosen independently of the other instances of the respective group and that each of the groups are chosen independently of the other groups. For example, each instance of a first group could be different from every instance, some other instances, or no other instances of a second group (or third, or fourth, etc., group).

"Component" as used herein in the context of a product, e.g., medical products, such as medical devices, is a part of a product that is structurally integrated with that product. A component may be applied to a substrate or to the surface or a surface of a product, contained within the substance of the product, retained in the interior of the product, or any other arrangement whereby that part is an integral element of the structure of the product. As an example, the silicone covering surrounding the mechanical part of a pacemaker is a component of the pacemaker. A component may be the lumen of a product where the lumen performs some function essential to the overall function of the product. The lumen of a tissue expander port is a component of the tissue expander. A component can refer to a reservoir or a discrete area within the product specifically adapted for the delivery of a fluid to a surface of the product. A reservoir within an implantable drug delivery device is a component of that device.

The phrase "effective amount," as used herein in the context of a coating, generally refers to the amount of the coating applied to the implant in order to provide one or more clinically measurable endpoints, such as reduced foreign body response compared to an uncoated implant, an implant coated with an unmodified coating, or another suitable control. The phrase "effective amount," as used herein in the context of a cell, capsule, product, device, material, composition, or compound, refers to a nontoxic but sufficient amount of the cell, capsule, product, device, material, composition, or compound to provide the desired result. The exact amount required may vary from subject to subject, depending on the species, age, and general condition of the subject; the severity of the disease that is being treated; the particular cell, capsule, product, device, material, composition, or compound used; its mode of administration; and other routine variables. An appropriate effective amount can be determined by one of ordinary skill in the art using only routine experimentation.

"Singularly modified," as used herein, refers to a modified product that contains one or more covalently attached compounds, non-covalently attached compounds, or both, wherein substantially all of the covalently attached compounds, non-covalently attached compounds, or both are the same compound. A singularly modified device includes, for example, a modified device wherein all the modifications are carried out using Z1-Y15 (see below).

"Multiply modified," as used herein, refers to a modified product that contains one or more covalently attached compounds, non-covalently attached compounds, or both, wherein substantially all of the covalently attached compounds, non-covalently attached compounds, or both are not formed using the same compound. A multiply modified device includes, for example, a modified device wherein the modifications are carried out using Z2-Y12, Z1-Y15 and Z1-Y19 (see below).

"Capsule," as used herein, refers to a particle having a mean diameter of about 150 µm to about 5 cm, formed of a cross-linked hydrogel, having a cross-linked hydrogel core that is surrounded by one or more polymeric shells, having one or more cross-linked hydrogel layers, having a cross-linked hydrogel coating, or a combination thereof. The capsule may have any shape suitable for, for example, cell encapsulation. The capsule may contain one or more cells dispersed in the cross-linked hydrogel, thereby "encapsulating" the cells. Reference to "capsules" herein refers to and includes microcapsules unless the context clearly indicates otherwise. Preferred capsules have a mean diameter of about 150 μm to about 8 mm.

"Microcapsule" and "microgel," as used herein, are used interchangeably to refer to a particle or capsule having a mean diameter of about 150 μm to about 1000 μm.

"Biological material" and "biomaterial," as used herein, refers to any biological substance, including, but not limited to, tissue, cells, biological micromolecules, such as a nucleotides, amino acids, cofactors, and hormones, biological macromolecules, such as nucleic acids, polypeptides, proteins (for example enzymes, receptors, secretory proteins, structural and signaling proteins, hormones, ligands, etc.), polysaccharides, and/or any combination thereof.

"Cell," as used herein, refers to individual cells, cell lines, primary cultures, or cultures derived from such cells unless specifically indicated. "Culture," as used herein, refers to a composition including cells, such as isolated cells, which can be of the same or a different type. "Cell line," as used herein, refers to a permanently established cell culture that will proliferate indefinitely given appropriate fresh medium and space, thus making the cell line "immortal." "Cell strain," as used herein, refers to a cell culture having a plurality of cells adapted to culture, but with finite division potential. "Cell culture," as used herein, is a population of cells grown on a medium such as agar.

Cells can be, for example, xenogeneic, autologous, or allogeneic. Cells can also be primary cells. Cells can also be cells derived from the culture and expansion of a cell obtained from a subject. For example, cells can also be stem cells or derived from stem cells. Cells can also be immortalized cells. Cells can also be genetically engineered to express or produce a protein, nucleic acid, or other product.

"Mammalian cell," as used herein, refers to any cell derived from a mammalian subject.

"Autologous," as used herein, refers to a transplanted biological material, such as cells, taken from the same individual.

"Allogeneic," as used herein, refers to a transplanted biological material, such as cells, taken from a different individual of the same species.

"Xenogeneic," as used herein, refers to a transplanted biological material, such as cells, taken from a different species.

"Endocrine cell," as used herein, refers to a cell of the endocrine system.

"Secreting endocrine cell," as used herein, refers to an endocrine cell that secretes one or more hormones.

"Islet cell," as used herein, refers to an endocrine cell derived from a mammalian pancreas. Islet cells include alpha cells that secrete glucagon, beta cells that secrete insulin and amylin, delta cells that secrete somatostatin, PP cells that secrete pancreatic polypeptide, or epsilon cells that secrete ghrelin. The term includes homogenous and heterogeneous populations of these cells. In preferred embodiments, a population of islet cells contains at least beta cells. In certain embodiments, an islet cell is a human islet cell.

"Hormone-producing cell," as used herein, refers to a cell that produces one or more hormones. Preferred hormone-producing cells produce hormone in response to physiological stimulus, such as the physiological stimulus that cause secretion of the hormone from an endocrine cell that naturally secretes the hormone. Secreting endocrine cells, hormone-producing cells derived from stem cells, and cells genetically engineered to produce hormone are examples of hormone-producing cells.

"Insulin-producing cell," as used herein, refers to a cell that produces insulin. Preferred insulin-producing cells produce insulin in response to glucose levels. Islet beta cells, insulin-producing cells derived from stem cells, and cells genetically engineered to produce insulin are examples of insulin-producing cells.

"Transplant," as used herein, refers to the transfer of a cell, tissue, or organ to a subject from another source. The term is not limited to a particular mode of transfer. Encapsulated cells may be transplanted by any suitable method, such as by injection or surgical implantation.

"Primary cells," "primary cell lines," and "primary cultures," as used herein, are used interchangeably to refer to cells and cells cultures that have been derived from a subject and allowed to grow in vitro for a limited number of passages, that is, splittings, of the culture.

"Mesenchymal stem cell" or "MSC," as used herein, refer to multipotent stem cells present in or derived from mesenchymal tissue that can differentiate into a variety of cell types, including: osteoblasts, chondrocytes, and adipocytes.

"Derived from," as used herein, with respect to cells, refer to cells obtained from tissue, cell lines, or cells, which optionally are then cultured, passaged, differentiated, induced, etc., to produce the derived cells. For example, induced pluripotent stem cells are derived from somatic cells.

"Pluripotency," as used herein, refers to the ability of cells to differentiate into multiple types of cells in an organism. By "pluripotent stem cells," it is meant cells that can self-renew and differentiate to produce all types of cells in an organism. By "multipotency" it is meant the ability of cells to differentiate into some types of cells in an organism but not all, typically into cells of a particular tissue or cell lineage.

"Multi-potent cells" and "adult stem cells," as used herein, refer to any type of stem cell that is not derived from an embryo or fetus and generally has a limited capacity to generate new cell types (referred to as "multipotency") and being committed to a particular lineage.

"Induced pluripotent stem cell," as used herein, encompasses pluripotent stem cells, that, like embryonic stem (ES) cells, can be cultured over a long period of time while maintaining the ability to differentiate into all types of cells in an organism, but that, unlike ES cells (which are derived from the inner cell mass of blastocysts), are derived from somatic cells.

"Analog" and "Derivative," in the context of chemical compounds, are used herein interchangeably, and refer to a compound having a structure similar to that of a parent compound, but varying from the parent compound by a difference in one or more certain components. (Designation as a parent compound does not mean that the parent compound is used as a starting material or intermediate but is rather a structural relationship.) Analogs or derivatives differ from the parent compound in one or more atoms, functional groups, or substructures, which are replaced with other atoms, groups, or substructures. An analog or derivative can be imagined to be formed, at least theoretically, from the parent compound via some chemical or physical process. The terms analog and derivative encompass compounds which retain the same basic ring structure as the parent compound, but possess one or more different substituents on the ring(s). For example, an analog or derivative of Z2-Y12 refers to a compound that retains the core of Z2-Y12, e.g., but differs in or more substituents on any of the rings. In some embodiments, an analog or derivative retains at least, 20, 30, 40, 50, 60, 70, 80, 90, or 100% of a selected activity of a reference compound, e.g., a parent compound.

"Substantially," as used herein, specifies an amount of 95% or more, 96% or more, 97% or more, 98% or more, or 99% or more.

"Click chemistry," as used herein, refers to chemical reactions used to couple two compounds together which are high yielding, wide in scope, create only byproducts that can be removed without chromatography, are stereospecific, simple to perform, and can be conducted in easily removable or benign solvents. Examples of reactions which fulfill these criteria include the nucleophilic ring opening of epoxides and aziridines, non-aldol type carbonyl reactions, including the formation of hydrazones and heterocycles, additions to carbon-carbon multiple bonds, including Michael Additions, and cycloaddition reactions, such as a 1,3-dipolar cycloaddition reaction (i.e., a Huisgen cycloaddition reaction). See, for example, Moses, and Moorhouse, Chem Soc. Rev. 36:1249-1262 (2007); Kolb and Sharpless, Drug Discovery Today. 8(24): 1128-1137 (2003); and Kolb et al., Angew. Chem. Int. Ed. 40:2004-2021 (2001).

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Except where specifically and expressly provided to the contrary, the term "substituted" refers to a structure, e.g., a chemical compound or a moiety on a larger chemical compound, regardless of how the structure was formed. The structure is not limited to a structure made by any specific method.

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with an heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkyl," as used herein, refers to the radical of saturated aliphatic groups, including straight-chain alkyl, alkenyl, or alkynyl groups, branched-chain alkyl, cycloalkyl (alicyclic), alkyl substituted cycloalkylgroups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfoxide, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —$CF_3$, —$CH_2$—$CF_3$, —$CCl_3$); —CN; —$NCOCOCH_2CH_2$; —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl, sulfoxide, and sulfonate), and silyl groups, as well as ethers, alkylthios, carbonyls (including ketones, aldehydes, carboxylates, and esters), haloalkyls, —CN and the like. Cycloalkyls can be substituted in the same manner.

The terms "alkenyl" and "alkynyl" refer to unsaturated aliphatic groups analogous in length and possible substitution to the alkyls described above, but that contain at least one double or triple bond, respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenyl" is art recognized, and refers to the aromatic moiety —$C_6H_5$, i.e., a benzene ring without one hydrogen atom.

The term "substituted phenyl" refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Amino" and "Amine," as used herein, are art-recognized and refer to both substituted and unsubstituted amines, e.g., a moiety that can be represented by the general formula:

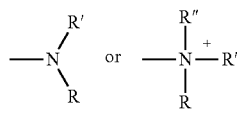

wherein, R, R', and R" each independently represent a hydrogen, substituted or unsubstituted alkyl, substituted or unsubstituted alkenyl, substituted or unsubstituted alkynyl, substituted or unsubstituted carbonyl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —$(CH_2)_m$—R'''. Thus, the term 'alkylamine' as used herein refers to an amine group, as defined above, having a substituted or unsubstituted alkyl attached thereto (i.e. at least one of R, R', or R" is an alkyl group).

"Carbonyl," as used herein, is art-recognized and includes such moieties as can be represented by the general formula:

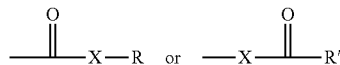

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R", or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —$(CH_2)_m$—R"; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

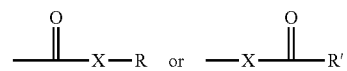

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "carboxyl" is as defined above for the formula

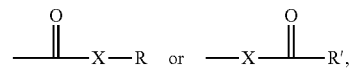

and is defined more specifically by the formula —$R^{iv}COOH$, wherein $R^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in $R^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The terms "alkoxyl" or "alkoxy," "aroxy" or "aryloxy," generally describe compounds represented by the formula —OR$^v$, wherein R$^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenoxy" is art recognized, and refers to a compound of the formula —OR$^v$ wherein R$^v$ is (i.e., —O—C$_6$H$_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenylthio" is art recognized, and refers to —S—C$_6$H$_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylalkyl," as used herein, refers to an alkyl group that is substituted with a substituted or unsubstituted aryl or heteroaryl group.

"Alkylaryl," as used herein, refers to an aryl group (e.g., an aromatic or hetero aromatic group), substituted with a substituted or unsubstituted alkyl group.

The terms "amide" or "amido" are used interchangeably, refer to both "unsubstituted amido" and "substituted amido" and are represented by the general formula:

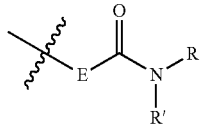

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or —(CH$_2$)$_m$—R'. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

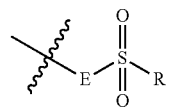

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

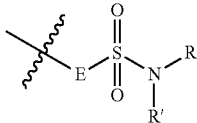

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the N atom to which they are attached complete a heterocycle having from 3 to 14 atoms in the ring structure; $R'''$ represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide.

The term "sulfoxide" is represented by the formula

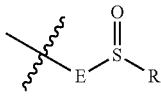

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or E and R taken together with the S atom to which they are attached complete a heterocycle having from 3 to 14 atoms in the ring structure; $R'''$ represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "phosphonyl" is represented by the formula

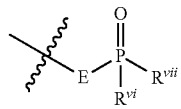

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, $R^{vi}$ and $R^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the P atom to which they are attached complete a heterocycle having from 3 to 14 atoms in the ring structure; $R'''$ represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phosphoryl" defines a phoshonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof.

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —$NO_2$.

The term "phosphate" refers to —O—$PO_3$.

The term "azide" or "azido" are used interchangeably to refer to —$N_3$.

The term "substituted $C_1$-$C_x$ alkyl" refers to alkyl groups having from one to x carbon atoms, wherein at least one carbon atom is substituted, wherein "x" is an integer from one to ten. The term "unsubstituted $C_1$-$C_x$ alkyl" refers to alkyl groups having from one to x carbon atoms that are not substituted, wherein "x" is an integer from one to ten.

The term "substituted $C_1$-$C_x$ alkylene" refers to alkylene groups having from one to x carbon atoms, wherein at least one carbon atom is substituted, wherein "x" is an integer from one to ten. The term "unsubstituted $C_1$-$C_x$ alkylene" refers to alkylene groups having from one to x carbon atoms that are not substituted, wherein "x" is an integer from one to ten. The term "alkylene" as used herein, refers to a moiety with the formula —$(CH_2)_a$—, wherein "a" is an integer from one to ten.

The term "substituted $C_2$-$C_x$ alkenyl" refers to alkenyl groups having from two to x carbon atoms, wherein at least one carbon atom is substituted, wherein "x" is an integer from two to ten. The term "unsubstituted $C_2$-$C_x$ alkenyl" refers to alkenyl groups having from two to x carbon atoms that are not substituted, wherein "x" is an integer from two to ten.

The term "substituted $C_2$-$C_x$ alkynyl" refers to alkynyl groups having from two to x carbon atoms, wherein at least one carbon atom is substituted, wherein "x" is an integer from two to ten. The term "unsubstituted $C_2$-$C_x$ alkynyl" refers to alkynyl groups having from two to x carbon atoms that are not substituted, wherein "x" is an integer from two to ten.

The term "substituted $C_1$-$C_x$ alkoxy" refers to alkoxy groups having from one to x carbon atoms, wherein at least one carbon atom is substituted, wherein "x" is an integer from one to ten. The term "unsubstituted $C_1$-$C_x$ alkoxy" refers to alkoxy groups having from one to x carbon atoms that are not substituted, wherein "x" is an integer from one to ten.

The term "substituted $C_1$-$C_x$ alkylamino" refers to alkylamino groups having from one to x carbon atoms, wherein at least one carbon atom is substituted, wherein "x" is an integer from one to ten. The term "unsubstituted $C_1$-$C_x$ alkylamino" refers to alkyl groups having from one to x carbon atoms that are not substituted, wherein "x" is an integer from one to ten. The terms "alkylamine" and "alkylamino" are used interchangeably. In any alkylamino, where the nitrogen atom is substituted with one, two, or three substituents, the nitrogen atom can be referred to as a secondary, tertiary, or quarternary nitrogen atom, respectively.

The term "substituted $C_1$-$C_x$ alkylthio" refers to alkylthio groups having from one to x carbon atoms, wherein at least one carbon atom is substituted, wherein "x" is an integer from one to ten. The term "unsubstituted $C_1$-$C_x$ alkylthio" refers to alkylthio groups having from one to x carbon atoms that are not substituted, wherein "x" is an integer from one to ten.

The term "substituted $C_1$-$C_x$ carbonyl" refers to carbonyl groups having from one to x carbon atoms, wherein at least one carbon atom is substituted, wherein "x" is an integer from one to ten. The term "unsubstituted $C_1$-$C_x$ carbonyl" refers to carbonyl groups having from one to x carbon atoms that are not substituted, wherein "x" is an integer from one to ten.

The term "substituted $C_1$-$C_x$ carboxyl" refers to carboxyl groups having from one to x carbon atoms, wherein at least one carbon atom is substituted, wherein "x" is an integer from one to ten. The term "unsubstituted $C_1$-$C_x$ carboxyl" refers to carboxyl groups having from one to x carbon atoms that are not substituted, wherein "x" is an integer from one to ten.

The term "substituted $C_1$-$C_x$ amido" refers to amido groups having from one to x carbon atoms, wherein at least one carbon atom is substituted, wherein "x" is an integer from one to ten. The term "unsubstituted $C_1$-$C_x$ amido" refers to amido groups having from one to x carbon atoms that are not substituted, wherein "x" is an integer from one to ten.

The term "substituted $C_1$-$C_x$ sulfonyl" refers to sulfonyl groups having from one to x carbon atoms, wherein at least one carbon atom is substituted, wherein "x" is an integer from one to ten. The term "unsubstituted $C_1$-$C_x$ sulfonyl" refers to sulfonyl groups having from one to x carbon atoms that are not substituted, wherein "x" is an integer from one to ten.

The term "substituted $C_1$-$C_x$ sulfonic acid" refers to sulfonic acid groups having from one to x carbon atoms, wherein at least one carbon atom is substituted, wherein "x" is an integer from one to ten. The term "unsubstituted $C_1$-$C_x$ sulfonic acid" refers to sulfonic acid groups having from one to x carbon atoms that are not substituted, wherein "x" is an integer from one to ten.

The term "substituted $C_1$-$C_x$ sulfamoyl" refers to sulfamoyl groups having from one to x carbon atoms, wherein at least one carbon atom is substituted, wherein "x" is an integer from one to ten. The term "unsubstituted $C_1$-$C_x$ sulfamoyl" refers to sulfamoyl groups having from one to x carbon atoms that are not substituted, wherein "x" is an integer from one to ten.

The term "substituted $C_1$-$C_x$ sulfoxide" refers to sulfoxide groups having from one to x carbon atoms, wherein at least one carbon atom is substituted, wherein "x" is an integer from one to ten. The term "unsubstituted $C_1$-$C_x$ sulfoxide" refers to sulfoxide groups having from one to x carbon atoms that are not substituted, wherein "x" is an integer from one to ten.

The term "substituted $C_1$-$C_x$ phosphoryl" refers to phosphoryl groups having from one to x carbon atoms, wherein at least one carbon atom is substituted, wherein "x" is an integer from one to ten. The term "unsubstituted $C_1$-$C_x$ phosphoryl" refers to phosphoryl groups having from one to x carbon atoms that are not substituted, wherein "x" is an integer from one to ten.

The term "substituted $C_1$-$C_x$ phosphonyl" refers to phosphonyl groups having from one to x carbon atoms, wherein at least one carbon atom is substituted, wherein "x" is an integer from one to ten. The term "unsubstituted $C_1$-$C_x$ phosphonyl" refers to phosphonyl groups having from one to x carbon atoms that are not substituted, wherein "x" is an integer from one to ten.

The term "substituted $C_0$-$C_x$ sulfonyl" refers to sulfonyl groups having from zero to x carbon atoms, wherein, if present, at least one carbon atom is substituted, wherein "x" is an integer from zero to ten. The term "unsubstituted $C_0$-$C_x$ sulfonyl" refers to sulfonyl groups having from zero to x carbon atoms that are not substituted, wherein "x" is an integer from zero to ten.

The term "substituted $C_0$-$C_x$ sulfonic acid" refers to sulfonic acid groups having from zero to x carbon atoms, wherein, if present, at least one carbon atom is substituted, wherein "x" is an integer from zero to ten. The term "unsubstituted $C_0$-$C_x$ sulfonic acid" refers to sulfonic acid groups having from zero to x carbon atoms that are not substituted, wherein "x" is an integer from zero to ten.

The term "substituted $C_0$-$C_x$ sulfamoyl" refers to sulfamoyl groups having from zero to x carbon atoms, wherein, if present, at least one carbon atom is substituted, wherein "x" is an integer from zero to ten. The term "unsubstituted $C_0$-$C_x$ sulfamoyl" refers to sulfamoyl groups having from zero to x carbon atoms that are not substituted, wherein "x" is an integer from zero to ten.

The term "substituted $C_0$-$C_x$ sulfoxide" refers to sulfoxide groups having from zero to x carbon atoms, wherein at least one carbon atom is substituted, wherein "x" is an integer from zero to ten. The term "unsubstituted $C_0$-$C_x$ sulfoxide" refers to sulfoxide groups having from zero to x carbon atoms that are not substituted, wherein "x" is an integer from zero to ten.

The term "substituted $C_0$-$C_x$ phosphoryl" refers to phosphoryl groups having from zero to x carbon atoms, wherein, if present, at least one carbon atom is substituted, wherein "x" is an integer from zero to ten. The term "unsubstituted $C_0$-$C_x$ phosphoryl" refers to phosphoryl groups having from zero to x carbon atoms that are not substituted, wherein "x" is an integer from zero to ten.

The term "substituted $C_0$-$C_x$ phosphonyl" refers to phosphonyl groups having from zero to x carbon atoms, wherein, if present, at least one carbon atom is substituted, wherein "x" is an integer from zero to ten. The term "unsubstituted $C_0$-$C_x$ phosphonyl" refers to phosphonyl groups having from zero to x carbon atoms that are not substituted, wherein "x" is an integer from zero to ten.

The terms substituted "$C_x$ alkyl," "$C_x$ alkylene," "$C_x$ alkenyl," "$C_x$ alkynyl," "$C_x$ alkoxy," "$C_x$ alkylamino," "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms, wherein at least one carbon atom is substituted, wherein "x" is an integer from one to ten. The terms unsubstituted "$C_x$ alkyl," "$C_x$ alkylene," "$C_x$ alkenyl," "$C_x$ alkynyl," "$C_x$ alkoxy," "$C_x$ alkylamino", "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms that are not substituted, wherein "x" is an integer from one to ten.

The terms unsubstituted "$C_0$ sulfonyl," "$C_0$ sulfonic acid," "$C_0$ sulfamoyl," "$C_0$ phosphoryl," and "$C_0$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having zero carbon atoms that are not substituted.

"Halogen," as used herein, refers to fluorine, chlorine, bromine, or iodine.

As used herein, $U_1$ represents the organic groups alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, and polypeptide group.

As used herein, $U_2$ represents the organic groups alkylamino, dialkylamino, hydroxy, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, and polypeptide group.

As used herein, $U_3$ represents the organic groups alkylamino, dialkylamino, hydroxy, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, and polypeptide group.

As used herein, $U_4$ represents the organic groups alkyl, substituted alkyl, alkenyl, substituted alkenyl, alkynyl, substituted alkynyl, aryl, substituted aryl, heteroaryl, substituted heteroaryl, alkoxy, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, and substituted heterocyclic.

As used herein, $Q_1$ represents the organic groups arylalkyl and substituted arylalkyl.

As used herein, $Q_2$ represents the organic groups sulfonyl, substituted sulfonyl, sulfonic acid, phosphoryl, substituted phosphoryl, phosphonyl, and substituted phosphonyl.

As used herein, $Q_3$ represents the organic group poly (lactic-co-glycolic acid).

As used herein, $Q_4$ represents the organic groups phenyl and substituted phenyl.

As used herein, $Q_5$ represents the organic groups alkylamino, dialkylamino, and hydroxy.

As used herein, $Q_6$ represents the organic groups aroxy, substituted aroxy, carbonyl, substituted carbonyl, and poly (ethylene glycol).

As used herein, $Q_7$ represents the organic groups alkylthio, substituted alkylthio, arylthio, substituted arylthio, phenoxy, substituted phenoxy, phenylthio, substituted phenylthio, polyaryl, and substituted polyaryl.

As used herein, $Q_8$ represents the organic groups amino acid, peptide, and polypeptide group.

In some embodiments, groups $Q_1$, $Q_2$, $Q_3$, or any combination thereof, can be used along with any one of $U_1$, $U_2$, and $U_3$. For example, $U_1$ can be combined with $Q_1$, with $Q_2$, with $Q_3$, with $Q_1$ and $Q_2$, with $Q_1$ and $Q_3$, with $Q_2$ and $Q_3$, and with $Q_1$, $Q_2$, and $Q_3$. Such combinations can be referred to as $U_1+Q_1$, $U_1+Q_2$, $U_1+Q_3$, $U_1+Q_1+Q_2$, $U_1+Q_1+Q_3$, $U_1+Q_2+Q_3$, and $U_1+Q_1+Q_2+Q_3$, respectively. Similarly, $U_2$ can be combined with $Q_1$, with $Q_2$, with $Q_3$, with $Q_1$ and $Q_2$, with $Q_1$ and $Q_3$, with $Q_2$ and $Q_3$, and with $Q_1$, $Q_2$, and $Q_3$. Such combinations can be referred to as $U_2+Q_1$, $U_2+Q_2$, $U_2+Q_3$, $U_2+Q_1+Q_2$, $U_2+Q_1+Q_3$, $U_2+Q_2+Q_3$, and $U_2+Q_1+Q_2+Q_3$, respectively. Similarly, $U_3$ can be combined with $Q_1$, with $Q_2$, with $Q_3$, with $Q_1$ and $Q_2$, with $Q_1$ and $Q_3$, with $Q_2$ and $Q_3$, and with $Q_1$, $Q_2$, and $Q_3$. Such combinations can be referred to as $U_3+Q_1$, $U_3+Q_2$, $U_3+Q_3$, $U_3+Q_1+Q_2$, $U_3+Q_1+Q_3$, $U_3+Q_2+Q_3$, and $U_3+Q_1+Q_2+Q_3$, respectively.

In some embodiments, groups $Q_1$, $Q_2$, $Q_3$, $Q_5$, or any combination thereof, can be used along with $U_1$. For example, $U_1$ can be combined with $Q_1$, with $Q_2$, with $Q_3$, with $Q_5$, with $Q_1$ and $Q_2$, with $Q_1$ and $Q_3$, with $Q_1$ and $Q_5$, with $Q_2$ and $Q_3$, with $Q_2$ and $Q_5$, with $Q_3$ and $Q_5$, with $Q_1$, $Q_2$, and $Q_3$, with $Q_1$, $Q_2$, and $Q_5$, with $Q_1$, $Q_3$, and $Q_5$, with $Q_2$, $Q_3$, and $Q_5$, and with $Q_1$, $Q_2$, $Q_3$, and $Q_5$. Such combinations can be referred to as $U_1+Q_1$, $U_1+Q_2$, $U_1+Q_3$, $U_1+Q_5$, $U_1+Q_1+Q_2$, $U_1+Q_1+Q_3$, $U_1+Q_1+Q_5$, $U_1+Q_2+Q_3$, $U_1+Q_2+Q_5$, $U_1+Q_3+Q_5$, $U_1+Q_1+Q_2+Q_3$, $U_1+Q_1+Q_2+Q_5$, $U_1+Q_1+Q_3+Q_5$, $U_1+Q_2+Q_3+Q_5$, respectively.

In some embodiments, groups $Q_1$, $Q_2$, $Q_3$, $Q_4$, $Q_5$, $Q_6$, $Q_7$, $Q_8$ or any combination thereof, can be used along with $U_4$. For example, $U_4$ can be combined with $Q_1$, with $Q_2$, with $Q_3$, with $Q_4$, with $Q_5$, with $Q_6$, with $Q_7$, with $Q_8$, with $Q_1+Q_2$, with $Q_1+Q_3$, with $Q_1+Q_4$, with $Q_1+Q_5$, with $Q_1+Q_6$, with $Q_1+Q_7$, with $Q_1+Q_8$, with $Q_2+Q_3$, with $Q_2+Q_4$, with $Q_2+Q_5$, with $Q_2+Q_6$, with $Q_2+Q_7$, with $Q_2+Q_8$, with $Q_3+Q_4$, with $Q_3+Q_5$, with $Q_3+Q_6$, with $Q_3+Q_7$, with $Q_3+Q_8$, with $Q_4+Q_5$, with $Q_4+Q_6$, with $Q_4+Q_7$, with $Q_4+Q_8$, with $Q_5+Q_6$, with $Q_5+Q_7$, with $Q_5+Q_8$, with $Q_6+Q_7$, with $Q_6+Q_8$, with $Q_7+Q_8$, with $Q_1+Q_2+Q_3$, with $Q_1+Q_2+Q_4$, with $Q_1+Q_2+Q_5$, with $Q_1+Q_2+Q_6$, with $Q_1+Q_2+Q_7$, with $Q_1+Q_2+Q_8$, with $Q_1+Q_3+Q_4$, with $Q_1+Q_3+Q_5$, with $Q_1+Q_3+Q_6$, with $Q_1+Q_3+Q_7$, with $Q_1+Q_3+Q_8$, with $Q_1+Q_4+Q_5$, with $Q_1+Q_4+Q_6$, with $Q_1+Q_4+Q_7$, with $Q_1+Q_4+Q_8$, with $Q_1+Q_5+Q_6$, with $Q_1+Q_5+Q_7$, with $Q_1+Q_5+Q_8$, with $Q_1+Q_6+Q_7$, with $Q_1+Q_6+Q_8$, with $Q_1+Q_7+Q_8$, with $Q_2+Q_3+Q_4$, with $Q_2+Q_3+Q_5$, with $Q_2+Q_3+Q_6$, with $Q_2+Q_3+Q_7$, with $Q_2+Q_3+Q_8$, with $Q_2+Q_4+Q_5$, with $Q_2+Q_4+Q_6$, with $Q_2+Q_4+Q_7$, with $Q_2+Q_4+Q_8$, with $Q_2+Q_5+Q_6$, with $Q_2+Q_5+Q_7$, with $Q_2+Q_5+Q_8$, with $Q_2+Q_6+Q_7$, with $Q_2+Q_6+Q_8$, with $Q_2+Q_7+Q_8$, with $Q_3+Q_4+Q_5$, with $Q_3+Q_4+Q_6$, with $Q_3+Q_4+Q_7$, with $Q_3+Q_4+Q_8$, with $Q_3+Q_5+Q_6$, with $Q_3+Q_5+Q_7$, with $Q_3+Q_5+Q_8$, with $Q_3+Q_6+Q_7$, with $Q_3+Q_6+Q_8$, with $Q_3+Q_7+Q_8$, with $Q_4+Q_5+Q_6$, with $Q_4+Q_5+Q_7$, with $Q_4+Q_5+Q_8$, with $Q_4+Q_6+Q_7$, with $Q_4+Q_6+Q_8$, with $Q_4+Q_7+Q_8$, with $Q_5+Q_6+Q_7$, with $Q_5+Q_6+Q_8$, with $Q_5+Q_7+Q_8$, with $Q_6+Q_7+Q_8$, with $Q_1+Q_2+Q_3+Q_4$, with $Q_1+Q_2+Q_3+Q_5$, with $Q_1+Q_2+Q_3+Q_6$, with $Q_1+Q_2+Q_3+Q_7$, with $Q_1+Q_2+Q_3+Q_8$, with $Q_1+Q_3+Q_4+Q_5$, with $Q_1+Q_3+Q_4+Q_6$, with $Q_1+Q_3+Q_4+Q_7$, with $Q_1+Q_3+Q_4+Q_8$, with $Q_1+Q_4+Q_5+Q_6$, with $Q_1+Q_4+Q_5+Q_7$, with $Q_1+Q_4+Q_5+Q_8$, with $Q_1+Q_5+Q_6+Q_7$, with $Q_1+Q_5+Q_6+Q_8$, with $Q_1+Q_6+Q_7+Q_8$, with $Q_2+Q_3+Q_4+Q_5$, with $Q_2+Q_3+Q_4+Q_6$, with $Q_2+Q_3+Q_4+Q_7$, with $Q_2+Q_3+Q_4+Q_8$, with $Q_2+Q_4+Q_5+Q_6$, with $Q_2+Q_4+Q_5+Q_7$, with $Q_2+Q_4+Q_5+Q_8$, with $Q_2+Q_5+Q_6+Q_7$, with $Q_2+Q_5+Q_6+Q_8$, with $Q_2+Q_6+Q_7+Q_8$, with $Q_3+Q_4+Q_5+Q_6$, with $Q_3+Q_4+Q_5+Q_7$, with $Q_3+Q_4+Q_5+Q_8$, with $Q_3+Q_5+Q_6+Q_7$, with $Q_3+Q_5+Q_6+Q_8$, with $Q_3+Q_6+Q_7+Q_8$, with $Q_4+Q_5+Q_6+Q_7$, with $Q_4+Q_5+Q_6+Q_8$, with $Q_4+Q_6+Q_7+Q_8$, with $Q_5+Q_6+Q_7+Q_8$, with $Q_1+Q_2+Q_3+Q_4+Q_5$, with $Q_1+Q_2+Q_3+Q_4+Q_6$, with $Q_1+Q_2+Q_3+Q_4+Q_7$, with $Q_1+Q_2+Q_3+Q_4+Q_8$, with $Q_1+Q_3+Q_4+Q_5+Q_6$, with $Q_1+Q_3+Q_4+Q_5+Q_7$, with $Q_1+Q_3+Q_4+Q_5+Q_8$, with $Q_1+Q_4+Q_5+Q_6+Q_7$, with $Q_1+Q_4+Q_5+Q_6+Q_8$, with $Q_1+Q_5+Q_6+Q_7+Q_8$, with $Q_2+Q_3+Q_4+Q_5+Q_6$, with $Q_2+Q_3+Q_4+Q_5+Q_7$, with $Q_2+Q_3+Q_4+Q_5+Q_8$, with $Q_2+Q_4+Q_5+Q_6+Q_7$, with $Q_2+Q_4+Q_5+Q_6+Q_8$, with $Q_2+Q_5+Q_6+Q_7+Q_8$, with $Q_3+Q_4+Q_5+Q_6+Q_7$, with $Q_3+Q_4+Q_5+Q_6+Q_8$, with $Q_3+Q_5+Q_6+Q_7+Q_8$, with $Q_4+Q_5+Q_6+Q_7+Q_8$, with $Q_1+Q_2+Q_3+Q_4+Q_5+Q_6$, with $Q_1+Q_2+Q_3+Q_4+Q_5+Q_7$, with $Q_1+Q_2+Q_3+Q_4+Q_5+Q_8$, with $Q_1+Q_3+Q_4+Q_5+Q_6+Q_7$, with $Q_1+Q_2+Q_3+Q_4+Q_5+Q_6+Q_8$, with $Q_1+Q_3+Q_4+Q_5+Q_6+Q_7+Q_8$, with $Q_2+Q_3+Q_4+Q_5+Q_6+Q_7+Q_8$, or with $Q_1+Q_2+Q_3+Q_4+Q_5+Q_6+Q_7+Q_8$. Such combinations can be referred to as $U_4+Q_1$, $U_4+Q_2$, $U_4+Q_3$, $U_4+Q_4$, $U_4+Q_5$, $U_4+Q_6$, $U_4+Q_7$, $U_4+Q_8$, $U_4+Q_1+Q_2$, $U_4+Q_1+Q_3$, $U_4+Q_1+Q_4$, $U_4+Q_1+Q_5$, $U_4+Q_1+Q_6$, $U_4+Q_1+Q_7$, $U_4+Q_1+Q_8$, $U_4+Q_2+Q_3$, $U_4+Q_2+Q_4$, $U_4+Q_2+Q_5$, $U_4+Q_2+Q_6$, $U_4+Q_2+Q_7$, $U_4+Q_2+Q_8$, $U_4+Q_3+Q_4$, $U_4+Q_3+Q_5$, $U_4+Q_3+Q_6$, $U_4+Q_3+Q_7$, $U_4+Q_3+Q_8$, $U_4+Q_4+Q_5$, $U_4+Q_4+Q_6$, $U_4+Q_4+Q_7$, $U_4+Q_4+Q_8$, $U_4+Q_5+Q_6$, $U_4+Q_5+Q_7$, $U_4+Q_5+Q_8$, $U_4+Q_6+Q_7$, $U_4+Q_6+Q_8$, $U_4+Q_7+Q_8$, $U_4+Q_1+Q_2+Q_3$, $U_4+Q_1+Q_2+Q_4$, $U_4+Q_1+Q_2+Q_5$, $U_4+Q_1+Q_2+Q_6$, $U_4+Q_1+Q_2+Q_7$, $U_4+Q_1+Q_2+Q_8$, $U_4+Q_1+Q_3+Q_4$, $U_4+Q_1+Q_3+Q_5$, $U_4+Q_1+Q_3+Q_6$, $U_4+Q_1+Q_3+Q_7$, $U_4+Q_1+Q_3+Q_8$, $U_4+Q_1+Q_4+Q_5$, $U_4+Q_1+Q_4+Q_6$, $U_4+Q_1+Q_4+Q_7$, $U_4+Q_1+Q_4+Q_8$, $U_4+Q_1+Q_5+Q_6$, $U_4+Q_1+Q_5+Q_7$, $U_4+Q_1+Q_5+Q_8$, $U_4+Q_1+Q_6+Q_7$, $U_4+Q_1+Q_6+Q_8$, $U_4+Q_1+Q_7+Q_8$, $U_4+Q_2+Q_3+Q_4$, $U_4+Q_2+Q_3+Q_5$, $U_4+Q_2+Q_3+Q_6$, $U_4+Q_2+Q_3+Q_7$, $U_4+Q_2+Q_3+Q_8$, $U_4+Q_2+Q_4+Q_5$, $U_4+Q_2+Q_4+Q_6$, $U_4+Q_2+Q_4+Q_7$, $U_4+Q_2+Q_4+Q_8$, $U_4+Q_2+Q_5+Q_6$, $U_4+Q_2+Q_5+Q_7$, $U_4+Q_2+Q_5+Q_8$, $U_4+Q_2+Q_6+Q_7$, $U_4+Q_2+Q_6+Q_8$, $U_4+Q_2+Q_7+Q_8$, $U_4+Q_3+Q_4+Q_5$, $U_4+Q_3+Q_4+Q_6$, $U_4+Q_3+Q_4+Q_7$, $U_4+Q_3+Q_4+Q_8$, $U_4+Q_3+Q_5+Q_6$, $U_4+Q_3+Q_5+Q_7$, $U_4+Q_3+Q_5+Q_8$, $U_4+Q_3+Q_6+Q_7$, $U_4+Q_3+Q_6+Q_8$, $U_4+Q_3+Q_7+Q_8$, $U_4+Q_4+Q_5+Q_6$, $U_4+Q_4+Q_5+Q_7$, $U_4+Q_4+Q_5+Q_8$, $U_4+Q_4+Q_6+Q_7$, $U_4+Q_4+Q_6+Q_8$, $U_4+Q_4+Q_7+Q_8$, $U_4+Q_5+Q_6+Q_7$, $U_4+Q_5+Q_6+Q_8$, $U_4+Q_5+Q_7+Q_8$, $U_4+Q_6+Q_7+Q_8$, $U_4+Q_1+Q_2+Q_3+Q_4$, $U_4+Q_1+Q_2+Q_3+Q_5$, $U_4+Q_1+Q_2+Q_3+Q_6$, $U_4+Q_1+Q_2+Q_3+Q_7$, $U_4+Q_1+Q_2+Q_3+Q_8$, $U_4+Q_1+Q_3+Q_4+Q_5$, $U_4+Q_1+Q_3+Q_4+Q_6$, $U_4+Q_1+Q_3+Q_4+Q_7$, $U_4+Q_1+Q_3+Q_4+Q_8$, $U_4+Q_1+Q_4+Q_5+Q_6$, $U_4+Q_1+Q_4+Q_5+Q_7$, $U_4+Q_1+Q_4+Q_5+Q_8$, $U_4+Q_1+Q_5+Q_6+Q_7$, $U_4+Q_1+Q_5+Q_6+Q_8$, $U_4+Q_1+Q_6+Q_7+$ $Q_8$, $U_4+Q_2+Q_3+Q_4+Q_5$, $U_4+Q_2+Q_3+Q_4+Q_6$, $U_4+Q_2+Q_3+Q_4+Q_7$, $U_4+Q_2+Q_3+Q_4+Q_8$, $U_4+Q_2+Q_4+Q_5+Q_6$, $U_4+Q_2+Q_4+Q_5+Q_7$, $U_4+Q_2+Q_4+Q_5+Q_8$, $U_4+Q_2+Q_5+Q_6+Q_7$, $U_4+Q_2+Q_5+Q_6+Q_8$, $U_4+Q_2+Q_6+Q_7+Q_8$, $U_4+Q_3+Q_4+Q_5+Q_6$, $U_4+Q_3+Q_4+Q_5+Q_7$, $U_4+Q_3+Q_4+Q_5+Q_8$, $U_4+Q_3+Q_5+Q_6+Q_7$, $U_4+Q_3+Q_4+Q_6+Q_8$, $U_4+Q_3+Q_6+Q_7+Q_8$, $U_4+Q_4+Q_5+Q_6+Q_7$, $U_4+Q_4+Q_5+Q_6+Q_8$, $U_4+Q_4+Q_6+Q_7+Q_8$, $U_4+Q_5+Q_6+Q_7+Q_8$, $U_4+Q_1+Q_2+Q_3+Q_4+Q_5$, $U_4+Q_1+Q_2+Q_3+Q_4+Q_6$, $U_4+Q_1+Q_2+Q_3+Q_4+Q_7$, $U_4+Q_1+Q_2+Q_3+Q_4+Q_8$, $U_4+Q_1+Q_3+Q_4+Q_5+Q_6$, $U_4+Q_1+Q_3+Q_4+Q_5+Q_7$, $U_4+Q_1+Q_3+Q_4+Q_5+Q_8$, $U_4+Q_1+Q_4+Q_5+Q_6+Q_7$, $U_4+Q_1+Q_4+Q_5+Q_6+Q_8$, $U_4+Q_1+Q_5+Q_6+Q_7+Q_8$, $U_4+Q_2+Q_3+Q_4+Q_5+Q_6$, $U_4+Q_2+Q_3+Q_4+Q_5+Q_7$, $U_4+Q_2+Q_3+Q_4+Q_5+Q_8$, $U_4+Q_2+Q_4+Q_5+Q_6+Q_7$, $U_4+Q_2+Q_4+Q_5+Q_6+Q_8$, $U_4+Q_2+Q_5+Q_6+Q_7+Q_8$, $U_4+Q_3+Q_4+Q_5+Q_6+Q_7$, $U_4+Q_3+Q_4+Q_5+Q_6+Q_8$, $U_4+Q_3+Q_5+Q_6+Q_7+Q_8$, $U_4+Q_4+Q_5+Q_6+Q_7+Q_8$, $U_4+Q_1+Q_2+Q_3+Q_4+Q_5+Q_6$, $U_4+Q_1+Q_2+Q_3+Q_4+Q_5+Q_7$, $U_4+Q_1+Q_2+Q_3+Q_4+Q_5+Q_8$, $U_4+Q_1+Q_3+Q_4+Q_5+Q_6+Q_7$, $U_4+Q_1+Q_3+Q_4+Q_5+Q_6+Q_8$, $U_4+Q_1+Q_4+Q_5+Q_6+Q_7+Q_8$, $U_4+Q_2+Q_3+Q_4+Q_5+Q_6+Q_7$, $U_4+Q_2+Q_3+Q_4+Q_5+Q_6+Q_8$, $U_4+Q_2+Q_4+Q_5+Q_6+Q_7+Q_8$, $U_4+Q_3+Q_4+Q_5+Q_6+Q_7+Q_8$, $U_4+Q_1+Q_2+Q_3+Q_4+Q_5+Q_6+Q_7$, $U_4+Q_1+Q_2+Q_3+Q_4+Q_5+Q_6+Q_8$, $U_4+Q_1+Q_3+Q_4+Q_5+Q_6+Q_7+Q_8$, $U_4+Q_2+Q_3+Q_4+Q_5+Q_6+Q_7+Q_8$, and $U_4+Q_1+Q_2+Q_3+Q_4+Q_5+Q_6+Q_7+Q_8$, respectively.

As used herein, $J_1$ represents the organic groups substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, $C_1$-$C_9$ alkyl, $C_1$-$C_9$ alkylene, $C_2$-$C_9$ alkenyl, $C_2$-$C_9$ alkynyl, $C_1$-$C_9$ alkoxy, $C_1$-$C_9$ alkylamino, $C_1$-$C_9$ alkylthio, $C_1$-$C_9$ carbonyl, $C_1$-$C_9$ carboxyl, $C_1$-$C_9$ amido, $C_1$-$C_9$ sulfonyl, $C_1$-$C_9$ sulfonic acid, $C_1$-$C_9$ sulfamoyl, $C_1$-$C_9$ sulfoxide, $C_1$-$C_9$ phosphoryl, $C_1$-$C_9$ phosphonyl, $C_1$-$C_8$ alkyl, $C_1$-$C_8$ alkylene, $C_2$-$C_8$ alkenyl, $C_2$-$C_8$ alkynyl, $C_1$-$C_8$ alkoxy, $C_1$-$C_8$ alkylamino, $C_1$-$C_8$ alkylthio, $C_1$-$C_8$ carbonyl, $C_1$-$C_8$ carboxyl, $C_1$-$C_8$ amido, $C_1$-$C_8$ sulfonyl, $C_1$-$C_8$ sulfonic acid, $C_1$-$C_8$ sulfamoyl, $C_1$-$C_8$ sulfoxide, $C_1$-$C_8$ phosphoryl, $C_1$-$C_8$ phosphonyl, $C_1$-$C_7$ alkyl, $C_1$-$C_7$ alkylene, $C_2$-$C_7$ alkenyl, $C_2$-$C_7$ alkynyl, $C_1$-$C_7$ alkoxy, $C_1$-$C_7$ alkylamino, $C_1$-$C_7$ alkylthio, $C_1$-$C_7$ carbonyl, $C_1$-$C_7$ carboxyl, $C_1$-$C_7$ amino, $C_1$-$C_7$ amido, $C_1$-$C_7$ sulfonyl, $C_1$-$C_7$ sulfonic acid, $C_1$-$C_7$ sulfamoyl, $C_1$-$C_7$ sulfoxide, $C_1$-$C_7$ phosphoryl, $C_1$-$C_7$ phosphonyl, $C_1$-$C_6$ alkyl, $C_1$-$C_6$ alkylene, $C_2$-$C_6$ alkenyl, $C_2$-$C_6$ alkynyl, $C_1$-$C_6$ alkoxy, $C_1$-$C_6$ alkylamino, $C_1$-$C_6$ alkylthio, $C_1$-$C_6$ carbonyl, $C_1$-$C_6$ carboxyl, $C_1$-$C_6$ amido, $C_1$-$C_6$ sulfonyl, $C_1$-$C_6$ sulfonic acid, $C_1$-$C_6$ sulfamoyl, $C_1$-$C_6$ sulfoxide, $C_2$-$C_6$ phosphoryl, $C_2$-$C_6$ phosphonyl, $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_5$ carbonyl, $C_1$-$C_5$ carboxyl, $C_1$-$C_8$ amido, $C_1$-$C_5$ sulfonyl, $C_1$-$C_5$ sulfonic acid, $C_1$-$C_5$ sulfamoyl, $C_1$-$C_5$ sulfoxide, $C_1$-$C_5$ phosphoryl, $C_1$-$C_5$ phosphonyl, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_{10}$ sulfonyl, $C_0$-$C_{10}$ sulfonic acid, $C_0$-$C_{10}$ sulfamoyl, $C_0$-$C_{10}$ sulfoxide, $C_0$-$C_{10}$ phosphoryl, $C_0$-$C_{10}$ phosphonyl, $C_0$-$C_9$ sulfonyl, $C_0$-$C_9$ sulfonic acid, $C_0$-$C_9$ sulfamoyl, $C_0$-$C_9$ sulfoxide, $C_0$-$C_9$ phosphoryl, $C_0$-$C_9$ phosphonyl, $C_0$-$C_8$ sulfonyl, $C_0$-$C_8$ sulfonic acid, $C_0$-$C_8$ sulfamoyl, $C_0$-$C_8$ sulfoxide, $C_0$-$C_8$ phosphoryl, $C_0$-$C_8$ phosphonyl, $C_0$-$C_7$ sulfonyl, $C_0$-$C_7$ sulfonic acid, $C_0$-$C_7$ sulfamoyl, $C_0$-$C_7$ sulfoxide, $C_0$-$C_7$ phosphoryl, $C_0$-$C_7$ phosphonyl, $C_0$-$C_6$ sulfonyl, $C_0$-$C_6$ sulfonic acid, $C_0$-$C_6$ sulfamoyl, $C_0$-$C_6$ sulfoxide, $C_0$-$C_6$ phosphoryl, $C_0$-$C_6$ phosphonyl, $C_0$-$C_5$ sulfonyl, $C_0$-$C_5$ sulfonic acid, $C_0$-$C_5$ sulfamoyl, $C_0$-$C_5$ sulfoxide, $C_0$-$C_5$ phosphoryl, $C_0$-$C_5$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_{10}$ carbonyl, $C_{10}$ carboxyl, $C_{10}$ amido, $C_{10}$ sulfonyl, $C_{10}$ sulfonic acid, $C_{10}$ sulfamoyl, $C_{10}$ sulfoxide, $C_{10}$ phosphoryl, $C_{10}$ phosphonyl, $C_9$ alkyl, $C_9$ alkylene, $C_9$ alkenyl, $C_9$ alkynyl, $C_9$ alkoxy, $C_9$ alkylamino, $C_9$ alkylthio, $C_9$ carbonyl, $C_9$ carboxyl, $C_9$ amido, $C_9$ sulfonyl, $C_9$ sulfonic acid, $C_9$ sulfamoyl, $C_9$ sulfoxide, $C_9$ phosphoryl, $C_9$ phosphonyl, $C_8$ alkyl, $C_8$ alkylene, $C_8$ alkenyl, $C_8$ alkynyl, $C_8$ alkoxy, $C_8$ alkylamino, $C_8$ alkylthio, $C_8$ carbonyl, $C_8$ carboxyl, $C_8$ amido, $C_8$ sulfonyl, $C_8$ sulfonic acid, $C_8$ sulfamoyl, $C_8$ sulfoxide, $C_8$ phosphoryl, $C_8$ phosphonyl, $C_7$ alkyl, $C_7$ alkylene, $C_7$ alkenyl, $C_7$ alkynyl, $C_7$ alkoxy, $C_7$ alkylamino, $C_7$ alkylthio, $C_7$ carbonyl, $C_7$ carboxyl, $C_7$ amido, $C_7$ sulfonyl, $C_7$ sulfonic acid, $C_7$ sulfamoyl, $C_7$ sulfoxide, $C_7$ phosphoryl, $C_7$ phosphonyl, $C_6$ alkyl, $C_6$ alkylene, $C_6$ alkenyl, $C_6$ alkynyl, $C_6$ alkoxy, $C_6$ alkylamino, $C_6$ alkylthio, $C_6$ carbonyl, $C_6$ carboxyl, $C_6$ amido, $C_6$ sulfonyl, $C_6$ sulfonic acid, $C_6$ sulfamoyl, $C_6$ sulfoxide, $C_6$ phosphoryl, $C_6$ phosphonyl, $C_5$ alkyl, $C_5$ alkylene, $C_5$ alkenyl, $C_5$ alkynyl, $C_5$ alkoxy, $C_5$ alkylamino, $C_5$ alkylthio, $C_5$ carbonyl, $C_5$ carboxyl, $C_5$ amido, $C_8$ sulfonyl, $C_5$ sulfonic acid, $C_5$ sulfamoyl, $C_5$ sulfoxide, $C_5$ phosphoryl, $C_5$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, and $C_0$ phosphonyl.

As used herein, $J_2$ represents the organic groups substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_9$ alkyl, $C_1$-$C_9$ alkylene, $C_2$-$C_9$ alkenyl, $C_2$-$C_9$ alkynyl, $C_1$-$C_9$ alkoxy, $C_1$-$C_9$ alkylamino, $C_1$-$C_9$ alkylthio, $C_1$-$C_8$ alkyl, $C_1$-$C_8$ alkylene, $C_2$-$C_8$ alkenyl, $C_2$-$C_8$ alkynyl, $C_1$-$C_8$ alkoxy, $C_1$-$C_8$ alkylamino, $C_1$-$C_8$ alkylthio, $C_1$-$C_7$ alkyl, $C_1$-$C_7$ alkylene, $C_2$-$C_7$ alkenyl, $C_2$-$C_7$ alkynyl, $C_1$-$C_7$ alkoxy, $C_1$-$C_7$ alkylamino, $C_1$-$C_7$ alkylthio, $C_1$-$C_6$ alkyl, $C_1$-$C_6$ alkylene, $C_2$-$C_6$ alkenyl, $C_2$-$C_6$ alkynyl, $C_1$-$C_6$ alkoxy, $C_1$-$C_6$ alkylamino, $C_1$-$C_6$ alkylthio, $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_8$ alkenyl, $C_8$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, and $C_1$ alkylthio.

II. Compounds

Described herein, are compounds, such as chemical compounds, for use to modify a product, such as the surface of a product, a surface of a product, the surface of the product, a surface of the product, the face of a surface of a product, a face of a surface of a product, the face of the surface of a product, a face of the surface of a product, the face of a surface of the product, a face of a surface of the product, the face of the surface of the product, and a face of the surface of the product. Generally, the surface(s) and face(s) of the product to be modified can be those that, when the device is administered to (e.g., implanted in) a subject, would be in contact with fluid, cells, or other components of the subjects body. The compounds are represented by the general formula:

      Formula I wherein X is oxygen, sulfur, $NR_2$, or another group compatible with attachment or coupling of the compound to a product or surface;

$R_1$ is hydrogen, or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_1$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$); and $R_2$ is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

X is preferably oxygen, sulfur, or $NR_2$.

In some embodiments, $R_1$ is, independently in one or more sites of chemical modification,

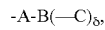      Formula XII wherein

A is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$);

B, and C are, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and δ is an integer from, as valency permits, 0 to 30.

X is preferably oxygen, sulfur, or $NR_2$.

In some embodiments, $R_1$ is, independently in one or more sites of chemical modification,

      Formula II wherein $R_3$ is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_3$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and $R^b$ is absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R^b$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In some embodiments of $R_1$, $R_2$, $R_3$, $R_4$, $R_5$, $R^b$, A, B, and C, and independently in combination with any embodiments of any other relevant substituent classes, $R_1$, $R_2$, $R_3$, $R_4$, $R_5$, $R^b$, A, B, and C can be, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_1$, $R_2$, $R_3$, $R_4$, $R_5$, $R^b$, A, B, and C organic groupings being those present in $U_1+Q_1+Q_2+Q_3$, $U_1+Q_5$, $U_1+Q_1+Q_5$, $U_1+Q_2+Q_5$, $U_1+Q_3+Q_5$, $U_1+Q_1+Q_2+Q_5$, $U_1+Q_1+Q_3+Q_5$, $U_1+Q_2+Q_3+Q_5$, or $+Q_1+Q_2+Q_3+Q_5$.

In some embodiments of $R_1$, $R_2$, $R_3$, $R_4$, $R_5$, $R^b$, A, B, and C, and independently in combination with any embodiments of any other relevant substituent classes, $R_1$, $R_2$, $R_3$, $R_4$, $R_5$, $R^b$, A, B, and C can be, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_1$, $R_2$, $R_3$, $R_4$, $R_5$, $R^b$, A, B, and C organic groupings being those present in $U_4$, $U_4+Q_1$, $U_4+Q_2$, $U_4+Q_3$, $U_4+Q_4$, $U_4+Q_5$, $U_4+Q_6$, $U_4+Q_7$, $U_4+Q_8$, $U_4+Q_1+Q_2$, $U_4+Q_1+Q_3$, $U_4+Q_1+Q_4$, $U_4+Q_1+Q_5$, $U_4+Q_1+Q_6$, $U_4+Q_1+Q_7$, $U_4+Q_1+Q_8$, $U_4+Q_2+Q_3$, $U_4+Q_2+Q_4$, $U_4+Q_2+Q_5$, $U_4+Q_2+Q_6$, $U_4+Q_2+Q_7$, $U_4+Q_2+Q_8$, $U_4+Q_3+Q_4$, $U_4+Q_3+Q_5$, $U_4+Q_3+Q_6$, $U_4+Q_3+Q_7$, $U_4+Q_3+Q_8$, $U_4+Q_4+Q_5$, $U_4+Q_4+Q_6$, $U_4+Q_4+Q_7$, $U_4+Q_4+Q_8$, $U_4+Q_5+Q_6$, $U_4+Q_5+Q_7$, $U_4+Q_5+Q_8$, $U_4+Q_6+Q_7$, $U_4+Q_6+Q_8$, $U_4+Q_7+Q_8$, $U_4+Q_1+Q_2+Q_3$, $U_4+Q_1+Q_2+Q_4$, $U_4+Q_1+Q_2+Q_5$, $U_4+Q_1+Q_2+Q_6$, $U_4+Q_1+Q_2+Q_7$, $U_4+Q_1+Q_2+Q_8$, $U_4+Q_1+Q_3+Q_4$, $U_4+Q_1+Q_3+Q_5$, $U_4+Q_1+Q_3+Q_6$, $U_4+Q_1+Q_3+Q_7$, $U_4+Q_1+Q_3+Q_8$, $U_4+Q_1+Q_4+Q_5$, $U_4+Q_1+Q_4+Q_6$, $U_4+Q_1+Q_4+Q_7$, $U_4+Q_1+Q_4+Q_8$, $U_4+Q_1+Q_5+Q_6$, $U_4+Q_1+Q_5+Q_7$, $U_4+Q_1+Q_5+Q_8$, $U_4+Q_1+Q_6+Q_7$, $U_4+Q_1+Q_6+Q_8$, $U_4+Q_1+Q_7+Q_8$, $U_4+Q_2+Q_3+Q_4$, $U_4+Q_2+Q_3+Q_5$, $U_4+Q_2+Q_3+Q_6$, $U_4+Q_2+Q_3+Q_7$, $U_4+Q_2+Q_3+Q_8$, $U_4+Q_2+Q_4+Q_5$, $U_4+Q_2+Q_4+Q_6$, $U_4+Q_2+Q_4+Q_7$, $U_4+Q_2+Q_4+Q_8$, $U_4+Q_2+Q_5+Q_6$, $U_4+Q_2+Q_5+Q_7$, $U_4+Q_2+Q_5+Q_8$, $U_4+Q_2+Q_6+Q_7$, $U_4+Q_2+Q_6+Q_8$, $U_4+Q_2+Q_7+Q_8$, $U_4+Q_3+Q_4+Q_5$, $U_4+Q_3+Q_4+Q_6$, $U_4+Q_3+Q_4+Q_7$, $U_4+Q_3+Q_4+Q_8$, $U_4+Q_3+Q_5+Q_6$, $U_4+Q_3+Q_5+Q_7$, $U_4+Q_3+Q_5+Q_8$, $U_4+Q_3+Q_6+Q_7$, $U_4+Q_3+Q_6+Q_8$, $U_4+Q_3+Q_7+Q_8$, $U_4+Q_4+Q_5+Q_6$, $U_4+Q_4+Q_5+Q_7$, $U_4+Q_4+Q_5+Q_8$, $U_4+Q_4+Q_6+Q_7$, $U_4+Q_4+Q_6+Q_8$, $U_4+Q_4+Q_7+Q_8$, $U_4+Q_5+Q_6+Q_7$, $U_4+Q_5+Q_6+Q_8$, $U_4+Q_5+Q_7+Q_8$, $U_4+Q_6+Q_7+Q_8$, $U_4+Q_1+Q_2+Q_3+Q_4$, $U_4+Q_1+Q_2+Q_3+Q_5$, $U_4+Q_1+Q_2+Q_3+Q_6$, $U_4+Q_1+Q_2+Q_3+Q_7$, $U_4+Q_1+Q_2+Q_3+Q_8$, $U_4+Q_1+Q_3+Q_4+Q_5$, $U_4+Q_1+Q_3+Q_4+Q_6$, $U_4+Q_1+Q_3+Q_4+Q_7$, $U_4+Q_1+Q_3+Q_4+Q_8$, $U_4+Q_1+Q_4+Q_5+Q_6$, $U_4+Q_1+Q_4+Q_5+Q_7$, $U_4+Q_1+Q_4+Q_5+Q_8$, $U_4+Q_1+Q_5+Q_6+Q_7$, $U_4+Q_1+Q_5+Q_6+Q_8$, $U_4+Q_1+Q_6+Q_7+Q_8$, $U_4+Q_2+Q_3+Q_4+Q_5$, $U_4+Q_2+Q_3+Q_4+Q_6$, $U_4+Q_2+Q_3+Q_4+Q_7$, $U_4+Q_2+Q_3+Q_4+Q_8$, $U_4+Q_2+Q_4+Q_5+Q_6$, $U_4+Q_2+Q_4+Q_5+Q_7$, $U_4+Q_2+Q_4+Q_5+Q_8$, $U_4+Q_2+Q_5+Q_6+Q_7$, $U_4+Q_2+Q_5+Q_6+Q_8$, $U_4+Q_2+Q_6+Q_7+Q_8$, $U_4+Q_3+Q_4+Q_5+Q_6$, $U_4+Q_3+Q_4+Q_5+Q_7$, $U_4+Q_3+Q_4+Q_5+Q_8$, $U_4+Q_3+Q_5+Q_6+Q_7$, $U_4+Q_3+Q_5+Q_6+Q_8$, $U_4+Q_3+Q_6+Q_7+Q_8$, $U_4+Q_4+Q_5+Q_6+Q_7$, $U_4+Q_4+Q_5+Q_6+Q_8$, $U_4+Q_4+Q_6+Q_7+Q_8$, $U_4+Q_5+Q_6+Q_7+Q_8$, $U_4+Q_1+Q_2+Q_3+Q_4+Q_5$, $U_4+Q_1+Q_2+Q_3+Q_4+Q_6$, $U_4+Q_1+Q_2+Q_3+Q_4+Q_7$, $U_4+Q_1+Q_2+Q_3+Q_4+Q_8$, $U_4+Q_1+Q_3+Q_4+Q_5+Q_6$, $U_4+Q_1+Q_3+Q_4+Q_5+Q_7$, $U_4+Q_1+Q_3+Q_4+Q_5+Q_8$, $U_4+Q_1+Q_4+Q_5+Q_6+Q_7$, $U_4+Q_1+Q_4+Q_5+Q_6+Q_8$, $U_4+Q_1+Q_5+Q_6+Q_7+Q_8$, $U_4+Q_2+Q_3+Q_4+Q_5+Q_6$, $U_4+Q_2+Q_3+Q_4+Q_5+Q_7$, $U_4+Q_2+Q_3+Q_4+Q_5+Q_8$, $U_4+Q_1+Q_3+Q_4+Q_5+Q_6+Q_7$, $U_4+Q_1+Q_3+Q_4+Q_5+Q_6+Q_8$, $U_4+Q_1+Q_4+Q_5+Q_6+Q_7+Q_8$, $U_4+Q_2+Q_3+Q_4+Q_5+Q_6+Q_7$, $U_4+Q_2+Q_3+Q_4+Q_5+Q_6+Q_8$, $U_4+Q_2+Q_4+Q_5+Q_6+Q_7+Q_8$, $U_4+Q_3+Q_4+Q_5+Q_6+Q_7+Q_8$, $U_4+Q_1+Q_2+Q_3+Q_4+Q_5+Q_6+Q_7$, $U_4+Q_1+Q_2+Q_3+Q_4+Q_5+$ $Q_6+Q_8$, $U_4+Q_1+Q_3+Q_4+Q_5+Q_6+Q_7+Q_8$, $U_4+Q_2+Q_3+Q_4+$ $Q_5+Q_6+Q_7+Q_8$, or $U_4+Q_1+Q_2+Q_3+Q_4+Q_5+Q_6+Q_7+Q_8$.

Independently in some embodiments of A and $R_3$, and independently in combination with any embodiments of any other relevant substituent classes, A and $R_3$ can be, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of B, C, and $R^b$, and independently in combination with any embodiments of any other relevant substituent classes, B, C, and $R^b$ can be, independently, absent, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of A and $R_3$, and independently in combination with any embodiments of any other relevant substituent classes, A and $R_3$ can be, independently, hydrogen, amino, hydroxyl, thiol, oxo, phosphate, or $J_1$.

Independently in some embodiments of A and $R_3$, and independently in combination with any embodiments of any other relevant substituent classes, A and $R_3$ can be, independently, hydrogen, amino, hydroxyl, thiol, oxo, phosphate, or $J_2$.

Independently in some embodiments of B, C, and $R^b$, and independently in combination with any embodiments of any other relevant substituent classes, B, C, and $R^b$ can be, independently, absent, hydrogen, amino, hydroxyl, thiol, oxo, phosphate, or $J_1$.

Independently in some embodiments of B, C, and $R^b$, and independently in combination with any embodiments of any other relevant substituent classes, B, C, and $R^b$ can be, independently, absent, hydrogen, amino, hydroxyl, thiol, oxo, phosphate, or $J_2$.

Independently in some embodiments of A and $R_3$, and independently in combination with any embodiments of any other relevant substituent classes, A and $R_3$ can be, independently,

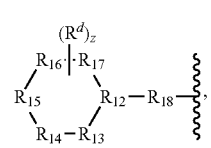

Formula VI

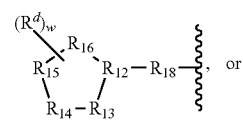

Formula IX

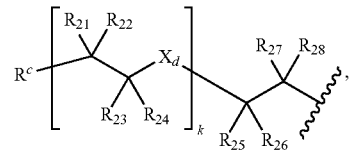

Formula VIII wherein z is an integer from 0-11; wherein w is an integer from 0-9; wherein k is an integer from 0 to 20;

wherein $R^d$ are independently B, C, —B(—C)$_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $X_d$ are independently absent, O, or S;

wherein $R^c$ is B, C, —B(—C)$_\delta$, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$);

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently B, C, absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently B, C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of B, and independently in combination with any embodiments of any other relevant substituent classes, B can be

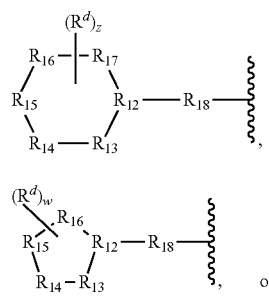

Formula VI

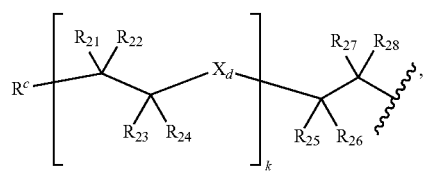

Formula IX

Formula VIII wherein z is an integer from 0-11; wherein w is an integer from 0-9; wherein k is an integer from 0 to 20;

wherein $R^d$ are independently C, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $X_d$ are independently absent, O, or S;

wherein $R^c$ is C, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$);

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently C, $R^b$, absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R^b$, and independently in combination with any embodiments of any other relevant substituent classes, $R^b$ can be

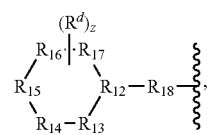

Formula VI

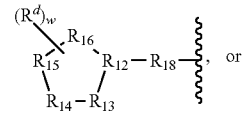

Formula IX

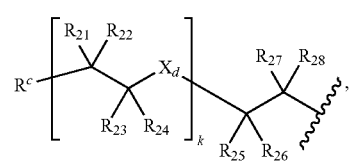

Formula VIII wherein z is an integer from 0-11; wherein w is an integer from 0-9; wherein k is an integer from 0 to 20;

wherein $R^d$ are independently C, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $X_d$ are independently absent, O, or S;

wherein $R^c$ is C, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$);

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently C, absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of C, and independently in combination with any embodiments of any other relevant substituent classes C can be

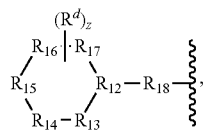

Formula VI

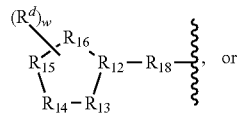

Formula IX

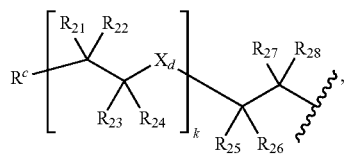

Formula VIII wherein z is an integer from 0-11; wherein w is an integer from 0-9; wherein k is an integer from 0 to 20;

wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $X_d$ are independently absent, O, or S;

wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$);

wherein $R_{12}$, $R_{13}$, $R_{14}$, $R_{15}$, $R_{16}$, and $R_{17}$ are independently C, O, N, S, S(O), or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —$S(O)_2$—, or $NR_{20}$, wherein each $R_{19}$ is, as valency permits, independently absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of A and $R_3$, and independently in combination with any embodiments of any other relevant substituent classes, A and $R_3$ can be, independently,

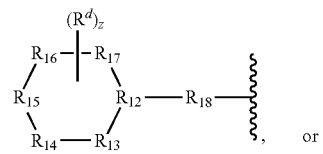

Formula VI

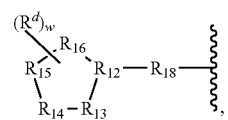

Formula IX wherein z is an integer from 0-11; wherein w is an integer from 0-9;

wherein $R^d$ are independently B, C, —B(—C)$_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —$S(O)_2$—, or $NR_{20}$, wherein each $R_{19}$ is, as valency permits, independently B, C, absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of B, and independently in combination with any embodiments of any other relevant substituent classes, B can be

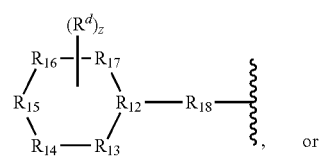

Formula VI

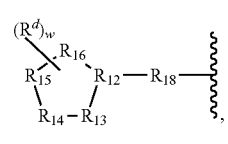

Formula IX wherein z is an integer from 0-11; wherein w is an integer from 0-9;

wherein $R^d$ are independently C, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+$ $Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently C, $R^b$, absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of $R^b$, and independently in combination with any embodiments of any other relevant substituent classes, $R^b$ can be

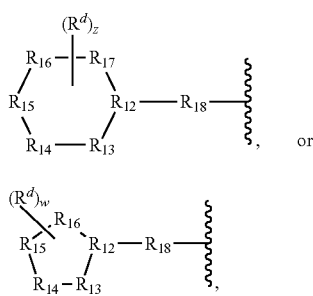

, or wherein z is an integer from 0-11; wherein w is an integer from 0-9;

wherein $R^d$ are independently C, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently C, absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of C, and independently in combination with any embodiments of any other relevant substituent classes, C can be

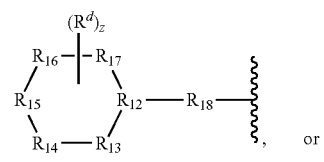

Formula VI

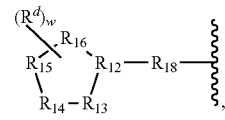

Formula IX wherein z is an integer from 0-11; wherein w is an integer from 0-9;

wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of A and $R_3$, and independently in combination with any embodiments of any other relevant substituent classes, A and $R_3$ can be, independently,

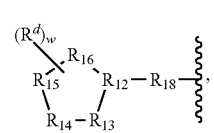

Formula IX wherein w is an integer from 0-9;

wherein $R^d$ are independently B, C, —B(—C)$_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C, O, N, S, S(O), or S(O)$_2$, wherein the bonds between adjacent $R_{12}$ to $R_{16}$ are double or single according to valency, and wherein $R_{12}$ to $R_{16}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —S(O)$_2$—, or $NR_{20}$, wherein each $R_{19}$ is, as valency permits, independently B, C, absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of B, and independently in combination with any embodiments of any other relevant substituent classes, B can be

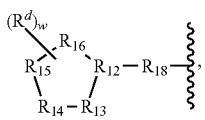

Formula IX wherein w is an integer from 0-9;
wherein $R^d$ are independently C, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, and $R_{16}$ are independently C, O, N, S, S(O), or S(O)$_2$, wherein the bonds between adjacent $R_{12}$ to $R_{16}$ are double or single according to valency, and wherein $R_{12}$ to $R_{16}$ are bound to none, one, or two hydrogens according to valency; and
wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —S(O)$_2$—, or $NR_{20}$, wherein each $R_{19}$ is, as valency permits, independently C, $R^b$, absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of $R^b$, and independently in combination with any embodiments of any other relevant substituent classes, $R^b$ can be

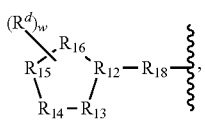

Formula IX wherein w is an integer from 0-9;
wherein $R^d$ are independently C, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, and $R_{16}$ are independently C, O, N, S, S(O), or S(O)$_2$, wherein the bonds between adjacent $R_{12}$ to $R_{16}$ are double or single according to valency, and wherein $R_{12}$ to $R_{16}$ are bound to none, one, or two hydrogens according to valency; and
wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —S(O)$_2$—, or $NR_{20}$, wherein each $R_{19}$ is, as valency permits, independently C, absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of C, and independently in combination with any embodiments of any other relevant substituent classes, C can be

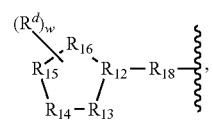

Formula IX wherein w is an integer from 0-9;
wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, and $R_{16}$ are independently C, O, N, S, S(O), or S(O)$_2$, wherein the bonds between adjacent $R_{12}$ to $R_{16}$ are double or single according to valency, and wherein $R_{12}$ to $R_{16}$ are bound to none, one, or two hydrogens according to valency; and
wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —S(O)$_2$—, or $NR_{20}$, wherein each $R_{19}$ is, as valency permits, independently absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of A and $R_3$, and independently in combination with any embodiments of any other relevant substituent classes, A and $R_3$ can be, independently,

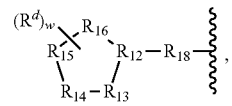

Formula IX wherein w is an integer from 0-9;
wherein $R^d$ are independently B, C, —B(—C)$_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently B, C, absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of B, and independently in combination with any embodiments of any other relevant substituent classes, B can be

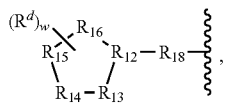

Formula IX wherein w is an integer from 0-9;
wherein $R^d$ are independently C, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently C, $R^b$, absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of $R^b$, and independently in combination with any embodiments of any other relevant substituent classes, $R^b$ can be

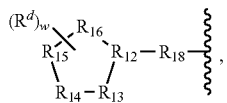

Formula IX wherein w is an integer from 0-9;
wherein $R^d$ are independently C, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+$ $Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently C, absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of C, and independently in combination with any embodiments of any other relevant substituent classes, C can be

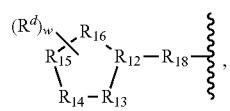

Formula IX wherein w is an integer from 0-9;
wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of A and $R_3$, and independently in combination with any embodiments of any other relevant substituent classes, A and $R_3$ can be, independently,

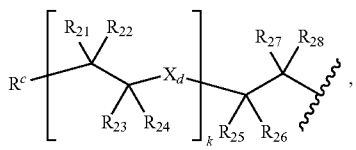

Formula VIII wherein k is an integer from 0 to 20;
wherein $X_d$ are independently absent, O, or S;
wherein $R^c$ is B, C, —B(—C)$_\delta$, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently B, C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of B, and independently in combination with any embodiments of any other relevant substituent classes, B can be

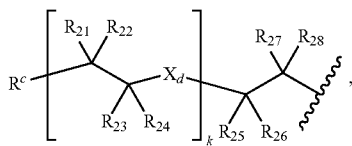

Formula VIII wherein k is an integer from 0 to 20;
wherein $X_d$ are independently absent, O, or S;
wherein $R^c$ is C, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R^b$, and independently in combination with any embodiments of any other relevant substituent classes, $R^b$ can be

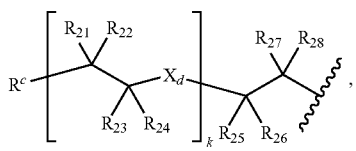

Formula VIII wherein k is an integer from 0 to 20;
wherein $X_d$ are independently absent, O, or S;
wherein $R^c$ is C, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of C, and independently in combination with any embodiments of any other relevant substituent classes, C can be

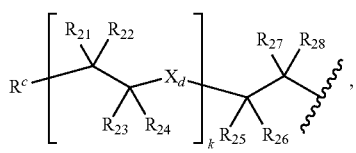

Formula VIII wherein k is an integer from 0 to 20;
wherein $X_d$ are independently absent, O, or S;
wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of A and $R_3$, and independently in combination with any embodiments of any other relevant substituent classes, A and $R_3$ can be, independently,

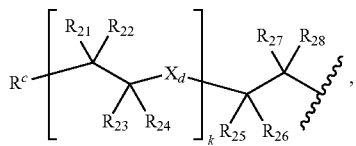

Formula VIII wherein k is an integer from 0 to 20;
wherein $X_d$ are independently O or S;
wherein $R^c$ is B, C, —B(—C)$_\delta$, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently B, C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of B, and independently in combination with any embodiments of any other relevant substituent classes, B can be

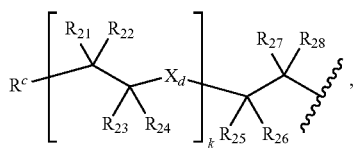

Formula VIII wherein k is an integer from 0 to 20;
wherein $X_d$ are independently O or S;
wherein R is C, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R^b$, and independently in combination with any embodiments of any other relevant substituent classes, $R^b$ can be

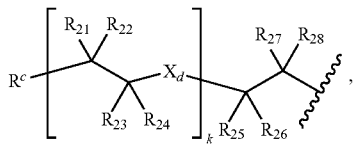

Formula VIII wherein k is an integer from 0 to 20;
wherein $X_d$ are independently O or S;
wherein $R^c$ is C, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of C, and independently in combination with any embodiments of any other relevant substituent classes, C can be

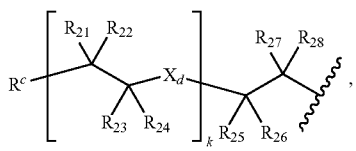

Formula VIII wherein k is an integer from 0 to 20;
wherein $X_d$ are independently O or S;
wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of A and $R_3$, and independently in combination with any embodiments of any other relevant substituent classes, A and $R_3$ can be, independently,

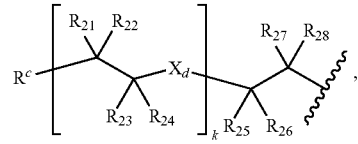

Formula VIII wherein k is an integer from 1 to 20;
wherein $X_d$ are O;
wherein $R^c$ is B, C, —B(—C)$_\delta$, $R^b$, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently B, C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of B, and independently in combination with any embodiments of any other relevant substituent classes, B can be

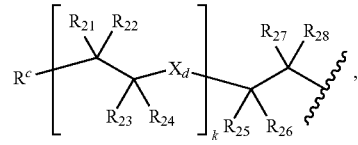

Formula VIII wherein k is an integer from 1 to 20;
wherein $X_d$ are O;
wherein $R^c$ is C, $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently C, $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R^b$, and independently in combination with any embodiments of any other relevant substituent classes, $R^b$ can be

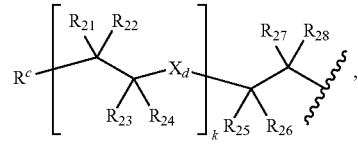

Formula VIII wherein k is an integer from 1 to 20;
wherein $X_d$ are O;
wherein $R^c$ is C, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently C, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of C, and independently in combination with any embodiments of any other relevant substituent classes, C can be

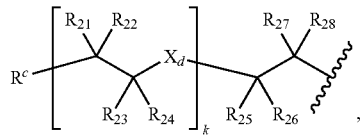

Formula VIII wherein k is an integer from 1 to 20;

wherein $X_d$ are O;

wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, A is

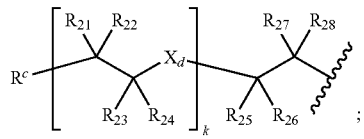

Formula VIII wherein each k is, independently, an integer from 0 to 20;

wherein $R^c$ is B;

wherein each $X_d$ is, independently, absent, O, or S; and wherein each $R_{21}$, $R_{22}$, $R_{23}$, $R_{24}$, $R_{25}$, $R_{26}$, $R_{27}$, and $R_{28}$ is, independently, hydrogen, amino, hydroxyl, thiol, oxo, phosphate, or $J_1$;

wherein preferably k is 1, 2, 3, 4, 5, 6, or 7; each $X_d$ is O; and each $R_{21}$, $R_{22}$, $R_{23}$, $R_{24}$, $R_{25}$, $R_{26}$, $R_{27}$, and $R_{28}$ is, independently, hydrogen, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio;

wherein more preferably k is 2, 3, or 4; each $X_d$ is O; and each $R_{21}$, $R_{22}$, $R_{23}$, $R_{24}$, $R_{25}$, $R_{26}$, $R_{27}$, and $R_{28}$ is hydrogen; and wherein most preferably A is —$CH_2$—$CH_2$—(O—$CH_2$—$CH_2$)$_3$—; and B and C are, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In some embodiments, B is

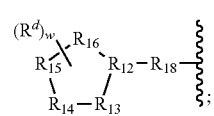

Formula IX wherein each w is, independently, an integer from 0-9;

wherein $R^d$ is C;

wherein each $R_{12}$, $R_{13}$, $R_{14}$, $R_{15}$, and $R_{16}$ is, independently, C, O, N, S, S(O), or S(O)$_2$, wherein the bonds between adjacent $R_{12}$ to $R_{16}$ are double or single according to valency, and wherein $R_{12}$ to $R_{16}$ are bound to none, one, or two hydrogens according to valency;

preferably w is 1, 2, 3, or 4; and none, one, two, three, four, or five of $R_{12}$, $R_{13}$, $R_{14}$, $R_{15}$, and $R_{16}$ are N, none, one, two, three, four, or five of $R_{12}$, $R_{13}$, $R_{14}$, $R_{15}$, and $R_{16}$ is O, and the others are C;

more preferably w is 1 or 2; and one, two, or three of $R_{12}$, $R_{13}$, $R_{14}$, $R_{15}$, and $R_{16}$ are N, none or one of $R_{12}$, $R_{13}$, $R_{14}$, $R_{15}$, and $R_{16}$ is O, and the others are C;

even more preferably w is 1 or 2; and three of $R_{12}$, $R_{13}$, $R_{14}$, $R_{15}$, and $R_{16}$ are N, none of $R_{12}$, $R_{13}$, $R_{14}$, $R_{15}$, and $R_{16}$ is O, and the others are C; and most preferably

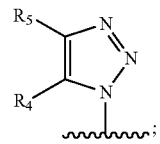

wherein $R_4$ is hydrogen and $R_5$ is C;

A is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and each C is, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In some embodiments, C is

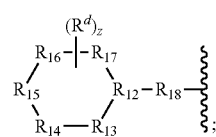

Formula VI wherein z is an integer from 0-11;

wherein each $R_{12}$, $R_{13}$, $R_{14}$, $R_{15}$, $R_{16}$, and $R_{17}$ is, independently, C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency;

wherein each $R_{18}$ is, independently, absent, —(CR$_{19}$R$_{19}$)$_p$—, or —(CR$_{19}$R$_{19}$)$_p$—X$_b$—(CR$_{19}$R$_{19}$)$_q$—, wherein each p and q is, independently, an integer from 0 to 5, wherein X$_b$ is absent, —O—, —S—, —S(O)—, —S(O)$_2$—, or NR$_{20}$, wherein each R$_{19}$ is, as valency permits, independently absent, hydrogen, =O, =S, —OH, —SH, or —NR$_{20}$, wherein each R$_{20}$ is, independently, J$_2$;

wherein each $R^d$ is, independently, J$_1$;

preferably z is 0, 1, 2, 3, 4, or 5; none, one, two, three, four, five, or six of $R_{12}$, $R_{13}$, $R_{14}$, $R_{15}$, $R_{16}$, and $R_{17}$ are N, none, one, two, three, four, five, or six of $R_{12}$, $R_{13}$, $R_{14}$, $R_{15}$, $R_{16}$, and $R_{17}$ is O, none or one is S(O)$_2$, and the others are C; each $R_{18}$ is, independently, absent, —(CR$_{19}$R$_{19}$)$_p$—, or —(CR$_{19}$R$_{19}$)$_p$—X$_b$—(CR$_{19}$R$_{19}$)$_q$—, wherein each p is, independently, 0, 1, 2, or 3, each q is, independently, 0, 1, or 2, and X$_b$ is O; and $R^d$ is, independently, C$_1$-C$_2$ carbonyl, C$_1$-C$_2$ carboxyl, C$_1$-C$_2$ amino, C$_1$-C$_2$ amido, C$_1$-C$_2$ sulfonyl, C$_1$-C$_2$ sulfonic acid, C$_2$-C$_3$ phosphoryl, or C$_2$-C$_3$ phosphonyl;

more preferably z is 0, 1, 2, or 3; none, one, two, or three of $R_{12}$, $R_{13}$, $R_{14}$, $R_{15}$, $R_{16}$, and $R_{17}$ are N, none, one, or two of $R_{12}$, $R_{13}$, $R_{14}$, $R_{15}$, $R_{16}$, and $R_{17}$ is O, none or one is S(O)$_2$, and the others are C; each $R_{18}$ is, independently, absent, —(CR$_{19}$R$_{19}$)$_p$—, or —(CR$_{19}$R$_{19}$)$_p$—X$_b$—(CR$_{19}$R$_{19}$)$_q$—, wherein each p is, independently, 0 or 1, each q is, independently, 0 or 1, and X$_b$ is O; and $R^d$ is, independently, C$_1$ carbonyl, C$_1$ carboxyl, C$_1$ amino, C$_1$ amido, C$_1$ sulfonyl, C$_1$ sulfonic acid, C$_2$ phosphoryl, or C$_2$ phosphonyl; and even more preferably z is 0 or 1; none or one of $R_{12}$, $R_{13}$, $R_{14}$, $R_{15}$, $R_{16}$, and $R_{17}$ are N, none or one of $R_{12}$, $R_{13}$, $R_{14}$, $R_{15}$, $R_{16}$, and $R_{17}$ is O, none or one is S(O)$_2$, and the others are C; each $R_{18}$ is, independently, absent, —(CR$_{19}$R$_{19}$)$_p$—, or —(CR$_{19}$R$_{19}$)$_p$—X$_b$—(CR$_{19}$R$_{19}$)$_q$—, wherein each p is, independently, 0 or 1, each q is, independently, 0 or 1, and X$_b$ is O; and $R^d$ is, independently, C$_1$ carbonyl, C$_1$ carboxyl, C$_1$ amino, or C$_1$ sulfonyl; and most preferably C is

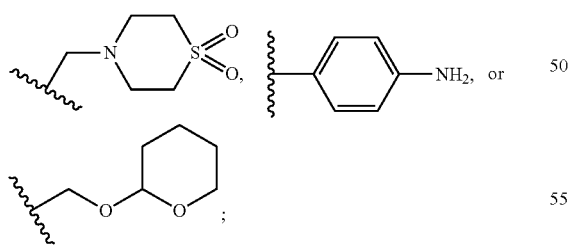

A is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in U$_1$, U$_1$+Q$_1$, U$_1$+Q$_2$, U$_1$+Q$_3$, U$_1$+Q$_1$+Q$_2$, U$_1$+Q$_1$+Q$_3$, U$_1$+Q$_2$+Q$_3$, or U$_1$+Q$_1$+Q$_2$+Q$_3$ (preferably, in these embodiments, U$_1$+Q$_1$+Q$_3$); and B is absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in U$_1$, U$_1$+Q$_1$, U$_1$+Q$_2$, U$_1$+Q$_3$, U$_1$+Q$_1$+Q$_2$, U$_1$+Q$_1$+Q$_3$, U$_1$+Q$_2$+Q$_3$, or U$_1$+Q$_1$+Q$_2$+Q$_3$ (preferably, in these embodiments, U$_1$+Q$_1$+Q$_3$).

In some embodiments

A is 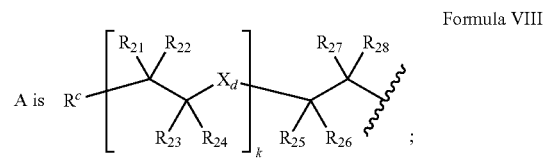  Formula VIII

B is 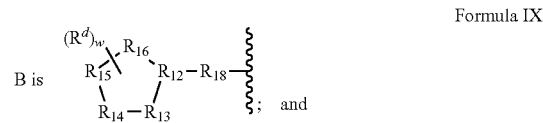  Formula IX ; and each $R_4$, $R_5$, and C are, independently,

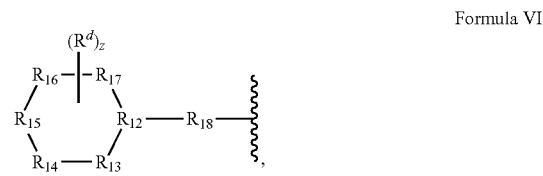  Formula VI

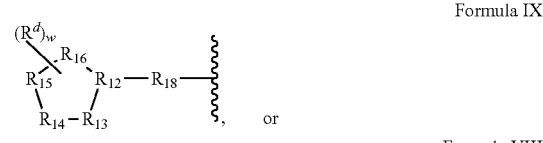  Formula IX , or

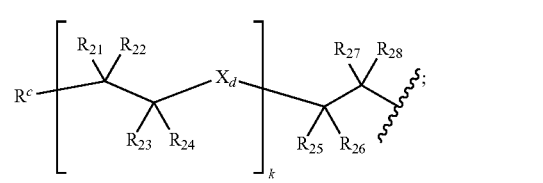  Formula VIII wherein each z is, independently, an integer from 0-11;
wherein each w is, independently, an integer from 0-9;
wherein each k is, independently, an integer from 0 to 20;
wherein in A, $R^c$ is B,
wherein in B, $R^c$ and $R^d$ are C,
wherein each $X_d$ is, independently, absent, O, or S;
wherein each $R_{12}$, $R_{13}$, $R_{14}$, $R_{15}$, $R_{16}$, and $R_{17}$ is, independently, C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein each $R_{18}$ is, independently, absent, —(CR$_{19}$R$_{19}$)$_p$—, or —(CR$_{19}$R$_{19}$)$_p$—X$_b$—(CR$_{19}$R$_{19}$)$_q$—, wherein each p and q is, independently, an integer from 0 to 5, wherein X$_b$ is absent, —O—, —S—, —S(O)—, —S(O)$_2$—, or NR$_{20}$, wherein each R$_{19}$ is, as valency permits, independently absent, hydrogen, =O, =S, —OH, —SH, or —NR$_{20}$, wherein each R$_{20}$ is, independently, U$_1$, U$_1$+Q$_1$, U$_1$+Q$_2$, U$_1$+Q$_3$, U$_1$+Q$_1$+Q$_2$, U$_1$+Q$_1$+Q$_3$, U$_1$+Q$_2$+Q$_3$, or U$_1$+Q$_1$+Q$_2$+Q$_3$ (preferably, in these embodiments, U$_1$+Q$_1$+Q$_3$); and wherein each R$_{21}$, R$_{22}$, R$_{23}$, R$_{24}$, R$_{25}$, R$_{26}$, R$_{27}$, and R$_{28}$ is, independently, hydrogen, U$_1$, U$_1$+Q$_1$, U$_1$+Q$_2$, U$_1$+Q$_3$, U$_1$+Q$_1$+Q$_2$, U$_1$+Q$_1$+Q$_3$, U$_1$+Q$_2$+Q$_3$, or U$_1$+Q$_1$+Q$_2$+Q$_3$ (preferably, in these embodiments, U$_1$+Q$_1$+Q$_2$+Q$_3$).

In some embodiments, each R$_{20}$ is, independently, J$_2$.

In some embodiments, each R$_{21}$, R$_{22}$, R$_{23}$, R$_{24}$, R$_{25}$, R$_{26}$, R$_{27}$, and R$_{28}$ is, independently, hydrogen, amino, hydroxyl, thiol, oxo, phosphate, or J$_1$.

In some embodiments, independently in each Formula VI, none, one, two, three, four, five, or six of R$_{12}$, R$_{13}$, R$_{14}$, R$_{15}$, R$_{16}$, and R$_{17}$ are N, none, one, two, three, four, five, or six of R$_{12}$, R$_{13}$, R$_{14}$, R$_{15}$, R$_{16}$, and R$_{17}$ is O, and the others are C. In some embodiments, independently in each Formula IX, none, one, two, three, four, or five of R$_{12}$, R$_{13}$, R$_{14}$, R$_{15}$, and R$_{16}$ are N, none, one, two, three, four, or five of R$_{12}$, R$_{13}$, R$_{14}$, R$_{15}$, and R$_{16}$ is O, and the others are C.

In some embodiments, independently in each C, none, one, two, or three of R$_{12}$, R$_{13}$, R$_{14}$, R$_{15}$, R$_{16}$, and R$_{17}$ are N, none, one, two, or three of R$_{12}$, R$_{13}$, R$_{14}$, R$_{15}$, R$_{16}$, and R$_{17}$ is O, and the others are C. In some embodiments, in B, three of R$_{12}$, R$_{13}$, R$_{14}$, R$_{15}$, and R$_{16}$ are N, none of R$_{12}$, R$_{13}$, R$_{14}$, R$_{15}$, and R$_{16}$ is O, and the others are C.

In some embodiments, R$_3$ and A are —CH$_2$—Ar— or —CH$_2$—CH$_2$—(O—CH$_2$—CH$_2$)$_3$—; R$_2$ is hydrogen; R$_4$ and C are hydrogen, methyl, or —CH$_2$—OH; and R$_5$ and C are methyl, —COCH$_3$, —CH$_2$—N(CH$_2$—CH$_3$)$_2$,

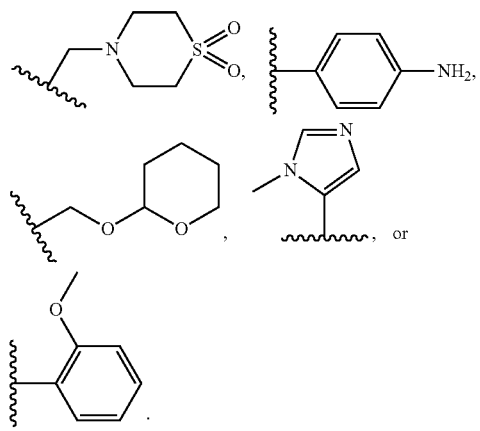

In some embodiments, R$_4$ is hydrogen; and R$_5$ and C are

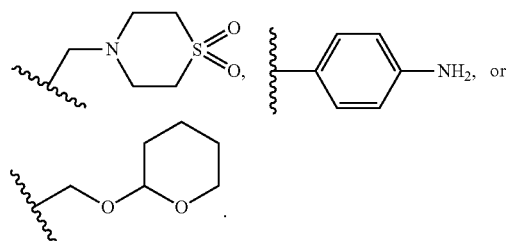

In some embodiments, R$_4$ is hydrogen; and R$_5$ and C are

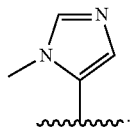

In some embodiments, R$_5$ and C are methyl, —COCH$_3$, or —CH$_2$—N(CH$_2$—CH$_3$)$_2$.

In some embodiments, X is oxygen or NR$_2$, wherein R$_2$ is hydrogen, methyl, or —CH$_2$—CH$_3$; and R$_1$ is —CH$_2$—CH$_2$—CH$_2$—CH$_2$—OH, —CH$_2$—CH$_2$—(O—CH$_2$—CH$_2$)$_n$—O—CH$_3$, —CH$_2$—CH$_2$—O—CH$_2$—CH$_2$—OH, —(CH$_2$—CH$_2$)$_3$—NH—CH$_3$,

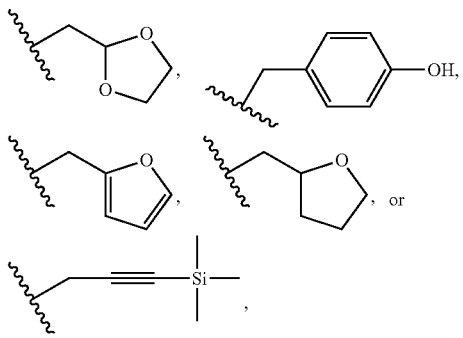

where n is an integer from 3 to 16.

Independently in some embodiments of R$^c$, and independently in combination with any embodiments of any other relevant substituent classes, R$^c$ can be B, C, —B(—C)$_\delta$, R$^b$, amino, hydroxyl, thiol, oxo, phosphate, or J$_1$.

Independently in some embodiments of R$^c$, and independently in combination with any embodiments of any other relevant substituent classes, R$^c$ can be B, C, —B(—C)$_\delta$, R$^b$, amino, hydroxyl, thiol, oxo, phosphate, or J$_2$.

Independently in some embodiments of R$^c$, and independently in combination with any embodiments of any other relevant substituent classes, R$^c$ can be B, C, —B(—C)$_\delta$, R$^b$, amino, hydroxyl, thiol, oxo, phosphate, or substituted or unsubstituted C$_1$-C$_5$ alkyl, C$_1$-C$_5$ alkylene, C$_2$-C$_5$ alkenyl, C$_2$-C$_5$ alkynyl, C$_1$-C$_5$ alkoxy, C$_1$-C$_5$ alkylamino, C$_1$-C$_5$ alkylthio, C$_1$-C$_5$ carbonyl, C$_1$-C$_5$ carboxyl, C$_1$-C$_8$ amido, C$_1$-C$_8$ sulfonyl, C$_1$-C$_5$ sulfonic acid, C$_1$-C$_5$ sulfamoyl, C$_1$-C$_5$ sulfoxide, C$_1$-C$_5$ phosphoryl, C$_1$-C$_5$ phosphonyl, C$_1$-C$_4$ alkyl, C$_1$-C$_4$ alkylene, C$_2$-C$_4$ alkenyl, C$_2$-C$_4$ alkynyl, C$_1$-C$_4$ alkoxy, C$_1$-C$_4$ alkylamino, C$_1$-C$_4$ alkylthio, C$_1$-C$_4$ carbonyl, C$_1$-C$_4$ carboxyl, C$_1$-C$_4$ amino, C$_1$-C$_4$ amido, C$_1$-C$_4$ sulfonyl, C$_1$-C$_4$ sulfonic acid, C$_1$-C$_4$ sulfamoyl, C$_1$-C$_4$ sulfoxide, C$_1$-C$_4$ phosphoryl, C$_1$-C$_4$ phosphonyl, C$_1$-C$_3$ alkyl, C$_1$-C$_3$ alkylene, C$_2$-C$_3$ alkenyl, C$_2$-C$_3$ alkynyl, C$_1$-C$_3$ alkoxy, C$_1$-C$_3$ alkylamino, C$_1$-C$_3$ alkylthio, C$_1$-C$_3$ carbonyl, C$_1$-C$_3$ carboxyl, C$_1$-C$_3$ amino, C$_1$-C$_3$ amido, C$_1$-C$_3$ sulfonyl, C$_1$-C$_3$ sulfonic acid, C$_1$-C$_3$ sulfamoyl, C$_1$-C$_3$ sulfoxide, C$_1$-C$_3$ phosphoryl, C$_1$-C$_3$ phosphonyl, C$_1$-C$_2$ alkyl, C$_1$-C$_2$ alkylene, C$_1$-C$_2$ alkoxy, C$_1$-C$_2$ alkylamino, C$_1$-C$_2$ alkylthio, C$_1$-C$_2$ carbonyl, C$_1$-C$_2$ carboxyl, C$_1$-C$_2$ amido, C$_1$-C$_2$ sulfonyl, C$_1$-C$_2$ sulfonic acid, C$_1$-C$_2$ sulfamoyl, C$_1$-C$_2$ sulfoxide, C$_1$-C$_2$ phosphoryl, C$_1$-C$_2$ phosphonyl, C$_0$-C$_8$ sulfonyl, C$_0$-C$_5$ sulfonic acid, C$_0$-C$_5$ sulfamoyl, C$_0$-C$_5$ sulfoxide, C$_0$-C$_5$ phosphoryl, C$_0$-C$_5$ phosphonyl, C$_0$-C$_4$ sulfonyl, C$_0$-C$_4$ sulfonic acid, C$_0$-C$_4$ sulfamoyl, C$_0$-C$_4$ sulfoxide, C$_0$-C$_4$ phosphoryl, C$_0$-C$_4$ phosphonyl, C$_0$-C$_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_5$ alkyl, $C_5$ alkylene, $C_5$ alkenyl, $C_5$ alkynyl, $C_5$ alkoxy, $C_5$ alkylamino, $C_5$ alkylthio, $C_5$ carbonyl, $C_5$ carboxyl, $C_5$ amido, $C_5$ sulfonyl, $C_5$ sulfonic acid, $C_5$ sulfamoyl, $C_5$ sulfoxide, $C_5$ phosphoryl, $C_5$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl Independently in some embodiments of $R^c$, and independently in combination with any embodiments of any other relevant substituent classes, $R^c$ can be B, C, —B(—C)$_\delta$, $R^b$, amino, hydroxyl, thiol, oxo, phosphate, or substituted or unsubstituted $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

Independently in some embodiments of $R^c$, and independently in combination with any embodiments of any other relevant substituent classes, $R^c$ can be B, C, —B(—C)$_\delta$, $R^b$, amino, hydroxyl, thiol, oxo, phosphate, or substituted or unsubstituted $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl Independently in some embodiments of $R^c$, and independently in combination with any embodiments of any other relevant substituent classes, $R^c$ can be B, C, —B(—C)$_\delta$, $R^b$, amino, hydroxyl, thiol, oxo, phosphate, or substituted or unsubstituted $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

Independently in some embodiments of $R^c$, and independently in combination with any embodiments of any other relevant substituent classes, $R^c$ can be B, C, —B(—C)$_\delta$, $R^b$, amino, hydroxyl, thiol, oxo, phosphate, or substituted or unsubstituted $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl Independently in some embodiments of $R^c$, and independently in combination with any embodiments of any other relevant substituent classes, $R^c$ can be B, C, —B(—C)$_8$, $R^b$, amino, hydroxyl, thiol, oxo, phosphate, or substituted or unsubstituted $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

Independently in some embodiments of $R_{21}$, $R_{22}$, $R_{23}$, $R_{24}$, $R_{25}$, $R_{26}$, $R_{27}$, and $R_{28}$, and independently in combination with any embodiments of any other relevant substituent classes, $R_{21}$, $R_{22}$, $R_{23}$, $R_{24}$, $R_{25}$, $R_{26}$, $R_{27}$, and $R_{28}$ can be, independently, $R^b$, hydrogen, amino, hydroxyl, thiol, oxo, phosphate, or $J_1$.

Independently in some embodiments of $R_{21}$, $R_{22}$, $R_{23}$, $R_{24}$, $R_{25}$, $R_{26}$, $R_{27}$, and $R_{28}$, and independently in combination with any embodiments of any other relevant substituent classes, $R_{21}$, $R_{22}$, $R_{23}$, $R_{24}$, $R_{25}$, $R_{26}$, $R_{27}$, and $R_{28}$ can be, independently, $R^b$, hydrogen, amino, hydroxyl, thiol, oxo, phosphate, or $J_2$.

Independently in some embodiments of $R_{21}$, $R_{22}$, $R_{23}$, $R_{24}$, $R_{25}$, $R_{26}$, $R_{27}$, and $R_{28}$, and independently in combination with any embodiments of any other relevant substituent classes, $R_{21}$, $R_{22}$, $R_{23}$, $R_{24}$, $R_{25}$, $R_{26}$, $R_{27}$, and $R_{28}$ can be, independently, $R^b$, hydrogen, amino, hydroxyl, thiol, oxo, phosphate, or substituted or unsubstituted $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_5$ carbonyl, $C_1$-$C_5$ carboxyl, $C_1$-$C_8$ amido, $C_1$-$C_8$ sulfonyl, $C_1$-$C_5$ sulfonic acid, $C_1$-$C_5$ sulfamoyl, $C_1$-$C_5$ sulfoxide, $C_1$-$C_5$ phosphoryl, $C_1$-$C_5$ phosphonyl, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_8$ sulfonyl, $C_0$-$C_5$ sulfonic acid, $C_0$-$C_5$ sulfamoyl, $C_0$-$C_5$ sulfoxide, $C_0$-$C_5$ phosphoryl, $C_0$-$C_5$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_5$ alkyl, $C_5$ alkylene, $C_5$ alkenyl, $C_5$ alkynyl, $C_5$ alkoxy, $C_5$ alkylamino, $C_5$ alkylthio, $C_5$ carbonyl, $C_5$ carboxyl, $C_5$ amido, $C_5$ sulfonyl, $C_5$ sulfonic acid, $C_5$ sulfamoyl, $C_5$ sulfoxide, $C_5$ phosphoryl, $C_5$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

Independently in some embodiments of $R_{21}$, $R_{22}$, $R_{23}$, $R_{24}$, $R_{25}$, $R_{26}$, $R_{27}$, and $R_{28}$, and independently in combination with any embodiments of any other relevant substituent classes, $R_{21}$, $R_{22}$, $R_{23}$, $R_{24}$, $R_{25}$, $R_{26}$, $R_{27}$, and $R_{28}$ can be, independently, $R^b$, hydrogen, amino, hydroxyl, thiol, oxo, phosphate, or substituted or unsubstituted $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

Independently in some embodiments of $R_{21}$, $R_{22}$, $R_{23}$, $R_{24}$, $R_{25}$, $R_{26}$, $R_{27}$, and $R_{28}$, and independently in combination with any embodiments of any other relevant substituent classes, $R_{21}$, $R_{22}$, $R_{23}$, $R_{24}$, $R_{25}$, $R_{26}$, $R_{27}$, and $R_{28}$ can be, independently, $R^b$, hydrogen, amino, hydroxyl, thiol, oxo, phosphate, or substituted or unsubstituted $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

Independently in some embodiments of $R_{21}$, $R_{22}$, $R_{23}$, $R_{24}$, $R_{25}$, $R_{26}$, $R_{27}$, and $R_{28}$, and independently in combination with any embodiments of any other relevant substituent classes, $R_{21}$, $R_{22}$, $R_{23}$, $R_{24}$, $R_{25}$, $R_{26}$, $R_{27}$, and $R_{28}$ can be, independently, $R^b$, hydrogen, amino, hydroxyl, thiol, oxo, phosphate, or substituted or unsubstituted $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

Independently in some embodiments of $R_{21}$, $R_{22}$, $R_{23}$, $R_{24}$, $R_{25}$, $R_{26}$, $R_{27}$, and $R_{28}$, and independently in combination with any embodiments of any other relevant substituent classes, $R_{21}$, $R_{22}$, $R_{23}$, $R_{24}$, $R_{25}$, $R_{26}$, $R_{27}$, and $R_{28}$ can be, independently, $R^b$, hydrogen, amino, hydroxyl, thiol, oxo, phosphate, or substituted or unsubstituted $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

Independently in some embodiments of 6, and independently in combination with any embodiments of any other relevant substituent classes, 6 can be an integer from 1 to 30, 2 to 30, 3 to 30, 4 to 30, 5 to 30, 6 to 30, 7 to 30, 8 to 30, 9 to 30, 10 to 30, 11 to 30, 12 to 30, 13 to 30, 14 to 30, 15 to 30, 16 to 30, 17 to 30, 18 to 30, 19 to 30, 20 to 30, 21 to 30, 22 to 30, 23 to 30, 24 to 30, 25 to 30, 26 to 30, 27 to 30, 28 to 30, 29 to 30, 1 to 29, 2 to 29, 3 to 29, 4 to 29, 5 to 29, 6 to 29, 7 to 29, 8 to 29, 9 to 29, 10 to 29, 11 to 29, 12 to 29, 13 to 29, 14 to 29, 15 to 29, 16 to 29, 17 to 29, 18 to 29, 19 to 29, 20 to 29, 21 to 29, 22 to 29, 23 to 29, 24 to 29, 25 to 29, 26 to 29, 27 to 29, 28 to 29, 1 to 28, 2 to 28, 3 to 28, 4 to 28, 5 to 28, 6 to 28, 7 to 28, 8 to 28, 9 to 28, 10 to 28, 11 to 28, 12 to 28, 13 to 28, 14 to 28, 15 to 28, 16 to 28, 17 to 28, 18 to 28, 19 to 28, 20 to 28, 21 to 28, 22 to 28, 23 to 28, 24 to 28, 25 to 28, 26 to 28, 27 to 28, 1 to 27, 2 to 27, 3 to 27, 4 to 27, 5 to 27, 6 to 27, 7 to 27, 8 to 27, 9 to 27, 10 to 27, 11 to 27, 12 to 27, 13 to 27, 14 to 27, 15 to 27, 16 to 27, 17 to 27, 18 to 27, 19 to 27, 20 to 27, 21 to 27, 22 to 27, 23 to 27, 24 to 27, 25 to 27, 26 to 27, 1 to 26, 2 to 26, 3 to 26, 4 to 26, 5 to 26, 6 to 26, 7 to 26, 8 to 26, 9 to 26, 10 to 26, 11 to 26, 12 to 26, 13 to 26, 14 to 26, 15 to 26, 16 to 26, 17 to 26, 18 to 26, 19 to 26, 20 to 26, 21 to 26, 22 to 26, 23 to 26, 24 to 26, 25 to 26, 1 to 25, 2 to 25, 3 to 25, 4 to 25, 5 to 25, 6 to 25, 7 to 25, 8 to 25, 9 to 25, 10 to 25, 11 to 25, 12 to 25, 13 to 25, 14 to 25, 15 to 25, 16 to 25, 17 to 25, 18 to 25, 19 to 25, 20 to 25, 21 to 25, 22 to 25, 23 to 25, 24 to 25, 1 to 24, 2 to 24, 3 to 24, 4 to 24, 5 to 24, 6 to 24, 7 to 24, 8 to 24, 9 to 24, 10 to 24, 11 to 24, 12 to 24, 13 to 24, 14 to 24, 15 to 24, 16 to 24, 17 to 24, 18 to 24, 19 to 24, 20 to 24, 21 to 24, 22 to 24, 23 to 24, 1 to 23, 2 to 23, 3 to 23, 4 to 23, 5 to 23, 6 to 23, 7 to 23, 8 to 23, 9 to 23, 10 to 23, 11 to 23, 12 to 23, 13 to 23, 14 to 23, 15 to 23, 16 to 23, 17 to 23, 18 to 23, 19 to 23, 20 to 23, 21 to 23, 22 to 23, 1 to 22, 2 to 22, 3 to 22, 4 to 22, 5 to 22, 6 to 22, 7 to 22, 8 to 22, 9 to 22, 10 to 22, 11 to 22, 12 to 22, 13 to 22, 14 to 22, 15 to 22, 16 to 22, 17 to 22, 18 to 22, 19 to 22, 20 to 22, 21 to 22, 1 to 21, 2 to 21, 3 to 21, 4 to 21, 5 to 21, 6 to 21, 7 to 21, 8 to 21, 9 to 21, 10 to 21, 11 to 21, 12 to 21, 13 to 21, 14 to 21, 15 to 21, 16 to 21, 17 to 21, 18 to 21, 19 to 21, 20 to 21, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 1 to 17, 2 to 17, 3 to 17, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, 6 is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

Independently in some embodiments of 6, and independently in combination with any embodiments of any other relevant substituent classes, 6 can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of δ, and independently in combination with any embodiments of any other relevant substituent classes, δ can be 1, 2, 3, 4, 5, 6, 7, 8, 9, or 10.

Independently in some embodiments of δ, and independently in combination with any embodiments of any other relevant substituent classes, δ can be an integer from 1 to 5, 2 to 5, 3 to 5, 4 to 5, 1 to 4, 2 to 4, 3 to 4, 1 to 3, 2 to 3, or 1 to 2. Independently in some embodiments of δ, and independently in combination with any embodiments of any other relevant substituent classes, δ can be 1, 2, 3, 4, or 5.

Independently in some embodiments of k, and independently in combination with any embodiments of any other relevant substituent classes, k can be an integer from 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 1 to 17, 2 to 17, 3 to 17, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 1, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, k is 1, 2, 3, 4, 5, 6, 7, 8, 9, 10, 11, 12, 13, 14, 15, 16, 17, 18, 19, or 20.

Independently in some embodiments of k, and independently in combination with any embodiments of any other relevant substituent classes, k can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of k, and independently in combination with any embodiments of any other relevant substituent classes, k can be 1, 2, 3, 4, 5, 6, 7, 8, 9, or 10.

Independently in some embodiments of w, and independently in combination with any embodiments of any other relevant substituent classes, w can be an integer from 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of w, and independently in combination with any embodiments of any other relevant substituent classes, w can be 1, 2, 3, 4, 5, 6, 7, 8, or 9.

Independently in some embodiments of w, and independently in combination with any embodiments of any other relevant substituent classes, w can be an integer from 1 to 5, 2 to 5, 3 to 5, 4 to 5, 1 to 4, 2 to 4, 3 to 4, 1 to 3, 2 to 3, or 1 to 2. In preferred embodiments, w is 1, 2, 3, 4, or 5.

Independently in some embodiments of z, and independently in combination with any embodiments of any other relevant substituent classes, z can be an integer from 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of z, and independently in combination with any embodiments of any other relevant substituent classes, z can be 1, 2, 3, 4, 5, 6, 7, 8, 9, 10, or 11.

Independently in some embodiments of z, and independently in combination with any embodiments of any other relevant substituent classes, z can be an integer from 1 to 5, 2 to 5, 3 to 5, 4 to 5, 1 to 4, 2 to 4, 3 to 4, 1 to 3, 2 to 3, or 1 to 2. Independently in some embodiments of z, and independently in combination with any embodiments of any other relevant substituent classes, z can be 1, 2, 3, 4, or 5.

Independently in some embodiments of p and q, and independently in combination with any embodiments of any other relevant substituent classes, p and q can be, independently, an integer from 1 to 5, 2 to 5, 3 to 5, 4 to 5, 1 to 4, 2 to 4, 3 to 4, 1 to 3, 2 to 3, or 1 to 2. Independently in some embodiments of p and q, and independently in combination with any embodiments of any other relevant substituent classes, p and q can be, independently, 1, 2, 3, 4, or 5.

In some embodiments, $R_1$ is, independently in one or more sites of chemical modification,

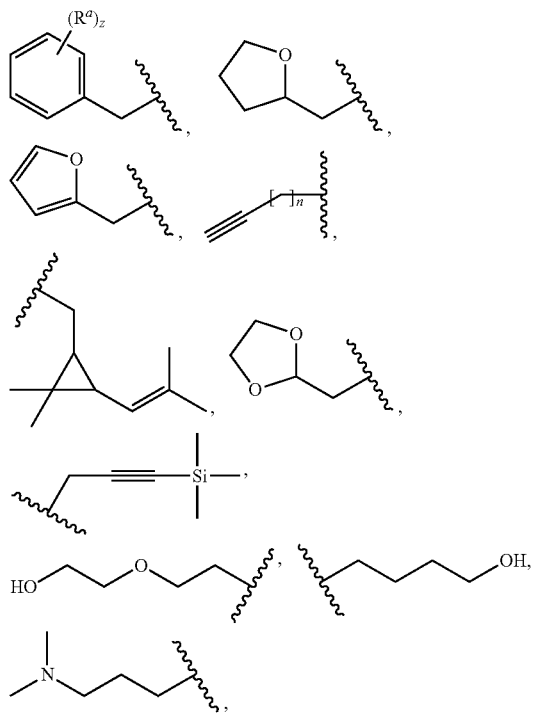

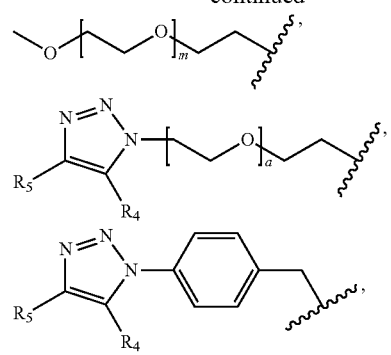

or —$R_3$—$R^b$  Formula II, wherein a is an integer from 1 to 30, z is an integer from 0-5, n is an integer from 1 to 12, m is an integer from 3 to 16, $R^a$ is independently selected from $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_2+Q_3$), and $R^b$, as valence permits, is

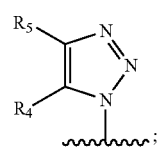

Formula III $R_2$ is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and $R_3$, $R_4$, and $R_5$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_3$, $R_4$, and $R_5$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, the surface or a surface of the product includes one or more covalent modifications defined by Formula I —X—$R_1$  Formula I wherein, X is oxygen, sulfur, $NR_2$, or another group compatible with attachment or coupling of the compound to a product or surface;

$R_1$ is, independently in the one or more modified monomers,

Formula VII

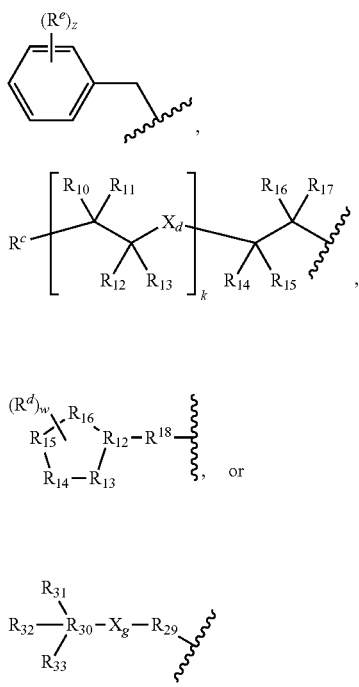

Formula VIII

Formula IX

Formula X wherein k is an integer from 1 to 10; wherein z is an integer from 0 to 5; wherein w is an integer from 0 to 4; wherein $X_d$ is absent, O or S;

wherein $R_{21}$, $R_{22}$, $R_{23}$, $R_{24}$, $R_{25}$, $R_{26}$, $R_{27}$, $R_{28}$, $R_{31}$, $R_{32}$, and $R_{33}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_2$);

wherein $R_{29}$ is C or Si;

wherein $X_g$ and $R_{30}$ are independently $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_2$); and wherein $R^a$ and $R^c$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1$); or together with the carbon atom to which they are attached, form a 3- to 8-membered unsubstituted or substituted carbocyclic, heterocyclic ring or Formula III

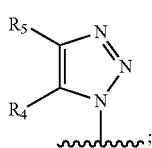

wherein $R_4$, $R_5$, or both are, independently, hydrogen, alkyl, substituted alkyl, alkoxy, amino, alkylamino, dialkylamino, hydroxy, alkenyl, alkynyl, substituted alkyl, substituted alkenyl, substituted alkynyl, carbonyl, substituted carbonyl, carbinol, Formula IV

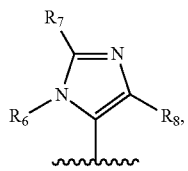

Formula V

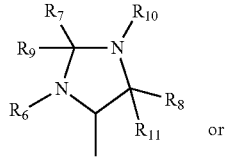

or

Formula VI

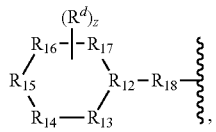

wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$);

wherein $R_6$, $R_9$, $R_{10}$, and $R_{11}$ are independently present or absent according to valency, and wherein the ring bonds are double or single according to valency;

wherein z is an integer from 0 to 11; wherein w is an integer from 0-9; wherein $R^d$ and $R^e$ are each independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, or S, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ is independently $—(CR_{19}R_{19})_p—$ or $—(CR_{19}R_{19})_p—X_b—(CR_{19}R_{19})_q—$, wherein p and q are independently integers from 0 to 5, wherein $X_b$ is absent, —O—, —S—, —SO$_2$—, or NR$_2$, wherein each $R_{19}$ is independently absent, hydrogen, =O, =S, —OH, —SH, —NR$_2$, wherein $R_2$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$);

wherein $R_4$, and $R_5$ are not both hydrogen; wherein at least one $R^b$ or $R^c$ is defined by Formula III;

wherein $R_2$ is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$).

X is preferably oxygen, sulfur, or NR$_2$.

In some embodiments, z in Formula VI is an integer from 0-3; $R^d$ is independently amino, hydroxyl, thiol, oxo, phosphate, or substituted or unsubstituted $C_1$-$C_6$ alkyl, $C_1$-$C_6$ alkoxy, $C_1$-$C_6$ alkylamino, or $C_1$-$C_6$ alkylthio;

where $R_{12}$, $R_{13}$, $R_{14}$, $R_{15}$, $R_{16}$, and $R_{17}$ are independently C, O, N, or S, where the bonds between adjacent $R_{12}$ to $R_{17}$ are double or single according to valency, and where $R_{12}$ to $R_{17}$ are bound to none, one, or two hydrogens according to valency; and where $R_{18}$ is independently —$(CR_{19}R_{19})_p$— or —$(CR_{19}R_{19})_p$—$X_b$—$(CR_{19}R_{19})_q$—, where p and q are independently integers from 0 to 3, where $X_b$ is absent, —O—, —S—, —$SO_2$—, or $NR_2$, where each $R_{19}$ is independently absent, hydrogen, =O, =S, —OH, —SH, —$NR_2$, where $R_2$ is substituted or unsubstituted $C_1$-$C_6$ alkyl, $C_1$-$C_6$ alkoxy, $C_1$-$C_6$ alkylamino, or $C_1$-$C_6$ alkylthio.

In some embodiments, z in Formula VI is 2, $R_{12}$ is N, $R_{13}$, $R_{14}$, $R_{15}$, $R_{16}$, or $R_{17}$ is S, both $R^d$ are oxo and are bonded to the S, and all of the bonds between adjacent $R_{12}$ to $R_{17}$ are single.

In some embodiments, z in Formula VI is 2, both $R^d$ are oxo and are bonded to $R_{15}$, $R_{12}$ is N, $R_{15}$ is S, and all of the bonds between adjacent $R_{12}$ to $R_{17}$ are single.

In some embodiments, z in Formula VI is 2, both $R^d$ are oxo and are bonded to $R_{15}$, $R_{12}$ is N, $R_{15}$ is S, and all of the bonds between adjacent $R_{12}$ to $R_{17}$ are single, $X_b$ is absent, q is 0, p is 1, and each $R_{19}$ is hydrogen.

In some embodiments, z in Formula VI is 1, $R^{ed}$ is amino, and three of the bonds between adjacent $R_{12}$ to $R_{17}$ are double and three of the bonds between adjacent $R_{12}$ to $R_{17}$ are single.

In some embodiments, z in Formula VI is 1, $R^d$ is amino and is bonded to $R_{15}$, and three of the bonds between adjacent $R_{12}$ to $R_{17}$ are double and three of the bonds between adjacent $R_{12}$ to $R_{17}$ are single.

In some embodiments, z in Formula VI is 1, $R^d$ is amino and is bonded to $R_{15}$, and three of the bonds between adjacent $R_{12}$ to $R_{17}$ are double and three of the bonds between adjacent $R_{12}$ to $R_{17}$ are single, $X_b$ is absent, p is 0 and q is 0.

In some embodiments, z in Formula VI is 0, $R_{13}$, $R_{14}$, $R_{15}$, $R_{16}$, or $R_{17}$ is O, and all of the bonds between adjacent $R_{12}$ to $R_{17}$ are single.

In some embodiments, z in Formula VI is 0, $R_{13}$ is O, and all of the bonds between adjacent $R_{12}$ to $R_{17}$ are single.

In some embodiments, z in Formula VI is 0, $R_{13}$ is O, all of the bonds between adjacent $R_{12}$ to $R_{17}$ are single, $X_b$ is oxygen, p is 1, q is 0 and each $R_{19}$ is hydrogen.

In some embodiments, $R_{13}$ and $R_{17}$ of Formula VI are O and all of the bonds between adjacent $R_{12}$ to $R_{17}$ are single.

In some embodiments, $R_{13}$ and $R_{17}$ of Formula VI are 0, the bonds between $R_{12}$ and $R_{13}$, and between $R_{15}$ and $R_{16}$ are double bonds, and the rest of the bonds in the ring are single bonds.

In some embodiments, z in Formula VI is 1, $R^d$ is alkoxy and is bonded to $R_{13}$, $R_{14}$, $R_{15}$, $R_{15}$, $R_{16}$, or $R_{17}$, three of the bonds between adjacent $R_{12}$ to $R_{17}$ are double and three of the bonds between adjacent $R_{12}$ to $R_{17}$ are single.

In some embodiments, z in Formula VI is 1, $R^d$ is alkoxy and is bonded to $R_{13}$, three of the bonds between adjacent $R_{12}$ to $R_{17}$ are double and three of the bonds between adjacent $R_{12}$ to $R_{17}$ are single.

In some embodiments, z in Formula VI is 1, $R^d$ is methoxy, and is bonded to $R_{13}$, $R_{12}$ to $R_{17}$ are carbon atoms, three of the bonds between adjacent $R_{12}$ to $R_{17}$ are double and three of the bonds between adjacent $R_{12}$ to $R_{17}$ are single, $X_b$ is absent, p is 0 and q is 0.

In some embodiments, z in Formula VI is 1, $R^d$ is hydroxyl.

In some embodiments, z in Formula VI is 1 and $R^d$ is hydroxyl bonded at the position para- to the methylene group.

In some embodiments, z in Formula VI is 1, $R^d$ is Formula III shown below:

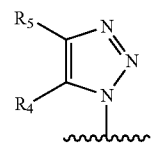

Formula III wherein $R_4$ is a substituted alkyl and $R_5$ is a dialkylamino, or $R_4$ is a dialkylamino and $R_5$ is a substituted alkyl, wherein the substituted alkyl is hydroxymethyl and the dialkylamino is N,N-diethylamino.

In some embodiments, z in Formula VI is 1, $R^d$ is Formula III, wherein $R_4$ is hydrogen and $R_5$ is Formula VI shown below:

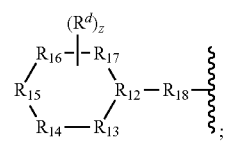

Formula VI or $R_4$ is Formula VI and $R_5$ is hydrogen. In some embodiments, z in Formula VI is 0, $R_{13}$, $R_{14}$, $R_{15}$, $R_{16}$, or $R_{17}$ is O, and all of the bonds between adjacent $R_{12}$ to $R_{17}$ are single. In some embodiments, z in Formula VI is 0, $R_{13}$ is O, and all of the bonds between adjacent $R_{12}$ to $R_{17}$ are single. In some embodiments, z in Formula VI is 0, $R_{13}$ is O, all of the bonds between adjacent $R_{12}$ to $R_{17}$ are single, $X_b$ is oxygen, p is 1, q is 0 and each $R_{19}$ is hydrogen.

In some embodiments, z in Formula VI is 1, $R^d$ is Formula III, wherein $R_4$ is hydrogen and $R_5$ is Formula IV or Formula V shown below:

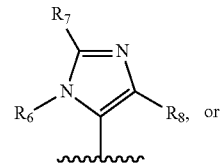

Formula IV

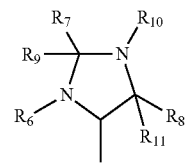

Formula V wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$);

wherein $R_6$, $R_9$, $R_{10}$, and $R_{11}$ are independently present or absent according to valency, and wherein the ring bonds are double or single according to valency.

In some embodiments $R_6$ of Formula IV is alkyl. In some embodiments, $R_6$ is methyl.

In some embodiments $R_6$ of Formula IV is methyl, $R_7$ and $R_8$ are hydrogen.

In some embodiments, z in Formula VI is 1 and $R^d$ is hydroxyl bonded at the position para- to the methylene group.

In some embodiments of Formula VIII, k is 1 and $R^c$ is hydroxyl.

In some embodiments of Formula VIII, k is 1, $R^c$ is hydroxyl, and $X_d$ is absent.

In some embodiments of Formula VIII, k is 1, $R^c$ is hydroxyl, $X_d$ is absent, and $R_{21}$—$R_{28}$ are hydrogen.

In some embodiments of Formula VIII, $R^c$ is alkoxy.

In some embodiments of Formula VIII, $R^c$ is methoxy and $X_d$ is O.

In some embodiments of Formula VIII, $R^c$ is methoxy, $X_d$ is O, and $R_{21}$—$R_{28}$ are hydrogen.

In some embodiments of Formula VIII, k is 2 and $R^c$ is alkylamino.

In some embodiments of Formula VIII, k is 2, $R^c$ is methylamino, and $X_d$ is absent.

In some embodiments of Formula VIII, k is 2, $R^c$ is methylamino, $X_d$ is absent, and $R_{21}$—$R_{28}$ are hydrogen.

In some embodiments of Formula VIII, k is 3, $X_d$ is O and $R^c$ is Formula III shown below:

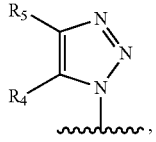

Formula III wherein $R_4$ and $R_5$ are alkyl.

In some embodiments of Formula VIII, k is 3, $X_d$ is O, and $R^c$ is Formula III, wherein $R_4$ and $R_5$ are methyl.

In some embodiments of Formula VIII, k is 3, $X_d$ is O and $R^c$ is Formula III, wherein $R_4$ is hydrogen, and $R_5$ is carbonyl, or $R_4$ is carbonyl, and $R_5$ is hydrogen.

In some embodiments of Formula VIII, k is 3, $X_d$ is O and $R^c$ is Formula III, wherein $R_4$ is hydrogen, and $R_5$ is acetyl, or $R_4$ is acetyl, and $R_5$ is hydrogen.

In some embodiments of Formula VIII, k is 3 and $R^c$ is Formula III, $R_4$ is hydrogen, and $R_5$ is Formula VI shown below:

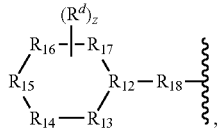

Formula VI or $R_4$ is hydrogen and $R_5$ is Formula VI.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 2, $R_{12}$ is N, $R_{13}$, $R_{14}$, $R_{15}$, $R_{16}$, or $R_{17}$ is S, both $R^d$ are oxo and are bonded to the S, and all of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 2, both $R^d$ are oxo and are bonded to $R_{15}$, $R_{12}$ is N, $R_{15}$ is S, and all of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 2, both $R^d$ are oxo and are bonded to $R_{15}$, $R_{12}$ is N, $R_{15}$ is S, and all of the bonds between adjacent $R_{12}$ to $R_{17}$ are single, $X_b$ is absent, q is 0, p is 1, and each $R_{19}$ is hydrogen.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 1, $R^d$ is amino, and three of the bonds between adjacent $R_{12}$ to $R_{17}$ are double and three of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 1, $R^d$ is amino and is bonded to $R_{15}$, and three of the bonds between adjacent $R_{12}$ to $R_{17}$ are double and three of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 1, $R^d$ is amino and is bonded to $R_{15}$, and three of the bonds between adjacent $R_{12}$ to $R_{17}$ are double and three of the bonds between adjacent $R_{12}$ to $R_{17}$ are single, $X_b$ is absent, p is 0 and q is 0.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 0, $R_{13}$, $R_{14}$, $R_{15}$, $R_{16}$, or $R_{17}$ is O, and all of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 0, $R_{13}$ is O, and all of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 0, $R_{13}$ is O, all of the bonds between adjacent $R_{12}$ to $R_{17}$ are single, $X_b$ is oxygen, p is 1, q is 0 and each $R_{19}$ is hydrogen.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 1, $R^d$ is alkoxy and is bonded to $R_{13}$, $R_{14}$, $R_{15}$, $R_{15}$, $R_{16}$, or $R_{17}$, three of the bonds between adjacent $R_{12}$ to $R_{17}$ are double and three of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 1, $R^d$ is alkoxy and is bonded to $R_{13}$, three of the bonds between adjacent $R_{12}$ to $R_{17}$ are double and three of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_4$ is hydrogen and $R_5$ is Formula VI, wherein z in Formula VI is 1, $R^d$ is alkoxy such as methoxy, and is bonded to $R_{13}$, $R_{12}$ to $R_{17}$ are carbon atoms, three of the bonds between adjacent $R_{12}$ to $R_{17}$ are double and three of the bonds between adjacent $R_{12}$ to $R_{17}$ are single, $X_b$ is absent, p is 0 and q is 0.

In some embodiments, w in Formula IX is 0, $R_{13}$, $R_{14}$, $R_{15}$, $R_{15}$, or $R_{16}$ is O, and, as valency permits, two of the bonds between adjacent $R_{12}$ to $R_{16}$ are double bonds, and three of the bonds between adjacent $R_{12}$ to $R_{16}$ are single bonds.

In some embodiments, w in Formula IX is 0, $R_{13}$ is O, $R_{12}$, $R_{14}$, $R_{15}$ and $R_{16}$ are C, the bonds between $R_{12}$ and $R_{16}$, and between $R_{14}$ and $R_{15}$, are double bonds, and the rest of the bonds in the ring are single bonds.

In some embodiments, w in Formula IX is 0, $R_{13}$ is O, $R_{12}$, $R_{14}$, $R_{15}$ and $R_{16}$ are C, the bonds between $R_{12}$ and $R_{16}$, and between $R_{14}$ and $R_{15}$, are double bonds, the rest of the bonds in the ring are single bonds, $X_b$ is absent, p is 1, q is 0, and each $R_{19}$ is hydrogen.

In some embodiments, w in Formula IX is 0, $R_{13}$, $R_{14}$, $R_{15}$, or $R_{16}$ is O, and, the bonds between adjacent $R_{12}$ to $R_{16}$ are single bonds.

In some embodiments, w in Formula IX is 0, $R_{13}$ is O, $R_{12}$, $R_{14}$, $R_{15}$ and $R_{16}$ are C, and the bonds between adjacent $R_{12}$ to $R_{16}$ are single bonds.

In some embodiments, w in Formula IX is 0, $R_{13}$ is O, $R_{12}$, $R_{14}$, $R_{15}$ and $R_{16}$ are C, the bonds between adjacent $R_{12}$ to $R_{16}$ are single bonds, $X_b$ is absent, p is 1, q is 0, and each $R_{19}$ is hydrogen.

In some embodiments, w in Formula IX is 0, $R_{13}$ and $R_{16}$ are O, and the bonds between adjacent $R_{12}$ to $R_{16}$ are single bonds.

In some embodiments, w in Formula IX is 0, $R_{13}$ and $R_{16}$ are O, $R_{12}$, $R_{14}$ and $R_{15}$ are C, the bonds between adjacent $R_{12}$ to $R_{16}$ are single bonds.

In some embodiments, w in Formula IX is 0, $R_{13}$ and $R_{16}$ are O, $R_{12}$, $R_{14}$ and $R_{15}$ are C, the bonds between adjacent $R_{12}$ to $R_{16}$ are single bonds, $X_b$ is absent, p is 1, q is 0, and each $R_{19}$ is hydrogen.

In some embodiments, w in Formula IX is 0, $R_{13}$, $R_{14}$, $R_{15}$, $R_{15}$, or $R_{16}$ is N, and, as valency permits, two of the bonds between adjacent $R_{12}$ to $R_{16}$ are double bonds, and three of the bonds between adjacent $R_{12}$ to $R_{16}$ are single bonds.

In some embodiments, w in Formula IX is 0, $R_{13}$ is N, $R_{12}$, $R_{14}$, $R_{15}$ and $R_{16}$ are C, the bonds between $R_{12}$ and $R_{16}$, and between $R_{14}$ and $R_{15}$, are double bonds, and the rest of the bonds in the ring are single bonds.

In some embodiments, w in Formula IX is 0, $R_{13}$ is N, $R_{12}$, $R_{14}$, $R_{15}$ and $R_{16}$ are C, the bonds between $R_{12}$ and $R_{16}$, and between $R_{14}$ and $R_{15}$, are double bonds, the rest of the bonds in the ring are single bonds, $X_b$ is absent, p is 1, q is 0, and each $R_{19}$ is hydrogen.

In some embodiments, w in Formula IX is 0, $R_{13}$, $R_{14}$, $R_{15}$, or $R_{16}$ is N, and, the bonds between adjacent $R_{12}$ to $R_{16}$ are single bonds.

In some embodiments, w in Formula IX is 0, $R_{13}$ is N, $R_{12}$, $R_{14}$, $R_{15}$ and $R_{16}$ are C, and the bonds between adjacent $R_{12}$ to $R_{16}$ are single bonds.

In some embodiments, w in Formula IX is 0, $R_{13}$ is N, $R_{12}$, $R_{14}$, $R_{15}$ and $R_{16}$ are C, the bonds between adjacent $R_{12}$ to $R_{16}$ are single bonds, $X_b$ is absent, p is 1, q is 0, and each $R_{19}$ is hydrogen.

In some embodiments, w in Formula IX is 0, $R_{13}$ and $R_{16}$ are N, and the bonds between adjacent $R_{12}$ to $R_{16}$ are single bonds.

In some embodiments, w in Formula IX is 0, $R_{13}$ and $R_{16}$ are N, $R_{12}$, $R_{14}$ and $R_{15}$ are C, the bonds between adjacent $R_{12}$ to $R_{16}$ are single bonds.

In some embodiments, w in Formula IX is 0, $R_{13}$ and $R_{16}$ are N, $R_{12}$, $R_{14}$ and $R_{15}$ are C, the bonds between adjacent $R_{12}$ to $R_{16}$ are single bonds, $X_b$ is absent, p is 1, q is 0, and each $R_{19}$ is hydrogen.

In some embodiments, w in Formula IX is 0, $R_{13}$, $R_{14}$, $R_{15}$, $R_{15}$, or $R_{16}$ is S, and, as valency permits, two of the bonds between adjacent $R_{12}$ to $R_{16}$ are double bonds, and three of the bonds between adjacent $R_{12}$ to $R_{16}$ are single bonds.

In some embodiments, w in Formula IX is 0, $R_{13}$ is S, $R_{12}$, $R_{14}$, $R_{15}$ and $R_{16}$ are C, the bonds between $R_{12}$ and $R_{16}$, and between $R_{14}$ and $R_{15}$, are double bonds, and the rest of the bonds in the ring are single bonds.

In some embodiments, w in Formula IX is 0, $R_{13}$ is S, $R_{12}$, $R_{14}$, $R_{15}$ and $R_{16}$ are C, the bonds between $R_{12}$ and $R_{16}$, and between $R_{14}$ and $R_{15}$, are double bonds, the rest of the bonds in the ring are single bonds, $X_b$ is absent, p is 1, q is 0, and each $R_{19}$ is hydrogen.

In some embodiments, w in Formula IX is 0, $R_{13}$, $R_{14}$, $R_{15}$, or $R_{16}$ is S, and, the bonds between adjacent $R_{12}$ to $R_{16}$ are single bonds.

In some embodiments, w in Formula IX is 0, $R_{13}$ is S, $R_{12}$, $R_{14}$, $R_{15}$ and $R_{16}$ are C, and the bonds between adjacent $R_{12}$ to $R_{16}$ are single bonds.

In some embodiments, w in Formula IX is 0, $R_{13}$ is S, $R_{12}$, $R_{14}$, $R_{15}$ and $R_{16}$ are C, the bonds between adjacent $R_{12}$ to $R_{16}$ are single bonds, $X_b$ is absent, p is 1, q is 0, and each $R_{19}$ is hydrogen.

In some embodiments, w in Formula IX is 0, $R_{13}$ and $R_{16}$ are S, and the bonds between adjacent $R_{12}$ to $R_{16}$ are single bonds.

In some embodiments, w in Formula IX is 0, $R_{13}$ and $R_{16}$ are S, $R_{12}$, $R_{14}$ and $R_{15}$ are C, the bonds between adjacent $R_{12}$ to $R_{16}$ are single bonds.

In some embodiments, w in Formula IX is 0, $R_{13}$ and $R_{16}$ are S, $R_{12}$, $R_{14}$ and $R_{15}$ are C, the bonds between adjacent $R_{12}$ to $R_{16}$ are single bonds, $X_b$ is absent, p is 1, q is 0, and each $R_{19}$ is hydrogen.

In some embodiments $R_{29}$ of Formula X is Si, and $X_g$ is alkynyl.

In some embodiments $R_{29}$ of Formula X is Si, $X_g$ is ethynyl, and $R_{30}$ is alkylene.

In some embodiments $R_{29}$ of Formula X is Si, $X_g$ is ethynyl, $R_{30}$ is methylene, and $R_{31}$, $R_{32}$, and $R_{33}$ are alkyl.

In some embodiments $R_{29}$ of Formula X is Si, $X_g$ is ethynyl, $R_{30}$ is methylene, and $R_{31}$, $R_{32}$, and $R_{33}$ are methyl.

Products can be either singularly modified or multiply modified. Singularly modified product s are products that contain one or more covalent modifications, wherein substantially all of the covalently modified products possess the same covalent modification (i.e. the product contains one 'type' or species of covalent modification). Multiply modified products are products that contain covalent modifications, wherein substantially all of the covalently modified products do not possess the same covalent modification (i.e. the product contains two or more 'types' or species of covalent modifications).

In some embodiments, the surface modified product is singularly modified. In some embodiments, the surface modification is:

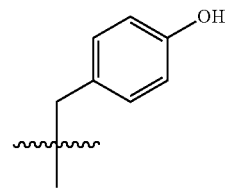

-continued

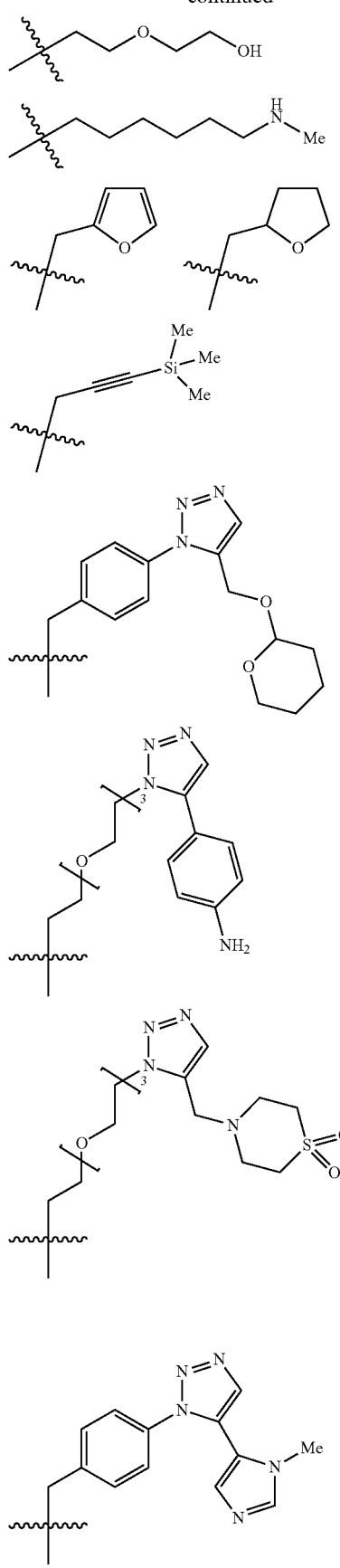

-continued

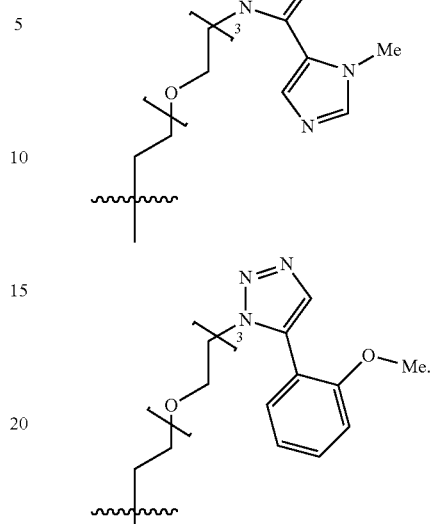

In preferred embodiments, the surface modified product is multiply modified containing a first species or type of covalent modification defined by Formula I, and a second species or type of covalent modification defined by Formula I. In some embodiments, the surface modifications are combinations of the modifications shown above. Example combinations include:

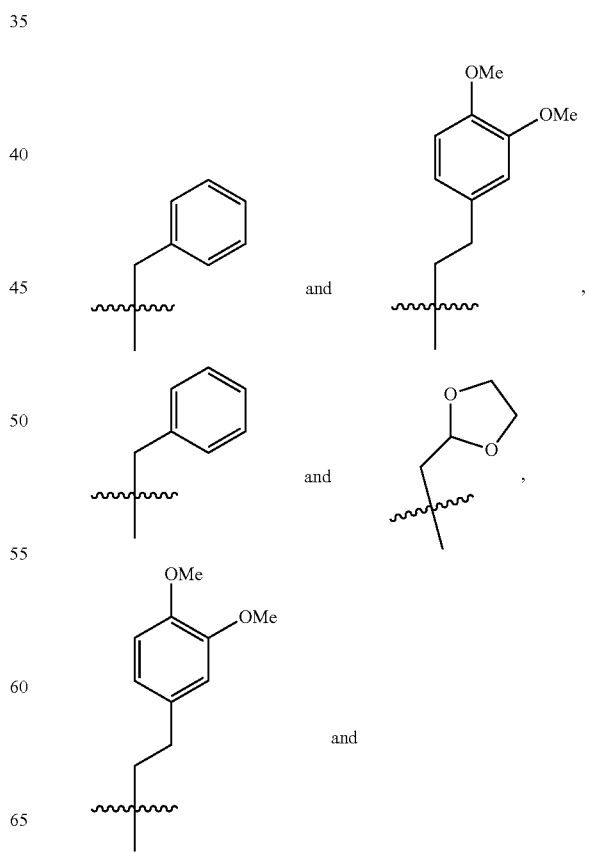

-continued
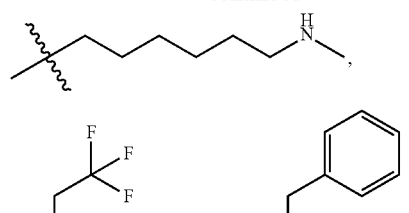
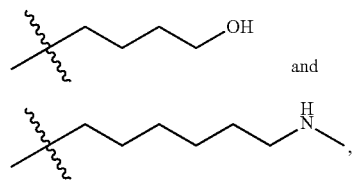
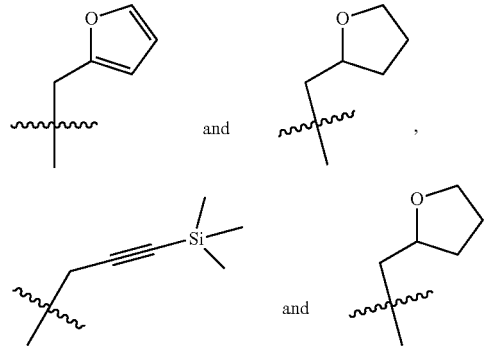
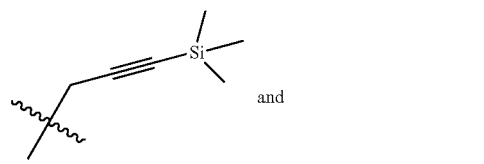
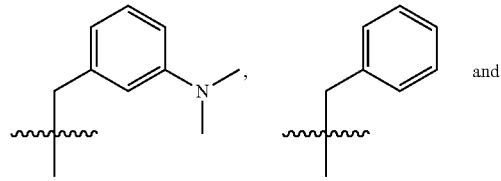
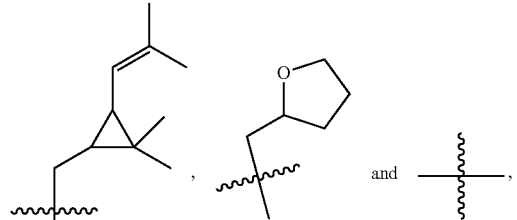
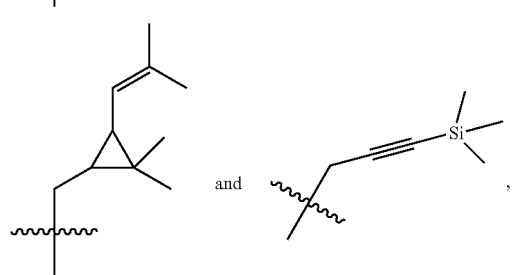
-continued
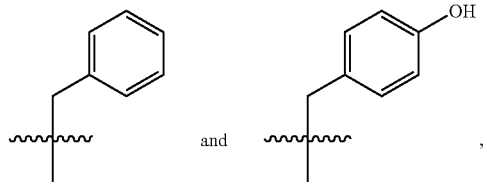
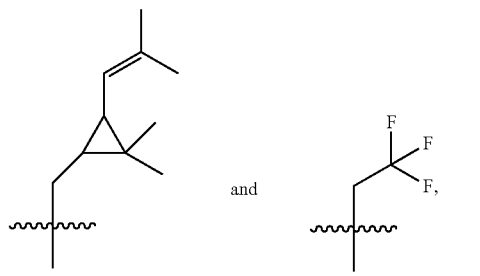
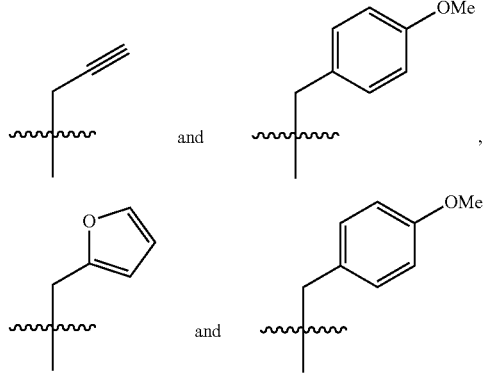
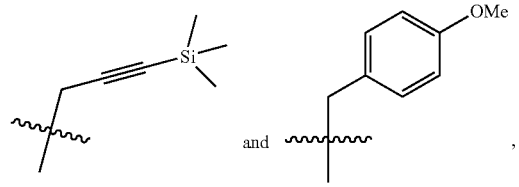
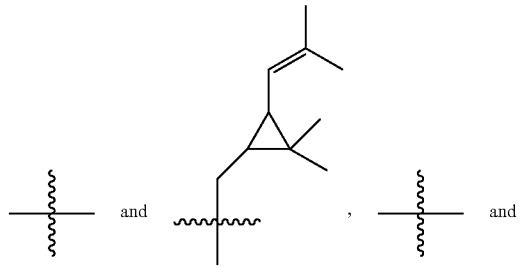
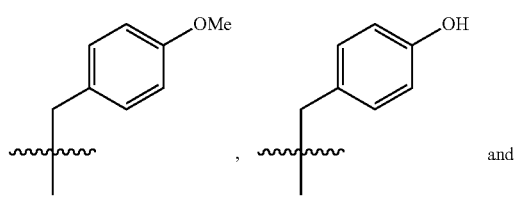
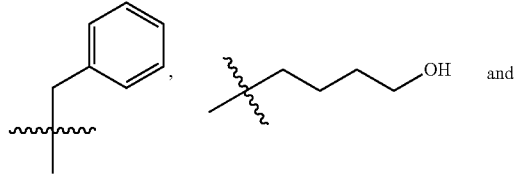

-continued
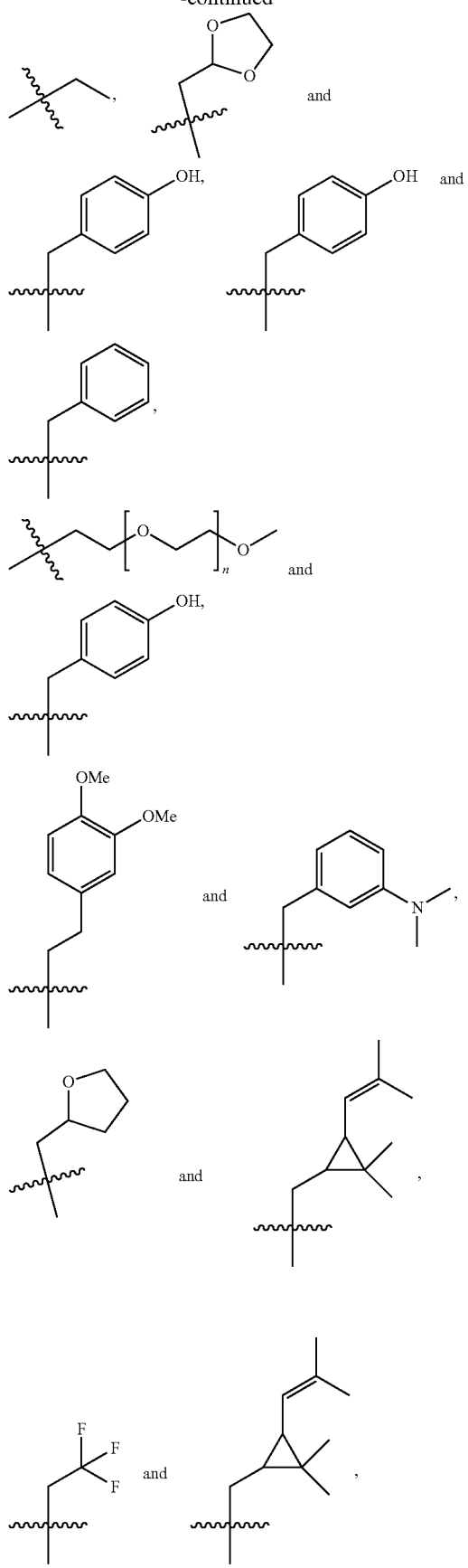
-continued
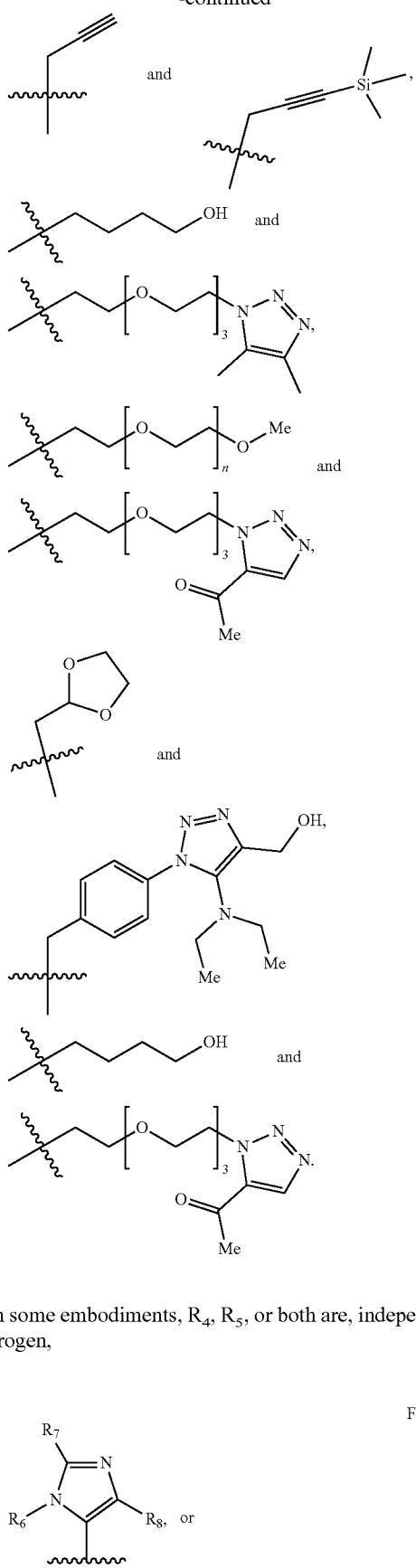
In some embodiments, R₄, R₅, or both are, independently, hydrogen,
Formula IV
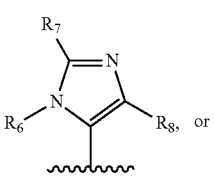
or -continued Formula V

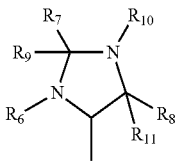

wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$);
  wherein $R_6$, $R_9$, $R_{10}$, and $R_{11}$ are independently present or absent according to valency, and wherein the ring bonds are double or single according to valency.

In some embodiments, $R_1$ is (A)

Formula VII

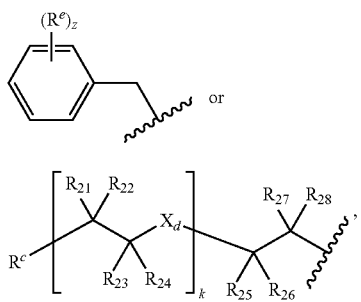

or

Formula VIII wherein k is independently an integer from 1 to 30; wherein z is an integer from 0 to 4; wherein $X_d$ is O or S; wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_2$); and wherein $R^a$ and $R^c$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1$); or together with the carbon atom to which they are attached, form a 3- to 8-membered unsubstituted or substituted carbocyclic, heterocyclic ring or Formula III

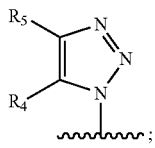

wherein $R_4$, $R_5$, or both are, independently, hydrogen,

Formula IV

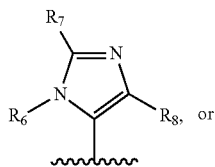

or

-continued

Formula V

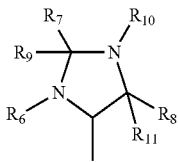

wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$);
  wherein $R_6$, $R_9$, $R_{10}$, and $R_{11}$ are independently present or absent according to valency, and wherein the ring bonds are double or single according to valency.

In some embodiments, the surface modified products contain one or more covalent modifications described by Formula I, wherein for each formula $R_2$, $R_3$, $R_4$, and $R_5$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$); and wherein $R_1$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$).

In some embodiments, the surface modified products contain one or more covalent modifications described by Formula I, wherein for each formula $R_1$, $R_2$, $R_3$, $R_4$, and $R_5$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$).

In some embodiments, the surface modified products contain one or more covalent modifications described by Formula I, wherein for each formula $R_1$, $R_3$, $R_4$, and $R_5$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$); and wherein $R_2$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$).

In some embodiments, the surface modified products contain one or more covalent modifications described by Formula I, wherein for each formula $R_1$, $R_2$, $R_4$, and $R_5$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$); and wherein $R_3$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$).

In some embodiments, the surface modified products contain one or more covalent modifications described by Formula I, wherein for each formula $R_1$, $R_2$, $R_3$, and $R_5$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$); and wherein $R_4$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$).

In some embodiments, the surface modified products contain one or more covalent modifications described by Formula I, wherein for each formula $R_1$, $R_2$, $R_3$, and $R_4$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1Q_1+Q_2$, $U_1+Q_1+Q_3$, $U_1+Q_2+Q_3$, or $U_1+Q_1+Q_2+Q_3$ (preferably, in these embodiments, $U_1+Q_1$); and wherein $R_5$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1$).

Independently in some embodiments of $R_4$ and $R_5$, and independently in combination with any embodiments of any other relevant substituent classes, $R_4$ and $R_5$ can be, independently,

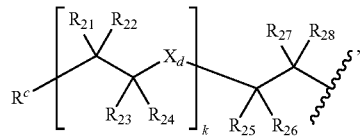

Formula VIII wherein k is an integer from 1 to 20;
wherein $X_d$ are O;
wherein $R^c$ is $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of Formula VI, and independently in combination with any embodiments of any other relevant substituent classes, all of $R_{12}$, $R_{13}$, $R_{14}$, $R_{15}$, $R_{16}$, and $R_{17}$ are C. Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is C.

Independently in some embodiments of Formula IX, and independently in combination with any embodiments of any other relevant substituent classes, all of $R_{12}$, $R_{13}$, $R_{14}$, $R_{15}$, and $R_{16}$ are C. Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are C. Independently in some embodiments of Formula IX, and independently in combination with any embodiments of any other relevant substituent classes, one or two of $R_{12}$, $R_{13}$, $R_{14}$, $R_{15}$, and $R_{16}$ are C. Independently in some embodiments of Formula IX, and independently in combination with any embodiments of any other relevant substituent classes, one of $R_{12}$, $R_{13}$, $R_{14}$, $R_{15}$, and $R_{16}$ is C.

Independently in some embodiments of Formula VI, and independently in combination with any embodiments of any other relevant substituent classes, all of $R_{12}$, $R_{13}$, $R_{14}$, $R_{15}$, $R_{16}$, and $R_{17}$ are N. Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are N. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are N. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are N. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are N. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N.

Independently in some embodiments of Formula IX, and independently in combination with any embodiments of any other relevant substituent classes, all of $R_{12}$, $R_{13}$, $R_{14}$, $R_{15}$, and $R_{16}$ are N. Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are N. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are N. Independently in some embodiments of Formula IX, and independently in combination with any embodiments of any other relevant substituent classes, one or two of $R_{12}$, $R_{13}$, $R_{14}$, $R_{15}$, and $R_{16}$ are N. Independently in some embodiments of Formula IX, and independently in combination with any embodiments of any other relevant substituent classes, one of $R_{12}$, $R_{13}$, $R_{14}$, $R_{15}$, and $R_{16}$ is N.

Independently in some embodiments of Formula VI, and independently in combination with any embodiments of any other relevant substituent classes, all of $R_{12}$, $R_{13}$, $R_{14}$, $R_{15}$, $R_{16}$, and $R_{17}$ are O. Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are O. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are O. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are O. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are O. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is O.

Independently in some embodiments of Formula IX, and independently in combination with any embodiments of any other relevant substituent classes, all of $R_{12}$, $R_{13}$, $R_{14}$, $R_{15}$, and $R_{16}$ are O. Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are O. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are O. Independently in some embodiments of Formula IX, and independently in combination with any embodiments of any other relevant substituent classes, one or two of $R_{12}$, $R_{13}$, $R_{14}$, $R_{15}$, and $R_{16}$ are O. Independently in some embodiments of Formula IX, and independently in combination with any embodiments of any other relevant substituent classes, one of $R_{12}$, $R_{13}$, $R_{14}$, $R_{15}$, and $R_{16}$ is O.

Independently in some embodiments of Formula VI, and independently in combination with any embodiments of any other relevant substituent classes, all of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is S.

Independently in some embodiments of Formula IX, and independently in combination with any embodiments of any other relevant substituent classes, all of $R_{12}$, $R_{13}$, $R_{14}$, $R_{15}$, and $R_{16}$ are S. Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are S. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are S. Independently in some embodiments of Formula IX, and independently in combination with any embodiments of any other relevant substituent classes, one or two of $R_{12}$, $R_{13}$, $R_{14}$, $R_{15}$, and $R_{16}$ are S. Independently in some embodiments of Formula IX, and independently in combination with any embodiments of any other relevant substituent classes, one of $R_{12}$, $R_{13}$, $R_{14}$, $R_{15}$, and $R_{16}$ is S.

Independently in some embodiments of Formula VI, and independently in combination with any embodiments of any other relevant substituent classes, all of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is $S(O)_2$.

Independently in some embodiments of Formula IX, and independently in combination with any embodiments of any other relevant substituent classes, all of $R_{12}$, $R_{13}$, $R_{14}$, $R_{15}$, and $R_{16}$ are $S(O)_2$. Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are $S(O)_2$. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are $S(O)_2$. Independently in some embodiments of Formula IX, and independently in combination with any embodiments of any other relevant substituent classes, one or two of $R_{12}$, $R_{13}$, $R_{14}$, $R_{15}$, and $R_{16}$ are $S(O)_2$. Independently in some embodiments of Formula IX, and independently in combination with any embodiments of any other relevant substituent classes, one of $R_{12}$, $R_{13}$, $R_{14}$, $R_{15}$, and $R_{16}$ is $S(O)_2$.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are N and one of $R_{12}$, $R_{13}$, $R_{14}$, $R_{15}$, $R_{16}$, and $R_{17}$ is O. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are N and one or two of $R_{12}$, $R_{13}$, $R_{14}$, $R_{15}$, $R_{16}$, and $R_{17}$ are O. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are N and one, two, or three of $R_{12}$, $R_{13}$, $R_{14}$, $R_{15}$, $R_{16}$, and $R_{17}$ are O. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are N and one, two, three, or four of $R_{12}$, $R_{13}$, $R_{14}$, $R_{15}$, $R_{16}$, and $R_{17}$ are O. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N and one, two, three, four, or five of $R_{12}$, $R_{13}$, $R_{14}$, $R_{15}$, $R_{16}$, and $R_{17}$ are 0.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are N and one of $R_{12}$, $R_{13}$, $R_{14}$, $R_{15}$, and $R_{16}$ is O. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are N and one or two of $R_{12}$, $R_{13}$, $R_{14}$, $R_{15}$, and $R_{16}$ are O. Independently in some embodiments of Formula IX, and independently in combination with any embodiments of any other relevant substituent classes, one or two of $R_{12}$, $R_{13}$, $R_{14}$, $R_{15}$, and $R_{16}$ are N and one, two, or three of $R_{12}$, $R_{13}$, $R_{14}$, $R_{15}$, and $R_{16}$ are O. Independently in some embodiments of Formula IX, and independently in combination with any embodiments of any other relevant substituent classes, one of $R_{12}$, $R_{13}$, $R_{14}$, $R_{15}$, and $R_{16}$ is N and one, two, three, or four of $R_{12}$, $R_{13}$, $R_{14}$, $R_{15}$, and $R_{16}$ are O.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are N and one of $R_{12}$, $R_{13}$, $R_{14}$, $R_{15}$, $R_{16}$, and $R_{17}$ is S. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are N and one or two of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are N and one, two, or three of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are N and one, two, three, or four of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N and one, two, three, four, or five of $R_{12}$, $R_{13}$, $R_{14}$, $R_{15}$, $R_{16}$, and $R_{17}$ are S.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are N and one of $R_{12}$, $R_{13}$, $R_{14}$, $R_{15}$, and $R_{16}$ is S. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are N and one or two of $R_{12}$, $R_{13}$, $R_{14}$, $R_{15}$, and $R_{16}$ are S. Independently in some embodiments of Formula IX, and independently in combination with any embodiments of any other relevant substituent classes, one or two of $R_{12}$, $R_{13}$, $R_{14}$, $R_{15}$, and $R_{16}$ are N and one, two, or three of $R_{12}$, $R_{13}$, $R_{14}$, $R_{15}$, and $R_{16}$ are S. Independently in some embodiments of Formula IX, and independently in combination with any embodiments of any other relevant substituent classes, one of $R_{12}$, $R_{13}$, $R_{14}$, $R_{15}$, and $R_{16}$ is N and one, two, three, or four of $R_{12}$, $R_{13}$, $R_{14}$, $R_{15}$, and $R_{16}$ are S.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are N and one of $R_{12}$, $R_{13}$, $R_{14}$, $R_{15}$, $R_{16}$, and $R_{17}$ is $S(O)_2$. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are N and one or two of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are N and one, two, or three of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are N and one, two, three, or four of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N and one, two, three, four, or five of $R_{12}$, $R_{13}$, $R_{14}$, $R_{15}$, $R_{16}$, and $R_{17}$ are $S(O)_2$.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are N and one of $R_{12}$, $R_{13}$, $R_{14}$, $R_{15}$, and $R_{16}$ is $S(O)_2$. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are N and one or two of $R_{12}$, $R_{13}$, $R_{14}$, $R_{15}$, and $R_{16}$ are $S(O)_2$. Independently in some embodiments of Formula IX, and independently in combination with any embodiments of any other relevant substituent classes, one or two of $R_{12}$, $R_{13}$, $R_{14}$, $R_{15}$, and $R_{16}$ are N and one, two, or three of $R_{12}$, $R_{13}$, $R_{14}$, $R_{15}$, and $R_{16}$ are $S(O)_2$. Independently in some embodiments of Formula IX, and independently in combination with any embodiments of any other relevant substituent classes, one of $R_{12}$, $R_{13}$, $R_{14}$, $R_{15}$, and $R_{16}$ is N and one, two, three, or four of $R_{12}$, $R_{13}$, $R_{14}$, $R_{15}$, and $R_{16}$ are $S(O)_2$.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are O and one of $R_{12}$, $R_{13}$, $R_{14}$, $R_{15}$, $R_{16}$, and $R_{17}$ is S. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are O and one or two of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are O and one, two, or three of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are O and one, two, three, or four of $R_{12}$, $R_{13}$, $R_{14}$, $R_{15}$, $R_{16}$, and $R_{17}$ are S. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N and one, two, three, four, or five of $R_{12}$, $R_{13}$, $R_{14}$, $R_{15}$, $R_{16}$, and $R_{17}$ are S.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are O and one of $R_{12}$, $R_{13}$, $R_{14}$, $R_{15}$, and $R_{16}$ is S. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are O and one or two of $R_{12}$, $R_{13}$, $R_{14}$, $R_{15}$, and $R_{16}$ are S. Independently in some embodiments of Formula IX, and independently in combination with any embodiments of any other relevant substituent classes, one or two of $R_{12}$, $R_{13}$, $R_{14}$, $R_{15}$, and $R_{16}$ are O and one, two, or three of $R_{12}$, $R_{13}$, $R_{14}$, $R_{15}$, and $R_{16}$ are S. Independently in some embodiments of Formula IX, and independently in combination with any embodiments of any other relevant substituent classes, one of $R_{12}$, $R_{13}$, $R_{14}$, $R_{15}$, and $R_{16}$ is O and one, two, three, or four of $R_{12}$, $R_{13}$, $R_{14}$, $R_{15}$, and $R_{16}$ are S.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are O and one of $R_{12}$, $R_{13}$, $R_{14}$, $R_{15}$, $R_{16}$, and $R_{17}$ is $S(O)_2$. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are O and one or two of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are O and one, two, or three of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are O and one, two, three, or four of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is O and one, two, three, four, or five of $R_{12}$, $R_{13}$, $R_{14}$, $R_{15}$, $R_{16}$, and $R_{17}$ are $S(O)_2$.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are O and one of $R_{12}$, $R_{13}$, $R_{14}$, $R_{15}$, and $R_{16}$ is $S(O)_2$. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are O and one or two of $R_{12}$, $R_{13}$, $R_{14}$, $R_{15}$, and $R_{16}$ are $S(O)_2$. Independently in some embodiments of Formula IX, and independently in combination with any embodiments of any other relevant substituent classes, one or two of $R_{12}$, $R_{13}$, $R_{14}$, $R_{15}$, and $R_{16}$ are O and one, two, or three of $R_{12}$, $R_{13}$, $R_{14}$, $R_{15}$, and $R_{16}$ are $S(O)_2$. Independently in some embodiments of Formula IX, and independently in combination with any embodiments of any other relevant substituent classes, one of $R_{12}$, $R_{13}$, $R_{14}$, $R_{15}$, and $R_{16}$ is O and one, two, three, or four of $R_{12}$, $R_{13}$, $R_{14}$, $R_{15}$, and $R_{16}$ are $S(O)_2$.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are S and one of $R_{12}$, $R_{13}$, $R_{14}$, $R_{15}$, $R_{16}$, and $R_{17}$ is $S(O)_2$. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are S and one or two of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are S and one, two, or three of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are S and one, two, three, or four of $R_{12}$, $R_{13}$, $R_{14}$, $R_{15}$, $R_{16}$, and $R_{17}$ are $S(O)_2$. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is S and one, two, three, four, or five of $R_{12}$, $R_{13}$, $R_{14}$, $R_{15}$, $R_{16}$, and $R_{17}$ are $S(O)_2$.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are S and one of $R_{12}$, $R_{13}$, $R_{14}$, $R_{15}$, and $R_{16}$ is $S(O)_2$. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are S and one or two of $R_{12}$, $R_{13}$, $R_{14}$, $R_{15}$, and $R_{16}$ are $S(O)_2$. Independently in some embodiments of Formula IX, and independently in combination with any other relevant substituent classes, one or two of $R_{12}$, $R_{13}$, $R_{14}$, $R_{15}$, and $R_{16}$ are S and one, two, or three of $R_{12}$, $R_{13}$, $R_{14}$, $R_{15}$, and $R_{16}$ are $S(O)_2$. Independently in some embodiments of Formula IX, and independently in combination with any embodiments of any other relevant substituent classes, one of $R_{12}$, $R_{13}$, $R_{14}$, $R_{15}$, and $R_{16}$ is S and one, two, three, or four of $R_{12}$, $R_{13}$, $R_{14}$, $R_{15}$, and $R_{16}$ are $S(O)_2$.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are N and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are N and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are N and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are N and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are N and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are N and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are N and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is N and the others are C.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are O and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are O and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are O and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are O and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is O and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are O and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are O and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are O and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is O and the others are C.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are S and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are S and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are S and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are S and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is S and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are S and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are S and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are S and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is S and the others are C.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are $S(O)_2$ and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are $S(O)_2$ and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are $S(O)_2$ and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are $S(O)_2$ and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is $S(O)_2$ and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are $S(O)_2$ and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are $S(O)_2$ and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are $S(O)_2$ and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is $S(O)_2$ and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are N, none, one, two, three, four, five, or six of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are N, none, one, two, three, four, or five of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are N, none, one, two, three, or four of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are N, none, one, two, or three of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are N, none, one, or two of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are N, none or one of $R_{12}$, $R_{13}$, $R_{14}$, $R_{15}$, $R_{16}$, and $R_{17}$ is O, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, and $R_{16}$ are N, none, one, two, three, four, or five of $R_{12}$, $R_{13}$, $R_{14}$, $R_{15}$, and $R_{16}$ is O, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, and $R_{16}$ are N, none, one, two, three, or four of $R_{12}$, $R_{13}$, $R_{14}$, $R_{15}$, and $R_{16}$ is O, and the others are C. Independently in some embodiments of Formula IX, and independently in combination with any embodiments of any other relevant substituent classes, none, one, two, or three of $R_{12}$, $R_{13}$, $R_{14}$, $R_{15}$, and $R_{16}$ are N, none, one, two, or three of $R_{12}$, $R_{13}$, $R_{14}$, $R_{15}$, and $R_{16}$ are O, and the others are C. Independently in some embodiments of Formula IX, and independently in combination with any embodiments of any other relevant substituent classes, none, one or two of $R_{12}$, $R_{13}$, $R_{14}$, $R_{15}$, and $R_{16}$ are N, none, one or two of $R_{12}$, $R_{13}$, $R_{14}$, $R_{15}$, and $R_{16}$ are O, and the others are C. Independently in some embodiments of Formula IX, and independently in combination with any embodiments of any other relevant substituent classes, none or one of $R_{12}$, $R_{13}$, $R_{14}$, $R_{15}$, and $R_{16}$ is N, none or one of $R_{12}$, $R_{13}$, $R_{14}$, $R_{15}$, and $R_{16}$ are O, and the others are C.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are N, one of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are N, one or two of $R_{12}$, $R_{13}$, $R_{14}$, $R_{15}$, $R_{16}$, and $R_{17}$ are O, and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are N, one, two, or three of $R_{12}$, $R_{13}$, $R_{14}$, $R_{15}$, $R_{16}$, and $R_{17}$ are O, and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are N, one, two, three, or four of $R_{12}$, $R_{13}$, $R_{14}$, $R_{15}$, $R_{16}$, and $R_{17}$ are O, and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N, one, two, three, four, or five of $R_{12}$, $R_{13}$, $R_{14}$, $R_{15}$, $R_{16}$, and $R_{17}$ are O, and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are N, one of $R_{12}$, $R_{13}$, $R_{14}$, $R_{15}$, and $R_{16}$ is O, and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are N, one or two of $R_{12}$, $R_{13}$, $R_{14}$, $R_{15}$, and $R_{16}$ are O, and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are N, one, two, or three of $R_{12}$, $R_{13}$, $R_{14}$, $R_{15}$, and $R_{16}$ are O, and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is N, one, two, three, or four of $R_{12}$, $R_{13}$, $R_{14}$, $R_{15}$, and $R_{16}$ are O, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are N, none, one, two, three, four, five, or six of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are N, none, one, two, three, four, or five of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are N, none, one, two, three, or four of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are N, none, one, two, or three of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are N, none, one, or two of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are N, none or one of $R_{12}$, $R_{13}$, $R_{14}$, $R_{15}$, $R_{16}$, and $R_{17}$ is S, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, and $R_{16}$ are N, none, one, two, three, four, or five of $R_{12}$, $R_{13}$, $R_{14}$, $R_{15}$, and $R_{16}$ is S, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, and $R_{16}$ are N, none, one, two, three, or four of $R_{12}$, $R_{13}$, $R_{14}$, $R_{15}$, and $R_{16}$ is S, and the others are C. Independently in some embodiments of Formula IX, and independently in combination with any embodiments of any other relevant substituent classes, none, one, two, or three of $R_{12}$, $R_{13}$, $R_{14}$, $R_{15}$, and $R_{16}$ are N, none, one, two, or three of $R_{12}$, $R_{13}$, $R_{14}$, $R_{15}$, and $R_{16}$ are S, and the others are C. Independently in some embodiments of Formula IX, and independently in combination with any embodiments of any other relevant substituent classes, none, one or two of $R_{12}$, $R_{13}$, $R_{14}$, $R_{15}$, and $R_{16}$ are N, none, one or two of $R_{12}$, $R_{13}$, $R_{14}$, $R_{15}$, and $R_{16}$ are S, and the others are C. Independently in some embodiments of Formula IX, and independently in combination with any embodiments of any other relevant substituent classes, none or one of $R_{12}$, $R_{13}$, $R_{14}$, $R_{15}$, and $R_{16}$ is N, none or one of $R_{12}$, $R_{13}$, $R_{14}$, $R_{15}$, and $R_{16}$ are S, and the others are C.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are N, one of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are N, one or two of $R_{12}$, $R_{13}$, $R_{14}$, $R_{15}$, $R_{16}$, and $R_{17}$ are S, and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are N, one, two, or three of $R_{12}$, $R_{13}$, $R_{14}$, $R_{15}$, $R_{16}$, and $R_{17}$ are S, and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are N, one, two, three, or four of $R_{12}$, $R_{13}$, $R_{14}$, $R_{15}$, $R_{16}$, and $R_{17}$ are S, and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N, one, two, three, four, or five of $R_{12}$, $R_{13}$, $R_{14}$, $R_{15}$, $R_{16}$, and $R_{17}$ are S, and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are N, one of $R_{12}$, $R_{13}$, $R_{14}$, $R_{15}$, and $R_{16}$ is S, and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are N, one or two of $R_{12}$, $R_{13}$, $R_{14}$, $R_{15}$, and $R_{16}$ are S, and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are N, one, two, or three of $R_{12}$, $R_{13}$, $R_{14}$, $R_{15}$, and $R_{16}$ are S, and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is N, one, two, three, or four of $R_{12}$, $R_{13}$, $R_{14}$, $R_{15}$, and $R_{16}$ are S, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are N, none, one, two, three, four, five, or six of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are N, none, one, two, three, four, or five of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are N, none, one, two, three, or four of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are N, none, one, two, or three of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are N, none, one, or two of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are N, none or one of $R_{12}$, $R_{13}$, $R_{14}$, $R_{15}$, $R_{16}$, and $R_{17}$ is $S(O)_2$, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, and $R_{16}$ are N, none, one, two, three, four, or five of $R_{12}$, $R_{13}$, $R_{14}$, $R_{15}$, and $R_{16}$ is $S(O)_2$, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, and $R_{16}$ are N, none, one, two, three, or four of $R_{12}$, $R_{13}$, $R_{14}$, $R_{15}$, and $R_{16}$ is $S(O)_2$, and the others are C. Independently in some embodiments of Formula IX, and independently in combination with any embodiments of any other relevant substituent classes, none, one, two, or three of $R_{12}$, $R_{13}$, $R_{14}$, $R_{15}$, and $R_{16}$ are N, none, one, two, or three of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, none, one or two of $R_{12}$, $R_{13}$, $R_{14}$, $R_{15}$, and $R_{16}$ are N, none, one or two of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, none or one of $R_{12}$, $R_{13}$, $R_{14}$, $R_{15}$, and $R_{16}$ is N, none or one of $R_{12}$, $R_{13}$, $R_{14}$, $R_{15}$, and $R_{16}$ are $S(O)_2$, and the others are C.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are N, one of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are N, one or two of $R_{12}$, $R_{13}$, $R_{14}$, $R_{15}$, $R_{16}$, and $R_{17}$ are $S(O)_2$, and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are N, one, two, or three of $R_{12}$, $R_{13}$, $R_{14}$, $R_{15}$, $R_{16}$, and $R_{17}$ are $S(O)_2$, and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are N, one, two, three, or four of $R_{12}$, $R_{13}$, $R_{14}$, $R_{15}$, $R_{16}$, and $R_{17}$ are $S(O)_2$, and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N, one, two, three, four, or five of $R_{12}$, $R_{13}$, $R_{14}$, $R_{15}$, $R_{16}$, and $R_{17}$ are $S(O)_2$, and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are N, one of $R_{12}$, $R_{13}$, $R_{14}$, $R_{15}$, and $R_{16}$ is $S(O)_2$, and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are N, one or two of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are N, one, two, or three of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is N, one, two, three, or four of $R_{12}$, $R_{13}$, $R_{14}$, $R_{15}$, and $R_{16}$ are $S(O)_2$, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are O, none, one, two, three, four, five, or six of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are O, none, one, two, three, four, or five of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are O, none, one, two, three, or four of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are O, none, one, two, or three of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are O, none, one, or two of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are O, none or one of $R_{12}$, $R_{13}$, $R_{14}$, $R_{15}$, $R_{16}$, and $R_{17}$ is S, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, and $R_{16}$ are O, none, one, two, three, four, or five of $R_{12}$, $R_{13}$, $R_{14}$, $R_{15}$, and $R_{16}$ is S, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, and $R_{16}$ are O, none, one, two, three, or four of $R_{12}$, $R_{13}$, $R_{14}$, $R_{15}$, and $R_{16}$ is S, and the others are C. Independently in some embodiments of Formula IX, and independently in combination with any embodiments of any other relevant substituent classes, none, one, two, or three of $R_{12}$, $R_{13}$, $R_{14}$, $R_{15}$, and $R_{16}$ are O, none, one, two, or three of $R_{12}$, $R_{13}$, $R_{14}$, $R_{15}$, and $R_{16}$ are S, and the others are C. Independently in some embodiments of Formula IX, and independently in combination with any embodiments of any other relevant substituent classes, none, one or two of $R_{12}$, $R_{13}$, $R_{14}$, $R_{15}$, and $R_{16}$ are O, none, one or two of $R_{12}$, $R_{13}$, $R_{14}$, $R_{15}$, and $R_{16}$ are S, and the others are C. Independently in some embodiments of Formula IX, and independently in combination with any embodiments of any other relevant substituent classes, none or one of $R_{12}$, $R_{13}$, $R_{14}$, $R_{15}$, and $R_{16}$ is O, none or one of $R_{12}$, $R_{13}$, $R_{14}$, $R_{15}$, and $R_{16}$ are S, and the others are C.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are O, one of $R_{12}$, $R_{13}$, $R_{14}$, $R_{15}$, $R_{16}$, and $R_{17}$ is S, and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are O, one or two of $R_{12}$, $R_{13}$, $R_{14}$, $R_{15}$, $R_{16}$, and $R_{17}$ are S, and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are O, one, two, or three of $R_{12}$, $R_{13}$, $R_{14}$, $R_{15}$, $R_{16}$, and $R_{17}$ are S, and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are O, one, two, three, or four of $R_{12}$, $R_{13}$, $R_{14}$, $R_{15}$, $R_{16}$, and $R_{17}$ are S, and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is N, one, two, three, four, or five of $R_{12}$, $R_{13}$, $R_{14}$, $R_{15}$, $R_{16}$, and $R_{17}$ are S, and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are O, one of $R_{12}$, $R_{13}$, $R_{14}$, $R_{15}$, and $R_{16}$ is S, and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are O, one or two of $R_{12}$, $R_{13}$, $R_{14}$, $R_{15}$, and $R_{16}$ are S, and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are O, one, two, or three of $R_{12}$, $R_{13}$, $R_{14}$, $R_{15}$, and $R_{16}$ are S, and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is O, one, two, three, or four of $R_{12}$, $R_{13}$, $R_{14}$, $R_{15}$, and $R_{16}$ are S, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are O, none, one, two, three, four, five, or six of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are O, none, one, two, three, four, or five of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are O, none, one, two, three, or four of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are O, none, one, two, or three of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are O, none, one, or two of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are O, none or one of $R_{12}$, $R_{13}$, $R_{14}$, $R_{15}$, $R_{16}$, and $R_{17}$ is $S(O)_2$, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, and $R_{16}$ are O, none, one, two, three, four, or five of $R_{12}$, $R_{13}$, $R_{14}$, $R_{15}$, and $R_{16}$ is $S(O)_2$, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, and $R_{16}$ are O, none, one, two, three, or four of $R_{12}$, $R_{13}$, $R_{14}$, $R_{15}$, and $R_{16}$ is $S(O)_2$, and the others are C. Independently in some embodiments of Formula IX, and independently in combination with any embodiments of any other relevant substituent classes, none, one, two, or three of $R_{12}$, $R_{13}$, $R_{14}$, $R_{15}$, and $R_{16}$ are O, none, one, two, or three of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, none, one or two of $R_{12}$, $R_{13}$, $R_{14}$, $R_{15}$, and $R_{16}$ are O, none, one or two of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, none or one of $R_{12}$, $R_{13}$, $R_{14}$, $R_{15}$, and $R_{16}$ is O, none or one of $R_{12}$, $R_{13}$, $R_{14}$, $R_{15}$, and $R_{16}$ are $S(O)_2$, and the others are C.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are O, one of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are O, one or two of $R_{12}$, $R_{13}$, $R_{14}$, $R_{15}$, $R_{16}$, and $R_{17}$ are $S(O)_2$, and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are O, one, two, or three of $R_{12}$, $R_{13}$, $R_{14}$, $R_{15}$, $R_{16}$, and $R_{17}$ are $S(O)_2$, and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are O, one, two, three, or four of $R_{12}$, $R_{13}$, $R_{14}$, $R_{15}$, $R_{16}$, and $R_{17}$ are $S(O)_2$, and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is O, one, two, three, four, or five of $R_{12}$, $R_{13}$, $R_{14}$, $R_{15}$, $R_{16}$, and $R_{17}$ are $S(O)_2$, and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are O, one of $R_{12}$, $R_{13}$, $R_{14}$, $R_{15}$, and $R_{16}$ is $S(O)_2$, and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are O, one or two of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are O, one, two, or three of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is O, one, two, three, or four of $R_{12}$, $R_{13}$, $R_{14}$, $R_{15}$, and $R_{16}$ are $S(O)_2$, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are S, none, one, two, three, four, five, or six of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any other relevant substituent classes, none, one, two, three, four, or five of $R_{12}$, $R_{13}$, $R_{14}$, $R_{15}$, $R_{16}$, and $R_{17}$ are S, none, one, two, three, four, or five of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are S, none, one, two, three, or four of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are S, none, one, two, or three of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are S, none, one, or two of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are S, none or one of $R_{12}$, $R_{13}$, $R_{14}$, $R_{15}$, $R_{16}$, and $R_{17}$ is $S(O)_2$, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, and $R_{16}$ are S, none, one, two, three, four, or five of $R_{12}$, $R_{13}$, $R_{14}$, $R_{15}$, and $R_{16}$ is $S(O)_2$, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, and $R_{16}$ are S, none, one, two, three, or four of $R_{12}$, $R_{13}$, $R_{14}$, $R_{15}$, and $R_{16}$ is $S(O)_2$, and the others are C. Independently in some embodiments of Formula IX, and independently in combination with any embodiments of any other relevant substituent classes, none, one, two, or three of $R_{12}$, $R_{13}$, $R_{14}$, $R_{15}$, and $R_{16}$ are S, none, one, two, or three of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, none, one or two of $R_{12}$, $R_{13}$, $R_{14}$, $R_{15}$, and $R_{16}$ are S, none, one or two of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, none or one of $R_{12}$, $R_{13}$, $R_{14}$, $R_{15}$, and $R_{16}$ is S, none or one of $R_{12}$, $R_{13}$, $R_{14}$, $R_{15}$, and $R_{16}$ are $S(O)_2$, and the others are C.

Independently in some embodiments of Formula VI, and independently in combination with any embodiments of any other relevant substituent classes, one, two, three, four, or five of $R_{12}$, $R_{13}$, $R_{14}$, $R_{15}$, $R_{16}$, and $R_{17}$ are S, one of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, one, two, three, or four of $R_{12}$, $R_{13}$, $R_{14}$, $R_{15}$, $R_{16}$, and $R_{17}$ are S, one or two of $R_{12}$, $R_{13}$, $R_{14}$, $R_{15}$, $R_{16}$, and $R_{17}$ are $S(O)_2$, and the others are C. Independently in some embodiments of Formula VI, and independently in combination with any embodiments of any other relevant substituent classes, one, two, or three of $R_{12}$, $R_{13}$, $R_{14}$, $R_{15}$, $R_{16}$, and $R_{17}$ are S, one, two, or three of $R_{12}$, $R_{13}$, $R_{14}$, $R_{15}$, $R_{16}$, and $R_{17}$ are $S(O)_2$, and the others are C. Independently in some embodiments of Formula VI, and independently in combination with any embodiments of any other relevant substituent classes, one or two of $R_{12}$, $R_{13}$, $R_{14}$, $R_{15}$, $R_{16}$, and $R_{17}$ are S, one, two, three, or four of $R_{12}$, $R_{13}$, $R_{14}$, $R_{15}$, $R_{16}$, and $R_{17}$ are $S(O)_2$, and the others are C. Independently in some embodiments of Formula VI, and independently in combination with any embodiments of any other relevant substituent classes, one of $R_{12}$, $R_{13}$, $R_{14}$, $R_{15}$, $R_{16}$, and $R_{17}$ is S, one, two, three, four, or five of $R_{12}$, $R_{13}$, $R_{14}$, $R_{15}$, $R_{16}$, and $R_{17}$ are $S(O)_2$, and the others are C.

Independently in some embodiments of Formula IX, and independently in combination with any embodiments of any other relevant substituent classes, one, two, three, or four of $R_{12}$, $R_{13}$, $R_{14}$, $R_{15}$, and $R_{16}$ are S, one of $R_{12}$, $R_{13}$, $R_{14}$, $R_{15}$, and $R_{16}$ is $S(O)_2$, and the others are C. Independently in some embodiments of Formula IX, and independently in combination with any embodiments of any other relevant substituent classes, one, two, or three of $R_{12}$, $R_{13}$, $R_{14}$, $R_{15}$, and $R_{16}$ are S, one or two of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, one or two of $R_{12}$, $R_{13}$, $R_{14}$, $R_{15}$, and $R_{16}$ are S, one, two, or three of $R_{12}$, $R_{13}$, $R_{14}$, $R_{15}$, and $R_{16}$ are $S(O)_2$, and the others are C. Independently in some embodiments of Formula IX, and independently in combination with any embodiments of any other relevant substituent classes, one of $R_{12}$, $R_{13}$, $R_{14}$, $R_{15}$, and $R_{16}$ is S, one, two, three, or four of $R_{12}$, $R_{13}$, $R_{14}$, $R_{15}$, and $R_{16}$ are $S(O)_2$, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are N, none, one, two, three, four, five, or six of $R_{12}$, $R_{13}$, $R_{14}$, $R_{15}$, $R_{16}$, and $R_{17}$ are S, none, one, two, three, four, five, or six of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are N, none, one, two, three, four, or five of $R_{12}$, $R_{13}$, $R_{14}$, $R_{15}$, $R_{16}$, and $R_{17}$ are S, none, one, two, three, four, or five of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are N, none, one, two, three, or four of $R_{12}$, $R_{13}$, $R_{14}$, $R_{15}$, $R_{16}$, and $R_{17}$ are S, none, one, two, three, or four of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are N, none, one, two, or three of $R_{12}$, $R_{13}$, $R_{14}$, $R_{15}$, $R_{16}$, and $R_{17}$ are S, none, one, two, or three of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are N, none, one, or two of $R_{12}$, $R_{13}$, $R_{14}$, $R_{15}$, $R_{16}$, and $R_{17}$ are S, none, one, or two of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are N, none or one of $R_{12}$, $R_{13}$, $R_{14}$, $R_{15}$, $R_{16}$, and $R_{17}$ are S, none or one of $R_{12}$, $R_{13}$, $R_{14}$, $R_{15}$, $R_{16}$, and $R_{17}$ is O, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, or $R_{16}$ are N, none, one, two, three, four, or five of $R_{12}$, $R_{13}$, $R_{14}$, $R_{15}$, or $R_{16}$ are S, none, one, two, three, four, or five of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, or $R_{16}$ are N, none, one, two, three, or four of $R_{12}$, $R_{13}$, $R_{14}$, $R_{15}$, or $R_{16}$ are S, none, one, two, three, or four of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, two, or three of $R_{12}$, $R_{13}$, $R_{14}$, $R_{15}$, or $R_{16}$ are N, none, one, two, or three of $R_{12}$, $R_{13}$, $R_{14}$, $R_{15}$, or $R_{16}$ are S, none, one, two, or three of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, or two of $R_{12}$, $R_{13}$, $R_{14}$, $R_{15}$, or $R_{16}$ are N, none, one, or two of $R_{12}$, $R_{13}$, $R_{14}$, $R_{15}$, or $R_{16}$ are S, none, one, or two of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none or one of $R_{12}$, $R_{13}$, $R_{14}$, $R_{15}$, or $R_{16}$ are N, none or one of $R_{12}$, $R_{13}$, $R_{14}$, $R_{15}$, or $R_{16}$ are S, none or one of $R_{12}$, $R_{13}$, $R_{14}$, $R_{15}$, or $R_{16}$ is O, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are N, none, one, two, three, four, five, or six of $R_{12}$, $R_{13}$, $R_{14}$, $R_{15}$, $R_{16}$, and $R_{17}$ are $S(O)_2$, none, one, two, three, four, five, or six of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are N, none, one, two, three, four, or five of $R_{12}$, $R_{13}$, $R_{14}$, $R_{15}$, $R_{16}$, and $R_{17}$ are $S(O)_2$, none, one, two, three, four, or five of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are N, none, one, two, three, or four of $R_{12}$, $R_{13}$, $R_{14}$, $R_{15}$, $R_{16}$, and $R_{17}$ are $S(O)_2$, none, one, two, three, or four of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are N, none, one, two, or three of $R_{12}$, $R_{13}$, $R_{14}$, $R_{15}$, $R_{16}$, and $R_{17}$ are $S(O)_2$, none, one, two, or three of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are N, none, one, or two of $R_{12}$, $R_{13}$, $R_{14}$, $R_{15}$, $R_{16}$, and $R_{17}$ are $S(O)_2$, none, one, or two of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are N, none or one of $R_{12}$, $R_{13}$, $R_{14}$, $R_{15}$, $R_{16}$, and $R_{17}$ are $S(O)_2$, none or one of $R_{12}$, $R_{13}$, $R_{14}$, $R_{15}$, $R_{16}$, and $R_{17}$ is O, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, or $R_{16}$ are N, none, one, two, three, four, or five of $R_{12}$, $R_{13}$, $R_{14}$, $R_{15}$, or $R_{16}$ are $S(O)_2$, none, one, two, three, four, or five of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, or $R_{16}$ are N, none, one, two, three, or four of $R_{12}$, $R_{13}$, $R_{14}$, $R_{15}$, or $R_{16}$ are $S(O)_2$, none, one, two, three, or four of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, two, or three of $R_{12}$, $R_{13}$, $R_{14}$, $R_{15}$, or $R_{16}$ are N, none, one, two, or three of $R_{12}$, $R_{13}$, $R_{14}$, $R_{15}$, or $R_{16}$ are $S(O)_2$, none, one, two, or three of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, or two of $R_{12}$, $R_{13}$, $R_{14}$, $R_{15}$, or $R_{16}$ are N, none, one, or two of $R_{12}$, $R_{13}$, $R_{14}$, $R_{15}$, or $R_{16}$ are $S(O)_2$, none, one, or two of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none or one of $R_{12}$, $R_{13}$, $R_{14}$, $R_{15}$, or $R_{16}$ are N, none or one of $R_{12}$, $R_{13}$, $R_{14}$, $R_{15}$, or $R_{16}$ are $S(O)_2$, none or one of $R_{12}$, $R_{13}$, $R_{14}$, $R_{15}$, or $R_{16}$ is O, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are N, none, one, two, three, four, five, or six of $R_{12}$, $R_{13}$, $R_{14}$, $R_{15}$, $R_{16}$, and $R_{17}$ are S, none, one, two, three, four, five, or six of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are N, none, one, two, three, four, or five of $R_{12}$, $R_{13}$, $R_{14}$, $R_{15}$, $R_{16}$, and $R_{17}$ are S, none, one, two, three, four, or five of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are N, none, one, two, three, or four of $R_{12}$, $R_{13}$, $R_{14}$, $R_{15}$, $R_{16}$, and $R_{17}$ are S, none, one, two, three, or four of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are N, none, one, two, or three of $R_{12}$, $R_{13}$, $R_{14}$, $R_{15}$, $R_{16}$, and $R_{17}$ are S, none, one, two, or three of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are N, none, one, or two of $R_{12}$, $R_{13}$, $R_{14}$, $R_{15}$, $R_{16}$, and $R_{17}$ are S, none, one, or two of $R_{12}$, $R_{13}$, $R_{14}$, $R_{15}$, $R_{16}$, and $R_{17}$ is $S(O)_2$, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are N, none or one of $R_{12}$, $R_{13}$, $R_{14}$, $R_{15}$, $R_{16}$, and $R_{17}$ are S, none or one of $R_{12}$, $R_{13}$, $R_{14}$, $R_{15}$, $R_{16}$, and $R_{17}$ is $S(O)_2$, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, or $R_{16}$ are N, none, one, two, three, four, or five of $R_{12}$, $R_{13}$, $R_{14}$, $R_{15}$, or $R_{16}$ are S, none, one, two, three, four, or five of $R_{12}$, $R_{13}$, $R_{14}$, $R_{15}$, or $R_{16}$ is $S(O)_2$, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, or $R_{16}$ are N, none, one, two, three, or four of $R_{12}$, $R_{13}$, $R_{14}$, $R_{15}$, or $R_{16}$ are S, none, one, two, three, or four of $R_{12}$, $R_{13}$, $R_{14}$, $R_{15}$, or $R_{16}$ is $S(O)_2$, and the others are C. Independently in some embodiments of Formula IX, and independently in combination with any embodiments of any other relevant substituent classes, none, one, two, or three of $R_{12}$, $R_{13}$, $R_{14}$, $R_{15}$, or $R_{16}$ are N, none, one, two, or three of $R_{12}$, $R_{13}$, $R_{14}$, $R_{15}$, or $R_{16}$ are S, none, one, two, or three of $R_{12}$, $R_{13}$, $R_{14}$, $R_{15}$, or $R_{16}$ is $S(O)_2$, and the others are C. Independently in some embodiments of Formula IX, and independently in combination with any embodiments of any other relevant substituent classes, none, one, or two of $R_{12}$, $R_{13}$, $R_{14}$, $R_{15}$, or $R_{16}$ are N, none, one, or two of $R_{12}$, $R_{13}$, $R_{14}$, $R_{15}$, or $R_{16}$ are S, none, one, or two of $R_{12}$, $R_{13}$, $R_{14}$, $R_{15}$, or $R_{16}$ is $S(O)_2$, and the others are C. Independently in some embodiments of Formula IX, and independently in combination with any embodiments of any other relevant substituent classes, none or one of $R_{12}$, $R_{13}$, $R_{14}$, $R_{15}$, or $R_{16}$ are N, none or one of $R_{12}$, $R_{13}$, $R_{14}$, $R_{15}$, or $R_{16}$ are S, none or one of $R_{12}$, $R_{13}$, $R_{14}$, $R_{15}$, or $R_{16}$ is $S(O)_2$, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are $S(O)_2$, none, one, two, three, four, five, or six of $R_{12}$, $R_{13}$, $R_{14}$, $R_{15}$, $R_{16}$, and $R_{17}$ are S, none, one, two, three, four, five, or six of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are $S(O)_2$, none, one, two, three, four, or five of $R_{12}$, $R_{13}$, $R_{14}$, $R_{15}$, $R_{16}$, and $R_{17}$ are S, none, one, two, three, four, or five of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are $S(O)_2$, none, one, two, three, or four of $R_{12}$, $R_{13}$, $R_{14}$, $R_{15}$, $R_{16}$, and $R_{17}$ are S, none, one, two, three, or four of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are $S(O)_2$, none, one, two, or three of $R_{12}$, $R_{13}$, $R_{14}$, $R_{15}$, $R_{16}$, and $R_{17}$ are S, none, one, two, or three of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are $S(O)_2$, none, one, or two of $R_{12}$, $R_{13}$, $R_{14}$, $R_{15}$, $R_{16}$, and $R_{17}$ are S, none, one, or two of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are $S(O)_2$, none or one of $R_{12}$, $R_{13}$, $R_{14}$, $R_{15}$, $R_{16}$, and $R_{17}$ are S, none or one of $R_{12}$, $R_{13}$, $R_{14}$, $R_{15}$, $R_{16}$, and $R_{17}$ is O, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, or $R_{16}$ are $S(O)_2$, none, one, two, three, four, or five of $R_{12}$, $R_{13}$, $R_{14}$, $R_{15}$, or $R_{16}$ are S, none, one, two, three, four, or five of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, or $R_{16}$ are $S(O)_2$, none, one, two, three, or four of $R_{12}$, $R_{13}$, $R_{14}$, $R_{15}$, or $R_{16}$ are S, none, one, two, three, or four of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, two, or three of $R_{12}$, $R_{13}$, $R_{14}$, $R_{15}$, or $R_{16}$ are $S(O)_2$, none, one, two, or three of $R_{12}$, $R_{13}$, $R_{14}$, $R_{15}$, or $R_{16}$ are S, none, one, two, or three of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, or two of $R_{12}$, $R_{13}$, $R_{14}$, $R_{15}$, or $R_{16}$ are $S(O)_2$, none, one, or two of $R_{12}$, $R_{13}$, $R_{14}$, $R_{15}$, or $R_{16}$ are S, none, one, or two of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none or one of $R_{12}$, $R_{13}$, $R_{14}$, $R_{15}$, or $R_{16}$ are $S(O)_2$, none or one of $R_{12}$, $R_{13}$, $R_{14}$, $R_{15}$, or $R_{16}$ are S, none or one of $R_{12}$, $R_{13}$, $R_{14}$, $R_{15}$, or $R_{16}$ is O, and the others are C.

Independently in some embodiments of Formula VI, and independently in combination with any embodiments of any other relevant substituent classes, none, one, two, three, four, five, or six of $R_{12}$, $R_{13}$, $R_{14}$, $R_{15}$, $R_{16}$, and $R_{17}$ are N, none, one, two, three, four, five, or six of $R_{12}$, $R_{13}$, $R_{14}$, $R_{15}$, $R_{16}$, and $R_{17}$ are S, none, one, two, three, four, five, or six of $R_{12}$, $R_{13}$, $R_{14}$, $R_{15}$, $R_{16}$, and $R_{17}$ are $S(O)_2$, none, one, two, three, four, five, or six of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, four, or five of $R_{12}$, $R_{13}$, $R_{14}$, $R_{15}$, $R_{16}$, and $R_{17}$ are N, none, one, two, three, four, or five of $R_{12}$, $R_{13}$, $R_{14}$, $R_{15}$, $R_{16}$, and $R_{17}$ are S, none, one, two, three, four, or five of $R_{12}$, $R_{13}$, $R_{14}$, $R_{15}$, $R_{16}$, and $R_{17}$ are $S(O)_2$, none, one, two, three, four, or five of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, three, or four of $R_{12}$, $R_{13}$, $R_{14}$, $R_{15}$, $R_{16}$, and $R_{17}$ are N, none, one, two, three, or four of $R_{12}$, $R_{13}$, $R_{14}$, $R_{15}$, $R_{16}$, and $R_{17}$ are S, none, one, two, three, or four of $R_{12}$, $R_{13}$, $R_{14}$, $R_{15}$, $R_{16}$, and $R_{17}$ are $S(O)_2$, none, one, two, three, or four of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, two, or three of $R_{12}$, $R_{13}$, $R_{14}$, $R_{15}$, $R_{16}$, and $R_{17}$ are N, none, one, two, or three of $R_{12}$, $R_{13}$, $R_{14}$, $R_{15}$, $R_{16}$, and $R_{17}$ are S, none, one, two, or three of $R_{12}$, $R_{13}$, $R_{14}$, $R_{15}$, $R_{16}$, and $R_{17}$ are $S(O)_2$, none, one, two, or three of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none, one, or two of $R_{12}$, $R_{13}$, $R_{14}$, $R_{15}$, $R_{16}$, and $R_{17}$ are N, none, one, or two of $R_{12}$, $R_{13}$, $R_{14}$, $R_{15}$, $R_{16}$, and $R_{17}$ are S, none, one, or two of $R_{12}$, $R_{13}$, $R_{14}$, $R_{15}$, $R_{16}$, and $R_{17}$ are $S(O)_2$, none, one, or two of $R_{12}$, $R_{13}$, $R_{14}$, $R_{15}$, $R_{16}$, and $R_{17}$ is O, and the others are C. Independently in some embodiments of Formula VI, and independently in combination with any embodiments of any other relevant substituent classes, none or one of $R_{12}$, $R_{13}$, $R_{14}$, $R_{15}$, $R_{16}$, and $R_{17}$ are N, none or one of $R_{12}$, $R_{13}$, $R_{14}$, $R_{15}$, $R_{16}$, and $R_{17}$ are S, none or one of $R_{12}$, $R_{13}$, $R_{14}$, $R_{15}$, $R_{16}$, and $R_{17}$ are $S(O)_2$, none or one of $R_{12}$, $R_{13}$, $R_{14}$, $R_{15}$, $R_{16}$, and $R_{17}$ is O, and the others are C.

Independently in some embodiments of Formula IX, and independently in combination with any embodiments of any other relevant substituent classes, none, one, two, three, four, or five of $R_{12}$, $R_{13}$, $R_{14}$, $R_{15}$, or $R_{16}$ are N, none, one, two, three, four, or five of $R_{12}$, $R_{13}$, $R_{14}$, $R_{15}$, or $R_{16}$ are S, none, one, two, three, four, or five of $R_{12}$, $R_{13}$, $R_{14}$, $R_{15}$, or $R_{16}$ are $S(O)_2$, none, one, two, three, four, or five of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, two, three, or four of $R_{12}$, $R_{13}$, $R_{14}$, $R_{15}$, or $R_{16}$ are N, none, one, two, three, or four of $R_{12}$, $R_{13}$, $R_{14}$, $R_{15}$, or $R_{16}$ are S, none, one, two, three, or four of $R_{12}$, $R_{13}$, $R_{14}$, $R_{15}$, or $R_{16}$ are $S(O)_2$, none, one, two, three, or four of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, two, or three of $R_{12}$, $R_{13}$, $R_{14}$, $R_{15}$, or $R_{16}$ are N, none, one, two, or three of $R_{12}$, $R_{13}$, $R_{14}$, $R_{15}$, or $R_{16}$ are S, none, one, two, or three of $R_{12}$, $R_{13}$, $R_{14}$, $R_{15}$, or $R_{16}$ are $S(O)_2$, none, one, two, or three of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none, one, or two of $R_{12}$, $R_{13}$, $R_{14}$, $R_{15}$, or $R_{16}$ are N, none, one, or two of $R_{12}$, $R_{13}$, $R_{14}$, $R_{15}$, or $R_{16}$ are S, none, one, or two of $R_{12}$, $R_{13}$, $R_{14}$, $R_{15}$, or $R_{16}$ are $S(O)_2$, none, one, or two of $R_{12}$, $R_{13}$, $R_{14}$, $R_{15}$, or $R_{16}$ is O, and the others are C. Independently in some embodiments of Formula IX, and independently in combination with any embodiments of any other relevant substituent classes, none or one of $R_{12}$, $R_{13}$, $R_{14}$, $R_{15}$, or $R_{16}$ are N, none or one of $R_{12}$, $R_{13}$, $R_{14}$, $R_{15}$, or $R_{16}$ are S, none or one of $R_{12}$, $R_{13}$, $R_{14}$, $R_{15}$, or $R_{16}$ are $S(O)_2$, none or one of $R_{12}$, $R_{13}$, $R_{14}$, $R_{15}$, or $R_{16}$ is O, and the others are C.

In some embodiments, $R_4$ and $R_5$ are independently hydrogen, alkyl, alkoxy, amino, alkylamino, dialkylamino, hydroxy, alkenyl, alkynyl, substituted alkyl, substituted alkenyl, substituted alkynyl, carbonyl, substituted carbonyl, carbinol,

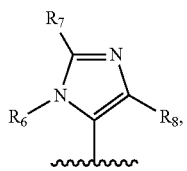

Formula IV

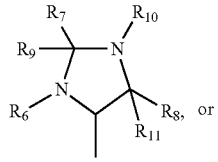

Formula V

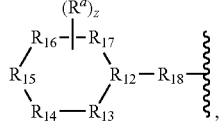

Formula VI wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$);

wherein $R_6$, $R_9$, $R_{10}$, and $R_{11}$ are independently present or absent according to valency, and wherein the ring bonds are double or single according to valency;

wherein z is an integer from 0-11; wherein $R^d$ is independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ is independently —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —$S(O)_2$—, or $NR_{20}$, wherein each $R_{19}$ is, as valency permits, independently absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of $R_{18}$, and independently in combination with any embodiments of any other relevant substituent classes, $R_{18}$ can be

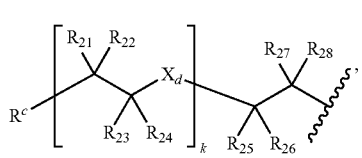

Formula VIII wherein k is an integer from 0 to 20;
wherein $X_d$ are absent or 0;
wherein $R^c$ is $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R_{18}$, and independently in combination with any embodiments of any other relevant substituent classes, $R_{18}$ can be

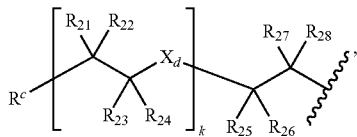

Formula VIII wherein k is an integer from 1 to 20;
wherein $X_d$ are O;
wherein $R^c$ is $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R_{18}$, and independently in combination with any embodiments of any other relevant substituent classes, $R_{18}$ can be

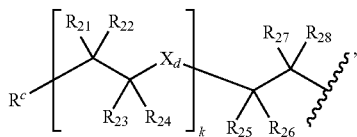

Formula VIII wherein k is an integer from 1 to 20;
wherein $X_d$ are absent;
wherein $R^c$ is $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $R_{18}$, and independently in combination with any embodiments of any other relevant substituent classes, $R_{18}$ can be absent or $-(CR_{19}R_{19})_p-$, wherein p is 1.

Independently in some embodiments of -A-B(—C)$_\delta$, —B(—C)$_\delta$, —B, C, $R_3$, $R_4$, $R_5$, $R^a$, $R^b$, $R^c$, $R^d$, and $R^e$, and independently in combination with any embodiments of any other relevant substituent classes, -A-B(—C)$_\delta$, —B(—C)$_\delta$, —B, C, $R_3$, $R_4$, $R_5$, $R^a$, $R^b$, $R^c$, $R^d$, and $R^e$ can be, independently, an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R^b$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of -A-B(—C)$_\delta$, —B(—C)$_\delta$, A, B, C, $R_3$, $R_4$, $R_5$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_3$, $R_4$, $R_5$, $R^a$, $R^b$, $R^c$, $R^d$, and $R^e$ can be, independently, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of -A-B(—C)$_\delta$, —B(—C)$_\delta$, A, B, C, $R_3$, $R_4$, $R_5$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_3$, $R_4$, $R_5$, $R^a$, $R^b$, $R^c$, $R^d$, and $R^e$ can be, independently, amino, hydroxyl, thiol, oxo, phosphate, or $J_1$.

Independently in some embodiments of -A-B(—C)$_\delta$, —B(—C)$_\delta$, A, B, C, $R_3$, $R_4$, $R_5$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_3$, $R_4$, $R_5$, $R^a$, $R^b$, $R^c$, $R^d$, and $R^e$ can be, independently, amino, hydroxyl, thiol, oxo, phosphate, or $J_2$.

Independently in some embodiments of -A-B(—C)$_\delta$, —B(—C)$_\delta$, A, B, C, $R_3$, $R_4$, $R_5$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_3$, $R_4$, $R_5$, $R^a$, $R^b$, $R^c$, $R^d$, and $R^e$ can be, independently,

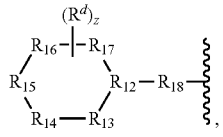

Formula VI

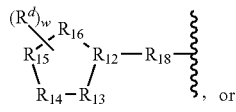

Formula IX

, or

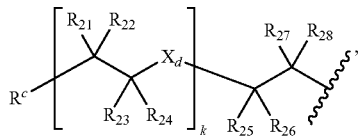

Formula VIII wherein z is an integer from 0-11; wherein w is an integer from 0-9; wherein k is an integer from 0 to 20;
wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $X_d$ are independently absent, O, or S;
wherein $R^e$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$);

wherein $R_{12}$, $R_{13}$, $R_{14}$, $R_{15}$, $R_{16}$, and $R_{17}$ are independently C, O, N, S, S(O), or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of $-A-B(-C)_\delta$, $-B(-C)_\delta$, A, B, C, $R_3$, $R_4$, $R_5$, $R^a$, $R^b$, $R^c$, $R^d$, and $R^e$, and independently in combination with any embodiments of any other relevant substituent classes, $-A-B(-C)_\delta$, $-B(-C)_\delta$, A, B, C, $R_3$, $R_4$, $R_5$, $R^a$, $R^b$, $R^c$, $R^d$, and $R^e$ can be, independently,

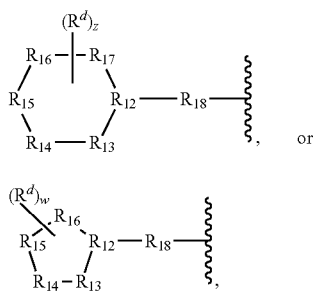

Formula VI or

Formula IX wherein z is an integer from 0-11; wherein w is an integer from 0-9;

wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, $R_{16}$, and $R_{17}$ are independently C, O, N, S, S(O), or $S(O)_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of $-A-B(-C)_\delta$, $-B(-C)_\delta$, A, B, C, $R_3$, $R_4$, $R_5$, $R^a$, $R^b$, $R^c$, $R^d$, and $R^e$, and independently in combination with any embodiments of any other relevant substituent classes, $-A-B(-C)_\delta$, $-B(-C)_\delta$, A, B, C, $R_3$, $R_4$, $R_5$, $R^a$, $R^b$, $R^c$, $R^d$, and $R^e$ can be, independently,

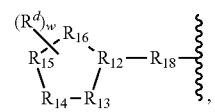

Formula IX wherein w is an integer from 0-9;

wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C, O, N, S, S(O), or $S(O)_2$, wherein the bonds between adjacent $R_{12}$ to $R_{16}$ are double or single according to valency, and wherein $R_{12}$ to $R_{16}$ are bound to none, one, or two hydrogens according to valency; and wherein $R_{18}$ are independently absent, $-(CR_{19}R_{19})_p-$ or $-(CR_{19}R_{19})_p-X_b-(CR_{19}R_{19})_q-$, wherein p and q are independently integers from 0 to 5, wherein $X_b$ is absent, $-O-$, $-S-$, $-S(O)-$, $-S(O)_2-$, or $NR_{20}$, wherein each $R_{19}$ is, as valency permits, independently absent, hydrogen, $=O$, $=S$, $-OH$, $-SH$, or $-NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of $-A-B(-C)_\delta$, $-B(-C)_\delta$, A, B, C, $R_3$, $R_4$, $R_5$, $R^a$, $R^b$, $R^c$, $R^d$, and $R^e$, and independently in combination with any embodiments of any other relevant substituent classes, $-A-B(-C)_\delta$, $-B(-C)_\delta$, A, B, C, $R_3$, $R_4$, $R_5$, $R^a$, $R^b$, $R^c$, $R^d$, and $R^e$ can be, independently,

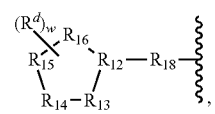

Formula IX wherein w is an integer from 0-9;

wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and wherein $R_{18}$ are independently absent, —$(CR_{19}R_{19})_p$— or —$(CR_{19}R_{19})_p$—$X_b$—$(CR_{19}R_{19})_q$—, wherein p and q are independently integers from 0 to 5, wherein $X_b$ is absent, —O—, —S—, —S(O)—, —S(O)$_2$—, or $NR_{20}$, wherein each $R_{19}$ is, as valency permits, independently absent, hydrogen, =O, =S, —OH, —SH, or —$NR_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Independently in some embodiments of -A-B(—C)$_\delta$, —B(—C)$_\delta$, A, B, C, $R_3$, $R_4$, $R_5$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_3$, $R_4$, $R_5$, $R^a$, $R^b$, $R^c$, $R^d$, and $R^e$ can be, independently,

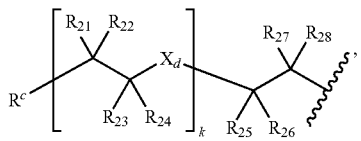

Formula VIII wherein k is an integer from 0 to 20;
wherein $X_d$ are independently absent, O, or S;
wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of -A-B(—C)$_\delta$, —B(—C)$_\delta$, A, B, C, $R_3$, $R_4$, $R_5$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_3$, $R_4$, $R_5$, $R^a$, $R^b$, $R^c$, $R^d$, and $R^e$ can be, independently,

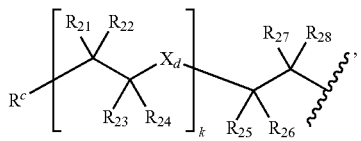

Formula VIII wherein k is an integer from 0 to 20;
wherein $X_d$ are independently O or S;
wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Independently in some embodiments of -A-B(—C)$_\delta$, —B(—C)$_\delta$, A, B, C, $R_3$, $R_4$, $R_5$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_3$, $R_4$, $R_5$, $R^a$, $R^b$, $R^c$, $R^d$, and $R^e$ can be, independently,

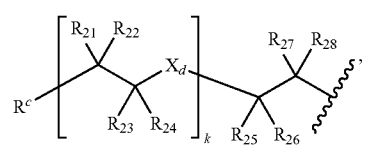

Formula VIII wherein k is an integer from 1 to 20;
wherein $X_d$ are O;
wherein $R^c$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, $R_4$, $R_5$, or both are not hydrogen. In some embodiments, neither $R_4$ nor $R_5$ is hydrogen. In some embodiments, either $R_4$ or $R_5$ is hydrogen. In some embodiments, $R_4$ and $R_5$ both hydrogen.

In some embodiments, the compounds are represented by Formula I
wherein X is oxygen, sulfur, or $NR_2$,
$R_1$ is, independently in one or more sites of chemical modification,

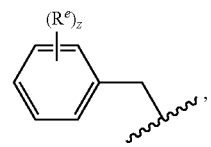

Formula VII

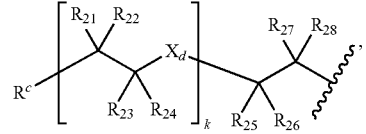

Formula VIII

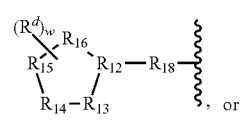

Formula IX

, or

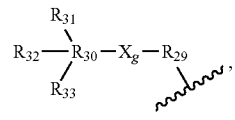

Formula X wherein k is an integer from 1 to 10; wherein w is an integer from 0-4; wherein $X_d$ are independently absent, O or S;
wherein $R_{21}$, $R_{22}$, $R_{23}$, $R_{24}$, $R_{25}$, $R_{26}$, $R_{27}$, $R_{28}$, $R_{31}$, $R_{32}$, and $R_{33}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$);
wherein $R_{30}$ is C or Si;

wherein $X_g$ and $R_{29}$ are independently $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$); and wherein $R^e$ and $R^c$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic, heterocyclic ring or

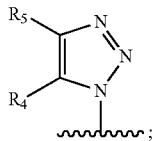

Formula III wherein $R_4$, $R_5$, or both are, independently, hydrogen, alkyl, substituted alkyl, alkoxy, amino, alkylamino, dialkylamino, hydroxy, alkenyl, alkynyl, substituted alkyl, substituted alkenyl, substituted alkynyl, carbonyl, substituted carbonyl, carbinol,

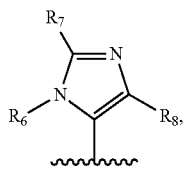

Formula IV

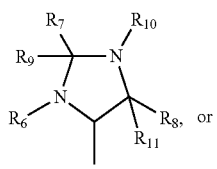

Formula V

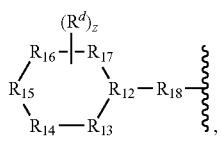

Formula VI wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$);

wherein $R_6$, $R_9$, $R_{10}$, and $R_{11}$ are independently present or absent according to valency, and wherein the ring bonds are double or single according to valency;

wherein in $R_4$ or $R_5$;

z is an integer from 0-11;

$R^d$ is independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

$R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and $R_{18}$ is independently —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein X$_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$);

wherein $R_4$, $R_5$, or both are not hydrogen; wherein at least one $R^b$ or $R^c$ is defined by Formula III.

In some embodiments, z in Formula VI is an integer from 0-3; $R^d$ is independently amino, hydroxyl, thiol, oxo, phosphate, or substituted or unsubstituted $C_1$-$C_6$ alkyl, $C_1$-$C_6$ alkoxy, $C_1$-$C_6$ alkylamino, or $C_1$-$C_6$ alkylthio;

where $R_{12}$, $R_{13}$, $R_{14}$, $R_{15}$, $R_{16}$, and $R_{17}$ are independently C, O, N, S, S(O), or S(O)$_2$, where the bonds between adjacent $R_{12}$ to $R_{17}$ are double or single according to valency, and where $R_{18}$ to $R_{23}$ are bound to none, one, or two hydrogens according to valency; and where $R_{18}$ is independently —(CR$_{19}$R$_{19}$)$_p$— or —(CR$_{19}$R$_{19}$)$_p$—X$_b$—(CR$_{19}$R$_{19}$)$_q$—, where p and q are independently integers from 0 to 3, where X$_b$ is absent, —O—, —S—, —S(O)—, —S(O)$_2$—, or NR$_{20}$, where each $R_{19}$ is, as valency permits, independently absent, hydrogen, =O, =S, —OH, —SH, or —NR$_{20}$, where $R_{20}$ is substituted or unsubstituted $C_1$-$C_6$ alkyl, $C_1$-$C_6$ alkoxy, $C_1$-$C_6$ alkylamino, or $C_1$-$C_6$ alkylthio.

In some embodiments, z in Formula VI is 2, $R_{12}$ is N, $R_{13}$, $R_{14}$, $R_{15}$, $R_{16}$, or $R_{17}$ is S, both $R^d$ are oxo and are bonded to the S, and all of the bonds between adjacent $R_{12}$ to $R_{17}$ are single.

In some embodiments, z in Formula VI is 2, both $R^d$ are oxo and are bonded to $R_{15}$, $R_{12}$ is N, $R_{15}$ is S, and all of the bonds between adjacent $R_{12}$ to $R_{17}$ are single.

In some embodiments, z in Formula VI is 2, both $R^d$ are oxo and are bonded to $R_{15}$, $R_{12}$ is N, $R_{15}$ is S, and all of the bonds between adjacent $R_{12}$ to $R_{17}$ are single, $X_b$ is absent, q is 0, p is 1, and each $R_{19}$ is hydrogen.

In some embodiments, z in Formula VI is 1, $R^d$ is amino, and three of the bonds between adjacent $R_{12}$ to $R_{17}$ are double and three of the bonds between adjacent $R_{12}$ to $R_{17}$ are single.

In some embodiments, z in Formula VI is 1, $R^d$ is amino and is bonded to $R_{15}$, and three of the bonds between adjacent $R_{12}$ to $R_{17}$ are double and three of the bonds between adjacent $R_{12}$ to $R_{17}$ are single.

In some embodiments, z in Formula VI is 1, $R^d$ is amino and is bonded to $R_{15}$, and three of the bonds between adjacent $R_{12}$ to $R_{17}$ are double and three of the bonds between adjacent $R_{12}$ to $R_{17}$ are single, $X_b$ is absent, p is 0 and q is 0.

In some embodiments, z in Formula VI is 0, $R_{13}$, $R_{14}$, $R_{15}$, $R_{16}$, or $R_{17}$ is O, and all of the bonds between adjacent $R_{12}$ to $R_{17}$ are single.

In some embodiments, z in Formula VI is 0, $R_{13}$ is O, and all of the bonds between adjacent $R_{12}$ to $R_{17}$ are single.

In some embodiments, z in Formula VI is 0, $R_{13}$ is O, all of the bonds between adjacent $R_{12}$ to $R_{17}$ are single, $X_b$ is oxygen, p is 1, q is 0 and each $R_{19}$ is hydrogen.

In some embodiments, $R_{13}$ and $R_{17}$ of Formula VI are O and all of the bonds between adjacent $R_{12}$ to $R_{17}$ are single.

In some embodiments, z in Formula VI is 1, $R^d$ is alkoxy and is bonded to $R_{13}$, $R_{14}$, $R_{15}$, $R_{16}$, or $R_{17}$, three of the bonds between adjacent $R_{12}$ to $R_{17}$ are double and three of the bonds between adjacent $R_{12}$ to $R_{17}$ are single.

In some embodiments, z in Formula VI is 1, $R^d$ is alkoxy and is bonded to $R_{13}$, three of the bonds between adjacent $R_{12}$ to $R_{17}$ are double and three of the bonds between adjacent $R_{12}$ to $R_{17}$ are single.

In some embodiments, z in Formula VI is 1, $R^d$ is methoxy, and is bonded to $R_{13}$, $R_{12}$ to $R_{17}$ are carbon atoms, three of the bonds between adjacent $R_{12}$ to $R_{17}$ are double and three of the bonds between adjacent $R_{12}$ to $R_{17}$ are single, $X_b$ is absent, p is 0 and q is 0.

In some embodiments, z in Formula VII is 1, $R^e$ is hydroxyl.

In some embodiments, z in Formula VII is 1 and $R^e$ is hydroxyl bonded at the position para- to the methylene group.

In some embodiments, z in Formula VII is 1, $R^e$ is Formula III shown below:

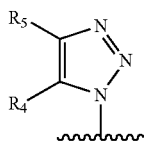

Formula III wherein $R_4$ is a substituted alkyl and $R_5$ is a dialkylamino, or $R_4$ is a dialkylamino and $R_5$ is a substituted alkyl, wherein the substituted alkyl is hydroxymethyl and the dialkylamino is N,N-diethylamino.

In some embodiments, z in Formula VII is 1, $R^e$ is Formula III, wherein $R_4$ is hydrogen and $R_5$ is Formula VI shown below:

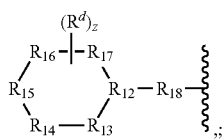

Formula VI or $R_4$ is Formula VI and $R_5$ is hydrogen. In some embodiments, z in Formula VI is 0, $R_{13}$, $R_{15}$, $R_{15}$, $R_{16}$, or $R_{17}$ is O, and all of the bonds between adjacent $R_{12}$ to $R_{17}$ are single. In some embodiments, z in Formula VI is 0, $R_{13}$ is O, and all of the bonds between adjacent $R_{12}$ to $R_{17}$ are single. In some embodiments, z in Formula VI is 0, $R_{13}$ is O, all of the bonds between adjacent $R_{12}$ to $R_{17}$ are single, $X_b$ is oxygen, p is 1, q is 0 and each $R_{19}$ is hydrogen.

In some embodiments, z in Formula VI is 1, $R^e$ is Formula III, wherein $R_4$ is hydrogen and $R_5$ is Formula IV or Formula V shown below:

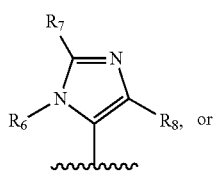

Formula IV

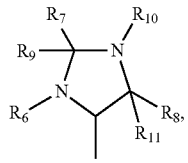

Formula V wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In some embodiments $R_6$ of Formula IV is alkyl. In some embodiments, $R_6$ is methyl.

In some embodiments $R_6$ of Formula IV is methyl, $R_7$ and $R_8$ are hydrogen.

In some embodiments, z in Formula VII is 1 and $R^e$ is hydroxyl bonded at the position para- to the methylene group.

In some embodiments of Formula VIII, k is 1 and $R^c$ is hydroxyl.

In some embodiments of Formula VIII, k is 1, $R^c$ is hydroxyl, and $X_d$ is absent.

In some embodiments of Formula VIII, k is 1, $R^c$ is hydroxyl, $X_d$ is absent, and $R_{21}$—$R_{28}$ are hydrogen.

In some embodiments of Formula VIII, $R^c$ is alkoxy.

In some embodiments of Formula VIII, $R^c$ is methoxy and $X_d$ is O.

In some embodiments of Formula VIII, $R^c$ is methoxy, $X_d$ is O, and $R_{21}$—$R_{28}$ are hydrogen.

In some embodiments of Formula VIII, k is 2 and $R^c$ is alkylamino.

In some embodiments of Formula VIII, k is 2, $R^c$ is methylamino, and $X_d$ is absent.

In some embodiments of Formula VIII, k is 2, $R^c$ is methylamino, $X_d$ is absent, and $R_{21}$—$R_{28}$ are hydrogen.

In some embodiments of Formula VIII, k is 3, $X_d$ is O and $R^c$ is Formula III shown below:

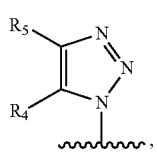

Formula III wherein $R_4$ and $R_5$ are alkyl.

In some embodiments of Formula VIII, k is 3, $X_d$ is O, and $R^c$ is Formula III, wherein $R_4$ and $R_5$ are methyl.

In some embodiments of Formula VIII, k is 3, $X_d$ is O and $R^c$ is Formula III, wherein $R_4$ is hydrogen, and $R_5$ is carbonyl, or $R_4$ is carbonyl, and $R_5$ is hydrogen.

In some embodiments of Formula VIII, k is 3, $X_d$ is O and $R^c$ is Formula III, wherein $R_4$ is hydrogen, and $R_5$ is acetyl, or $R_4$ is acetyl, and $R_5$ is hydrogen.

In some embodiments of Formula VIII, k is 3 and $R^c$ is Formula III, $R_4$ is hydrogen, and $R_5$ is Formula VI shown below:

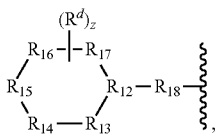

Formula VI or $R_4$ is hydrogen and $R_5$ is Formula VI.

In some embodiments of Formula VIII, k is 3 and $R^c$ is Formula III, wherein $R_4$ is hydrogen, and $R_5$ is Formula IX, or $R_5$ is hydrogen and $R_4$ is Formula VI, wherein z in Formula VI is 2, $R_{12}$ is N, $R_{13}$, $R_{14}$, $R_{15}$, $R_{16}$, or $R_{17}$ is S, both $R^d$ are oxo and are bonded to the S, and all of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 2, both $R^d$ are oxo and are bonded to $R_{15}$, $R_{12}$ is N, $R_{15}$ is S, and all of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 2, both $R^d$ are oxo and are bonded to $R_{15}$, $R_{12}$ is N, $R_{15}$ is S, and all of the bonds between adjacent $R_{12}$ to $R_{17}$ are single, $X_b$ is absent, q is 0, p is 1, and each $R_{19}$ is hydrogen.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 1, $R^d$ is amino, and three of the bonds between adjacent $R_{12}$ to $R_{17}$ are double and three of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 1, $R^d$ is amino and is bonded to $R_{15}$, and three of the bonds between adjacent $R_{12}$ to $R_{17}$ are double and three of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 1, $R^d$ is amino and is bonded to $R_{15}$, and three of the bonds between adjacent $R_{12}$ to $R_{17}$ are double and three of the bonds between adjacent $R_{12}$ to $R_{17}$ are single, $X_b$ is absent, p is 0 and q is 0.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein w in Formula IX is 0, $R_{13}$, $R_{14}$, $R_{15}$, or $R_{16}$ is O, and all of the bonds between adjacent $R_{12}$ to $R_{16}$ are single.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 0, $R_{13}$ is O, and all of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 0, $R_{13}$ is O, all of the bonds between adjacent $R_{12}$ to $R_{17}$ are single, $X_b$ is oxygen, p is 1, q is 0 and each $R_{19}$ is hydrogen.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 1, $R^d$ is alkoxy and is bonded to $R_{13}$, $R_{14}$, $R_{15}$, $R_{16}$, $R_{17}$, or $R_{18}$, three of the bonds between adjacent $R_{12}$ to $R_{17}$ are double and three of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 1, $R^d$ is alkoxy and is bonded to $R_{13}$, three of the bonds between adjacent $R_{12}$ to $R_{17}$ are double and three of the bonds between adjacent $R_{12}$ to $R_{17}$ are single.

In some embodiments of Formula VIII, k is 3 and $R^c$ is Formula III, wherein $R_4$ is hydrogen, and $R_5$ is Formula VI, or $R_5$ is hydrogen and $R_4$ is Formula VI, wherein z in Formula VI is 1, $R^d$ is alkoxy such as methoxy, and is bonded to $R_{13}$, $R_{12}$ to $R_{17}$ are carbon atoms, three of the bonds between adjacent $R_{12}$ to $R_{17}$ are double and three of the bonds between adjacent $R_{12}$ to $R_{17}$ are single, $X_b$ is absent, p is 0 and q is 0.

In some embodiments of Formula VIII, k is 3 and $R^c$ is Formula III, wherein $R_4$ is hydrogen, and $R_5$ is Formula IV or Formula V, or $R_5$ is hydrogen and $R_4$ is Formula IV or Formula V, wherein $R_6$ is alkyl.

In some embodiments of Formula VIII, k is 3 and $R^c$ is Formula III, wherein $R_4$ is hydrogen, and $R_5$ is Formula IV or Formula V, or $R_5$ is hydrogen and $R_4$ is Formula IV or Formula V, wherein $R_6$ is alkyl.

In some embodiments of Formula VIII, k is 3 and $R^c$ is Formula III, wherein $R_4$ is hydrogen, and $R_5$ is Formula IV, or $R_5$ is hydrogen and $R_4$ is Formula IV, wherein $R_6$ is an alkyl such as a methyl, $R_7$ and $R_8$ are hydrogen.

In some embodiments, w in Formula IX is 0, $R_{13}$, $R_{14}$, $R_{15}$, or $R_{16}$ is O, and, as valency permits, two of the bonds between adjacent $R_{12}$ to $R_{16}$ are double bonds, and three of the bonds between adjacent $R_{12}$ to $R_{16}$ are single bonds.

In some embodiments, w in Formula IX is 0, $R_{13}$ is O, $R_{12}$, $R_{14}$, $R_{15}$ and $R_{16}$ are C, the bonds between $R_{12}$ and $R_{16}$, and between $R_{14}$ and $R_{15}$, are double bonds, and the rest of the bonds in the ring are single bonds.

In some embodiments, w in Formula IX is 0, $R_{13}$ is O, $R_{12}$, $R_{14}$, $R_{15}$ and $R_{16}$ are C, the bonds between $R_{12}$ and $R_{16}$, and between $R_{15}$ and $R_{15}$, are double bonds, the rest of the bonds in the ring are single bonds, $R_{18}$ is —$(CR_{19}R_{19})_p$—$X_b$—$(CR_{19}R_{19})_q$—, $X_b$ is absent, p is 1, q is 0, and each $R_{19}$ is hydrogen.

In some embodiments, w in Formula IX is 0, $R_{13}$, $R_{14}$, $R_{15}$, or $R_{16}$ is O, and, the bonds between adjacent $R_{12}$ to $R_{16}$ are single bonds.

In some embodiments, w in Formula IX is 0, $R_{13}$ is O, $R_{12}$, $R_{14}$, $R_{15}$ and $R_{16}$ are C, and the bonds between adjacent $R_{12}$ to $R_{16}$ are single bonds.

In some embodiments, w in Formula IX is 0, $R_{13}$ is O, $R_{12}$, $R_{14}$, $R_{15}$ and $R_{16}$ are C, the bonds between adjacent $R_{12}$ to $R_{16}$ are single bonds, $R_{18}$ is —$(CR_{19}R_{19})_p$—$X_b$—$(CR_{19}R_{19})_q$—, $X_b$ is absent, p is 1, q is 0, and each $R_{19}$ is hydrogen.

In some embodiments, w in Formula IX is 0, $R_{13}$ and $R_{16}$ are O, and the bonds between adjacent $R_{12}$ to $R_{16}$ are single bonds.

In some embodiments, w in Formula IX is 0, $R_{13}$ and $R_{16}$ are O, $R_{12}$, $R_{15}$ and $R_{16}$ are C, the bonds between adjacent $R_{12}$ to $R_{16}$ are single bonds.

In some embodiments, w in Formula IX is 0, $R_{13}$ and $R_{16}$ are O, $R_{12}$, $R_{15}$ and $R_{16}$ are C, the bonds between adjacent $R_{12}$ to $R_{16}$ are single bonds, $R_{18}$ is —$(CR_{19}R_{19})_p$—$X_b$—$(CR_{19}R_{19})_q$—, $X_b$ is absent, p is 1, q is 0, and each $R_{19}$ is hydrogen.

In some embodiments $R_{30}$ of Formula X is Si, and $X_g$ is alkynyl.

In some embodiments $R_{30}$ of Formula X is Si, $X_g$ is ethynyl, and $R_{29}$ is alkylene.

In some embodiments $R_{30}$ of Formula X is Si, $X_g$ is ethynyl, $R_{29}$ is methylene, and $R_{31}$, $R_{32}$, and $R_{33}$ are alkyl.

In some embodiments $R_{30}$ of Formula X is Si, $X_g$ is ethynyl, $R_{29}$ is methylene, and $R_{31}$, $R_{32}$, and $R_{33}$ are methyl.

In preferred embodiments, the surface or a surface of the product described herein, is covalently modified.

In some embodiments the modified product is singularly modified. In specific embodiments, the singularly modified product contains one or more covalent modifications defined by Formula I, wherein $R_1$ includes an azide group, an alkyne group, or a 1,2,3-triazole ring.

In some embodiments, the surface or a surface of the product is modified with a compound that contains an azide group. The azide group is further reacted with a second molecule containing a terminal or internal alkyne. Upon reaction, the azide and the alkyne groups undergo an intramolecular 1,3-dipolar cycloaddition reaction forming a 1,2,3-triazole ring, coupling the second molecule to the modified surface.

In alternative embodiments, the surface or a surface of the product is modified with a compound that contains an alkyne group. The alkyne group is further reacted with a second molecule containing an azide group. Upon reaction, the azide and the alkyne groups undergo an intramolecular 1,3-dipolar cycloaddition reaction forming a 1,2,3-triazole ring, coupling the second molecule to the modified surface.

Examples of the azide-containing compounds include $X_c$—$R_w$—$N_3$, where $X_c$ is absent, —OH, —SH, or —NH$_2$ and $R_w$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

Alkynes for use as reagents in 1,3-dipolarcycloaddition reactions include alkynes having side groups corresponding to of the moieties described herein for any of the organic groups, R groups, and substituents. For example, the alkynes can have side groups corresponding to of the moieties described herein for $R_4$ and $R_5$.

In some embodiments, alkynes for use as reagents in 1,3-dipolarcycloaddition reactions can be

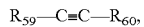
$R_{59}$—C≡C—$R_{60}$, Formula XIII wherein $R_{59}$ and $R_{60}$ are independently hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_{59}$ and $R_{60}$ organic groupings being those present in $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In some embodiments, $R_{59}$ and $R_{60}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In some embodiments, $R_{59}$ and $R_{60}$ are independently hydrogen, amino, hydroxyl, thiol, oxo, phosphate, or $J_1$.

In some embodiments, $R_{59}$ and $R_{60}$ are independently hydrogen, amino, hydroxyl, thiol, oxo, phosphate, or $J_2$.

In some embodiments, $R_{59}$ and $R_{60}$ are independently,

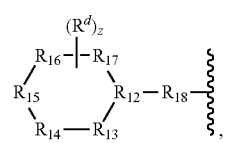

Formula VI

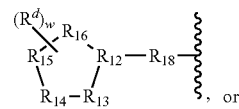

Formula IX

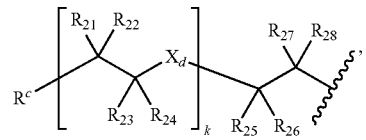

Formula VIII wherein z is an integer from 0-11; wherein w is an integer from 0-9; wherein k is an integer from 0 to 20;

wherein $R^d$ are independently absent, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;

wherein $X_d$ are independently absent, O, or S;

wherein $R^e$ is absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$);

wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein $R_{21}$, $R_{22}$, $R_{23}$, $R_{24}$, $R_{25}$, $R_{26}$, $R_{27}$, and $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, $R_{59}$ and $R_{60}$ are independently,

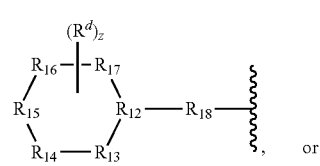

Formula VI or

-continued

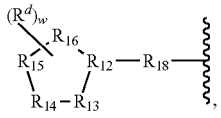
Formula IX wherein z is an integer from 0-11; wherein w is an integer from 0-9;
wherein $R^d$ are independently absent, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and
wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein X$_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).
In some embodiments, $R_{59}$ and $R_{60}$ are independently,

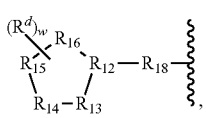
Formula IX wherein w is an integer from 0-9;
wherein $R^d$ are independently absent, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, and $R_{16}$ are independently C, O, N, S, S(O), or S(O)$_2$, wherein the bonds between adjacent $R_{12}$ to $R_{16}$ are double or single according to valency, and wherein $R_{12}$ to $R_{16}$ are bound to none, one, or two hydrogens according to valency; and
wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein X$_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In some embodiments, $R_{59}$ and $R_{60}$ are independently,

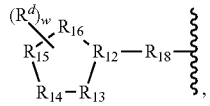
Formula IX wherein w is an integer from 0-9;
wherein $R^d$ are independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring;
wherein $R_{12}$, $R_{13}$, $R_{14}$, $R_{15}$, and $R_{16}$ are independently C or N, wherein the bonds between adjacent $R_{12}$ to $R_{16}$ are double or single according to valency, wherein one, two, three, or four of $R_{12}$, $R_{13}$, $R_{14}$, $R_{15}$, and $R_{16}$ are N and the others are C, and wherein $R_{12}$ to $R_{16}$ are bound to none, one, or two hydrogens according to valency; and
wherein $R_{18}$ are independently absent, —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein X$_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).
In some embodiments, $R_{59}$ and $R_{60}$ are independently,

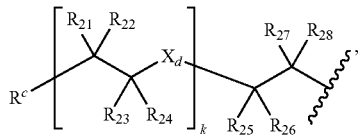
Formula VIII wherein k is an integer from 0 to 20;
wherein $X_d$ are independently absent, O, or S;
wherein $R^c$ is $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and
wherein $R_{21}$, $R_{22}$, $R_{23}$, $R_{24}$, $R_{25}$, $R_{26}$, $R_{27}$, and $R_{28}$ are independently $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).
In some embodiments, $R_{59}$ and $R_{60}$ are independently,

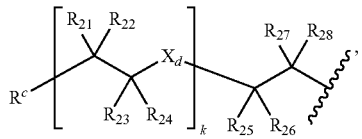
Formula VIII wherein k is an integer from 1 to 20;

wherein $X_d$ are independently O or S;

wherein $R^c$ is $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, $R_{59}$ and $R_{60}$ are independently,

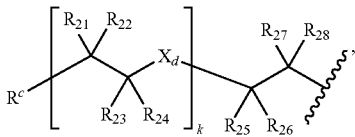

Formula VIII wherein k is an integer from 1 to 20;

wherein $X_d$ are O;

wherein $R^c$ is $R^b$, absent, hydrogen, $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); and wherein $R_{21}$, $R_{22}$, $R_{23}$, $R_{24}$, $R_{25}$, $R_{26}$, $R_{27}$, and $R_{28}$ are independently $R^b$, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments of $R_6$, $R_7$, $R_8$, $R_9$, $R_{10}$, $R_{11}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{59}$, $R_{60}$, $R^a$, $R^c$, $R^d$, $R^e$, $R_w$, $R_x$, $R_z$, $X_g$, -A-B(—C)$_\delta$, and —B(—C)$_\delta$, and independently in combination with any embodiments of any other relevant substituent classes, $R_6$, $R_7$, $R_8$, $R_9$, $R_{10}$, $R_{11}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{59}$, $R_{60}$, $R^a$, $R^c$, $R^d$, $R^e$, $R_w$, $R_x$, $R_z$, $X_g$, -A-B(—C)$_\delta$, and —B(—C)$_\delta$ can be, independently, absent, hydrogen, $U_1+Q_1+Q_2+Q_3$, $U_1+Q_5$, $U_1+Q_1+Q_5$, $U_1+Q_2+Q_5$, $U_1+Q_3+Q_5$, $U_1+Q_1+Q_2+Q_5$, $U_1+Q_1+Q_3+Q_5$, $U_1+Q_2+Q_3+Q_5$, or $U_1+Q_1+Q_2+Q_3+Q_5$.

In some embodiments of $R_6$, $R_7$, $R_8$, $R_9$, $R_{10}$, $R_{11}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{59}$, $R_{60}$, $R^a$, $R^c$, $R^d$, $R^e$, $R_w$, $R_x$, $R_z$, $X_g$, -A-B(—C)$_\delta$, and —B(—C)$_\delta$, and independently in combination with any embodiments of any other relevant substituent classes, $R_6$, $R_7$, $R_8$, $R_9$, $R_{10}$, $R_{11}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{59}$, $R_{60}$, $R^a$, $R^c$, $R^d$, $R^e$, $R_w$, $R_x$, $R_z$, $X_g$, -A-B(—C)$_\delta$, and —B(—C)$_\delta$ can be, independently, absent, hydrogen, $U_4$, $U_4+Q_1$, $U_4+Q_2$, $U_4+Q_3$, $U_4+Q_4$, $U_4+Q_5$, $U_4+Q_6$, $U_4+Q_7$, $U_4+Q_8$, $U_4+Q_1+Q_2$, $U_4+Q_1+Q_3$, $U_4+Q_1+Q_4$, $U_4+Q_1+Q_5$, $U_4+Q_1+Q_6$, $U_4+Q_1+Q_7$, $U_4+Q_1+Q_8$, $U_4+Q_2+Q_3$, $U_4+Q_2+Q_4$, $U_4+Q_2+Q_5$, $U_4+Q_2+Q_6$, $U_4+Q_2+Q_7$, $U_4+Q_2+Q_8$, $U_4+Q_3+Q_4$, $U_4+Q_3+Q_5$, $U_4+Q_3+Q_6$, $U_4+Q_3+Q_7$, $U_4+Q_3+Q_8$, $U_4+Q_4+Q_5$, $U_4+Q_4+Q_6$, $U_4+Q_4+Q_7$, $U_4+Q_4+Q_8$, $U_4+Q_5+Q_6$, $U_4+Q_5+Q_7$, $U_4+Q_5+Q_8$, $U_4+Q_6+Q_7$, $U_4+Q_6+Q_8$, $U_4+Q_7+Q_8$, $U_4+Q_1+Q_2+Q_3$, $U_4+Q_1+Q_2+Q_4$, $U_4+Q_1+Q_2+Q_5$, $U_4+Q_1+Q_2+Q_6$, $U_4+Q_1+Q_2+Q_7$, $U_4+Q_1+Q_2+Q_8$, $U_4+Q_1+Q_3+Q_4$, $U_4+Q_1+Q_3+Q_5$, $U_4+Q_1+Q_3+Q_6$, $U_4+Q_1+Q_3+Q_7$, $U_4+Q_1+Q_3+Q_8$, $U_4+Q_1+Q_4+Q_5$, $U_4+Q_1+Q_4+Q_6$, $U_4+Q_1+Q_4+Q_7$, $U_4+Q_1+Q_4+Q_8$, $U_4+Q_1+Q_5+Q_6$, $U_4+Q_1+Q_5+Q_7$, $U_4+Q_1+Q_5+Q_8$, $U_4+Q_1+Q_6+Q_7$, $U_4+Q_1+Q_6+Q_8$, $U_4+Q_1+Q_7+Q_8$, $U_4+Q_2+Q_3+Q_4$, $U_4+Q_2+Q_3+Q_5$, $U_4+Q_2+Q_3+Q_6$, $U_4+Q_2+Q_3+Q_7$, $U_4+Q_2+Q_3+Q_8$, $U_4+Q_2+Q_4+Q_5$, $U_4+Q_2+Q_4+Q_6$, $U_4+Q_2+Q_4+Q_7$, $U_4+Q_2+Q_4+Q_8$, $U_4+Q_2+Q_5+Q_6$, $U_4+Q_2+Q_5+Q_7$, $U_4+Q_2+Q_5+Q_8$, $U_4+Q_2+Q_6+Q_7$, $U_4+Q_2+Q_6+Q_8$, $U_4+Q_2+Q_7+Q_8$, $U_4+Q_3+Q_4+Q_5$, $U_4+Q_3+Q_4+Q_6$, $U_4+Q_3+Q_4+Q_7$, $U_4+Q_3+Q_4+Q_8$, $U_4+Q_3+Q_5+Q_6$, $U_4+Q_3+Q_5+Q_7$, $U_4+Q_3+Q_5+Q_8$, $U_4+Q_3+Q_6+Q_7$, $U_4+Q_3+Q_6+Q_8$, $U_4+Q_3+Q_7+Q_8$, $U_4+Q_4+Q_5+Q_6$, $U_4+Q_4+Q_5+Q_7$, $U_4+Q_4+Q_5+Q_8$, $U_4+Q_4+Q_6+Q_7$, $U_4+Q_4+Q_6+Q_8$, $U_4+Q_4+Q_7+Q_8$, $U_4+Q_5+Q_6+Q_7$, $U_4+Q_5+Q_6+Q_8$, $U_4+Q_5+Q_7+Q_8$, $U_4+Q_6+Q_7+Q_8$, $U_4+Q_1+Q_2+Q_3+Q_4$, $U_4+Q_1+Q_2+Q_3+Q_5$, $U_4+Q_1+Q_2+Q_3+Q_6$, $U_4+Q_1+Q_2+Q_3+Q_7$, $U_4+Q_1+Q_2+Q_3+Q_8$, $U_4+Q_1+Q_3+Q_4+Q_5$, $U_4+Q_1+Q_3+Q_4+Q_6$, $U_4+Q_1+Q_3+Q_4+Q_7$, $U_4+Q_1+Q_3+Q_4+Q_8$, $U_4+Q_1+Q_5+Q_6$, $U_4+Q_1+Q_5+Q_7$, $U_4+Q_1+Q_5+Q_8$, $U_4+Q_1+Q_5+Q_6+Q_7$, $U_4+Q_1+Q_5+Q_6+Q_8$, $U_4+Q_1+Q_6+Q_7+Q_8$, $U_4+Q_2+Q_3+Q_4+Q_5$, $U_4+Q_2+Q_3+Q_4+Q_6$, $U_4+Q_2+Q_3+Q_4+Q_7$, $U_4+Q_2+Q_3+Q_4+Q_8$, $U_4+Q_2+Q_4+Q_5+Q_6$, $U_4+Q_2+Q_4+Q_5+Q_7$, $U_4+Q_2+Q_4+Q_5+Q_8$, $U_4+Q_2+Q_5+Q_6+Q_7$, $U_4+Q_2+Q_5+Q_6+Q_8$, $U_4+Q_2+Q_6+Q_7+Q_8$, $U_4+Q_3+Q_4+Q_5+Q_6$, $U_4+Q_3+Q_4+Q_5+Q_7$, $U_4+Q_3+Q_4+Q_5+Q_8$, $U_4+Q_3+Q_4+Q_6+Q_7$, $U_4+Q_3+Q_4+Q_6+Q_8$, $U_4+Q_3+Q_5+Q_6+Q_7+Q_8$, $U_4+Q_4+Q_5+Q_6+Q_7+Q_8$, $U_4+Q_1+Q_2+Q_3+Q_4+Q_5+Q_6$, $U_4+Q_1+Q_2+Q_3+Q_4+Q_5+Q_7$, $U_4+Q_1+Q_2+Q_3+Q_4+Q_5+Q_8$, $U_4+Q_1+Q_3+Q_4+Q_5+Q_6+Q_7$, $U_4+Q_1+Q_3+Q_4+Q_5+Q_6+Q_8$, $U_4+Q_1+Q_4+Q_5+Q_6+Q_7+Q_8$, $U_4+Q_2+Q_3+Q_4+Q_5+Q_6+Q_7$, $U_4+Q_2+Q_3+Q_4+Q_5+Q_6+Q_8$, $U_4+Q_2+Q_4+Q_5+Q_6+Q_7+Q_8$, $U_4+Q_3+Q_4+Q_5+Q_6+Q_7+Q_8$, $U_4+Q_1+Q_2+Q_3+Q_4+Q_5+Q_6+Q_7$, $U_4+Q_1+Q_2+Q_3+Q_4+Q_5+Q_6+Q_8$, $U_4+Q_1+Q_3+Q_4+Q_5+Q_6+Q_7+Q_8$, $U_4+Q_2+Q_3+Q_4+Q_5+Q_6+Q_7+Q_8$, or $U_4+Q_1+Q_2+Q_3+Q_4+Q_5+Q_6+Q_7+Q_8$.

In some embodiments of $R_5$, and independently in combination with any embodiments of any other relevant substituent classes, $R_5$ can be —$CH_2$—OH, —$CH_3$, —O—$CH_3$, or —CO—$CH_3$, preferably —$CH_2$—OH. Preferably in these embodiments, $R_4$ is hydrogen.

In some embodiments of C, and independently in combination with any embodiments of any other relevant substituent classes, C can be —$CH_2$—OH, —$CH_3$, —O—$CH_3$, or —CO—$CH_3$, preferably —$CH_2$—OH. Preferably in these embodiments, C is in Formula XII, B is triazole, and $\delta$ is 1.

In some embodiments of $R^d$, and independently in combination with any embodiments of any other relevant substituent classes, $R^d$ can be —$CH_2$—OH, —$CH_3$, —O—$CH_3$, or —CO—$CH_3$, preferably —$CH_2$—OH. Preferably in these embodiments, $R_{12}$, $R_{13}$, and $R_{14}$ are N, $R_{15}$ and $R_{16}$ are C, and w is 1.

Preferred alkynes for use as reagents in 1,3-dipolarcycloaddition reactions include those shown below.

-continued

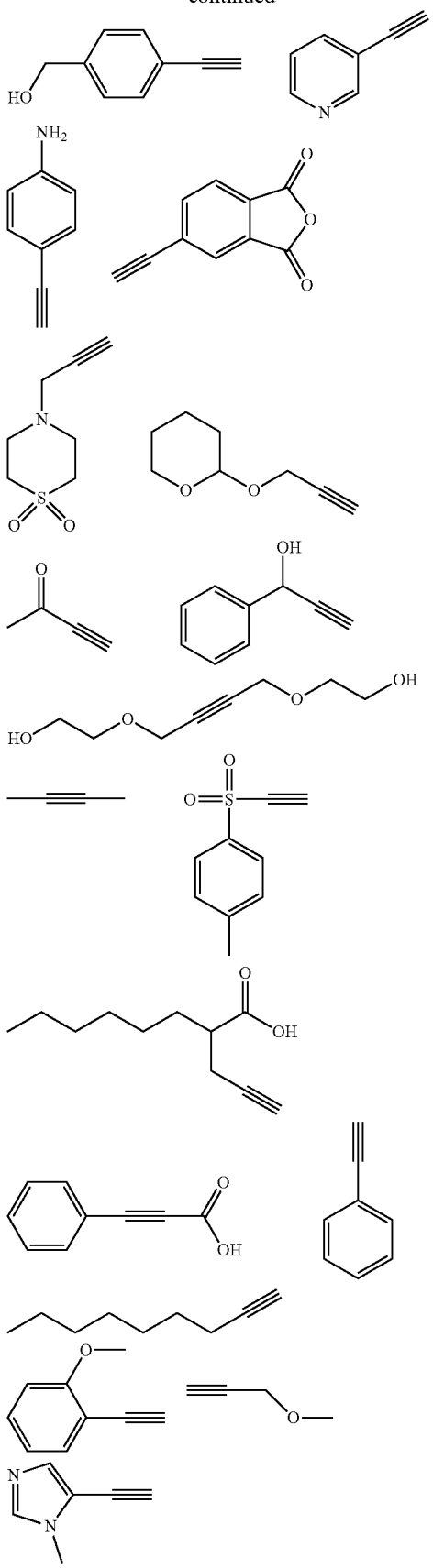

In alternative embodiments, the modified product is multiply modified. In preferred embodiments, the multiply modified product is covalently modified with a first species or type of a compound defined by Formula I, and also covalently modified with a second different species or type of compound by Formula I. In other embodiments, the multiply modified product is covalently modified with three or more different types of compounds defined by Formula I.

In some embodiments, the multiply product contains two different species of compounds defined by Formula I, which covalently modify a surface of the product, wherein in both species X is $NR_2$.

In some embodiments, the multiply product contains two different species of compounds defined by Formula I, which covalently modify a surface of the product, wherein in both species X is oxygen.

In some embodiments, the multiply product contains two different species of compounds defined by Formula I, which covalently modify a surface of the product, wherein in both species X is sulfur.

In some embodiments, the multiply modified product contains two different species of compounds defined by Formula I, which covalently modify a surface of the product, wherein in one species X is oxygen, and in the second species X is $NR_2$ or sulfur.

In some embodiments, the multiply modified product contains two different species of compounds defined by Formula I, which covalently modify a surface of the product, wherein in one species X is sulfur, and in the second species X is $NR_2$.

In some embodiments, the multiply modified product contains three different species of compounds defined by Formula I, which covalently modify a surface of the product, wherein in the first species X is oxygen, in the second species X is sulfur, and in the third species X is $NR_2$.

In some embodiments, the multiply modified product contains two different species of compounds defined by Formula I, wherein in at least one of the species of compounds, $R_1$ includes one or more cyclic moieties. In preferred embodiments, the multiply modified product contains two different species of covalent modifications defined by Formula I, wherein in one or more sites of chemical modification, $R_1$ includes a phenyl ring, furan ring, oxolane ring, dioxolane ring, or a 1,2,3-triazole ring.

In certain embodiments, the multiply modified product contains two different species of compounds defined by Formula I, wherein in one or more sites of chemical modification, $R_1$ includes one or more halogen moieties, an azide group, or an alkyne.

In some embodiments, $R_1$ through $R_5$, $R^a$, $R^b$, $R^c$, $R^d$ and $R^e$ are independently hydrogen, amino, hydroxyl, thiol, oxo, phosphate, or $J_1$.

In some embodiments, $R_1$ through $R_5$, $R^a$, $R^b$, $R^c$, $R^d$ and $R^e$ are independently hydrogen, amino, hydroxyl, thiol, oxo, phosphate, or $J_2$.

In some embodiments, -A-B(—C)$_\delta$, —B(—C)$_\delta$, A, B, C, $R_1$, $R_2$, $R_3$, $R_4$, $R_5$, $R_6$, $R_7$, $R_8$, $R_9$, $R_{10}$, $R_{11}$, $R_{59}$, $R_{60}$, $R^a$, $R^c$, $R^d$, and $R^e$ are independently —$R_h$—($R_g$)$_j$—$R_f$, wherein $R_h$ is absent, $C(R_{39}R_{40})$, O, S, $S(O)_2$, $S(O)_3$, or $NR_{41}$; wherein each $R_g$ is independently absent (i.e., j is 0), $C(R_{42}R_{43})$, O, S, $S(O)_2$, $S(O)_3$, or $NR_{44}$; and wherein $R_f$ is hydrogen, $C(R_{45}R_{46}R_{47})$, OH, SH, $S(O)_2$, $S(O)_3$, $Si(R_{100}R_{101}R_{102})$, or $NR_{48}R_{49}R_{50}$;

wherein j is an integer from 0 to 30, wherein $R_{39}$, $R_{40}$, $R_{41}$, $R_{42}$, $R_{43}$, and $R_{44}$ are each independently, as valency permits, absent, hydrogen, =O, —$OR_{51}$, —$SR_{52}$, —$NR_{53}R_{54}R_{55}$, —$C(R_{56}R_{57}R_{58})$, or —$R_{hx}$—$(R_{gx})_{jx}$—$R_{fx}$, wherein $R_{45}$, $R_{46}$, $R_{47}$, $R_{48}$, $R_{49}$, $R_{50}$, $R_{51}$, $R_{52}$, $R_{53}$, $R_{54}$, $R_{55}$, $R_{56}$, $R_{57}$, and $R_{58}$ are each independently, as valency permits, absent, hydrogen, fluorine, —OH, =O, —SH, =NH, —$NH_2$, —$NH_3$, —$CH_3$, or —COOH, wherein $R_{100}$, $R_{101}$, and $R_{102}$ are each independently alkyl, phenyl, aryl, or $C_3$-$C_{20}$ cyclic, wherein the bond between $R_h$ and $R_g$, if present, is single, double, or triple depending on the valency, wherein the bond between $R_g$ and $R_f$, if present, is single, double, or triple depending on the valency, wherein the bond between each adjacent $R_g$ is single, double, or triple depending on the valency, wherein the bond between $R_h$ and $R_f$, if present, is single, double, or triple depending on the valency; wherein when $R_h$ is O, S, $S(O)_2$, or $S(O)_3$, the bond between $R_h$ and $R_g$ is not a double or triple bond; wherein when $R_h$ is $NR_{41}$, the bond between $R_h$ and $R_g$ is not a triple bond; wherein when $R_g$ is O, S, $S(O)_2$, or $S(O)_3$, the bond between $R_g$ and $R_h$ is not a double or triple bond; wherein when $R_h$ is $NR_{44}$, the bond between $R_g$ and $R_h$ is not a triple bond; wherein when $R_g$ is O, S, $S(O)_2$, or $S(O)_3$, the bond between $R_g$ and $R_f$ is not a double or triple bond; wherein when $R_g$ is $NR_{44}$, the bond between $R_g$ and $R_f$ is not a triple bond; wherein when $R_h$ is O, $R_g$ is not O, S, or $NR_{44}$, and vice versa; wherein when $R_h$ is S, $R_g$ is not O, $S(O)_2$, $S(O)_3$, or $NR_{44}$, and vice versa; wherein when $R_h$ is $S(O)_2$, $R_g$ is not S, $S(O)_2$, or $S(O)_3$, and vice versa; wherein when $R_h$ is $S(O)_3$, $R_g$ is not S, $S(O)_2$, or $S(O)_3$, and vice versa; wherein when $R_h$ is $NR_{41}$, $R_g$ is not O, or S, and vice versa; wherein when $R_g$ is O, $R_f$ is not OH, SH, or $NR_{48}R_{49}R_{50}$, and vice versa; wherein when $R_g$ is S, $R_f$ is not OH, SH, $S(O)_2$ or $NR_{48}R_{49}R_{50}$, and vice versa; wherein when $R_g$ is $S(O)_2$, $R_f$ is not SH, $S(O)_2$, or $S(O)_3$, and vice versa; wherein when $R_g$ is $S(O)_3$, $R_f$ is not SH, $S(O)_2$, or $S(O)_3$, and vice versa; and wherein when $R_g$ is $NR_{44}$, $R_f$ is not OH, SH, or $S(O)_2$, and vice versa;

wherein each $R_{hx}$ is independently absent, $C(R_{39x}R_{40x})$, O, S, $S(O)_2$, $S(O)_3$, or $NR_{41x}$; wherein each $R_{gx}$ is independently absent (i.e., jx is 0), $C(R_{42x}R_{43x})$, O, S, $S(O)_2$, $S(O)_3$, or $NR_{44x}$; and wherein each $R_{fx}$ is independently hydrogen, $C(R_{45x}R_{46x}R_{47x})$, OH, SH, $S(O)_2$, $S(O)_3$, $Si(R_{100x}R_{101x}R_{102x})$, or $NR_{48x}R_{49x}R_{50x}$;

wherein jx is an integer from 0 to 20, wherein $R_{39x}$, $R_{40x}$, $R_{41x}$, $R_{42x}$, $R_{43x}$, and $R_{44x}$ are each independently, as valency permits, absent, hydrogen, =O, —$OR_{51x}$, —$SR_{52x}$, —$NR_{53x}R_{54x}R_{55x}$, —$C(R_{56x}R_{57x}R_{58x})$, or —$R_{hy}$—$(R_{gy})_{jy}$—$R_{fy}$, wherein $R_{45x}$, $R_{46x}$, $R_{47x}$, $R_{48x}$, $R_{49x}$, $R_{50x}$, $R_{51x}$, $R_{52x}$, $R_{53x}$, $R_{54x}$, $R_{55x}$, $R_{56x}$, $R_{57x}$, and $R_{58x}$ are each independently, as valency permits, absent, hydrogen, —OH, =O, —SH, =NH, —$NH_2$, —$NH_3$, —$CH_3$, or —COOH, wherein $R_{100x}$, $R_{101x}$, and $R_{102x}$ are each independently alkyl, phenyl, aryl, or $C_3$-$C_{20}$ cyclic, wherein the bond between each $R_{hx}$ and each respective $R_{gx}$, if present, is single, double, or triple depending on the valency, wherein the bond between each $R_{gx}$ and each respective $R_{fx}$, if present, is single, double, or triple depending on the valency, wherein the bond between each adjacent $R_{gx}$ is single, double, or triple depending on the valency, wherein the bond between each $R_{hx}$ and each respective $R_{fx}$, if present, is single, double, or triple depending on the valency; wherein when $R_{hx}$ is O, S, $S(O)_2$, or $S(O)_3$, the bond between $R_{hx}$ and $R_{gx}$ is not a double or triple bond; wherein when $R_{hx}$ is $NR_{41x}$, the bond between $R_{hx}$ and $R_{gx}$ is not a triple bond; wherein when $R_{gx}$ is O, S, $S(O)_2$, or $S(O)_3$, the bond between $R_{gx}$ and $R_{hx}$ is not a double or triple bond; wherein when $R_{hx}$ is $NR_{44x}$, the bond between $R_{gx}$ and $R_{hx}$ is not a triple bond; wherein when $R_{gx}$ is O, S, $S(O)_2$, or $S(O)_3$, the bond between $R_{gx}$ and $R_{fx}$ is not a double or triple bond; wherein when $R_{gx}$ is $NR_{44x}$, the bond between $R_{gx}$ and $R_{fx}$ is not a triple bond; wherein when $R_{hx}$ is O, $R_{gx}$ is not O, S, or $NR_{44x}$, and vice versa; wherein when $R_{hx}$ is S, $R_{gx}$ is not O, $S(O)_2$, $S(O)_3$, or $NR_{44x}$, and vice versa; wherein when $R_{hx}$ is $S(O)_2$, $R_{gx}$ is not S, $S(O)_2$, or $S(O)_3$, and vice versa; wherein when $R_{hx}$ is $S(O)_3$, $R_{gx}$ is not S, $S(O)_2$, or $S(O)_3$, and vice versa; wherein when $R_{hx}$ is $NR_{41x}$, $R_{gx}$ is not O, or S, and vice versa; wherein when $R_{gx}$ is O, $R_{fx}$ is not OH, SH, or $NR_{48x}R_{49x}R_{50x}$, and vice versa; wherein when $R_{gx}$ is S, $R_{fx}$ is not OH, SH, $S(O)_2$ or $NR_{48x}R_{49x}R_{50x}$, and vice versa; wherein when $R_{gx}$ is $S(O)_2$, $R_{fx}$ is not SH, $S(O)_2$, or $S(O)_3$, and vice versa; wherein when $R_{gx}$ is $S(O)_3$, $R_{fx}$ is not SH, $S(O)_2$, or $S(O)_3$, and vice versa; and wherein when $R_{gx}$ is $NR_{44x}$, $R_{fx}$ is not OH, SH, or $S(O)_2$, and vice versa;

wherein each $R_{hy}$ is independently absent, $C(R_{39y}R_{40y})$, O, S, $S(O)_2$, $S(O)_3$, or $NR_{41y}$; wherein each $R_{gy}$ is independently absent (i.e., jy is 0), $C(R_{42y}R_{43y})$, O, S, $S(O)_2$, $S(O)_3$, or $NR_{44y}$; and wherein each $R_{fy}$ is independently hydrogen, $C(R_{45y}R_{46y}R_{47y})$, OH, SH, $S(O)_2$, $S(O)_3$, $Si(R_{100y}R_{101y}R_{102y})$, or $NR_{48y}R_{49y}R_{50y}$;

wherein jy is an integer from 0 to 10, wherein $R_{39y}$, $R_{40y}$, $R_{41y}$, $R_{42y}$, $R_{43y}$, and $R_{44y}$ are each independently, as valency permits, absent, hydrogen, =O, —$OR_{51y}$, —$SR_{52y}$, —$NR_{53y}R_{54y}R_{55y}$, —$C(R_{56y}R_{57y}R_{58y})$, or —$R_{hz}$—$(R_{gz})_{jz}$—$R_{fz}$, wherein $R_{45y}$, $R_{46y}$, $R_{47y}$, $R_{48y}$, $R_{49y}$, $R_{50y}$, $R_{51y}$, $R_{52y}$, $R_{53y}$, $R_{54y}$, $R_{55y}$, $R_{56y}$, $R_{57y}$, and $R_{58y}$ are each independently, as valency permits, absent, hydrogen, —OH, =O, —SH, =NH, —$NH_2$, —$NH_3$, —$CH_3$, or —COOH, wherein $R_{100y}$, $R_{101y}$, and $R_{102y}$ are each independently alkyl, phenyl, aryl, or $C_3$-$C_{20}$ cyclic, wherein the bond between each $R_{hy}$ and each respective $R_{gy}$, if present, is single, double, or triple depending on the valency, wherein the bond between each $R_{gy}$ and each respective $R_{fy}$, if present, is single, double, or triple depending on the valency, wherein the bond between each adjacent $R_{gy}$ is single, double, or triple depending on the valency, wherein the bond between each $R_{hy}$ and each respective $R_{fy}$, if present, is single, double, or triple depending on the valency; wherein when $R_{hy}$ is O, S, $S(O)_2$, or $S(O)_3$, the bond between $R_{hy}$ and $R_{gy}$ is not a double or triple bond; wherein when $R_{hy}$ is $NR_{41y}$, the bond between $R_{hy}$ and $R_{gy}$ is not a triple bond; wherein when $R_{gy}$ is O, S, $S(O)_2$, or $S(O)_3$, the bond between $R_{gy}$ and $R_{hy}$ is not a double or triple bond; wherein when $R_{hy}$ is $NR_{44y}$, the bond between $R_{gy}$ and $R_{hy}$ is not a triple bond; wherein when $R_{gy}$ is O, S, $S(O)_2$, or $S(O)_3$, the bond between $R_{gy}$ and $R_{fy}$ is not a double or triple bond; wherein when $R_{gy}$ is $NR_{44y}$, the bond between $R_{gy}$ and $R_{fy}$ is not a triple bond; wherein when $R_{hy}$ is O, $R_{gy}$ is not O, S, or $NR_{44y}$, and vice versa; wherein when $R_{hy}$ is S, $R_{gy}$ is not O, $S(O)_2$, $S(O)_3$, or $NR_{44y}$, and vice versa; wherein when $R_{hy}$ is $S(O)_2$, $R_{gy}$ is not S, $S(O)_2$, or $S(O)_3$, and vice versa; wherein when $R_{hy}$ is $S(O)_3$, $R_{gy}$ is not S, $S(O)_2$, or S(O)$_3$, and vice versa; wherein when R$_{hy}$ is NR$_{41y}$, R$_{gy}$ is not O, or S, and vice versa; wherein when R$_{gy}$ is O, R$_{fy}$ is not OH, SH, or NR$_{48y}$R$_{49y}$R$_{50y}$, and vice versa; wherein when R$_{gy}$ is S, R$_{fy}$ is not OH, SH, S(O)$_2$ or NR$_{48y}$R$_{49y}$R$_{50y}$, and vice versa; wherein when R$_{gy}$ is S(O)$_2$, R$_{fy}$ is not SH, S(O)$_2$, or S(O)$_3$, and vice versa; wherein when R$_{gy}$ is S(O)$_3$, R$_{fy}$ is not SH, S(O)$_2$, or S(O)$_3$, and vice versa; and wherein when R$_{gy}$ is NR$_{44y}$, R$_{fy}$ is not OH, SH, or S(O)$_2$, and vice versa;

wherein each R$_{hz}$ is independently absent, C(R$_{39z}$R$_{40z}$), O, S, S(O)$_2$, S(O)$_3$, or NR$_{41z}$; wherein each R$_{gz}$ is independently absent (i.e., jz is 0), C(R$_{42z}$R$_{43z}$), O, S, S(O)$_2$, S(O)$_3$, or NR$_{44z}$; and wherein each R$_{fz}$ is independently hydrogen, C(R$_{45z}$R$_{46z}$R$_{47z}$), OH, SH, S(O)$_2$, S(O)$_3$, Si(R$_{100z}$R$_{101z}$R$_{102z}$), or NR$_{48z}$R$_{49z}$R$_{50z}$;

wherein jz is an integer from 0 to 6, wherein R$_{39z}$, R$_{40z}$, R$_{41z}$, R$_{42z}$, R$_{43z}$, and R$_{44z}$ are each independently, as valency permits, absent, hydrogen, =O, —OR$_{51z}$, —SR$_{52z}$, —NR$_{53z}$R$_{54z}$R$_{55z}$, or —C(R$_{56z}$R$_{57z}$R$_{58z}$), wherein R$_{45z}$, R$_{46z}$, R$_{47z}$, R$_{48z}$, R$_{49z}$, R$_{50z}$, R$_{51z}$, R$_{52z}$, R$_{53z}$, R$_{54z}$, R$_{55z}$, R$_{56z}$, R$_{57z}$, and R$_{58z}$ are each independently, as valency permits, absent, hydrogen, —OH, =O, —SH, =NH, —NH$_2$, —NH$_3$, —CH$_3$, or —COOH, wherein R$_{100z}$, R$_{101z}$, and R$_{102z}$ are each independently alkyl, phenyl, aryl, or C$_3$-C$_{20}$ cyclic, wherein the bond between each R$_{hz}$ and each respective R$_{gz}$, if present, is single, double, or triple depending on the valency, wherein the bond between each R$_{gz}$ and each respective R$_{fz}$, if present, is single, double, or triple depending on the valency, wherein the bond between each adjacent R$_{gz}$ is single, double, or triple depending on the valency, wherein the bond between each R$_{hz}$ and each respective R$_{fz}$, if present, is single, double, or triple depending on the valency; wherein when R$_{hz}$ is O, S, S(O)$_2$, or S(O)$_3$, the bond between R$_{hz}$ and R$_{gz}$ is not a double or triple bond; wherein when R$_{hz}$ is NR$_{41z}$, the bond between R$_{hz}$ and R$_{gz}$ is not a triple bond; wherein when R$_{gz}$ is O, S, S(O)$_2$, or S(O)$_3$, the bond between R$_{gz}$ and R$_{hz}$ is not a double or triple bond; wherein when R$_{hz}$ is NR$_{44z}$, the bond between R$_{gz}$ and R$_{hz}$ is not a triple bond; wherein when R$_{gz}$ is O, S, S(O)$_2$, or S(O)$_3$, the bond between R$_{gz}$ and R$_{fz}$ is not a double or triple bond; wherein when R$_{gz}$ is NR$_{44z}$, the bond between R$_{gz}$ and R$_{fz}$ is not a triple bond; wherein when R$_{hz}$ is O, R$_{gz}$ is not O, S, or NR$_{44z}$, and vice versa; wherein when R$_{hz}$ is S, R$_{gz}$ is not O, S(O)$_2$, S(O)$_3$, or NR$_{44z}$, and vice versa; wherein when R$_{hz}$ is S(O)$_2$, R$_{gz}$ is not S, S(O)$_2$, or S(O)$_3$, and vice versa; wherein when R$_{hz}$ is S(O)$_3$, R$_{gz}$ is not S, S(O)$_2$, or S(O)$_3$, and vice versa; wherein when R$_{hz}$ is NR$_{41z}$, R$_{gz}$ is not O, or S, and vice versa; wherein when R$_{gz}$ is O, R$_{fz}$ is not OH, SH, or NR$_{48z}$R$_{49z}$R$_{50z}$, and vice versa; wherein when R$_{gz}$ is S, R$_{fz}$ is not OH, SH, S(O)$_2$ or NR$_{48z}$R$_{49z}$R$_{50z}$, and vice versa; wherein when R$_{gz}$ is S(O)$_2$, R$_{fz}$ is not SH, S(O)$_2$, or S(O)$_3$, and vice versa; wherein when R$_{gz}$ is S(O)$_3$, R$_{fz}$ is not SH, S(O)$_2$, or S(O)$_3$, and vice versa; and wherein when R$_{gz}$ is NR$_{44z}$, R$_{fz}$ is not OH, SH, or S(O)$_2$, and vice versa.

Independently in some embodiments of j, and independently in combination with any embodiments of any other relevant substituent classes, j can be an integer from 1 to 30, 2 to 30, 3 to 30, 4 to 30, 5 to 30, 6 to 30, 7 to 30, 8 to 30, 9 to 30, 10 to 30, 11 to 30, 12 to 30, 13 to 30, 14 to 30, 15 to 30, 16 to 30, 17 to 30, 18 to 30, 19 to 30, 20 to 30, 21 to 30, 22 to 30, 23 to 30, 24 to 30, 25 to 30, 26 to 30, 27 to 30, 28 to 30, 29 to 30, 1 to 29, 2 to 29, 3 to 29, 4 to 29, 5 to 29, 6 to 29, 7 to 29, 8 to 29, 9 to 29, 10 to 29, 11 to 29, 12 to 29, 13 to 29, 14 to 29, 15 to 29, 16 to 29, 17 to 29, 18 to 29, 19 to 29, 20 to 29, 21 to 29, 22 to 29, 23 to 29, 24 to 29, 25 to 29, 26 to 29, 27 to 29, 28 to 29, 1 to 28, 2 to 28, 3 to 28, 4 to 28, 5 to 28, 6 to 28, 7 to 28, 8 to 28, 9 to 28, 10 to 28, 11 to 28, 12 to 28, 13 to 28, 14 to 28, 15 to 28, 16 to 28, 17 to 28, 18 to 28, 19 to 28, 20 to 28, 21 to 28, 22 to 28, 23 to 28, 24 to 28, 25 to 28, 26 to 28, 27 to 28, 1 to 27, 2 to 27, 3 to 27, 4 to 27, 5 to 27, 6 to 27, 7 to 27, 8 to 27, 9 to 27, 10 to 27, 11 to 27, 12 to 27, 13 to 27, 14 to 27, 15 to 27, 16 to 27, 17 to 27, 18 to 27, 19 to 27, 20 to 27, 21 to 27, 22 to 27, 23 to 27, 24 to 27, 25 to 27, 26 to 27, 1 to 26, 2 to 26, 3 to 26, 4 to 26, 5 to 26, 6 to 26, 7 to 26, 8 to 26, 9 to 26, 10 to 26, 11 to 26, 12 to 26, 13 to 26, 14 to 26, 15 to 26, 16 to 26, 17 to 26, 18 to 26, 19 to 26, 20 to 26, 21 to 26, 22 to 26, 23 to 26, 24 to 26, 25 to 26, 1 to 25, 2 to 25, 3 to 25, 4 to 25, 5 to 25, 6 to 25, 7 to 25, 8 to 25, 9 to 25, 10 to 25, 11 to 25, 12 to 25, 13 to 25, 14 to 25, 15 to 25, 16 to 25, 17 to 25, 18 to 25, 19 to 25, 20 to 25, 21 to 25, 22 to 25, 23 to 25, 24 to 25, 1 to 24, 2 to 24, 3 to 24, 4 to 24, 5 to 24, 6 to 24, 7 to 24, 8 to 24, 9 to 24, 10 to 24, 11 to 24, 12 to 24, 13 to 24, 14 to 24, 15 to 24, 16 to 24, 17 to 24, 18 to 24, 19 to 24, 20 to 24, 21 to 24, 22 to 24, 23 to 24, 1 to 23, 2 to 23, 3 to 23, 4 to 23, 5 to 23, 6 to 23, 7 to 23, 8 to 23, 9 to 23, 10 to 23, 11 to 23, 12 to 23, 13 to 23, 14 to 23, 15 to 23, 16 to 23, 17 to 23, 18 to 23, 19 to 23, 20 to 23, 21 to 23, 22 to 23, 1 to 22, 2 to 22, 3 to 22, 4 to 22, 5 to 22, 6 to 22, 7 to 22, 8 to 22, 9 to 22, 10 to 22, 11 to 22, 12 to 22, 13 to 22, 14 to 22, 15 to 22, 16 to 22, 17 to 22, 18 to 22, 19 to 22, 20 to 22, 21 to 22, 1 to 21, 2 to 21, 3 to 21, 4 to 21, 5 to 21, 6 to 21, 7 to 21, 8 to 21, 9 to 21, 10 to 21, 11 to 21, 12 to 21, 13 to 21, 14 to 21, 15 to 21, 16 to 21, 17 to 21, 18 to 21, 19 to 21, 20 to 21, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 1 to 17, 2 to 17, 3 to 17, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, j is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

Independently in some embodiments of j, and independently in combination with any embodiments of any other relevant substituent classes, j can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of j, and independently in combination with any embodiments of any other relevant substituent classes, j can be 1, 2, 3, 4, 5, 6, 7, 8, 9, or 10.

Independently in some embodiments of j, and independently in combination with any embodiments of any other relevant substituent classes, j can be an integer from 1 to 5, 2 to 5, 3 to 5, 4 to 5, 1 to 4, 2 to 4, 3 to 4, 1 to 3, 2 to 3, or 1 to 2. In preferred embodiments, j is 1, 2, 3, 4, or 5.

Independently in some embodiments of jx, and independently in combination with any embodiments of any other relevant substituent classes, jx can be an integer from 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 1 to 17, 2 to 17, 3 to 17, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, jx is 1, 2, 3, 4, 5, 6, 7, 8, 9, 10, 11, 12, 13, 14, 15, 16, 17, 18, 19, or 20.

Independently in some embodiments of jx, and independently in combination with any embodiments of any other relevant substituent classes, jx can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of jx, and independently in combination with any embodiments of any other relevant substituent classes, jx can be 1, 2, 3, 4, 5, 6, 7, 8, 9, or 10.

Independently in some embodiments of jx, and independently in combination with any embodiments of any other relevant substituent classes, jx can be an integer from 1 to 5, 2 to 5, 3 to 5, 4 to 5, 1 to 4, 2 to 4, 3 to 4, 1 to 3, 2 to 3, or 1 to 2. In preferred jx, jx is 1, 2, 3, 4, or 5.

Independently in some embodiments of jy, and independently in combination with any embodiments of any other relevant substituent classes, jy can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of jy, and independently in combination with any embodiments of any other relevant substituent classes, jy can be 1, 2, 3, 4, 5, 6, 7, 8, 9, or 10.

Independently in some embodiments of jy, and independently in combination with any embodiments of any other relevant substituent classes, jy can be an integer from 1 to 5, 2 to 5, 3 to 5, 4 to 5, 1 to 4, 2 to 4, 3 to 4, 1 to 3, 2 to 3, or 1 to 2. In preferred embodiments, jy is 1, 2, 3, 4, or 5.

Independently in some embodiments of jz, and independently in combination with any embodiments of any other relevant substituent classes, jz can be an integer from 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In preferred embodiments, jz is 1, 2, 3, 4, or 5.

N1

In some embodiments, in Formula VI, $R_{12}$, $R_{13}$, $R_{14}$, $R_{15}$, $R_{16}$, and $R_{17}$ are carbon, z is 2, $R^d$ is —O—$CH_3$, the ring of Formula VI is aromatic, $R_{18}$ is —$(CR_{19}R_{19})_p$—, both $R_{19}$ are hydrogen, and p is 1. In some embodiments, $R_d$ is at positions $R_{14}$ and $R_{15}$.

N2

In some embodiments, $R_2$ is methyl, in Formula IX, $R_{13}$ and $R_{16}$ are oxygen, $R_{12}$, $R_{14}$, and $R_{15}$ are carbon, w is 0, the ring of Formula IX has no double bonds, $R_{18}$ is —$(CR_{19}R_{19})_p$—, both $R_{19}$ are hydrogen, and p is 1.

N3

In some embodiments $R_h$ is absent, j is 3, and each $R_g$ is $C(R_{42}R_{43})$, wherein $R_{42}$ and $R_{43}$ are hydrogen. In some embodiments $R_h$ is absent, j is 0 to 10, and each $R_g$ is $C(R_{42}R_{43})$, wherein $R_{42}$ and $R_{43}$ are hydrogen. In some embodiments $R_h$ is absent, j is 3, each $R_g$ is $C(R_{42}R_{43})$, and $R_f$ is $NR_{48}R_{49}R_{50}$, wherein $R_{48}$ and $R_{49}$ are —$CH_3$, $R_{50}$ is absent, and $R_{42}$ and $R_{43}$ are hydrogen. In some embodiments $R_h$ is absent, j is 0 to 10, each $R_g$ is $C(R_{42}R_{43})$, and $R_f$ is $NR_{48}R_{49}R_{50}$, wherein $R_{48}$ and $R_{49}$ are —$CH_3$, $R_{50}$ is absent, and $R_{42}$ and $R_{43}$ are hydrogen. In some embodiments j is 0. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

N4

In some embodiments, $R_2$ is methyl, and in Formula VI, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, both $R_{19}$ are hydrogen, and p is 1.

N5

In some embodiments, in Formula VI, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, both $R_{19}$ are hydrogen, and p is 1.

N6

In some embodiments $R_h$ is $C(R_{39}R_{40})$, and j is 11, wherein the first, third, fourth, sixth, seventh, ninth, and tenth $R_g$ are $C(R_{42}R_{43})$ and the second, fifth, eighth, and eleventh $R_g$ are O, wherein $R_{39}$, $R_{40}$, $R_{42}$, and $R_{43}$ are hydrogen.

In some embodiments $R_h$ is $C(R_{39}R_{40})$, j is 11, and $R_f$ is $C(R_{45}R_{46}R_{47})$, wherein the first, third, fourth, sixth, seventh, ninth, and tenth $R_g$ are $C(R_{42}R_{43})$ and the second, fifth, eighth, and eleventh $R_g$ are O, wherein $R_{39}$, $R_{40}$, $R_{42}$, $R_{43}$, $R_{45}$, $R_{46}$, and $R_{47}$ are hydrogen.

In some embodiments $R_h$ is $C(R_{39}R_{40})$, and j is 5, 8, 11, 14, 17, 20, 23, 26, 29, or 32, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, twenty-ninth, and thirty-second $R_g$, if present, are O, wherein $R_{39}$, $R_{40}$, $R_{42}$, and $R_{43}$ are hydrogen.

In some embodiments $R_h$ is $C(R_{39}R_{40})$, j is 5, 8, 11, 14, 17, 20, 23, 26, 29, or 32, and $R_f$ is $C(R_{45}R_{46}R_{47})$, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, twenty-ninth, and thirty-second $R_g$, if present, are O, wherein $R_{39}$, $R_{40}$, $R_{42}$, $R_{43}$, $R_{45}$, $R_{46}$, and $R_{47}$ are hydrogen.

In some embodiments $R_h$ is $C(R_{39}R_{40})$, and j is 11, wherein the first, third, fourth, sixth, seventh, ninth, and tenth $R_g$ are $C(R_{42}R_{43})$ and the second, fifth, eighth, and eleventh $R_g$ are O, wherein $R_{39}$, $R_{40}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

In some embodiments $R_h$ is $C(R_{39}R_{40})$, j is 11, and $R_f$ is hydrogen, $C(R_{45}R_{46}R_{47})$, OH, SH, $S(O)_2$, $S(O)_3$, $Si(R_{100}R_{101}R_{102})$, or $NR_{48}R_{49}R_{50}$, wherein the first, third, fourth, sixth, seventh, ninth, and tenth $R_g$ are $C(R_{42}R_{43})$ and the second, fifth, eighth, and eleventh $R_g$ are O, wherein $R_{39}$, $R_{40}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

In some embodiments $R_h$ is $C(R_{39}R_{40})$, and j is 5, 8, 11, 14, 17, 20, 23, 26, 29, or 32, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, twenty-ninth, and thirty-second $R_g$, if present, are O, wherein $R_{39}$, $R_{40}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

In some embodiments $R_h$ is $C(R_{39}R_{40})$, j is 5, 8, 11, 14, 17, 20, 23, 26, 29, or 32, and $R_f$ is hydrogen, $C(R_{45}R_{46}R_{47})$, OH, SH, $S(O)_2$, $S(O)_3$, $Si(R_{100}R_{101}R_{102})$, or $NR_{48}R_{49}R_{50}$, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, twenty-ninth, and thirty-second $R_g$, if present, are O, wherein $R_{39}$, $R_{40}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

N7

In some embodiments $R_2$ is methyl, $R_h$ is $NR_{41}$, j is 6, and $R_g$ is $C(R_{42}R_{43})$, wherein $R_{41}$ is —$C(R_{56}R_{57}R_{58})$, wherein $R_{42}$, $R_{43}$, $R_{56}$, $R_{57}$, and $R_{58}$ are hydrogen. In some embodiments $R_2$ is methyl, $R_h$ is $NR_{41}$, j is 1 to 12, and each $R_g$ is $C(R_{42}R_{43})$, wherein $R_{41}$ is —$C(R_{56}R_{57}R_{58})$, wherein $R_{42}$, $R_{43}$, $R_{56}$, $R_{57}$, and $R_{58}$ are hydrogen. In some embodiments $R_2$ is methyl, $R_h$ is $NR_{41}$, j is 6, $R_g$ is $C(R_{42}R_{43})$, and $R_f$ is $NR_{48}R_{49}R_{50}$, wherein $R_{41}$ is —$C(R_{56}R_{57}R_{58})$, wherein $R_{42}$, $R_{43}$, $R_{49}$, $R_{56}$, $R_{57}$, and $R_{58}$ are hydrogen, $R_{48}$ is —CH$_3$, and $R_{50}$ is absent. In some embodiments $R_2$ is methyl, $R_h$ is $NR_{41}$, j is 1 to 12, each $R_g$ is $C(R_{42}R_{43})$, and $R_f$ is $NR_{48}R_{49}R_{50}$, wherein $R_{41}$ is —$C(R_{56}R_{57}R_{58})$, wherein $R_{42}$, $R_{43}$, $R_{49}$, $R_{56}$, $R_{57}$, and $R_{58}$ are hydrogen, $R_{48}$ is —CH$_3$, and $R_{50}$ is absent. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10. In some embodiments j is 11. In some embodiments j is 12. In some embodiments $R_2$ is hydrogen, methyl, ethyl, or butyl.

N8

In some embodiments $R_h$ is $C(R_{39}R_{40})$, j is 4, the first, third, and fourth $R_g$ are $C(R_{42}R_{43})$, and the second $R_g$ is O, wherein $R_{39}$, $R_{40}$, $R_{42}$, and $R_{43}$ are hydrogen. In some embodiments $R_h$ is $C(R_{39}R_{40})$, j is 4, the first, third, and fourth $R_g$ are $C(R_{42}R_{43})$, the second $R_g$ is O, and $R_f$ is OH, wherein $R_{39}$, $R_{40}$, $R_{42}$, and $R_{43}$ are hydrogen.

In some embodiments $R_h$ is $C(R_{39}R_{40})$, j is 1, 4, 7, 10, 13, or 16, the first, third, fourth, sixth, seventh, ninth, tenth, twelfth, thirteenth, fifteenth, and sixteenth $R_g$, if present, are $C(R_{42}R_{43})$, and the second, fifth, eighth, eleventh, and fourteenth $R_g$, if present, are O, wherein $R_{39}$, $R_{40}$, $R_{42}$, and $R_{43}$ are hydrogen.

In some embodiments $R_h$ is $C(R_{39}R_{40})$, j is 1, 4, 7, 10, 13, or 16, the first, third, fourth, sixth, seventh, ninth, tenth, twelfth, thirteenth, fifteenth, and sixteenth $R_g$, if present, are $C(R_{42}R_{43})$, the second, fifth, eighth, eleventh, and fourteenth $R_g$, if present, are O, and $R_f$ is OH, wherein $R_{39}$, $R_{40}$, $R_{42}$, and $R_{43}$ are hydrogen.

In some embodiments $R_h$ is $C(R_{39}R_{40})$, j is 4 to 16, one $R_g$ is O, and the other $R_g$ are $C(R_{42}R_{43})$, wherein $R_{39}$, $R_{40}$, $R_{42}$, and $R_{43}$ are hydrogen. In some embodiments the first $R_g$ is O. In some embodiments the second $R_g$ is O. In some embodiments the third $R_g$ is O. In some embodiments the fourth $R_g$ is O. In some embodiments the fifth $R_g$ is O. In some embodiments the sixth $R_g$ is O. In some embodiments the fifth from the last $R_g$ is O. In some embodiments the fourth from the last $R_g$ is O. In some embodiments the antepenultimate $R_g$ is O. In some embodiments the penultimate $R_g$ is not O. In some embodiments the last $R_g$ is not O. In some embodiments neither the penultimate $R_g$ nor the last $R_g$ is O.

In some embodiments $R_h$ is $C(R_{39}R_{40})$, j is 4 to 16, one $R_g$ is O, the other $R_g$ are $C(R_{42}R_{43})$, and $R_f$ is OH, wherein $R_{39}$, $R_{40}$, $R_{42}$, and $R_{43}$ are hydrogen. In some embodiments the first $R_g$ is O. In some embodiments the second $R_g$ is O. In some embodiments the third $R_g$ is O. In some embodiments the fourth $R_g$ is O. In some embodiments the fifth $R_g$ is O. In some embodiments the sixth $R_g$ is O. In some embodiments the fifth from the last $R_g$ is O. In some embodiments the fourth from the last $R_g$ is O. In some embodiments the antepenultimate $R_g$ is O. In some embodiments the penultimate $R_g$ is not O. In some embodiments the last $R_g$ is not O. In some embodiments neither the penultimate $R_g$ nor the last $R_g$ is O.

N9

In some embodiments $R_2$ is methyl, $R_h$ is $NR_{41}$, j is 4, and $R_g$ is $C(R_{42}R_{43})$, wherein $NR_{41}$ is —$R_{hx}$—$(R_{gx})_{jx}$—$R_{fx}$ and $R_{42}$ and $R_{43}$ are hydrogen, wherein $R_{hx}$ is $C(R_{39x}R_{40x})$, jx=0, and $R_{fx}$ is $C(R_{45x}R_{46x}R_{47x})$, and wherein $R_{39x}$, $R_{40x}$, $R_{45x}$, $R_{46x}$, $R_{47x}$ are hydrogen.

In some embodiments $R_2$ is methyl, $R_h$ is $NR_{41}$, j is 4, $R_g$ is $C(R_{42}R_{43})$, and $R_f$ is OH, wherein $NR_{41}$ is —$R_{hx}$—$(R_{gx})_{jx}$—$R_{fx}$ and $R_{42}$ and $R_{43}$ are hydrogen, wherein $R_{hx}$ is $C(R_{39x}R_{40x})$, jx=0, and $R_{fx}$ is $C(R_{45x}R_{46x}R_{47x})$, and wherein $R_{39x}$, $R_{40x}$, $R_{45x}$, $R_{46x}$, $R_{47x}$ are hydrogen.

In some embodiments $R_2$ is methyl, $R_h$ is $NR_{41}$, j is 0 to 10, and $R_g$ is $C(R_{42}R_{43})$, wherein $NR_{41}$ is —$R_{hx}$—$(R_{gx})_{jx}$—$R_{fx}$ and $R_{42}$ and $R_{43}$ are hydrogen, wherein $R_{hx}$ is $C(R_{39x}R_{40x})$, jx=0 to 10, and $R_{fx}$ is $C(R_{45x}R_{46x}R_{47x})$, and wherein $R_{39x}$, $R_{40x}$, $R_{45x}$, $R_{46x}$, $R_{47x}$ are hydrogen. In some embodiments $R_2$ is methyl, $R_h$ is $NR_{41}$, j is 0 to 10, $R_g$ is $C(R_{42}R_{43})$, and $R_f$ is OH, wherein $NR_{41}$ is —$R_{hx}$—$(R_{gx})_{jx}$—$R_{fx}$ and $R_{42}$ and $R_{43}$ are hydrogen, wherein $R_{hx}$ is $C(R_{39x}R_{40x})$, jx=0 to 10, and $R_{fx}$ is $C(R_{45x}R_{46x}R_{47x})$, and wherein $R_{39x}$, $R_{40x}$, $R_{45x}$, $R_{46x}$, $R_{47x}$ are hydrogen. In some embodiment j is 0. In some embodiments j is 1. In some embodiment j is 2. In some embodiments j is 3. In some embodiment j is 4. In some embodiments j is 5. In some embodiments j is 6. In some embodiments j is 7. In some embodiment j is 8. In some embodiments j is 9. In some embodiments j is 10. In some embodiment jx is 0. In some embodiments jx is 1. In some embodiment jx is 2. In some embodiments jx is 3. In some embodiment jx is 4. In some embodiments jx is 5. In some embodiments jx is 6. In some embodiments jx is 7. In some embodiment jx is 8. In some embodiments jx is 9. In some embodiments jx is 10. In some embodiments j=jx. In some embodiments j=jx+4. In some embodiments j=2*jx. In some embodiments $R_2$ is hydrogen, methyl, ethyl, or butyl.

In some embodiments $R_2$ is methyl, $R_h$ is $NR_{41}$, j is 0 to 10, and $R_g$ is $C(R_{42}R_{43})$, wherein $NR_{41}$ is —$R_{hx}$—$(R_{gx})_{jx}$—$R_{fx}$ and $R_{42}$ and $R_{43}$ are hydrogen, wherein $R_{hx}$ is $C(R_{39x}R_{40x})$, jx=0 to 10, and $R_{fx}$ is hydrogen, and wherein $R_{39x}$, $R_{40x}$, $R_{45x}$, $R_{46x}$, $R_{47x}$ are hydrogen. In some embodiments $R_2$ is methyl, $R_h$ is $NR_{41}$, j is 0 to 10, $R_g$ is $C(R_{42}R_{43})$, and $R_f$ is OH, wherein $NR_{41}$ is —$R_{hx}$—$(R_{gx})_{jx}$—$R_{fx}$ and $R_{42}$ and $R_{43}$ are hydrogen, wherein $R_{hx}$ is $C(R_{39x}R_{40x})$, jx=0 to 10, and $R_{fx}$ is hydrogen, and wherein $R_{39x}$, $R_{40x}$, $R_{45x}$, $R_{46x}$, $R_{47x}$ are hydrogen. In some embodiment j is 0. In some embodiments j is 1. In some embodiment j is 2. In some embodiments j is 3. In some embodiment j is 4. In some embodiments j is 5. In some embodiments j is 6. In some embodiments j is 7. In some embodiment j is 8. In some embodiments j is 9. In some embodiments j is 10. In some embodiment jx is 0. In some embodiments jx is 1. In some embodiment jx is 2. In some embodiments jx is 3. In some embodiment jx is 4. In some embodiments jx is 5. In some embodiments jx is 6. In some embodiments jx is 7. In some embodiment jx is 8. In some embodiments jx is 9. In some embodiments jx is 10. In some embodiments j=jx. In some embodiments j=jx+4. In some embodiments j=2*jx. In some embodiments $R_2$ is hydrogen, methyl, ethyl, or butyl.

O1

In some embodiments, in Formula VI, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, both $R_{19}$ are hydrogen, and p is 1.

O3

In some embodiments, in Formula IX, $R_{13}$ is oxygen, $R_{12}$, $R_{14}$, $R_{15}$, and $R_{16}$ are carbon, w is 0, the ring of Formula IX has no double bonds, $R_{18}$ is —$(CR_{19}R_{19})_p$—, both $R_{19}$ are hydrogen, and p is 1.

O4

In some embodiments, $R_h$ is $C(R_{39}R_{40})$, j is 0, $R_f$ is $C(R_{45}R_{46}R_{47})$, wherein $R_{45}$, $R_{46}$, and $R_{47}$ are fluorine, wherein $R_{39}$ and $R_{40}$ are hydrogen. In some embodiments, j is an integer from 0 to 5, wherein each $R_g$ is $C(R_{42}R_{43})$, wherein $R_{42}$ and $R_{43}$ are hydrogen. In some embodiments, j is 1. In some embodiments, j is 2. In some embodiments, j is 3. In some embodiments, j is 4. In some embodiments, j is 5.

O5

In some embodiments $R_h$ is $C(R_{39}R_{40})$, j is 2, and $R_g$ is $C(R_{42}R_{43})$, wherein $R_{42}$ and $R_{43}$ are absent and $R_{39}$ and $R_{40}$ are hydrogen. In some embodiments $R_h$ is $C(R_{39}R_{40})$, j is 2, $R_g$ is $C(R_{42}R_{43})$, and $R_f$ is hydrogen, wherein $R_{42}$ and $R_{43}$ are absent and $R_{39}$ and $R_{40}$ are hydrogen. In some embodiments $R_h$ is $C(R_{39}R_{40})$, j is 2 to 12, and $R_g$ is $C(R_{42}R_{43})$, wherein $R_{42}$ and $R_{43}$ are absent on one pair of adjacent $R_g$, $R_{42}$ and $R_{43}$ are hydrogen on the other $R_g$, and $R_{39}$ and $R_{40}$ are hydrogen. In some embodiments $R_h$ is $C(R_{39}R_{40})$, j is 2 to 12, $R_g$ is $C(R_{42}R_{43})$, and $R_f$ is hydrogen, wherein $R_{42}$ and $R_{43}$ are absent on one pair of adjacent $R_g$, $R_{42}$ and $R_{43}$ are hydrogen on the other $R_g$, and $R_{39}$ and $R_{40}$ are hydrogen. In some embodiments $R_{42}$ and $R_{43}$ are absent on the first and second $R_g$. In some embodiments $R_{42}$ and $R_{43}$ are absent on the second and third $R_g$. In some embodiments $R_{42}$ and $R_{43}$ are absent on the third and fourth $R_g$. In some embodiments $R_{42}$ and $R_{43}$ are absent on the fourth and fifth $R_g$. In some embodiments $R_{42}$ and $R_{43}$ are absent on the fifth and sixth $R_g$. In some embodiments $R_{42}$ and $R_{43}$ are absent on the sixth and seventh $R_g$. In some embodiments $R_{42}$ and $R_{43}$ are absent on the seventh and eighth $R_g$. In some embodiments $R_{42}$ and $R_{43}$ are absent on the eighth and ninth $R_g$. In some embodiments $R_{42}$ and $R_{43}$ are absent on the ninth and tenth $R_g$. In some embodiments $R_{42}$ and $R_{43}$ are absent on the tenth and eleventh $R_g$. In some embodiments $R_{42}$ and $R_{43}$ are absent on the eleventh and twelfth $R_g$.

O6

In some embodiments, in Formula IX, $R_{13}$ is oxygen, $R_{12}$, $R_{14}$, $R_{15}$, and $R_{16}$ are carbon, w is 0, the ring of Formula IX has no double bonds, $R_{18}$ is —$(CR_{19}R_{19})_p$—, both $R_{19}$ are hydrogen, and p is 1.

O7 Left

In some embodiments, in Formula IX, $R_{15}$ and $R_{16}$ are absent, $R_{12}$, $R_{13}$, and $R_{14}$ are carbon, w is 3, the ring of Formula IX has no double bonds, $R_{18}$ is —$(CR_{19}R_{19})_p$—, and p is 0, wherein each $R^d$ is independently —$CH_3$ or —$CH_2$—OH. In some embodiments, one $R^d$ is —$CH_3$ and two $R^d$ are —$CH_2$—OH. In some embodiments, one $R^d$ is —$CH_2$—OH and two $R^d$ are —$CH_3$. In some embodiments, each $R^d$ is —$CH_2$—OH. In some embodiments, each $R^d$ is —$CH_3$. In some embodiments, w is 4. In some embodiments, w is 3. In some embodiments, w is 2. In some embodiments, w is 1. In some embodiments, w is 0.

O7 Right

In some embodiments, $R_h$ is $C(R_{39}R_{40})$, j is 0, $R_f$ is $C(R_{45}R_{46}R_{47})$, wherein $R_{39}$, $R_{40}$, $R_{45}$, $R_{46}$, and $R_{47}$ are hydrogen. In some embodiments, j is an integer from 0 to 5, wherein each $R_g$ is $C(R_{42}R_{43})$, wherein $R_{42}$ and $R_{43}$ are hydrogen. In some embodiments, j is 1. In some embodiments, j is 2. In some embodiments, j is 3. In some embodiments, j is 4. In some embodiments, j is 5.

O8

In some embodiments $R_h$ is $C(R_{39}R_{40})$, and j is 0, wherein $R_{39}$ and $R_{40}$ are hydrogen. In some embodiments $R_h$ is $C(R_{39}R_{40})$, and j is 0 to 10, wherein $R_{39}$ and $R_{40}$ are hydrogen. In some embodiments $R_h$ is $C(R_{39}R_{40})$, j is 0, and $R_f$ is $C(R_{45}R_{46}R_{47})$, wherein $R_{39}$, $R_{40}$, $R_{45}$, $R_{46}$, and $R_{47}$ are hydrogen. In some embodiments $R_h$ is $C(R_{39}R_{40})$, j is 0 to 10, and $R_f$ is $C(R_{45}R_{46}R_{47})$, wherein $R_{39}$, $R_{40}$, $R_{45}$, $R_{46}$, and $R_{47}$ are hydrogen. In some embodiment j is 0. In some embodiments j is 1. In some embodiment j is 2. In some embodiments j is 3. In some embodiment j is 4. In some embodiments j is 5. In some embodiments j is 6. In some embodiments j is 7. In some embodiment j is 8. In some embodiments j is 9. In some embodiments j is 10.

O9

In some embodiments $R_h$ is $C(R_{39}R_{40})$, j is 2, and $R_g$ is $C(R_{42}R_{43})$, wherein $R_{42}$ and $R_{43}$ are absent and $R_{39}$ and $R_{40}$ are hydrogen. In some embodiments $R_h$ is $C(R_{39}R_{40})$, j is 2 to 12, and $R_g$ is $C(R_{42}R_{43})$, wherein $R_{42}$ and $R_{43}$ are absent on one pair of adjacent $R_g$, $R_{42}$ and $R_{43}$ are hydrogen on the other $R_g$, and $R_{39}$ and $R_{40}$ are hydrogen. In some embodiments, $R_{100}$, $R_{101}$, and $R_{102}$ are each independently $C_1$-$C_6$ alkyl, phenyl, aryl, or $C_5$-$C_6$ cyclic. In some embodiments $R_h$ is $C(R_{39}R_{40})$, j is 2, $R_g$ is $C(R_{42}R_{43})$, and $R_f$ is $Si(R_{100}R_{101}R_{102})$, wherein $R_{100}$, $R_{101}$, and $R_{102}$ are methyl, $R_{42}$ and $R_{43}$ are absent and $R_{39}$ and $R_{40}$ are hydrogen. In some embodiments $R_h$ is $C(R_{39}R_{40})$, j is 2 to 12, $R_g$ is $C(R_{42}R_{43})$, and $R_f$ is $Si(R_{100}R_{101}R_{102})$, wherein $R_{100}$, $R_{101}$, and $R_{102}$ are each independently alkyl, phenyl, aryl, or $C_3$-$C_{20}$ cyclic, $R_{42}$ and $R_{43}$ are absent on one pair of adjacent $R_g$, $R_{42}$ and $R_{43}$ are hydrogen on the other $R_g$, and $R_{39}$ and $R_{40}$ are hydrogen.

In some embodiments, $R_{100}$, $R_{101}$, and $R_{102}$ are each independently $C_1$-$C_3$ alkyl. In some embodiments $R_{42}$ and $R_{43}$ are absent on the first and second $R_g$. In some embodiments, $R_{100}$, $R_{101}$, and $R_{102}$ are each independently $C_1$-$C_6$ alkyl, phenyl, aryl, or $C_5$-$C_6$ cyclic. In some embodiments, $R_{100}$, $R_{101}$, and $R_{102}$ are each independently $C_1$-$C_3$ alkyl.

In some embodiments $R_{42}$ and $R_{43}$ are absent on the first and second $R_g$. In some embodiments $R_{42}$ and $R_{43}$ are absent on the second and third $R_g$. In some embodiments $R_{42}$ and $R_{43}$ are absent on the third and fourth $R_g$. In some embodiments $R_{42}$ and $R_{43}$ are absent on the fourth and fifth $R_g$. In some embodiments $R_{42}$ and $R_{43}$ are absent on the fifth and sixth $R_g$. In some embodiments $R_{42}$ and $R_{43}$ are absent on the sixth and seventh $R_g$. In some embodiments $R_{42}$ and $R_{43}$ are absent on the seventh and eighth $R_g$. In some embodiments $R_{42}$ and $R_{43}$ are absent on the eighth and ninth $R_g$. In some embodiments $R_{42}$ and $R_{43}$ are absent on the ninth and tenth $R_g$. In some embodiments $R_{42}$ and $R_{43}$ are absent on the tenth and eleventh $R_g$. In some embodiments $R_{42}$ and $R_{43}$ are absent on the eleventh and twelfth $R_g$.

O10

In some embodiments $R_h$ is $C(R_{39}R_{40})$, and j is 0, wherein $R_{39}$ and $R_{40}$ are hydrogen. In some embodiments $R_h$ is $C(R_{39}R_{40})$, and j is 0, wherein $R_{39}$ and $R_{40}$ are —$C(R_{56}R_{57}R_{58})$, and $R_{56}$, $R_{57}$, and $R_{58}$ are hydrogen. In some embodiments $R_h$ is $C(R_{39}R_{40})$, j is 0, and $R_f$ is hydrogen, wherein $R_{39}$ and $R_{40}$ are hydrogen. In some embodiments $R_h$ is $C(R_{39}R_{40})$, j is 0, and $R_f$ is $C(R_{45}R_{46}R_{47})$, wherein $R_{39}$, $R_{40}$, $R_{45}$, $R_{46}$, and $R_{47}$ are hydrogen. In some embodiments $R_h$ is $C(R_{39}R_{40})$, j is 0, and $R_f$ is $C(R_{45}R_{46}R_{47})$, wherein $R_{39}$ and $R_{40}$ are —$C(R_{56}R_{57}R_{58})$, and $R_{45}$, $R_{46}$, $R_{47}$, $R_{56}$, $R_{57}$, and $R_{58}$ are hydrogen.

O11

In some embodiments, in Formula VI, $R_{12}$, $R_{13}$, $R_{14}$, $R_{15}$, $R_{16}$, and $R_{17}$ are carbon, z is 1, $R^d$ is —OH, the ring of Formula VI is aromatic, $R_{18}$ is —$(CR_{19}R_{19})_p$—, both $R_{19}$ are hydrogen, and p is 1. In some embodiments, $R_d$ is at position $R_{15}$.

O12

In some embodiments, in Formula VI, $R_{12}$, $R_{13}$, $R_{14}$, $R_{15}$, $R_{16}$, and $R_{17}$ are carbon, z is 1, $R^d$ is —O—$CH_3$, the ring of Formula VI is aromatic, $R_{18}$ is —$(CR_{19}R_{19})_p$—, both $R_{19}$ are hydrogen, and p is 1. In some embodiments, $R_d$ is at position $R_{15}$.

Y1

In some embodiments, in Formula VI, $R_{12}$, $R_{13}$, $R_{14}$, $R_{15}$, $R_{16}$, and $R_{17}$ are carbon, z is 1, $R_d$ is hydroxy, the ring of Formula VI has no double bonds, $R_{18}$ is —$(CR_{19}R_{19})_p$—, and p is 0. In some embodiments, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$.

Y2

In some embodiments, in Formula VI, $R_{12}$, $R_{13}$, $R_{14}$, $R_{15}$, $R_{16}$, and $R_{17}$ are carbon, z is 1, $R_d$ is —O—$CH_3$, the ring of Formula VI is aromatic, $R_{18}$ is —$(CR_{19}R_{19})_p$—, and p is 0. In some embodiments, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$.

Y3

In some embodiments, in Formula IX, $R_{13}$ and $R_{14}$ are oxygen, $R_{12}$, $R_{15}$, and $R_{16}$ are carbon, w is 0, the ring of Formula IX has no double bonds, $R_{18}$ is —$(CR_{19}R_{19})_p$—, both $R_{19}$ are hydrogen, and p is 1.

Y4

In some embodiments, in Formula VI, $R_{12}$, $R_{13}$, $R_{14}$, $R_{15}$, $R_{16}$, and $R_{17}$ are carbon, z is 1, $R_d$ is —$CH_2$—OH, the ring of Formula VI is aromatic, $R_{18}$ is —$(CR_{19}R_{19})_p$—, and p is 0. In some embodiments, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$.

Y5

In some embodiments, in Formula VI, $R_{12}$, $R_{13}$, $R_{14}$, $R_{15}$, $R_{16}$, and $R_{17}$ are carbon, z is 1, $R_d$ is methyl, the ring of Formula VI is aromatic, $R_{18}$ is —$(CR_{19}R_{19})_p$—$X_b$—$(CR_{19}R_{19})_q$—, p is 0, q is 0, and $X_b$ is $S(O)_2$.

Y6 Left

In some embodiments $R_h$ is $NR_{41}$, j is 1, and $R_g$ is $C(R_{42}R_{43})$, wherein $R_{41}$ is —$R_{hx}$—$(R_{gx})_{jx}$—$R_{fx}$, and $R_{42}$ and $R_{43}$ are hydrogen, wherein $R_{hx}$ is absent, jx=1, $R_{gx}$ is $C(R_{42x}R_{43x})$, and $R_{fx}$ is $C(R_{45x}R_{46x}R_{47x})$, and wherein $R_{42x}$, $R_{43x}$, $R_{45x}$, $R_{46x}$, $R_{47x}$ are hydrogen. In some embodiments $R_h$ is $NR_{41}$, j is 1, $R_g$ is $C(R_{42}R_{43})$, and $R_f$ is $C(R_{45}R_{46}R_{47})$, wherein $R_{41}$ is —$R_{hx}$—$(R_{gx})_{jx}$—$R_{fx}$, and $R_{42}$, $R_{43}$, $R_{45}$, $R_{46}$, and $R_{47}$ are hydrogen, wherein $R_{hx}$ is absent, jx=1, $R_{gx}$ is $C(R_{42x}R_{43x})$, and $R_{fx}$ is $C(R_{45x}R_{46x}R_{47x})$, and wherein $R_{42x}$, $R_{43x}$, $R_{45x}$, $R_{46x}$, $R_{47x}$ are hydrogen.

In some embodiments $R_h$ is $NR_{41}$, j is 0 to 10, and each $R_g$ is $C(R_{42}R_{43})$, wherein $R_{41}$ is —$R_{hx}$—$(R_{gx})_{jx}$—$R_{fx}$, and $R_{42}$ and $R_{43}$ are hydrogen, wherein $R_{hx}$ is $C(R_{39x}R_{40x})$, jx=0 to 10, $R_{gx}$ is $C(R_{42x}R_{43x})$, and $R_{fx}$ is $C(R_{45x}R_{46x}R_{47x})$, and wherein $R_{39x}$, $R_{40x}$, $R_{42x}$, $R_{43x}$, $R_{45x}$, $R_{46x}$, $R_{47x}$ are hydrogen. In some embodiments $R_h$ is $NR_{41}$, j is 0 to 10, each $R_g$ is $C(R_{42}R_{43})$, and $R_f$ is $C(R_{45}R_{46}R_{47})$, wherein $R_{41}$ is —$R_{hx}$—$(R_{gx})_{jx}$—$R_{fx}$, and $R_{42}$, $R_{43}$, $R_{45}$, $R_{46}$, and $R_{47}$ are hydrogen, wherein $R_{hx}$ is $C(R_{39x}R_{40x})$, jx=0 to 10, $R_{gx}$ is $C(R_{42x}R_{43x})$, and $R_{fx}$ is $C(R_{45x}R_{46x}R_{47x})$, and wherein $R_{39x}$, $R_{40x}$, $R_{42x}$, $R_{43x}$, $R_{45x}$, $R_{46x}$, $R_{47x}$ are hydrogen.

In some embodiments j=jx. In some embodiments j and jx are 0. In some embodiment j and jx are 2. In some embodiments j and jx are 3. In some embodiments j and jx are 4.

Y6 Right

In some embodiments $R_h$ is $C(R_{39}R_{40})$, and j is 0, wherein $R_{39}$ and $R_{40}$ are hydrogen. In some embodiments $R_h$ is $C(R_{39}R_{40})$, j is 0 to 10, and each $R_g$ is $C(R_{42}R_{43})$, wherein $R_{39}$, $R_{40}$ $R_{42}$, $R_{43}$ are hydrogen. In some embodiments $R_h$ is $C(R_{39}R_{40})$, j is 0, and $R_f$ is OH, wherein $R_{39}$ and $R_{40}$ are hydrogen. In some embodiments $R_h$ is $C(R_{39}R_{40})$, j is 0 to 10, each $R_g$ is $C(R_{42}R_{43})$, and $R_f$ is OH, wherein $R_{39}$, $R_{40}$ $R_{42}$, $R_{43}$ are hydrogen. In some embodiments j is 1. In some embodiment j is 2. In some embodiments j is 3. In some embodiments j is 4.

Y7

In some embodiments $R_h$ is $C(R_{39}R_{40})$, j is 1, and $R_g$ is O, wherein $R_{39}$, $R_{40}$, $R_{45}$, $R_{46}$, and $R_{47}$ are hydrogen. In some embodiments $R_h$ is absent, j is 1, and $R_g$ is O. In some embodiments $R_h$ is $C(R_{39}R_{40})$, j is 1, $R_g$ is O, and $R_f$ is $C(R_{45}R_{46}R_{47})$, wherein $R_{39}$, $R_{40}$, $R_{45}$, $R_{46}$, and $R_{47}$ are hydrogen. In some embodiments $R_h$ is absent, j is 1, $R_g$ is O, and $R_f$ is $C(R_{45}R_{46}R_{47})$, wherein $R_{45}$, $R_{46}$, and $R_{47}$ are hydrogen.

In some embodiments $R_h$ is $C(R_{39}R_{40})$, j is 1 to 10, one $R_g$ is O, and the other $R_g$ are $C(R_{42}R_{43})$, wherein $R_{39}$, $R_{40}$, $R_{42}$, and $R_{43}$ are hydrogen. In some embodiments the last $R_g$ is O. In some embodiments the penultimate $R_g$ is O. In some embodiments the antepenultimate $R_g$ is O. In some embodiments the fourth from the last $R_g$ is O. In some embodiments the fifth from the last $R_g$ is O. In some embodiments the first $R_g$ is O. In some embodiments the second $R_g$ is O. In some embodiments the third $R_g$ is O. In some embodiments the fourth $R_g$ is O. In some embodiments the fifth $R_g$ is O.

In some embodiments $R_h$ is $C(R_{39}R_{40})$, j is 1 to 10, one $R_g$ is O, the other $R_g$ are $C(R_{42}R_{43})$, and $R_f$ is $C(R_{45}R_{46}R_{47})$, wherein $R_{39}$, $R_{40}$, $R_{42}$, $R_{43}$, $R_{45}$, $R_{46}$, and $R_{47}$ are hydrogen. In some embodiments the last $R_g$ is O. In some embodiments the penultimate $R_g$ is O. In some embodiments the antepenultimate $R_g$ is O. In some embodiments the fourth from the last $R_g$ is O. In some embodiments the fifth from the last $R_g$ is O. In some embodiments the first $R_g$ is O. In some embodiments the second $R_g$ is O. In some embodiments the third $R_g$ is O. In some embodiments the fourth $R_g$ is O. In some embodiments the fifth $R_g$ is O.

Y9 Left

In some embodiments, $R_4$ is —COOH and in Formula VI, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, and p is 0.

Y9 Right

In some embodiments $R_h$ is $C(R_{39}R_{40})$, and j is 0, wherein $R_{39}$ is =O and $R_{40}$ is —OH. In some embodiments $R_h$ is absent, j is 0 to 10, and each $R_g$ is $C(R_{42}R_{43})$, wherein $R_{42}$ and $R_{43}$ are hydrogen. In some embodiments $R_h$ is absent, j is 0, and $R_f$ is $C(R_{45}R_{46}R_{47})$, wherein $R_{45}$ is =O, $R_{46}$ is —OH, and $R_{47}$ is absent. In some embodiments $R_h$ is absent, j is 0 to 10, each $R_g$ is $C(R_{42}R_{43})$, and $R_f$ is $C(R_{45}R_{46}R_{47})$, wherein $R_{45}$ is =O, $R_{46}$ is —OH, $R_{47}$ is absent, and $R_{42}$ and $R_{43}$ are hydrogen.

Y10

In some embodiments $R_h$ is absent, j is 6, and each $R_g$ is $C(R_{42}R_{43})$, wherein $R_{42}$ and $R_{43}$ are hydrogen. In some embodiments $R_h$ is absent, j is 1 to 10, and each $R_g$ is $C(R_{42}R_{43})$, wherein $R_{42}$ and $R_{43}$ are hydrogen. In some embodiments $R_h$ is absent, j is 6, each $R_g$ is $C(R_{42}R_{43})$, and $R_f$ is $C(R_{45}R_{46}R_{47})$, wherein $R_{42}$, $R_{43}$, $R_{45}$, $R_{46}$, and $R_{47}$ are hydrogen. In some embodiments $R_h$ is absent, j is 1 to 10, each $R_g$ is $C(R_{42}R_{43})$, and $R_f$ is $C(R_{45}R_{46}R_{47})$, wherein $R_{42}$, $R_{43}$, $R_{45}$, $R_{46}$, and $R_{47}$ are hydrogen. In some embodiments j is 3. In some embodiment j is 4. In some embodiments j is 5. In some embodiments j is 7. In some embodiment j is 8. In some embodiments j is 9. In some embodiments j is 10.

Y11

In some embodiments $R_h$ is $C(R_{39}R_{40})$, j is 3, the first $R_g$ is O, and the second and third $R_g$ are $C(R_{42}R_{43})$, wherein $R_{39}$, $R_{40}$, $R_{42}$, and $R_{43}$ are hydrogen. In some embodiments $R_h$ is $C(R_{39}R_{40})$, j is 1 to 10, one $R_g$ is O, and the other $R_g$ are $C(R_{42}R_{43})$, wherein $R_{39}$, $R_{40}$, $R_{42}$, and $R_{43}$ are hydrogen. In some embodiments $R_h$ is $C(R_{39}R_{40})$, j is 3, the first $R_g$ is O, the second and third $R_g$ are $C(R_{42}R_{43})$, and $R_f$ is OH, wherein $R_{39}$, $R_{40}$, $R_{42}$, and $R_{43}$ are hydrogen. In some embodiments $R_h$ is $C(R_{39}R_{40})$, j is 1 to 10, one $R_g$ is O, the other $R_g$ are $C(R_{42}R_{43})$, and $R_f$ is OH, wherein $R_{39}$, $R_{40}$, $R_{42}$, and $R_{43}$ are hydrogen. In some embodiments the first $R_g$ is O. In some embodiments the second $R_g$ is O. In some embodiments the third $R_g$ is O. In some embodiments the fourth $R_g$ is O. In some embodiments the fifth $R_g$ is O. In some embodiments the fifth from the last $R_g$ is O.

In some embodiments the fourth from the last $R_g$ is O. In some embodiments the antepenultimate $R_g$ is O. In some embodiments the penultimate $R_g$ is O. In some embodiments the last $R_g$ is O.

In some embodiments $R_h$ is $C(R_{39}R_{40})$, j is 4 to 16, two $R_g$ are O, and the other $R_g$ are $C(R_{42}R_{43})$, wherein $R_{39}$, $R_{40}$, $R_{42}$, and $R_{43}$ are hydrogen. In some embodiments $R_h$ is $C(R_{39}R_{40})$, j is 4 to 16, two $R_g$ are O, the other $R_g$ are $C(R_{42}R_{43})$, and $R_f$ is OH, wherein $R_{39}$, $R_{40}$, $R_{42}$, and $R_{43}$ are hydrogen.

In some embodiments the first and third $R_g$ are O. In some embodiments the first and fourth $R_g$ are O. In some embodiments the first and fifth $R_g$ are O. In some embodiments the first and sixth $R_g$ are O. In some embodiments the first and seventh $R_g$ are O. In some embodiments the first and eighth $R_g$ are O. In some embodiments the first and ninth $R_g$ are O. In some embodiments the first and tenth $R_g$ are O. In some embodiments the first and eleventh $R_g$ are O. In some embodiments the first and twelfth $R_g$ are O. In some embodiments the first and thirteenth $R_g$ are O. In some embodiments the first and fourteenth $R_g$ are O. In some embodiments the first and fifteenth $R_g$ are O. In some embodiments the second and fourth $R_g$ are O. In some embodiments the second and fifth $R_g$ are O. In some embodiments the second and sixth $R_g$ are O. In some embodiments the second and seventh $R_g$ are O. In some embodiments the second and eighth $R_g$ are O. In some embodiments the second and ninth $R_g$ are O. In some embodiments the second and tenth $R_g$ are O. In some embodiments the second and eleventh $R_g$ are O. In some embodiments the second and twelfth $R_g$ are O. In some embodiments the second and thirteenth $R_g$ are O. In some embodiments the second and fourteenth $R_g$ are O. In some embodiments the second and fifteenth $R_g$ are O. In some embodiments the third and fifth $R_g$ are O. In some embodiments the third and sixth $R_g$ are O. In some embodiments the third and seventh $R_g$ are O. In some embodiments the third and eighth $R_g$ are O. In some embodiments the third and ninth $R_g$ are O. In some embodiments the third and tenth $R_g$ are O. In some embodiments the third and eleventh $R_g$ are O.

In some embodiments the third and twelfth $R_g$ are O. In some embodiments the third and thirteenth $R_g$ are O. In some embodiments the third and fourteenth $R_g$ are O. In some embodiments the third and fifteenth $R_g$ are O. In some embodiments the fourth and sixth $R_g$ are O. In some embodiments the fourth and seventh $R_g$ are O. In some embodiments the fourth and eighth $R_g$ are O. In some embodiments the fourth and ninth $R_g$ are O. In some embodiments the fourth and tenth $R_g$ are O. In some embodiments the fourth and eleventh $R_g$ are O. In some embodiments the fourth and twelfth $R_g$ are O. In some embodiments the fourth and thirteenth $R_g$ are O. In some embodiments the fourth and fourteenth $R_g$ are O. In some embodiments the fourth and fifteenth $R_g$ are O. In some embodiments the fifth and seventh $R_g$ are O. In some embodiments the fifth and eighth $R_g$ are O. In some embodiments the fifth and ninth $R_g$ are O. In some embodiments the fifth and tenth $R_g$ are O. In some embodiments the fifth and eleventh $R_g$ are O. In some embodiments the fifth and twelfth $R_g$ are O. In some embodiments the fifth and thirteenth $R_g$ are O. In some embodiments the fifth and fourteenth $R_g$ are O. In some embodiments the fifth and fifteenth $R_g$ are O. In some embodiments the sixth and eighth $R_g$ are O. In some embodiments the sixth and ninth $R_g$ are O. In some embodiments the sixth and tenth $R_g$ are O. In some embodiments the sixth and eleventh $R_g$ are O. In some embodiments the sixth and twelfth $R_g$ are O. In some embodiments the sixth and thirteenth $R_g$ are O. In some embodiments the sixth and fourteenth $R_g$ are O. In some embodiments the sixth and fifteenth $R_g$ are O. In some embodiments the seventh and ninth $R_g$ are O. In some embodiments the seventh and tenth $R_g$ are O. In some embodiments the seventh and eleventh $R_g$ are O. In some embodiments the seventh and twelfth $R_g$ are O. In some embodiments the seventh and thirteenth $R_g$ are O. In some embodiments the seventh and fourteenth $R_g$ are O. In some embodiments the seventh and fifteenth $R_g$ are O. In some embodiments the eighth and tenth $R_g$ are O. In some embodiments the eighth and eleventh $R_g$ are O. In some embodiments the eighth and twelfth $R_g$ are O. In some embodiments the eighth and thirteenth $R_g$ are O. In some embodiments the eighth and fourteenth $R_g$ are O. In some embodiments the eighth and fifteenth $R_g$ are O. In some embodiments the ninth and eleventh $R_g$ are O. In some embodiments the ninth and twelfth $R_g$ are O. In some embodiments the ninth and thirteenth $R_g$ are O. In some embodiments the ninth and fourteenth $R_g$ are O. In some embodiments the ninth and fifteenth $R_g$ are O. In some embodiments the tenth and twelfth $R_g$ are O. In some embodiments the tenth and thirteenth $R_g$ are O. In some embodiments the tenth and fourteenth $R_g$ are O. In some embodiments the tenth and fifteenth $R_g$ are O. In some embodiments the eleventh and thirteenth $R_g$ are O. In some embodiments the eleventh and fourteenth $R_g$ are O. In some embodiments the eleventh and fifteenth $R_g$ are O. In some embodiments the twelfth and fourteenth $R_g$ are O. In some embodiments the twelfth and fifteenth $R_g$ are O. In some embodiments the thirteenth and fifteenth $R_g$ are O.

Y12

In some embodiments, in Formula VI, $R_{13}$ is O, $R_{12}$, $R_{14}$, $R_{15}$, $R_{16}$, and $R_{17}$ are carbon, z is 0, the ring of Formula VI has no double bonds, $R_{18}$ is —$(CR_{19}R_{19})_p$—$X_h$—$(CR_{19}R_{19})_q$—, p is 0, q is 1, both $R_{19}$ are hydrogen, and $X_h$ is O.

Y13

In some embodiments, in Formula VI, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, one $R_{19}$ is —OH, the other $R_{19}$ is hydrogen, and p is 1.

Y14

In some embodiments, in Formula VI, $R_{14}$ is N, $R_{12}$, $R_{13}$, $R_{15}$, $R_{16}$, and $R_{17}$ are carbon, z is 0, the ring of Formula VI is aromatic, $R_{18}$ is —$(CR_{19}R_{19})_p$—, and p is 0).

Y15

In some embodiments, in Formula VI, $R_{12}$ is N, $R_{15}$ is $S(O)_2$, $R_{13}$, $R_{14}$, $R_{16}$, and $R_{17}$ are carbon, the ring of Formula VI has no double bonds, $R_{18}$ is —$(CR_{19}R_{19})_p$—, p is 1, both $R_{19}$ are hydrogen.

Y16

In some embodiments $R_h$ is $C(R_{39}R_{40})$, and j is 0, wherein $R_{39}$ and $R_{40}$ are hydrogen. In some embodiments $R_h$ is $C(R_{39}R_{40})$, j is 0 to 10, and each $R_g$ is $C(R_{42}R_{43})$, wherein $R_{39}$, $R_{40}$, $R_{42}$, and $R_{43}$ are hydrogen. In some embodiments $R_h$ is $C(R_{39}R_{40})$, j is 0, and $R_f$ is hydrogen, wherein $R_{39}$ and $R_{40}$ are hydrogen. In some embodiments $R_h$ is $C(R_{39}R_{40})$, j is 0 to 10, each $R_g$ is $C(R_{42}R_{43})$, and $R_f$ is hydrogen, wherein $R_{39}$, $R_{40}$, $R_{42}$, and $R_{43}$ are hydrogen. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

In some embodiments $R_h$ is $C(R_{39}R_{40})$, j is 0 to 10, and each $R_g$ is $C(R_{42}R_{43})$, wherein $R_{39}$ is —$R_{hx}$—$(R_{gx})_{jx}$—$R_{fx}$, and $R_{40}$, $R_{42}$, and $R_{43}$ are hydrogen, wherein $R_{hx}$ is $C(R_{39x}R_{40x})$, jx is 0, and $R_{fx}$ is hydrogen, wherein $R_{39x}$ and $R_{40x}$ are hydrogen. In some embodiments j is 0. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

In some embodiments $R_h$ is $C(R_{39}R_{40})$, j is 0 to 10, and each $R_g$ is $C(R_{42}R_{43})$, wherein $R_{39}$ is —$R_{hx}$—$(R_{gx})_{jx}$—$R_{fx}$, and $R_{40}$, $R_{42}$, and $R_{43}$ are hydrogen, wherein $R_{hx}$ is $C(R_{39x}R_{40x})$, jx is 0, and $R_{fx}$ is hydrogen, wherein $R_{39x}$ and $R_{40x}$ are hydrogen. In some embodiments $R_h$ is $C(R_{39}R_{40})$, j is 0 to 10, each $R_g$ is $C(R_{42}R_{43})$, and $R_f$ is hydrogen, wherein $R_{39}$ is —$R_{hx}$—$(R_{gx})_{jx}$—$R_{fx}$, and $R_{40}$, $R_{42}$, and $R_{43}$ are hydrogen, wherein $R_{hx}$ is $C(R_{39x}R_{40x})$, jx is 0, and $R_{fx}$ is hydrogen, wherein $R_{39x}$ and $R_{40x}$ are hydrogen. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10. In some embodiments jx is 1. In some embodiment jx is 2. In some embodiments jx is 3. In some embodiment jx is 4. In some embodiments jx is 5. In some embodiments jx is 7. In some embodiment jx is 8. In some embodiments jx is 9. In some embodiments jx is 10. In some embodiments j=jx.

Y17

In some embodiments, in Formula VI, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, and p is 0.

Y18

In some embodiments $R_h$ is $C(R_{39}R_{40})$, and j is 0, wherein $R_{39}$ is =O, and $R_{40}$ is absent. In some embodiments $R_h$ is $C(R_{39}R_{40})$, j is 0, and $R_f$ is $C(R_{45}R_{46}R_{47})$, wherein $R_{39}$ is =O, $R_{40}$ is absent, and $R_{45}$, $R_{46}$, and $R_{47}$ are hydrogen. In some embodiments $R_h$ is $C(R_{39}R_{40})$, j is 0 to 10, and each $R_g$ is $C(R_{42}R_{43})$, wherein $R_{39}$ is =O, $R_{40}$ is absent, and $R_{42}$ and $R_{43}$ are hydrogen. In some embodiments $R_h$ is $C(R_{39}R_{40})$, j is 0 to 10, each $R_g$ is $C(R_{42}R_{43})$, and $R_f$ is $C(R_{45}R_{46}R_{47})$, wherein $R_{39}$ is =O, $R_{40}$ is absent, and $R_{42}$, $R_{43}$, $R_{45}$, $R_{46}$, and $R_{47}$ are hydrogen. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

In some embodiments $R_h$ is $C(R_{39}R_{40})$, j is 1 to 10, and each $R_g$ is $C(R_{42}R_{43})$, wherein $R_{42}$ is =O and $R_{43}$ is absent for one $R_g$, $R_{42}$ and $R_{43}$ are hydrogen for the other $R_g$, and $R_{39}$ and $R_{40}$ are hydrogen. In some embodiments $R_h$ is $C(R_{39}R_{40})$, j is 1 to 10, each $R_g$ is $C(R_{42}R_{43})$, and $R_f$ is $C(R_{45}R_{46}R_{47})$, wherein $R_{42}$ is =O and $R_{43}$ is absent for one $R_g$, $R_{42}$ and $R_{43}$ are hydrogen for the other $R_g$, and $R_{39}$, $R_{40}$, $R_{45}$, $R_{46}$, and $R_{47}$ are hydrogen. In some embodiments $R_{42}$ is =O and $R_{43}$ is absent for the last $R_g$. In some embodiments $R_{42}$ is =O and $R_{43}$ is absent for the penultimate $R_g$. In some embodiments $R_{42}$ is =O and $R_{43}$ is absent for the antepenultimate $R_g$. In some embodiments $R_{42}$ is =O and $R_{43}$ is absent for the fourth from the last $R_g$. In some embodiments $R_{42}$ is =O and $R_{43}$ is absent for the fifth from the last $R_g$. In some embodiments $R_{42}$ is =O and $R_{43}$ is absent for the first $R_g$. In some embodiments $R_{42}$ is =O and $R_{43}$ is absent for the second $R_g$. In some embodiments $R_{42}$ is =O and $R_{43}$ is absent for the third $R_g$. In some embodiments $R_{42}$ is =O and $R_{43}$ is absent for the fourth $R_g$. In some embodiments $R_{42}$ is =O and $R_{43}$ is absent for the fifth $R_g$.

In some embodiments $R_h$ is $C(R_{39}R_{40})$, j is 1 to 15, and each $R_g$ is $C(R_{42}R_{43})$, wherein $R_{42}$ is =O and $R_{43}$ is absent for two $R_g$, $R_{42}$ and $R_{43}$ are hydrogen for the other $R_g$, and $R_{39}$ and $R_{40}$ are hydrogen. In some embodiments $R_h$ is $C(R_{39}R_{40})$, j is 1 to 15, each $R_g$ is $C(R_{42}R_{43})$, and $R_f$ is $C(R_{45}R_{46}R_{47})$, wherein $R_{42}$ is =O and $R_{43}$ is absent for two $R_g$, $R_{42}$ and $R_{43}$ are hydrogen for the other $R_g$, and $R_{39}$, $R_{40}$, $R_{45}$, $R_{46}$, and $R_{47}$ are hydrogen. In some embodiments $R_{42}$ is =O and $R_{43}$ is absent the first and third $R_g$. In some embodiments $R_{42}$ is =O and $R_{43}$ is absent the first and fourth $R_g$. In some embodiments $R_{42}$ is =O and $R_{43}$ is absent the first and fifth $R_g$. In some embodiments $R_{42}$ is =O and $R_{43}$ is absent the first and sixth $R_g$. In some embodiments $R_{42}$ is =O and $R_{43}$ is absent the first and seventh $R_g$. In some embodiments $R_{42}$ is =O and $R_{43}$ is absent the first and eighth $R_g$. In some embodiments $R_{42}$ is =O and $R_{43}$ is absent the first and ninth $R_g$. In some embodiments $R_{42}$ is =O and $R_{43}$ is absent the first and tenth $R_g$. In some embodiments $R_{42}$ is =O and $R_{43}$ is absent the first and eleventh $R_g$. In some embodiments $R_{42}$ is =O and $R_{43}$ is absent the first and twelfth $R_g$. In some embodiments $R_{42}$ is =O and $R_{43}$ is absent the first and thirteenth $R_g$. In some embodiments $R_{42}$ is =O and $R_{43}$ is absent the first and fourteenth $R_g$. In some embodiments $R_{42}$ is =O and $R_{43}$ is absent the first and fifteenth $R_g$. In some embodiments $R_{42}$ is =O and $R_{43}$ is absent the second and fourth $R_g$. In some embodiments $R_{42}$ is =O and $R_{43}$ is absent the second and fifth $R_g$. In some embodiments $R_{42}$ is =O and $R_{43}$ is absent the second and sixth $R_g$. In some embodiments $R_{42}$ is =O and $R_{43}$ is absent the second and seventh $R_g$. In some embodiments $R_{42}$ is =O and $R_{43}$ is absent the second and eighth $R_g$. In some embodiments $R_{42}$ is =O and $R_{43}$ is absent the second and ninth $R_g$. In some embodiments $R_{42}$ is =O and $R_{43}$ is absent the second and tenth $R_g$. In some embodiments $R_{42}$ is =O and $R_{43}$ is absent the second and eleventh $R_g$. In some embodiments $R_{42}$ is =O and $R_{43}$ is absent the second and twelfth $R_g$. In some embodiments $R_{42}$ is =O and $R_{43}$ is absent the second and thirteenth $R_g$. In some embodiments $R_{42}$ is =O and $R_{43}$ is absent the second and fourteenth $R_g$. In some embodiments $R_{42}$ is =O and $R_{43}$ is absent the second and fifteenth $R_g$. In some embodiments $R_{42}$ is =O and $R_{43}$ is absent the third and fifth $R_g$. In some embodiments $R_{42}$ is =O and $R_{43}$ is absent the third and sixth $R_g$. In some embodiments $R_{42}$ is =O and $R_{43}$ is absent the third and seventh $R_g$. In some embodiments $R_{42}$ is =O and $R_{43}$ is absent the third and eighth $R_g$. In some embodiments $R_{42}$ is =O and $R_{43}$ is absent the third and ninth $R_g$. In some embodiments $R_{42}$ is =O and $R_{43}$ is absent the third and tenth $R_g$. In some embodiments $R_{42}$ is =O and $R_{43}$ is absent the third and eleventh $R_g$. In some embodiments $R_{42}$ is =O and $R_{43}$ is absent the third and twelfth $R_g$. In some embodiments $R_{42}$ is =O and $R_{43}$ is absent the third and thirteenth $R_g$. In some embodiments $R_{42}$ is =O and $R_{43}$ is absent the third and fourteenth $R_g$. In some embodiments $R_{42}$ is =O and $R_{43}$ is absent the third and fifteenth $R_g$. In some embodiments $R_{42}$ is =O and $R_{43}$ is absent the fourth and sixth $R_g$. In some embodiments $R_{42}$ is =O and $R_{43}$ is absent the fourth and seventh $R_g$. In some embodiments $R_{42}$ is =O and $R_{43}$ is absent the fourth and eighth $R_g$. In some embodiments $R_{42}$ is =O and $R_{43}$ is absent the fourth and ninth $R_g$. In some embodiments $R_{42}$ is =O and $R_{43}$ is absent the fourth and tenth $R_g$. In some embodiments $R_{42}$ is =O and $R_{43}$ is absent the fourth and eleventh $R_g$. In some embodiments $R_{42}$ is =O and $R_{43}$ is absent the fourth and twelfth $R_g$. In some embodiments $R_{42}$ is =O and $R_{43}$ is absent the fourth and thirteenth $R_g$. In some embodiments $R_{42}$ is =O and $R_{43}$ is absent the fourth and fourteenth $R_g$. In some embodiments $R_{42}$ is =O and $R_{43}$ is absent the fourth and fifteenth $R_g$. In some embodiments $R_{42}$ is =O and $R_{43}$ is absent the fifth and seventh $R_g$. In some embodiments $R_{42}$ is =O and $R_{43}$ is absent the fifth and eighth $R_g$. In some embodiments $R_{42}$ is =O and $R_{43}$ is absent the fifth and ninth $R_g$. In some embodiments $R_{42}$ is =O and $R_{43}$ is absent the fifth and tenth $R_g$. In some embodiments $R_{42}$ is =O and $R_{43}$ is absent the fifth and eleventh $R_g$. In some embodiments $R_{42}$ is =O and $R_{43}$ is absent the fifth and twelfth $R_g$. In some embodiments $R_{42}$ is =O and $R_{43}$ is absent the fifth and thirteenth $R_g$. In some embodiments $R_{42}$ is =O and $R_{43}$ is absent the fifth and fourteenth $R_g$. In some embodiments $R_{42}$ is =O and $R_{43}$ is absent the fifth and fifteenth $R_g$. In some embodiments $R_{42}$ is =O and $R_{43}$ is absent the sixth and eighth $R_g$. In some embodiments $R_{42}$ is =O and $R_{43}$ is absent the sixth and ninth $R_g$. In some embodiments $R_{42}$ is =O and $R_{43}$ is absent the sixth and tenth $R_g$. In some embodiments $R_{42}$ is =O and $R_{43}$ is absent the sixth and eleventh $R_g$. In some embodiments $R_{42}$ is =O and $R_{43}$ is absent the sixth and twelfth $R_g$. In some embodiments $R_{42}$ is =O and $R_{43}$ is absent the sixth and thirteenth $R_g$. In some embodiments $R_{42}$ is =O and $R_{43}$ is absent the sixth and fourteenth $R_g$. In some embodiments $R_{42}$ is =O and $R_{43}$ is absent the sixth and fifteenth $R_g$. In some embodiments $R_{42}$ is =O and $R_{43}$ is absent the seventh and ninth $R_g$. In some embodiments $R_{42}$ is =O and $R_{43}$ is absent the seventh and tenth $R_g$. In some embodiments $R_{42}$ is =O and $R_{43}$ is absent the seventh and eleventh $R_g$. In some embodiments $R_{42}$ is =O and $R_{43}$ is absent the seventh and twelfth $R_g$. In some embodiments $R_{42}$ is =O and $R_{43}$ is absent the seventh and thirteenth $R_g$. In some embodiments $R_{42}$ is =O and $R_{43}$ is absent the seventh and fourteenth $R_g$. In some embodiments $R_{42}$ is =O and $R_{43}$ is absent the seventh and fifteenth $R_g$. In some embodiments $R_{42}$ is =O and $R_{43}$ is absent the eighth and tenth $R_g$. In some embodiments $R_{42}$ is =O and $R_{43}$ is absent the eighth and eleventh $R_g$. In some embodiments $R_{42}$ is =O and $R_{43}$ is absent the eighth and twelfth $R_g$. In some embodiments $R_{42}$ is =O and $R_{43}$ is absent the eighth and thirteenth $R_g$. In some embodiments $R_{42}$ is =O and $R_{43}$ is absent the eighth and fourteenth $R_g$. In some embodiments $R_{42}$ is =O and $R_{43}$ is absent the eighth and fifteenth $R_g$. In some embodiments $R_{42}$ is =O and $R_{43}$ is absent the ninth and eleventh $R_g$. In some embodiments $R_{42}$ is =O and $R_{43}$ is absent the ninth and twelfth $R_g$. In some embodiments $R_{42}$ is =O and $R_{43}$ is absent the ninth and thirteenth $R_g$. In some embodiments $R_{42}$ is =O and $R_{43}$ is absent the ninth and fourteenth $R_g$. In some embodiments $R_{42}$ is =O and $R_{43}$ is absent the ninth and fifteenth $R_g$. In some embodiments $R_{42}$ is =O and $R_{43}$ is absent the tenth and twelfth $R_g$. In some embodiments $R_{42}$ is =O and $R_{43}$ is absent the tenth and thirteenth $R_g$. In some embodiments $R_{42}$ is =O and $R_{43}$ is absent the tenth and fourteenth $R_g$. In some embodiments $R_{42}$ is =O and $R_{43}$ is absent the tenth and fifteenth $R_g$. In some embodiments $R_{42}$ is =O and $R_{43}$ is absent the eleventh and thirteenth $R_g$. In some embodiments $R_{42}$ is =O and $R_{43}$ is absent the eleventh and fourteenth $R_g$. In some embodiments $R_{42}$ is =O and $R_{43}$ is absent the eleventh and fifteenth $R_g$. In some embodiments $R_{42}$ is =O and $R_{43}$ is absent the twelfth and fourteenth $R_g$. In some embodiments $R_{42}$ is =O and $R_{43}$ is absent the twelfth and fifteenth $R_g$. In some embodiments the thirteenth and fifteenth $R_g$.

Y19

In some embodiments, in Formula VI, $R_{12}$, $R_{13}$, $R_{14}$, $R_{15}$, $R_{16}$, and $R_{17}$ are carbon, z is 1, $R^d$ is —$NH_2$, the ring of Formula VI is aromatic, $R_{18}$ is —$(CR_{19}R_{19})_p$—, and p is 0. In some embodiments, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$.

Y20

In some embodiments $R_h$ is $C(R_{39}R_{40})$, j is 6, each $R_g$ is $C(R_{42}R_{43})$, and $R_f$ is $C(R_{45}R_{46}R_{47})$, wherein $R_{39}$, $R_{40}$, $R_{45}$, $R_{46}$, and $R_{47}$ are hydrogen, wherein $R_{42}$ of the first $R_g$ is $C(R_{56}R_{57}R_{58})$, $R_{43}$ of the first through sixth $R_g$ are hydrogen, and $R_{42}$ of the second through sixth $R_g$ are hydrogen, wherein $R_{56}$ is =O, $R_{57}$ is —OH, and $R_{58}$ is absent. In some embodiments $R_h$ is $C(R_{39}R_{40})$, j is 6, and each $R_g$ is $C(R_{42}R_{43})$, wherein $R_{39}$ and $R_{40}$ are hydrogen, wherein $R_{42}$ of the first $R_g$ is $C(R_{56}R_{57}R_{58})$, $R_{43}$ of the first through sixth $R_g$ are hydrogen, and $R_{42}$ of the second through sixth $R_g$ are hydrogen, wherein $R_{56}$ is =O, $R_{57}$ is —OH, and $R_{58}$ is absent.

In some embodiments $R_h$ is $C(R_{39}R_{40})$, j is 1 to 10, each $R_g$ is $C(R_{42}R_{43})$, and $R_f$ is $C(R_{45}R_{46}R_{47})$, wherein $R_{39}$, $R_{40}$, $R_{45}$, $R_{46}$, and $R_{47}$ are hydrogen, wherein $R_{42}$ of one $R_g$ is $C(R_{56}R_{57}R_{58})$, $R_{42}$ of the other $R_g$ are hydrogen, and $R_{43}$ is hydrogen, and, wherein $R_{56}$ is =O, $R_{57}$ is —OH, and $R_{58}$ is absent. In some embodiments $R_{42}$ of the first $R_g$ is $C(R_{56}R_{57}R_{58})$. In some embodiments $R_h$ is $C(R_{39}R_{40})$, j is 1 to 10, and each $R_g$ is $C(R_{42}R_{43})$, wherein $R_{39}$ and $R_{40}$ are hydrogen, wherein $R_{42}$ of one $R_g$ is $C(R_{56}R_{57}R_{58})$, $R_{42}$ of the other $R_g$ are hydrogen, and $R_{43}$ is hydrogen, and, wherein $R_{56}$ is =O, $R_{57}$ is —OH, and $R_{58}$ is absent. In some embodiments $R_{42}$ of the first $R_g$ is $C(R_{56}R_{57}R_{58})$. In some embodiments $R_{42}$ of the second $R_g$ is $C(R_{56}R_{57}R_{58})$. In some embodiments $R_{42}$ of the third $R_g$ is $C(R_{56}R_{57}R_{58})$. In some embodiments $R_{42}$ of the fourth $R_g$ is $C(R_{56}R_{57}R_{58})$. In some embodiments $R_{42}$ of the fifth $R_g$ is $C(R_{56}R_{57}R_{58})$. In some embodiments $R_{42}$ of the sixth $R_g$ is $C(R_{56}R_{57}R_{58})$. In some embodiments $R_{42}$ of the seventh $R_g$ is $C(R_{56}R_{57}R_{58})$. In some embodiments $R_{42}$ of the eighth $R_g$ is $C(R_{56}R_{57}R_{58})$. In some embodiments $R_{42}$ of the ninth $R_g$ is $C(R_{56}R_{57}R_{58})$. In some embodiments $R_{42}$ of the tenth $R_g$ is $C(R_{56}R_{57}R_{58})$.

Z1

In some embodiments $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, wherein $R_{39}$, $R_{40}$, $R_{42}$, $R_{43}$, $R_{45}$, $R_{46}$, and $R_{47}$ are hydrogen. In some embodiments $R_h$ is $C(R_{39}R_{40})$, j is 10, and $R_f$ is $C(R_{45}R_{46}R_{47})$, wherein the first, third, fourth, sixth, seventh, ninth, and tenth $R_g$ are $C(R_{42}R_{43})$ and the second, fifth, and eighth $R_g$ are O, wherein $R_{39}$, $R_{40}$, $R_{42}$, $R_{43}$, $R_{45}$, $R_{46}$, and $R_{47}$ are hydrogen.

In some embodiments $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen. In some embodiments $R_h$ is $C(R_{39}R_{40})$, j is 4 to 31, and $R_f$ is $C(R_{45}R_{46}R_{47})$, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, $R_{43}$, $R_{45}$, $R_{46}$, and $R_{47}$ are hydrogen.

In some embodiments $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, wherein $R_{39}$, $R_{40}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —$NH_2$, —$NH_3$, —$CH_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

In some embodiments $R_h$ is $C(R_{39}R_{40})$, j is 10, and $R_f$ is hydrogen, $C(R_{45}R_{46}R_{47})$, OH, SH, $S(O)_2$, $S(O)_3$, $Si(R_{100}R_{101}R_{102})$, or $NR_{48}R_{49}R_{50}$, wherein the first, third, fourth, sixth, seventh, ninth, and tenth $R_g$ are $C(R_{42}R_{43})$ and the second, fifth, and eighth $R_g$ are O, wherein $R_{39}$, $R_{40}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —$NH_2$, —$NH_3$, —$CH_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

In some embodiments $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen.

In some embodiments $R_h$ is $C(R_{39}R_{40})$, j is 4 to 31, and $R_f$ is hydrogen, $C(R_{45}R_{46}R_{47})$, OH, SH, $S(O)_2$, $S(O)_3$, $Si(R_{100}R_{101}R_{102})$, or $NR_{48}R_{49}R_{50}$, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —$NH_2$, —$NH_3$, —$CH_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

In some embodiments, A, $R_3$, $R_{18}$, and $R^b$ are independently —$R_h$—$(R_g)_j$, wherein $R_h$ is $C(R_{39}R_{40})$, O, S, $S(O)_2$, $S(O)_3$, or $NR_{41}$; and wherein each $R_g$ is independently absent (i.e., j is 0), $C(R_{42}R_{43})$, O, S, $S(O)_2$, $S(O)_3$, or $NR_{44}$;
  wherein j is an integer from 0 to 30,
  wherein $R_{39}$, $R_{40}$, $R_{41}$, $R_{42}$, $R_{43}$, and $R_{44}$ are each independently, as valency permits, absent, hydrogen, =O, —$OR_{51}$, —$SR_{52}$, —$NR_{53}R_{54}R_{55}$, —$C(R_{56}R_{57}R_{58})$, or —$R_{hx}$—$(R_{gx})_{jx}$—$R_{fx}$,
  wherein $R_{51}$, $R_{52}$, $R_{53}$, $R_{54}$, $R_{55}$, $R_{56}$, $R_{57}$, and $R_{58}$ are each independently, as valency permits, absent, hydrogen, —OH, =O, —SH, =NH, —$NH_2$, —$NH_3$, —$CH_3$, or —COOH,
  wherein the bond between $R_h$ and $R_g$, if present, is single, double, or triple depending on the valency, wherein the bond between each adjacent $R_g$ is single, double, or triple depending on the valency; wherein when $R_h$ is O, S, $S(O)_2$, or $S(O)_3$, the bond between $R_h$ and $R_g$ is not a double or triple bond; wherein when $R_h$ is $NR_{41}$, the bond between $R_h$ and $R_g$ is not a triple bond; wherein when $R_g$ is O, S, $S(O)_2$, or $S(O)_3$, the bond between $R_g$ and $R_h$ is not a double or triple bond; wherein when $R_h$ is $NR_{44}$, the bond between $R_g$ and $R_h$ is not a triple bond; wherein when $R_h$ is O, $R_g$ is not O, S, or $NR_{44}$, and vice versa; wherein when $R_h$ is S, $R_g$ is not O, $S(O)_2$, $S(O)_3$, or $NR_{44}$, and vice versa; wherein when $R_h$ is $S(O)_2$, $R_g$ is not S, $S(O)_2$, or $S(O)_3$, and vice versa; wherein when $R_h$ is $S(O)_3$, $R_g$ is not S, $S(O)_2$, or $S(O)_3$, and vice versa; and wherein when $R_h$ is $NR_{41}$, $R_g$ is not O, or S, and vice versa.

Z2

In some embodiments where A or $R_3$ is Formula VI, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 0 to 10, and $R_{19}$ are independently hydrogen or $C_1$-$C_3$ alkyl. In some embodiments, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 1, and $R_{19}$ are hydrogen.

In some embodiments where A or $R_3$ is Formula VI, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

Z2-Y12, Z1-Y15, and Z1-Y19

Preferred compounds are represented by the general formula:

—X—$R_1$         Formula I wherein X is oxygen, sulfur, $NR_2$, or another group compatible with attachment or coupling of the compound to a product or surface;
  wherein $R_1$ is -A-B(—C)$_\delta$ or —$R_3$—$R^b$;
  wherein A and $R_3$ are —$R_h$—$(R_g)_j$ or

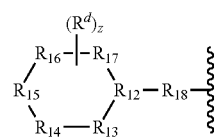

Formula VI wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein in Formula VI, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 0 to 10, and $R_{19}$ are independently hydrogen or $C_1$-$C_3$ alkyl;

wherein B and $R^b$ are:

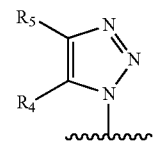

Formula III wherein each C, $R_4$, and $R_5$ are independently hydrogen or

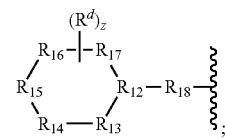

Formula VI wherein $R_{12}$ is carbon, one or two of nonadjacent $R_{13}$, $R_{14}$, $R_{15}$, $R_{16}$, and $R_{17}$ are O, the rest of $R_{13}$, $R_{14}$, $R_{15}$, $R_{16}$, and $R_{17}$ are carbon, z is 0 to 3, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI has no double bonds, $R_{18}$ is —$(CR_{19}R_{19})_p$—$X_b$—$(CR_{19}R_{19})_q$—, p is 0 to 5, q is 0 to 5, $R_{19}$ are independently hydrogen or $C_1$-$C_3$ alkyl, and $X_b$ is O;

wherein $R_{12}$ is N, $R_{15}$ is $S(O)_2$, $R_{13}$, $R_{14}$, $R_{16}$, and $R_{17}$ are carbon, the ring of Formula VI has no double bonds, $R_{18}$ is —$(CR_{19}R_{19})_p$—, p is 0 to 10, and $R_{19}$ are independently hydrogen or $C_1$-$C_3$ alkyl; or wherein $R_{12}$, $R_{13}$, $R_{14}$, $R_{15}$, $R_{16}$, and $R_{17}$ are carbon, z is 0 to 5, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI is aromatic, $R_{18}$ is —$(CR_{19}R_{19})_p$—, p is 0 to 5, and $R_{19}$ are independently hydrogen or $C_1$-$C_3$ alkyl;

wherein $R_4$ and $R_5$ are not both hydrogen, wherein at least one C is not hydrogen.

X is preferably oxygen, sulfur, or $NR_2$.

In some embodiments where A or $R_3$ is —$R_h$—$(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is —$R_h$—$(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments where A or $R_3$ is Formula VI, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where A or $R_3$ is Formula VI, in such A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 1, and $R_{19}$ are hydrogen.

In some embodiments where one or more of C, $R_4$, and $R_5$ are Formula VI, in such C, $R_4$, and $R_5$: $R_{12}$ is carbon, one or two of nonadjacent $R_{13}$, $R_{14}$, $R_{15}$, $R_{16}$, and $R_{17}$ are O, the rest of $R_{13}$, $R_{14}$, $R_{15}$, $R_{16}$, and $R_{17}$ are carbon, z is 0 to 3, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI has no double bonds, $R_{18}$ is —$(CR_{19}R_{19})_p$—$X_b$—$(CR_{19}R_{19})_q$—, p is 0 to 5, q is 0 to 5, $R_{19}$ are independently hydrogen or $C_1$-$C_3$ alkyl, and $X_b$ is O. In some embodiments $R_4$ is hydrogen. In some embodiments, $R_5$ is hydrogen. In some embodiments, $R_{13}$ is O and $R_{14}$, $R_{15}$, $R_{16}$, and $R_{17}$ are carbon. In some embodiments, $R_{14}$ is O and $R_{13}$, $R_{15}$, $R_{16}$, and $R_{17}$ are carbon. In some embodiments, $R_{15}$ is O and $R_{13}$, $R_{14}$, $R_{16}$, and $R_{17}$ are carbon. In some embodiments, $R_{16}$ is O and $R_{13}$, $R_{14}$, $R_{15}$, and $R_{17}$ are carbon. In some embodiments, $R_{17}$ is O and $R_{13}$, $R_{14}$, $R_{15}$, and $R_{16}$ are carbon. In some embodiments, $R_{13}$ and $R_{15}$ are O. In some embodiments, $R_{13}$ and $R_{16}$ are O. In some embodiments, $R_{13}$ and $R_{17}$ are O. In some embodiments, $R_{14}$ and $R_{16}$ are O. In some embodiments, $R_{14}$ and $R_{17}$ are O. In some embodiments, $R_{15}$ and $R_{17}$ are O. In some embodiments z is 0. In some embodiments z is 1. In some embodiments z is 2. In some embodiments z is 3. In some embodiments $R^d$ is independently methyl, ethyl, methoxy, ethoxy, amino methyl, amino ethyl, hydroxyl, or amino. In some embodiments, p is 0. In some embodiments p is 1. In some embodiment p is 2. In some embodiments p is 3. In some embodiments p is 4. In some embodiments p is 5. In some embodiments, q is 0. In some embodiments q is 1. In some embodiment q is 2. In some embodiments q is 3. In some embodiments q is 4. In some embodiments q is 5. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where at least one C is Formula VI, $R_4$ is hydrogen, and $R_5$ is Formula VI, in such C and $R_5$: $R_{13}$ is O, $R_{12}$, $R_{14}$, $R_{15}$, $R_{16}$, and $R_{17}$ are carbon, z is 0, the ring of Formula VI has no double bonds, $R_{18}$ is —$(CR_{19}R_{19})_p$—$X_b$—$(CR_{19}R_{19})_q$—, p is 0, q is 1, both $R_{19}$ are hydrogen, and $X_b$ is O.

In some embodiments where one or more of C, $R_4$, and $R_5$ are Formula VI, in such C, $R_4$, and $R_5$: $R_{12}$ is N, $R_{15}$ is $S(O)_2$, $R_{13}$, $R_{14}$, $R_{16}$, and $R_{17}$ are carbon, the ring of Formula VI has no double bonds, $R_{18}$ is —$(CR_{19}R_{19})_p$—, p is 0 to 10, and $R_{19}$ are independently hydrogen or $C_1$-$C_3$ alkyl. In some embodiments, p is 0. In some embodiments p is 1. In some embodiment p is 2. In some embodiments p is 3. In some embodiments p is 4. In some embodiments p is 5. In some embodiments p is 7. In some embodiment p is 8. In some embodiments p is 9. In some embodiments p is 10. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where at least one C is Formula VI, $R_4$ is hydrogen, and $R_5$ is Formula VI, in such C and $R_5$: $R_{12}$ is N, $R_{15}$ is $S(O)_2$, $R_{13}$, $R_{14}$, $R_{16}$, and $R_{17}$ are carbon, the ring of Formula VI has no double bonds, $R_{18}$ is —$(CR_{19}R_{19})_p$—, p is 1, and both $R_{19}$ are hydrogen.

In some embodiments where one or more of C, $R_4$, and $R_5$ are Formula VI, in such C, $R_4$, and $R_5$: $R_{12}$, $R_{13}$, $R_{14}$, $R_{15}$, $R_{16}$, and $R_{17}$ are carbon, z is 0 to 5, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI is aromatic, $R_{18}$ is —$(CR_{19}R_{19})_p$—, p is 0 to 5, and $R_{19}$ are independently hydrogen or $C_1$-$C_3$ alkyl. In some embodiments, z is 0. In some embodiments z is 1. In some embodiment z is 2. In some embodiments z is 3. In some embodiment z is 4. In some embodiments z is 5. In some embodiment, p is 0. In some embodiments p is 1. In some embodiment p is 2. In some embodiments p is 3. In some embodiment p is 4. In some embodiments p is 5. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen. In some embodiments, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$.

In some embodiments where at least one C is Formula VI, $R_4$ is hydrogen, and $R_5$ is Formula VI, in such C and $R_5$: $R_{12}$, $R_{13}$, $R_{14}$, $R_{15}$, $R_{16}$, and $R_{17}$ are carbon, z is 1, $R^d$ is —$NH_2$, the ring of Formula VI is aromatic, $R_{18}$ is —$(CR_{19}R_{19})_p$—, p is 0, and $R^d$ is at $R_{15}$.

Z2-Y12

In some embodiments, the compounds are represented by the general formula:

Formula I wherein X is oxygen, sulfur, $NR_2$, or another group compatible with attachment or coupling of the compound to a product or surface;
wherein $R_1$ is -A-B(—C)$_\delta$ or —$R_3$—$R^b$;
wherein A and $R_3$ are

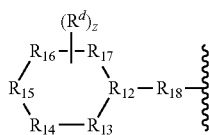
Formula VI wherein for A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 0 to 10, and $R_{19}$ are independently hydrogen or $C_1$-$C_3$ alkyl;
wherein B and $R^b$ are:

Formula III wherein each C, $R_4$, and $R_5$ are independently hydrogen or

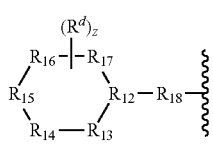
Formula VI wherein for C, $R_4$, and $R_5$, $R_{12}$ is carbon, one or two of nonadjacent $R_{13}$, $R_{14}$, $R_{15}$, $R_{16}$, and $R_{17}$ are O, the rest of $R_{13}$, $R_{14}$, $R_{15}$, $R_{16}$, and $R_{17}$ are carbon, z is 0 to 3, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI has no double bonds, $R_{18}$ is —$(CR_{19}R_{19})_p$—$X_b$—$(CR_{19}R_{19})_q$—, p is 0 to 5, q is 0 to 5, $R_{19}$ are independently hydrogen or $C_1$-$C_3$ alkyl, and $X_b$ is O.
X is preferably oxygen, sulfur, or $NR_2$.

In some embodiments where A or $R_3$ is Formula VI, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where A or $R_3$ is Formula VI, in such A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 1, and $R_{19}$ are hydrogen.

In some embodiments where one or more of C, $R_4$, and $R_5$ are Formula VI, in such C, $R_4$, and $R_5$: $R_{12}$ is carbon, one or two of nonadjacent $R_{13}$, $R_{14}$, $R_{15}$, $R_{16}$, and $R_{17}$ are O, the rest of $R_{13}$, $R_{14}$, $R_{15}$, $R_{16}$, and $R_{17}$ are carbon, z is 0 to 3, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI has no double bonds, $R_{18}$ is —$(CR_{19}R_{19})_p$—$X_b$—$(CR_{19}R_{19})_q$—, p is 0 to 5, q is 0 to 5, $R_{19}$ are independently hydrogen or $C_1$-$C_3$ alkyl, and $X_b$ is O. In some embodiments $R_4$ is hydrogen. In some embodiments, $R_5$ is hydrogen. In some embodiments, $R_{13}$ is O and $R_{14}$, $R_{15}$, $R_{16}$, and $R_{17}$ are carbon. In some embodiments, $R_{14}$ is O and $R_{13}$, $R_{15}$, $R_{16}$, and $R_{17}$ are carbon. In some embodiments, $R_{15}$ is O and $R_{13}$, $R_{14}$, $R_{16}$, and $R_{17}$ are carbon. In some embodiments, $R_{16}$ is O and $R_{13}$, $R_{14}$, $R_{15}$, and $R_{17}$ are carbon. In some embodiments, $R_{17}$ is O and $R_{13}$, $R_{14}$, $R_{15}$, and $R_{16}$ are carbon. In some embodiments, $R_{13}$ and $R_{15}$ are O. In some embodiments, $R_{13}$ and $R_{16}$ are O. In some embodiments, $R_{13}$ and $R_{17}$ are O. In some embodiments, $R_{14}$ and $R_{16}$ are O. In some embodiments, $R_{14}$ and $R_{17}$ are O. In some embodiments, $R_{15}$ and $R_{17}$ are O. In some embodiments z is 0. In some embodiments z is 1. In some embodiments z is 2. In some embodiments z is 3. In some embodiments $R^d$ is independently methyl, ethyl, methoxy, ethoxy, amino methyl, amino ethyl, hydroxyl, or amino. In some embodiments, p is 0. In some embodiments p is 1. In some embodiment p is 2. In some embodiments p is 3. In some embodiments p is 4. In some embodiments p is 5. In some embodiments, q is 0. In some embodiments q is 1. In some embodiment q is 2. In some embodiments q is 3. In some embodiments q is 4. In some embodiments q is 5. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where at least one C is Formula VI, $R_4$ is hydrogen, and $R_5$ is Formula VI, in such C and $R_5$: $R_{13}$ is O, $R_{12}$, $R_{14}$, $R_{15}$, $R_{16}$, and $R_{17}$ are carbon, z is 0, the ring of Formula VI has no double bonds, $R_{18}$ is —$(CR_{19}R_{19})_p$—$X_b$—$(CR_{19}R_{19})_q$—, p is 0, q is 1, both $R_{19}$ are hydrogen, and $X_b$ is O.

Z1-Y15

In some embodiments the compounds are represented by the general formula:

Formula I wherein X is oxygen, sulfur, $NR_2$, or another group compatible with attachment or coupling of the compound to a product or surface;

wherein $R_1$ is $-A-B(-C)_\delta$ or $-R_3-R^b$;

wherein A and $R_3$ are $-R_h-(R_g)_j$, wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein B and $R^b$ is:

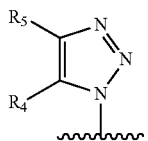

Formula III wherein each C, $R_4$, and $R_5$ are independently hydrogen or

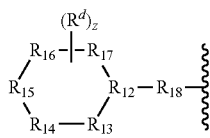

Formula VI wherein for C, $R_4$, and $R_5$, $R_{12}$ is N, $R_{15}$ is $S(O)_2$, $R_{13}$, $R_{14}$, $R_{16}$, and $R_{17}$ are carbon, the ring of Formula VI has no double bonds, $R_{18}$ is $-(CR_{19}R_{19})_p-$, p is 0 to 10, and $R_{19}$ are independently hydrogen or $C_1$-$C_3$ alkyl;

wherein $R_4$ and $R_5$ are not both hydrogen, wherein at least one C is not hydrogen.

X is preferably oxygen, sulfur, or $NR_2$.

In some embodiments where A or $R_3$ is $-R_h-(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where $R_3$ is $-R_h-(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments where one or more of C, $R_4$, and $R_5$ are Formula VI, in such C, $R_4$, and $R_5$: $R_{12}$ is N, $R_{15}$ is $S(O)_2$, $R_{13}$, $R_{14}$, $R_{16}$, and $R_{17}$ are carbon, the ring of Formula VI has no double bonds, $R_{18}$ is $-(CR_{19}R_{19})_p-$, p is 0 to 10, and $R_{19}$ are independently hydrogen or $C_1$-$C_3$ alkyl. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where at least one C is Formula VI, $R_4$ is hydrogen, and $R_5$ is Formula VI, in such C and $R_5$: $R_{12}$ is N, $R_{15}$ is $S(O)_2$, $R_{13}$, $R_{14}$, $R_{16}$, and $R_{17}$ are carbon, the ring of Formula VI has no double bonds, $R_{18}$ is $-(CR_{19}R_{19})_p-$, p is 1, and both $R_{19}$ are hydrogen.

Z1-Y19

In some embodiments, compounds are represented by the general formula:

$$-X-R_1$$  Formula I wherein X is oxygen, sulfur, $NR_2$, or another group compatible with attachment or coupling of the compound to a product or surface;

wherein $R_1$ is $-A-B(-C)_\delta$ or $-R_3-R^b$;

wherein A and $R_3$ are $-R_h-(R_g)_j$, wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein B and $R^b$ are:

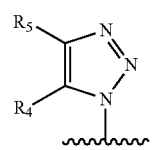

Formula III wherein each C, $R_4$, and $R_5$ are independently hydrogen or

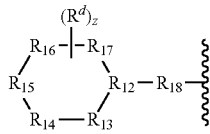
Formula VI wherein $R_{12}$, $R_{13}$, $R_{14}$, $R_{15}$, $R_{16}$, and $R_{17}$ are carbon, z is 0 to 5, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI is aromatic, $R_{18}$ is —$(CR_{19}R_{19})_p$—, p is 0 to 5, and $R_{19}$ are independently hydrogen or $C_1$-$C_3$ alkyl;

wherein $R_4$ and $R_5$ are not both hydrogen, wherein at least one of C is not hydrogen.

X is preferably oxygen, sulfur, or $NR_2$.

In some embodiments where A or $R_3$ is —$R_h$—$(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is —$R_h$—$(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments where one or more of C, $R_4$, and $R_5$ are Formula VI, in such C, $R_4$, and $R_5$: $R_{12}$, $R_{13}$, $R_{14}$, $R_{15}$, $R_{16}$, and $R_{17}$ are carbon, z is 0 to 5, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI is aromatic, $R_{18}$ is —$(CR_{19}R_{19})_p$—, p is 0 to 5, and $R_{19}$ are independently hydrogen or $C_1$-$C_3$ alkyl. In some embodiments, z is 0. In some embodiments z is 1. In some embodiment z is 2. In some embodiments z is 3. In some embodiment z is 4. In some embodiments z is 5. In some embodiments, p is 0. In some embodiment p is 1. In some embodiment p is 2. In some embodiment p is 3. In some embodiment p is 4. In some embodiment p is 5. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen. In some embodiments, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$.

In some embodiments where at least one C is Formula VI, $R_4$ is hydrogen, and $R_5$ is Formula VI, in such C and $R_5$: $R_{12}$, $R_{13}$, $R_{14}$, $R_{15}$, $R_{16}$, and $R_{17}$ are carbon, z is 1, $R^d$ is —$NH_2$, the ring of Formula VI is aromatic, $R_{18}$ is —$(CR_{19}R_{19})_p$—, p is 0, and $R^d$ is at $R_{15}$.

Z1-Y18

In some embodiments, compounds are represented by the general formula:

$$—X—R_1$$  Formula I wherein X is oxygen, sulfur, $NR_2$, or another group compatible with attachment or coupling of the compound to a product or surface;

wherein $R_1$ is -A-B(—C)$_\delta$ or —$R_3$—$R^b$;

wherein A and $R_3$ are —$R_h$—$(R_g)_j$, wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein B and $R^b$ are:

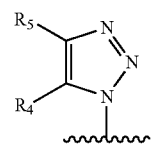
Formula III wherein each C, $R_4$, and $R_5$ are independently hydrogen or —$R_h$—$(R_g)_j$, wherein $R_h$ is $C(R_{39}R_{40})$, j is 1 to 15, and each $R_g$ is $C(R_{42}R_{43})$, wherein $R_{42}$ is =O and $R_{43}$ is absent for two $R_g$, $R_{42}$ and $R_{43}$ are hydrogen for the other $R_g$, and $R_{39}$ and $R_{40}$ are hydrogen;

wherein $R_4$ and $R_5$ are not both hydrogen, wherein at least one of C is not hydrogen.

X is preferably oxygen, sulfur, or $NR_2$.

In some embodiments where A or $R_3$ is —$R_h$—$(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is —$R_h$—$(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments $R_h$ is $C(R_{39}R_{40})$, and j is 0, wherein $R_{39}$ is =O, and $R_{40}$ is absent. In some embodiments $R_h$ is $C(R_{39}R_{40})$, j is 0 to 10, and each $R_g$ is $C(R_{42}R_{43})$, wherein $R_{39}$ is =O, $R_{40}$ is absent, and $R_{42}$ and $R_{43}$ are hydrogen. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

In some embodiments $R_h$ is $C(R_{39}R_{40})$, j is 1 to 10, and each $R_g$ is $C(R_{42}R_{43})$, wherein $R_{42}$ is =O and $R_{43}$ is absent for one $R_g$, $R_{42}$ and $R_{43}$ are hydrogen for the other $R_g$, and $R_{39}$ and $R_{40}$ are hydrogen. In some embodiments $R_{42}$ is =O and $R_{43}$ is absent for the last $R_g$. In some embodiments $R_{42}$ is =O and $R_{43}$ is absent for the penultimate $R_g$. In some embodiments $R_{42}$ is =O and $R_{43}$ is absent for the antepenultimate $R_g$. In some embodiments $R_{42}$ is =O and $R_{43}$ is absent for the fourth from the last $R_g$. In some embodiments $R_{42}$ is =O and $R_{43}$ is absent for the fifth from the last $R_g$. In some embodiments $R_{42}$ is =O and $R_{43}$ is absent for the first $R_g$. In some embodiments $R_{42}$ is =O and $R_{43}$ is absent for the second $R_g$. In some embodiments $R_{42}$ is =O and $R_{43}$ is absent for the third $R_g$. In some embodiments $R_{42}$ is =O and $R_{43}$ is absent for the fourth $R_g$. In some embodiments $R_{42}$ is =O and $R_{43}$ is absent for the fifth $R_g$.

In some embodiments $R_h$ is $C(R_{39}R_{40})$, j is 1 to 15, and each $R_g$ is $C(R_{42}R_{43})$, wherein $R_{42}$ is =O and $R_{43}$ is absent for two $R_g$, $R_{42}$ and $R_{43}$ are hydrogen for the other $R_g$, and $R_{39}$ and $R_{40}$ are hydrogen. In some embodiments $R_{42}$ is =O and $R_{43}$ is absent the first and third $R_g$. In some embodiments $R_{42}$ is =O and $R_{43}$ is absent the first and fourth $R_g$. In some embodiments $R_{42}$ is =O and $R_{43}$ is absent the first and fifth $R_g$. In some embodiments $R_{42}$ is =O and $R_{43}$ is absent the first and sixth $R_g$. In some embodiments $R_{42}$ is =O and $R_{43}$ is absent the first and seventh $R_g$. In some embodiments $R_{42}$ is =O and $R_{43}$ is absent the first and eighth $R_g$. In some embodiments $R_{42}$ is =O and $R_{43}$ is absent the first and ninth $R_g$. In some embodiments $R_{42}$ is =O and $R_{43}$ is absent the first and tenth $R_g$. In some embodiments $R_{42}$ is =O and $R_{43}$ is absent the first and eleventh $R_g$. In some embodiments $R_{42}$ is =O and $R_{43}$ is absent the first and twelfth $R_g$. In some embodiments $R_{42}$ is =O and $R_{43}$ is absent the first and thirteenth $R_g$. In some embodiments $R_{42}$ is =O and $R_{43}$ is absent the first and fourteenth $R_g$. In some embodiments $R_{42}$ is =O and $R_{43}$ is absent the first and fifteenth $R_g$. In some embodiments $R_{42}$ is =O and $R_{43}$ is absent the second and fourth $R_g$. In some embodiments $R_{42}$ is =O and $R_{43}$ is absent the second and fifth $R_g$. In some embodiments $R_{42}$ is =O and $R_{43}$ is absent the second and sixth $R_g$. In some embodiments $R_{42}$ is =O and $R_{43}$ is absent the second and seventh $R_g$. In some embodiments $R_{42}$ is =O and $R_{43}$ is absent the second and eighth $R_g$. In some embodiments $R_{42}$ is =O and $R_{43}$ is absent the second and ninth $R_g$. In some embodiments $R_{42}$ is =O and $R_{43}$ is absent the second and tenth $R_g$. In some embodiments $R_{42}$ is =O and $R_{43}$ is absent the second and eleventh $R_g$. In some embodiments $R_{42}$ is =O and $R_{43}$ is absent the second and twelfth $R_g$. In some embodiments $R_{42}$ is =O and $R_{43}$ is absent the second and thirteenth $R_g$. In some embodiments $R_{42}$ is =O and $R_{43}$ is absent the second and fourteenth $R_g$. In some embodiments $R_{42}$ is =O and $R_{43}$ is absent the second and fifteenth $R_g$. In some embodiments $R_{42}$ is =O and $R_{43}$ is absent the third and fifth $R_g$. In some embodiments $R_{42}$ is =O and $R_{43}$ is absent the third and sixth $R_g$. In some embodiments $R_{42}$ is =O and $R_{43}$ is absent the third and seventh $R_g$. In some embodiments $R_{42}$ is =O and $R_{43}$ is absent the third and eighth $R_g$. In some embodiments $R_{42}$ is =O and $R_{43}$ is absent the third and ninth $R_g$. In some embodiments $R_{42}$ is =O and $R_{43}$ is absent the third and tenth $R_g$. In some embodiments $R_{42}$ is =O and $R_{43}$ is absent the third and eleventh $R_g$. In some embodiments $R_{42}$ is =O and $R_{43}$ is absent the third and twelfth $R_g$. In some embodiments $R_{42}$ is =O and $R_{43}$ is absent the third and thirteenth $R_g$. In some embodiments $R_{42}$ is =O and $R_{43}$ is absent the third and fourteenth $R_g$. In some embodiments $R_{42}$ is =O and $R_{43}$ is absent the third and fifteenth $R_g$. In some embodiments $R_{42}$ is =O and $R_{43}$ is absent the fourth and sixth $R_g$. In some embodiments $R_{42}$ is =O and $R_{43}$ is absent the fourth and seventh $R_g$. In some embodiments $R_{42}$ is =O and $R_{43}$ is absent the fourth and eighth $R_g$. In some embodiments $R_{42}$ is =O and $R_{43}$ is absent the fourth and ninth $R_g$. In some embodiments $R_{42}$ is =O and $R_{43}$ is absent the fourth and tenth $R_g$. In some embodiments $R_{42}$ is =O and $R_{43}$ is absent the fourth and eleventh $R_g$. In some embodiments $R_{42}$ is =O and $R_{43}$ is absent the fourth and twelfth $R_g$. In some embodiments $R_{42}$ is =O and $R_{43}$ is absent the fourth and thirteenth $R_g$. In some embodiments $R_{42}$ is =O and $R_{43}$ is absent the fourth and fourteenth $R_g$. In some embodiments $R_{42}$ is =O and $R_{43}$ is absent the fourth and fifteenth $R_g$. In some embodiments $R_{42}$ is =O and $R_{43}$ is absent the fifth and seventh $R_g$. In some embodiments $R_{42}$ is =O and $R_{43}$ is absent the fifth and eighth $R_g$. In some embodiments $R_{42}$ is =O and $R_{43}$ is absent the fifth and ninth $R_g$. In some embodiments $R_{42}$ is =O and $R_{43}$ is absent the fifth and tenth $R_g$. In some embodiments $R_{42}$ is =O and $R_{43}$ is absent the fifth and eleventh $R_g$. In some embodiments $R_{42}$ is =O and $R_{43}$ is absent the fifth and twelfth $R_g$. In some embodiments $R_{42}$ is =O and $R_{43}$ is absent the fifth and thirteenth $R_g$. In some embodiments $R_{42}$ is =O and $R_{43}$ is absent the fifth and fourteenth $R_g$. In some embodiments $R_{42}$ is =O and $R_{43}$ is absent the fifth and fifteenth $R_g$. In some embodiments $R_{42}$ is =O and $R_{43}$ is absent the sixth and eighth $R_g$. In some embodiments $R_{42}$ is =O and $R_{43}$ is absent the sixth and ninth $R_g$. In some embodiments $R_{42}$ is =O and $R_{43}$ is absent the sixth and tenth $R_g$. In some embodiments $R_{42}$ is =O and $R_{43}$ is absent the sixth and eleventh $R_g$. In some embodiments $R_{42}$ is =O and $R_{43}$ is absent the sixth and twelfth $R_g$. In some embodiments $R_{42}$ is =O and $R_{43}$ is absent the sixth and thirteenth $R_g$. In some embodiments $R_{42}$ is =O and $R_{43}$ is absent the sixth and fourteenth $R_g$. In some embodiments $R_{42}$ is =O and $R_{43}$ is absent the sixth and fifteenth $R_g$. In some embodiments $R_{42}$ is =O and $R_{43}$ is absent the seventh and ninth $R_g$. In some embodiments $R_{42}$ is =O and $R_{43}$ is absent the seventh and tenth $R_g$. In some embodiments $R_{42}$ is =O and $R_{43}$ is absent the seventh and eleventh $R_g$. In some embodiments $R_{42}$ is =O and $R_{43}$ is absent the seventh and twelfth $R_g$. In some embodiments $R_{42}$ is =O and $R_{43}$ is absent the seventh and thirteenth $R_g$. In some embodiments $R_{42}$ is =O and $R_{43}$ is absent the seventh and fourteenth $R_g$. In some embodiments $R_{42}$ is =O and $R_{43}$ is absent the seventh and fifteenth $R_g$. In some embodiments $R_{42}$ is =O and $R_{43}$ is absent the eighth and tenth $R_g$. In some embodiments $R_{42}$ is =O and $R_{43}$ is absent the eighth and eleventh $R_g$. In some embodiments $R_{42}$ is =O and $R_{43}$ is absent the eighth and twelfth $R_g$. In some embodiments $R_{42}$ is =O and $R_{43}$ is absent the eighth and thirteenth $R_g$. In some embodiments $R_{42}$ is =O and $R_{43}$ is absent the eighth and fourteenth $R_g$. In some embodiments $R_{42}$ is =O and $R_{43}$ is absent the eighth and fifteenth $R_g$. In some embodiments $R_{42}$ is =O and $R_{43}$ is absent the ninth and eleventh $R_g$. In some embodiments $R_{42}$ is =O and $R_{43}$ is absent the ninth and twelfth $R_g$. In some embodiments $R_{42}$ is =O and $R_{43}$ is absent the ninth and thirteenth $R_g$. In some embodiments $R_{42}$ is =O and $R_{43}$ is absent the ninth and fourteenth $R_g$. In some embodiments $R_{42}$ is =O and $R_{43}$ is absent the ninth and fifteenth $R_g$. In some embodiments $R_{42}$ is =O and $R_{43}$ is absent the tenth and twelfth $R_g$. In some embodiments $R_{42}$ is =O and $R_{43}$ is absent the tenth and thirteenth $R_g$. In some embodiments $R_{42}$ is =O and $R_{43}$ is absent the tenth and fourteenth $R_g$. In some embodiments $R_{42}$ is =O and $R_{43}$ is absent the tenth and fifteenth $R_g$. In some embodiments $R_{42}$ is =O and $R_{43}$ is absent the eleventh and thirteenth $R_g$. In some embodiments $R_{42}$ is =O and $R_{43}$ is absent the eleventh and fourteenth $R_g$. In some embodiments $R_{42}$ is =O and $R_{43}$ is absent the eleventh and fifteenth $R_g$. In some embodiments $R_{42}$ is =O and $R_{43}$ is absent the twelfth and fourteenth $R_g$. In some embodiments $R_{42}$ is =O and $R_{43}$ is absent the twelfth and fifteenth $R_g$. In some embodiments the thirteenth and fifteenth $R_g$.

Z1-Y12

In some embodiments, compounds are represented by the general formula:

 Formula I wherein X is oxygen, sulfur, $NR_2$, or another group compatible with attachment or coupling of the compound to a product or surface;
wherein $R_1$ is -A-B(—C)$_\delta$ or —$R_3$—$R^b$;
wherein A and $R_3$ are —$R_h$—$(R_g)_j$,
wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;
wherein B and $R^b$ are:

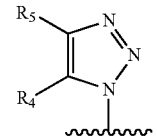 Formula III wherein each C, $R_4$, and $R_5$ are independently hydrogen or

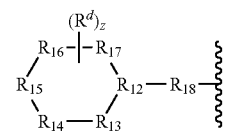 Formula VI wherein for C, $R_4$, and $R_5$, $R_{12}$ is carbon, one or two of nonadjacent $R_{13}$, $R_{14}$, $R_{15}$, $R_{16}$, and $R_{17}$ are O, the rest of $R_{13}$, $R_{14}$, $R_{15}$, $R_{16}$, and $R_{17}$ are carbon, z is 0 to 3, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI has no double bonds, $R_{18}$ is —$(CR_{19}R_{19})_p$—$X_b$—$(CR_{19}R_{19})_q$—, p is 0 to 5, q is 0 to 5, $R_{19}$ are independently hydrogen or $C_1$-$C_3$ alkyl, and $X_b$ is O;
wherein $R_4$ and $R_5$ are not both hydrogen, wherein at least one of C is not hydrogen.

X is preferably oxygen, sulfur, or $NR_2$.

In some embodiments where A or $R_3$ is —$R_h$—$(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is —$R_h$—$(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments where one or more of C, $R_4$, and $R_5$ are Formula VI, in such C, $R_4$, and $R_5$: $R_{12}$ is carbon, one or two of nonadjacent $R_{13}$, $R_{14}$, $R_{15}$, $R_{16}$, and $R_{17}$ are O, the rest of $R_{13}$, $R_{14}$, $R_{15}$, $R_{16}$, and $R_{17}$ are carbon, z is 0 to 3, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI has no double bonds, $R_{18}$ is —$(CR_{19}R_{19})_p$—$X_b$—$(CR_{19}R_{19})_q$—, p is 0 to 5, q is 0 to 5, $R_{19}$ are independently hydrogen or $C_1$-$C_3$ alkyl, and $X_b$ is O.

In some embodiments where one or more of C, $R_4$, and $R_5$ are Formula VI, in such C, $R_4$, and $R_5$: $R_{12}$ is carbon, one or two of nonadjacent $R_{13}$, $R_{14}$, $R_{15}$, $R_{16}$, and $R_{17}$ are O, the rest of $R_{13}$, $R_{14}$, $R_{15}$, $R_{16}$, and $R_{17}$ are carbon, z is 0 to 3, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI has no double bonds, $R_{18}$ is —$(CR_{19}R_{19})_p$—$X_b$—$(CR_{19}R_{19})_q$—, p is 0 to 5, q is 0 to 5, $R_{19}$ are independently hydrogen or $C_1$-$C_3$ alkyl, and $X_b$ is O. In some embodiments $R_4$ is hydrogen. In some embodiments, $R_5$ is hydrogen. In some embodiments, $R_{13}$ is O and $R_{14}$, $R_{15}$, $R_{16}$, and $R_{17}$ are carbon. In some embodiments, $R_{14}$ is O and $R_{13}$, $R_{15}$, $R_{16}$, and $R_{17}$ are carbon. In some embodiments, $R_{15}$ is O and $R_{13}$, $R_{14}$, $R_{16}$, and $R_{17}$ are carbon. In some embodiments, $R_{16}$ is O and $R_{13}$, $R_{14}$, $R_{15}$, and $R_{17}$ are carbon. In some embodiments, $R_{17}$ is O and $R_{13}$, $R_{14}$, $R_{15}$, and $R_{16}$ are carbon. In some embodiments, $R_{13}$ and $R_{15}$ are O. In some embodiments, $R_{13}$ and $R_{16}$ are O. In some embodiments, $R_{13}$ and $R_{17}$ are O. In some embodiments, $R_{14}$ and $R_{16}$ are O. In some embodiments, $R_{14}$ and $R_{17}$ are O. In some embodiments, $R_{15}$ and $R_{17}$ are O. In some embodiments z is 0. In some embodiments z is 1. In some embodiments z is 2. In some embodiments z is 3. In some embodiments $R^d$ is independently methyl, ethyl, methoxy, ethoxy, amino methyl, amino ethyl, hydroxyl, or amino. In some embodiments, p is 0. In some embodiments p is 1. In some embodiment p is 2. In some embodiments p is 3. In some embodiments p is 4. In some embodiments p is 5. In some embodiments, q is 0. In some embodiments q is 1. In some embodiment q is 2. In some embodiments q is 3. In some embodiments q is 4. In some embodiments q is 5. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where at least one C is Formula VI, $R_4$ is hydrogen, and $R_5$ is Formula VI, in such C and $R_5$: $R_{13}$ is O, $R_{12}$, $R_{14}$, $R_{15}$, $R_{16}$, and $R_{17}$ are carbon, z is 0, the ring of Formula VI has no double bonds, $R_{18}$ is —$(CR_{19}R_{19})_p$—$X_b$—$(CR_{19}R_{19})_q$—, p is 0, q is 1, both $R_{19}$ are hydrogen, and $X_b$ is O.

Z1-Y17

In some embodiments, compounds are represented by the general formula:

—X—$R_1$     Formula I wherein X is oxygen, sulfur, $NR_2$, or another group compatible with attachment or coupling of the compound to a product or surface;

wherein $R_1$ is -A-B(—C)$_\delta$ or —$R_3$—$R^b$;

wherein A and $R_3$ are —$R_h$—$(R_g)_j$, wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein B and $R^b$ are:

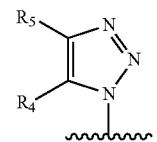

Formula III wherein each C, $R_4$, and $R_5$ are independently hydrogen or

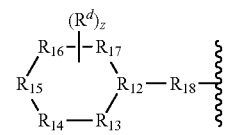

Formula VI wherein for C, $R_4$, and $R_5$, $R_{12}$, $R_{13}$, $R_{14}$, $R_{15}$, $R_{16}$, and $R_{17}$ are carbon, z is 0 to 3, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI is aromatic, $R_{18}$ is —$(CR_{19}R_{19})_p$—, and p is 0;

wherein $R_4$ and $R_5$ are not both hydrogen, wherein at least one of C is not hydrogen.

X is preferably oxygen, sulfur, or $NR_2$.

In some embodiments where A or $R_3$ is —$R_h$—$(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is —$R_h$—$(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments, in Formula VI, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, and p is 0.

In some embodiments, in Formula VI, $R_{12}$, $R_{13}$, $R_{14}$, $R_{15}$, $R_{16}$, and $R_{17}$ are carbon, z is 1, $R^d$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI is aromatic, $R_{18}$ is —$(CR_{19}R_{19})_p$—, and p is 0.

Z1-Y1

In some embodiments, compounds are represented by the general formula:

$$—X—R_1 \quad \text{Formula I}$$

wherein X is oxygen, sulfur, $NR_2$, or another group compatible with attachment or coupling of the compound to a product or surface;

wherein $R_1$ is -A-B(—C)$_\delta$ or —$R_3$—$R^b$;

wherein A and $R_3$ are —$R_h$—$(R_g)_j$, wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein B and $R^b$ are:

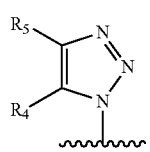
Formula III wherein each C, $R_4$, and $R_5$ are independently hydrogen or

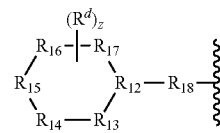
Formula VI wherein for C, $R_4$, and $R_5$, $R_{12}$, $R_{13}$, $R_{14}$, $R_{15}$, $R_{16}$, and $R_{17}$ are carbon, z is 1, $R^d$ is hydroxy, $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula VI has no double bonds, $R_{18}$ is —$(CR_{19}R_{19})_p$—, and p is 0;

wherein $R_4$ and $R_5$ are not both hydrogen, wherein at least one of C is not hydrogen.

X is preferably oxygen, sulfur, or $NR_2$.

In some embodiments where A or $R_3$ is —$R_h$—$(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is —$R_h$—$(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments, in Formula VI, $R_{12}$, $R_{13}$, $R_{14}$, $R_{15}$, $R_{16}$, and $R_{17}$ are carbon, z is 1, $R_d$ is hydroxy, the ring of Formula VI has no double bonds, $R_{18}$ is —$(CR_{19}R_{19})_p$—, and p is 0. In some embodiments, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$.

Z1-Y9

In some embodiments, compounds are represented by the general formula:

   Formula I wherein X is oxygen, sulfur, $NR_2$, or another group compatible with attachment or coupling of the compound to a product or surface;

wherein $R_1$ is -A-B(—C)$_\delta$ or —$R_3$—$R^b$;

wherein A and $R_3$ are —$R_h$—$(R_g)_j$, wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein B and $R^b$ are:

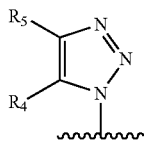   Formula III wherein C and $R_5$ are independently hydrogen or

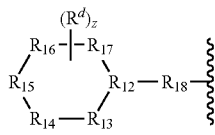   Formula VI wherein C and $R_4$, independently hydrogen or —$R_h$—$(R_g)_j$, wherein for C and $R_5$, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, and p is 0; wherein $R_h$ is $C(R_{39}R_{40})$, and j is 0, wherein $R_{39}$ is =O and $R_{40}$ is —OH. In some embodiments $R_h$ is absent, j is 0 to 10, and each $R_g$ is $C(R_{42}R_{43})$, wherein $R_{42}$ and $R_{43}$ are hydrogen;

wherein $R_4$ and $R_5$ are not both hydrogen, wherein at least one of C is not hydrogen.

X is preferably oxygen, sulfur, or $NR_2$.

In some embodiments where A or $R_3$ is —$R_h$—$(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is —$R_h$—$(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments, one C or $R_4$ is —$R_h$—$(R_g)_j$, and one C or $R_5$ is, wherein in Formula VI, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, and p is 0, wherein $R_h$ is $C(R_{39}R_{40})$, and j is 0, wherein $R_{39}$ is =O and $R_{40}$ is —OH. In some embodiments $R_h$ is absent, j is 0 to 10, and each $R_g$ is $C(R_{42}R_{43})$, wherein $R_{42}$ and $R_{43}$ are hydrogen.

Z1-Y2

In some embodiments, compounds are represented by the general formula:

   Formula I wherein X is oxygen, sulfur, $NR_2$, or another group compatible with attachment or coupling of the compound to a product or surface;

wherein $R_1$ is -A-B(—C)$_\delta$ or —$R_3$—$R^b$;

wherein A and $R_3$ are —$R_h$—$(R_g)_j$, wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein B and $R^b$ are:

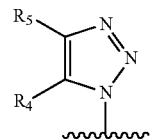   Formula III wherein each C, $R_4$, and $R_5$ are independently hydrogen or

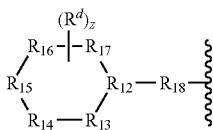

Formula VI wherein for C, $R_4$, and $R_5$, $R_{12}$, $R_{13}$, $R_{14}$, $R_{15}$, $R_{16}$, and $R_{17}$ are carbon, z is 1, $R^d$ is —O—$CH_3$, the ring of Formula VI is aromatic, $R_{18}$ is —$(CR_{19}R_{19})_p$—, and p is 0. In some embodiments, $R^d$ is at $R_{15}$;

wherein $R_4$ and $R_5$ are not both hydrogen, wherein at least one of C is not hydrogen.

X is preferably oxygen, sulfur, or $NR_2$.

In some embodiments where A or $R_3$ is —$R_h$—$(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is —$R_h$—$(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments, in Formula VI, $R_{12}$, $R_{13}$, $R_{14}$, $R_{15}$, $R_{16}$, and $R_{17}$ are carbon, z is 1, $R_d$ is —O—$CH_3$, the ring of Formula VI is aromatic, $R_{18}$ is —$(CR_{19}R_{19})_p$—, and p is 0.

In some embodiments, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$.

Z2-Y13

In some embodiments, the compounds are represented by the general formula:

—X—$R_1$     Formula I wherein X is oxygen, sulfur, $NR_2$, or another group compatible with attachment or coupling of the compound to a product or surface;

wherein $R_1$ is -A-B(—C)$_\delta$ or —$R_3$—$R^b$;

wherein A and $R_3$ are

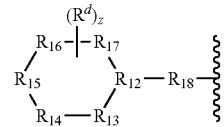

Formula VI wherein for A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 0 to 10, and $R_{19}$ are independently hydrogen or $C_1$-$C_3$ alkyl;

wherein B and $R^b$ are:

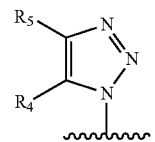

Formula III wherein each C, $R_4$, and $R_5$ are independently hydrogen or

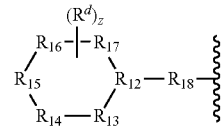

Formula VI wherein for C, $R_4$, and $R_5$, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, one $R_{19}$ is —OH, the other $R_{19}$ is hydrogen, and p is 1;

wherein $R_4$ and $R_5$ are not both hydrogen, wherein at least one of C is not hydrogen.

X is preferably oxygen, sulfur, or $NR_2$.

In some embodiments where A or $R_3$ is Formula VI, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where A or $R_3$ is Formula VI, in such A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 1, and $R_{19}$ are hydrogen.

In some embodiments, in Formula VI, $R_{12}$, $R_{13}$, $R_{14}$, $R_{15}$, $R_{16}$, and $R_{17}$ are carbon, z is 0, the ring of Formula VI is aromatic, $R_{18}$ is —$(CR_{19}R_{19})_p$—, one $R_{19}$ is —OH, the other $R_{19}$ is hydrogen, and p is 1.

Z2-Y5

In some embodiments, the compounds are represented by the general formula:

   Formula I wherein X is oxygen, sulfur, $NR_2$, or another group compatible with attachment or coupling of the compound to a product or surface;

wherein $R_1$ is -A-B(—C)$_\delta$ or —$R_3$—$R^b$;

wherein A and $R_3$ are

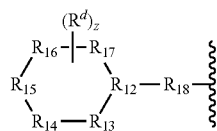   Formula VI wherein for A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 0 to 10, and $R_{19}$ are independently hydrogen or $C_1$-$C_3$ alkyl;

wherein B and $R^b$ are:

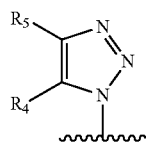   Formula III wherein each C, $R_4$, and $R_5$ are independently hydrogen or

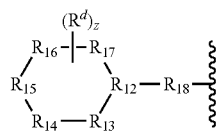   Formula VI wherein for C, $R_4$, and $R_5$, $R_{12}$, $R_{13}$, $R_{14}$, $R_{15}$, $R_{16}$, and $R_{17}$ are carbon, z is 1, $R^d$ is methyl, the ring of Formula VI is aromatic, $R_{18}$ is —$(CR_{19}R_{19})_p$—$X_b$—$(CR_{19}R_{19})_q$—, p is 0, q is 0, and $X_b$ is $S(O)_2$;

wherein $R_4$ and $R_5$ are not both hydrogen, wherein at least one of C is not hydrogen.

X is preferably oxygen, sulfur, or $NR_2$.

In some embodiments where A or $R_3$ is Formula VI, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiment p is 10. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where A or $R_3$ is Formula VI, in such A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 1, and $R_{19}$ are hydrogen.

In some embodiments, in Formula VI, $R_{12}$, $R_{13}$, $R_{14}$, $R_{15}$, $R_{16}$, and $R_{17}$ are carbon, z is 1, $R_d$ is methyl, the ring of Formula VI is aromatic, $R_{18}$ is —$(CR_{19}R_{19})_p$—$X_b$—$(CR_{19}R_{19})_q$—, p is 0, q is 0, and $X_b$ is $S(O)_2$.

Z2-Y7

In some embodiments, the compounds are represented by the general formula:

   Formula I wherein X is oxygen, sulfur, $NR_2$, or another group compatible with attachment or coupling of the compound to a product or surface;

wherein $R_1$ is -A-B(—C)$_\delta$ or —$R_3$—$R^b$;

wherein A and $R_3$ are

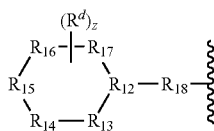   Formula VI wherein for A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 0 to 10, and $R_{19}$ are independently hydrogen or $C_1$-$C_3$ alkyl;

wherein B and $R^b$ are:

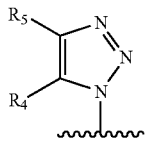   Formula III wherein each C, $R_4$, and $R_5$ are independently hydrogen or —$R_h$—$(R_g)_j$, wherein $R_h$ is $C(R_{39}R_{40})$, j is 1 to 10, one $R_g$ is O, the other $R_g$ are $C(R_{42}R_{43})$, and $R_f$ is $C(R_{45}R_{46}R_{47})$, wherein $R_{39}$, $R_{40}$, $R_{42}$, $R_{43}$, $R_{45}$, $R_{46}$, and $R_{47}$ are hydrogen;

wherein $R_4$ and $R_5$ are not both hydrogen, wherein at least one of C is not hydrogen.

X is preferably oxygen, sulfur, or $NR_2$.

In some embodiments where A or $R_3$ is Formula VI, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where A or $R_3$ is Formula VI, in such A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 1, and $R_{19}$ are hydrogen.

In some embodiments $R_h$ is $C(R_{39}R_{40})$, j is 1, $R_g$ is O, and $R_f$ is $C(R_{45}R_{46}R_{47})$, wherein $R_{39}$, $R_{40}$, $R_{45}$, $R_{46}$, and $R_{47}$ are hydrogen. In some embodiments $R_h$ is absent, j is 1, $R_g$ is O, and $R_f$ is $C(R_{45}R_{46}R_{47})$, wherein $R_{45}$, $R_{46}$, and $R_{47}$ are hydrogen.

In some embodiments $R_h$ is $C(R_{39}R_{40})$, j is 1 to 10, one $R_g$ is O, the other $R_g$ are $C(R_{42}R_{43})$, and $R_f$ is $C(R_{45}R_{46}R_{47})$, wherein $R_{39}$, $R_{40}$, $R_{42}$, $R_{43}$, $R_{45}$, $R_{46}$, and $R_{47}$ are hydrogen. In some embodiments the last $R_g$ is O. In some embodiments the penultimate $R_g$ is O. In some embodiments the antepenultimate $R_g$ is O. In some embodiments the fourth from the last $R_g$ is O. In some embodiments the fifth from the last $R_g$ is O. In some embodiments the first $R_g$ is O. In some embodiments the second $R_g$ is O. In some embodiments the third $R_g$ is O. In some embodiments the fourth $R_g$ is O. In some embodiments the fifth $R_g$ is O.

Z2-Y6

In some embodiments, the compounds are represented by the general formula:

Formula I wherein X is oxygen, sulfur, $NR_2$, or another group compatible with attachment or coupling of the compound to a product or surface;
wherein $R_1$ is -A-B(—C)$_\delta$ or —$R_3$—$R^b$;
wherein A and $R_3$ are

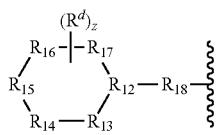

Formula VI wherein for A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 0 to 10, and $R_{19}$ are independently hydrogen or $C_1$-$C_3$ alkyl;
wherein B and $R^b$ are:

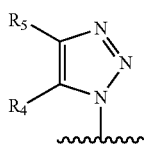

Formula III wherein each C, $R_4$, and $R_5$ are independently hydrogen or —$R_h$—$(R_g)_j$;
wherein for C and $R_5$, $R_h$ is $NR_{41}$, j is 0 to 10, and each $R_g$ is $C(R_{42}R_{43})$, wherein $R_{41}$ is —$R_{hx}$—$(R_{gx})_{jx}$—$R_{fx}$, and $R_{42}$ and $R_{43}$ are hydrogen, wherein $R_{hx}$ is $C(R_{39x}R_{40x})$, jx=0 to 10, $R_{gx}$ is $C(R_{42x}R_{43x})$, and $R_{fx}$ is $C(R_{45x}R_{46x}R_{47x})$, and wherein $R_{39x}$, $R_{40x}$, $R_{42x}$, $R_{43x}$, $R_{45x}$, $R_{46x}$, $R_{47x}$ are hydrogen; wherein for C and $R_4$, $R_h$ is $C(R_{39}R_{40})$, j is 0 to 10, and each $R_g$ is $C(R_{42}R_{43})$, wherein $R_{39}$, $R_{40}$ $R_{42}$, $R_{43}$ are hydrogen;
wherein $R_4$ and $R_5$ are not both hydrogen, wherein at least one of C is not hydrogen.

X is preferably oxygen, sulfur, or $NR_2$.

In some embodiments where A or $R_3$ is Formula VI, $R^d$ is at $R_{15}$. In some embodiments, $R^d$ is at $R_{13}$. In some embodiments, $R^d$ is at $R_{14}$. In some embodiments, $R^d$ is at $R_{16}$. In some embodiments, $R^d$ is at $R_{17}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{19}$ are hydrogen. In some embodiments all but one $R_{19}$ are hydrogen. In some embodiments all but two $R_{19}$ are hydrogen. In some embodiments all but three $R_{19}$ are hydrogen. In some embodiments all but four $R_{19}$ are hydrogen.

In some embodiments where A or $R_3$ is Formula VI, in such A and $R_3$, $R_{12}$, $R_{13}$, $R_{14}$, $R_{15}$, $R_{16}$, and $R_{17}$ are carbon, z is 1, $R^d$ is $R^b$, the ring of Formula VI is aromatic, $R_{18}$ is —$(CR_{19}R_{19})_p$—, p is 1, and $R_{19}$ are hydrogen.

In some embodiments $R_h$ is $NR_{41}$, j is 1, and $R_g$ is $C(R_{42}R_{43})$, wherein $R_{41}$ is —$R_{hx}$—$(R_{gx})_{jx}$—$R_{fx}$, and $R_{42}$ and $R_{43}$ are hydrogen, wherein $R_{hx}$ is absent, jx=1, $R_{gx}$ is $C(R_{42x}R_{43x})$, and $R_{fx}$ is $C(R_{45x}R_{46x}R_{47x})$, and wherein $R_{42x}$, $R_{43x}$, $R_{45x}$, $R_{46x}$, $R_{47x}$ are hydrogen.

In some embodiments $R_h$ is $NR_{41}$, j is 0 to 10, and each $R_g$ is $C(R_{42}R_{43})$, wherein $R_{41}$ is —$R_{hx}$—$(R_{gx})_{jx}$—$R_{fx}$, and $R_{42}$ and $R_{43}$ are hydrogen, wherein $R_{hx}$ is $C(R_{39x}R_{40x})$, jx=0 to 10, $R_{gx}$ is $C(R_{42x}R_{43x})$, and $R_{fx}$ is $C(R_{45x}R_{46x}R_{47x})$, and wherein $R_{39x}$, $R_{40x}$, $R_{42x}$, $R_{43x}$, $R_{45x}$, $R_{46x}$, $R_{47x}$ are hydrogen. In some embodiments j=jx. In some embodiments j and jx are 0. In some embodiment j and jx are 2. In some embodiments j and jx are 3. In some embodiments j and jx are 4.

In some embodiments $R_h$ is $C(R_{39}R_{40})$, and j is 0, wherein $R_{39}$ and $R_{40}$ are hydrogen. In some embodiments $R_h$ is $C(R_{39}R_{40})$, j is 0 to 10, and each $R_g$ is $C(R_{42}R_{43})$, wherein $R_{39}$, $R_{40}$ $R_{42}$, $R_{43}$ are hydrogen. In some embodiments j is 1. In some embodiment j is 2. In some embodiments j is 3. In some embodiments j is 4.

Z1-Y10

In some embodiments, compounds are represented by the general formula:

Formula I wherein X is oxygen, sulfur, $NR_2$, or another group compatible with attachment or coupling of the compound to a product or surface;
wherein $R_1$ is -A-B(—C)$_\delta$ or —$R_3$—$R^b$;
wherein A and $R_3$ are —$R_h$—$(R_g)_j$;
wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;
wherein B and $R^b$ are:

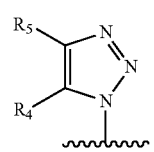

Formula III wherein each C, $R_4$, and $R_5$ are independently hydrogen or —$R_h$—$(R_g)_j$;

wherein $R_h$ is absent, j is 1 to 10, and each $R_g$ is $C(R_{42}R_{43})$, wherein $R_{42}$ and $R_{43}$ are hydrogen;

wherein $R_4$ and $R_5$ are not both hydrogen, wherein at least one of C is not hydrogen.

X is preferably oxygen, sulfur, or $NR_2$.

In some embodiments where A or $R_3$ is $-R_h-(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is $-R_h-(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments $R_h$ is absent, j is 6, and each $R_g$ is $C(R_{42}R_{43})$, wherein $R_{42}$ and $R_{43}$ are hydrogen. In some embodiments $R_h$ is absent, j is 1 to 10, and each $R_g$ is $C(R_{42}R_{43})$, wherein $R_{42}$ and $R_{43}$ are hydrogen. In some embodiments j is 3. In some embodiment j is 4. In some embodiments j is 5. In some embodiments j is 7. In some embodiment j is 8. In some embodiments j is 9. In some embodiments j is 10.

Z1-Y11

In some embodiments, compounds are represented by the general formula:

$-X-R_1$                                    Formula I wherein X is oxygen, sulfur, $NR_2$, or another group compatible with attachment or coupling of the compound to a product or surface;

wherein $R_1$ is -A-B($-C)_\delta$ or $-R_3-R^b$;

wherein A and $R_3$ are $-R_h-(R_g)_j$;

wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein B and $R^b$ are:

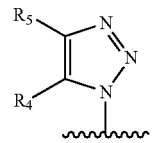

Formula III wherein each C, $R_4$, and $R_5$ are independently hydrogen or $-R_h-(R_g)_j$, wherein $R_h$ is $C(R_{39}R_{40})$, j is 1 to 10, one $R_g$ is O, and the other $R_g$ are $C(R_{42}R_{43})$, wherein $R_{39}$, $R_{40}$, $R_{42}$, and $R_{43}$ are hydrogen;

wherein $R_4$ and $R_5$ are not both hydrogen, wherein at least one of C is not hydrogen.

X is preferably oxygen, sulfur, or $NR_2$.

In some embodiments where A or $R_3$ is $-R_h-(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is $-R_h-(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments $R_h$ is $C(R_{39}R_{40})$, j is 3, the first $R_g$ is O, and the second and third $R_g$ are $C(R_{42}R_{43})$, wherein $R_{39}$, $R_{40}$, $R_{42}$, and $R_{43}$ are hydrogen. In some embodiments $R_h$ is $C(R_{39}R_{40})$, j is 1 to 10, one $R_g$ is O, and the other $R_g$ are $C(R_{42}R_{43})$, wherein $R_{39}$, $R_{40}$, $R_{42}$, and $R_{43}$ are hydrogen. In some embodiments the first $R_g$ is O. In some embodiments the second $R_g$ is O. In some embodiments the third $R_g$ is O. In some embodiments the fourth $R_g$ is O. In some embodiments the fifth $R_g$ is O. In some embodiments the fifth from the last $R_g$ is O. In some embodiments the fourth from the last $R_g$ is O. In some embodiments the antepenultimate $R_g$ is O. In some embodiments the penultimate $R_g$ is O. In some embodiments the last $R_g$ is O.

In some embodiments $R_h$ is $C(R_{39}R_{40})$, j is 4 to 16, two $R_g$ are O, and the other $R_g$ are $C(R_{42}R_{43})$, wherein $R_{39}$, $R_{40}$, $R_{42}$, and $R_{43}$ are hydrogen. In some embodiments the first and third $R_g$ are O. In some embodiments the first and fourth $R_g$ are O. In some embodiments the first and fifth $R_g$ are O. In some embodiments the first and sixth $R_g$ are O. In some embodiments the first and seventh $R_g$ are O. In some embodiments the first and eighth $R_g$ are O. In some embodiments the first and ninth $R_g$ are O. In some embodiments the first and tenth $R_g$ are O. In some embodiments the first and eleventh $R_g$ are O. In some embodiments the first and twelfth $R_g$ are O. In some embodiments the first and thirteenth $R_g$ are O. In some embodiments the first and fourteenth $R_g$ are O. In some embodiments the first and fifteenth $R_g$ are O. In some embodiments the second and fourth $R_g$ are O. In some embodiments the second and fifth $R_g$ are O. In some embodiments the second and sixth $R_g$ are O. In some embodiments the second and seventh $R_g$ are O. In some embodiments the second and eighth $R_g$ are O. In some embodiments the second and ninth $R_g$ are O. In some embodiments the second and tenth $R_g$ are O. In some embodiments the second and eleventh $R_g$ are O. In some embodiments the second and twelfth $R_g$ are O. In some embodiments the second and thirteenth $R_g$ are O. In some embodiments the second and fourteenth $R_g$ are O. In some embodiments the second and fifteenth $R_g$ are O. In some embodiments the third and fifth $R_g$ are O. In some embodiments the third and sixth $R_g$ are O. In some embodiments the third and seventh $R_g$ are O. In some embodiments the third and eighth $R_g$ are O. In some embodiments the third and ninth $R_g$ are O. In some embodiments the third and tenth $R_g$ are O. In some embodiments the third and eleventh $R_g$ are O. In some embodiments the third and twelfth $R_g$ are O. In some embodiments the third and thirteenth $R_g$ are O. In some embodiments the third and fourteenth $R_g$ are O. In some embodiments the third and fifteenth $R_g$ are O. In some embodiments the fourth and sixth $R_g$ are O. In some embodiments the fourth and seventh $R_g$ are O. In some embodiments the fourth and eighth $R_g$ are O. In some embodiments the fourth and ninth $R_g$ are O. In some embodiments the fourth and tenth $R_g$ are O. In some embodiments the fourth and eleventh $R_g$ are O. In some embodiments the fourth and twelfth $R_g$ are O. In some embodiments the fourth and thirteenth $R_g$ are O. In some embodiments the fourth and fourteenth $R_g$ are O. In some embodiments the fourth and fifteenth $R_g$ are O. In some embodiments the fifth and seventh $R_g$ are O. In some embodiments the fifth and eighth $R_g$ are O. In some embodiments the fifth and ninth $R_g$ are O. In some embodiments the fifth and tenth $R_g$ are O. In some embodiments the fifth and eleventh $R_g$ are O. In some embodiments the fifth and twelfth $R_g$ are O. In some embodiments the fifth and thirteenth $R_g$ are O. In some embodiments the fifth and fourteenth $R_g$ are O. In some embodiments the fifth and fifteenth $R_g$ are O. In some embodiments the sixth and eighth $R_g$ are O. In some embodiments the sixth and ninth $R_g$ are O. In some embodiments the sixth and tenth $R_g$ are O. In some embodiments the sixth and eleventh $R_g$ are O. In some embodiments the sixth and twelfth $R_g$ are O. In some embodiments the sixth and thirteenth $R_g$ are O. In some embodiments the sixth and fourteenth $R_g$ are O. In some embodiments the sixth and fifteenth $R_g$ are O. In some embodiments the seventh and ninth $R_g$ are O. In some embodiments the seventh and tenth $R_g$ are O. In some embodiments the seventh and eleventh $R_g$ are O. In some embodiments the seventh and twelfth $R_g$ are O. In some embodiments the seventh and thirteenth $R_g$ are O. In some embodiments the seventh and fourteenth $R_g$ are O. In some embodiments the seventh and fifteenth $R_g$ are O. In some embodiments the eighth and tenth $R_g$ are O. In some embodiments the eighth and eleventh $R_g$ are O. In some embodiments the eighth and twelfth $R_g$ are O. In some embodiments the eighth and thirteenth $R_g$ are O. In some embodiments the eighth and fourteenth $R_g$ are O. In some embodiments the eighth and fifteenth $R_g$ are O. In some embodiments the ninth and eleventh $R_g$ are O. In some embodiments the ninth and twelfth $R_g$ are O. In some embodiments the ninth and thirteenth $R_g$ are O. In some embodiments the ninth and fourteenth $R_g$ are O. In some embodiments the ninth and fifteenth $R_g$ are O. In some embodiments the tenth and twelfth $R_g$ are O. In some embodiments the tenth and thirteenth $R_g$ are O. In some embodiments the tenth and fourteenth $R_g$ are O. In some embodiments the tenth and fifteenth $R_g$ are O. In some embodiments the eleventh and thirteenth $R_g$ are O. In some embodiments the eleventh and fourteenth $R_g$ are O. In some embodiments the eleventh and fifteenth $R_g$ are O. In some embodiments the twelfth and fourteenth $R_g$ are O. In some embodiments the twelfth and fifteenth $R_g$ are O. In some embodiments the thirteenth and fifteenth $R_g$ are 0.

Z1-Y2

In some embodiments, compounds are represented by the general formula:

$$—X—R_1 \qquad \text{Formula I}$$

wherein X is oxygen, sulfur, $NR_2$, or another group compatible with attachment or coupling of the compound to a product or surface;

wherein $R_1$ is -A-B(—C)$_\delta$ or —$R_3$—$R^b$;

wherein A and $R_3$ are —$R_h$—$(R_g)_j$;

wherein $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are independently hydrogen or $C_1$-$C_3$ alkyl;

wherein B and $R^b$ are:

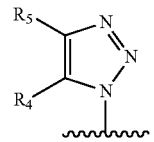

Formula III wherein each C, $R_4$, and $R_5$ are independently hydrogen or

Formula IX

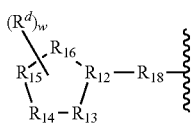

wherein for C, $R_4$, and $R_5$, $R_{13}$ and $R_{14}$ are oxygen, $R_{12}$, $R_{15}$, and $R_{16}$ are carbon, w is 0, the ring of Formula IX has no double bonds, $R_{18}$ is —$(CR_{19}R_{19})_p$—, both $R_{19}$ are hydrogen, and p is 1;

wherein $R_4$ and $R_5$ are not both hydrogen, wherein at least one of C is not hydrogen.

X is preferably oxygen, sulfur, or $NR_2$.

In some embodiments where A or $R_3$ is —$R_h$—$(R_g)_j$, $R_h$ is $C(R_{39}R_{40})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{39}$, $R_{40}$, $R_{42}$, and $R_{43}$ are hydrogen or $C_1$-$C_3$ alkyl. In some embodiments $R_{39}$ and $R_{40}$ are hydrogen. In some embodiments $R_{39}$ is hydrogen and $R_{40}$ is $C_1$-$C_3$ alkyl. In some embodiments $R_{39}$ and $R_{40}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_3$ is —$R_h$—$(R_g)_j$, $R_h$ is $C(R_{39}R_{40})$, and j is 10, wherein the first, third, fourth, sixth, seventh, ninth, and tenth $R_g$ are $C(R_{42}R_{43})$ and the second, fifth, and eighth $R_g$ are O, and wherein $R_{39}$, $R_{40}$, $R_{42}$, and $R_{43}$ are hydrogen.

In some embodiments, in Formula IX, $R_{13}$ and $R_{14}$ are oxygen, $R_{12}$, $R_{15}$, and $R_{16}$ are carbon, w is 0, the ring of Formula IX has no double bonds, $R_{18}$ is —$(CR_{19}R_{19})_p$—, both $R_{19}$ are hydrogen, and p is 1.

The hydrophobicity/hydrophilicity of surfaces of the surface-modified product can be varied by the incorporation of hydrophobic compounds, hydrophilic compounds, or both on the surfaces. In preferred embodiments, the modified surface contains one or more hydrophobic covalently attached compounds. The relative hydrophobicity/hydrophilicity of the surface or a surface of the surface-modified product can be quantitatively assessed by measuring the contact angle of a water droplet on such a surface. In some embodiments, the water droplet has a contact angle of less than 90° (i.e., the surface is hydrophilic). In preferred embodiments, the water droplet has a contact angle greater than or equal to 900 (i.e., the surface is hydrophobic). In some embodiments, the water droplet has a contact angle greater than or equal to 950, 1000, 105°, 110°, 115°, or 120°.

The compounds described herein, provide bioinert surfaces when used to coat the surfaces of products. In some embodiments the surface or a surface of the product is substantially covered with the compounds, wherein the surface or a surface is covalently modified as described herein.

Also contemplated are products containing a surface that has been modified using a compound that renders the surface or a surface bioinert, such as those described above, and another compound that renders the surface or a surface bioactive, such as those described by Franz, Ward and Slee, the contents of which are incorporated herein by reference.

III. Products

The disclosed products generally can be products that (1) are useful for treating a disease or disorder in a subject and (2) have a surface that can be chemically modified with a compound as disclosed herein. Useful products include, for example, devices, prostheses, and other materials for implantation in a subject or to be in long term contact with biomaterial, such as blood or body fluids, of a subject. A product can have any form, composition, use, and purpose that can be used to treat a subject. A product can include a biological material, such as cells, or other therapeutic agent, such as drugs, antibodies, nucleic acids, vaccines, and hormones.

The surfaces of products can be chemically modified as described herein to any desired density of modifications. The density of modifications is the average number of modifications (that is, attached compounds) per a given area of the surface or a surface of the product. Generally, a density at or above a threshold density can provide a beneficial effect, such as lower foreign body response. In some embodiments, a high density is not required. Without being bound to any particular theory of operation, it is believed that the chemical modifications signal to, indicate to, or are identified by, one or more immune system or other body components to result in a beneficial effect, such as a lower foreign body response. In some embodiments, a lower density of modifications can be effective for this purpose.

It has been discovered that coverage of products need not be at the same or at an even density. For example, in some embodiments, the density can vary over all or part of the product or surface, can be patchy, or can be uneven. Thus, in some embodiments, density can be referred to as the average over the entire product or surface or a portion or component of the product or surface. Density can be characterized as or by the local density of a portion of the product or surface. In such cases, other portions of the product or surface can have densities that are the same or different from the referenced local density (in other words, reference to the density of a portion of the product or surface does not preclude density of other parts of the product or surface from being the same or different). In some embodiments, the product, surface, or portions thereof, can also have smooth or uneven gradients of density. Gradients of density can vary through any of the density ranges disclosed herein.

Useful densities include densities of at least, of less than, of about, or of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, and 1000 modifications per square m. All ranges defined by any pair of these densities are also specifically contemplated and disclosed.

In some embodiments, the density of the modifications on a surface, surfaces, or portions of a surface(s) of a product that, when the product is administered to (e.g., implanted in the body of) a subject, would be in contact with fluid(s), cell(s), tissue(s), other component(s), or a combination thereof of the subject's body is greater than the density of the modifications on other surfaces of the product.

Density can also be expressed in terms of the concentration of the surface modifications as measured by X-ray photoelectron spectroscopy (XPS). XPS is a surface-sensitive quantitative spectroscopic technique that measures the elemental composition at the parts per thousand range of the elements that exist within a material. XPS spectra are obtained by irradiating a material with a beam of X-rays while simultaneously measuring the kinetic energy and number of electrons that escape from the top 0 to 10 nm of the material being analyzed. By measuring all elements present on the surface, the percentage of the elements that come from the surface modifications can be calculated. This can be accomplished by, for example, taking the percentage of nitrogen (and/or other elements in the surface modifications) in the total elemental signal measured. Nitrogen is a useful indicator for the surface modification because many substrated and materials forming the product contain little nitrogen. For convenience, the percent of the element(s) used to indicate the surface modifications can be stated as the percent surface modifications. Also for convenience, the percent surface modifications can be referred to as the concentration of surface modifications. Examples of XPS analysis and concentrations of surface modifications are shown in Tables 4-7.

Useful percent surface modifications include concentrations of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent surface modifications. All ranges defined by any pair of these concentrations are also specifically contemplated and disclosed.

Useful percent surface modifications also include concentrations of less than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent surface modifications. All ranges defined by any pair of these concentrations are also specifically contemplated and disclosed.

Useful percent surface modifications also include concentrations of 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent surface modifications. All ranges defined by any pair of these concentrations are also specifically contemplated and disclosed.

A. Materials

Useful materials that can constitute all or a part of a product (e.g., that includes its surface) include a variety of different substrates and substances that the disclosed chemical compounds can be, for example, applied to, absorbed into, or coupled to. Examples of suitable materials include metals, metallic materials, ceramics, polymers, fibers, inert materials such as silicon, and combinations thereof.

Suitable metallic materials include, but are not limited to, metals and alloys based on titanium (such as nitinol, nickel titanium alloys, thermo-memory alloy materials), platinum, platinum group alloys, stainless steel, tantalum, palladium, zirconium, niobium, molybdenum, nickel-chrome, or certain cobalt alloys including cobalt-chromium and cobalt-chromium-nickel alloys such as ELGILOY® and PHYNOX®. Useful examples include stainless steel grade 316 (SS 316L) (comprised of Fe, <0.3% C, 16-18.5% Cr, 10-14% Ni, 2-3% Mo, <2% Mn, <1% Si, <0.45% P, and <0.03% S), tantalum, chromium molybdenum alloys, nickel-titanium alloys (such as nitinol) and cobalt chromium alloys (such as MP35N, ASTM Material Designation: 35Co-35Ni-20Cr-10Mo). Typical metals currently in use for stents include SS 316L steel and MP35N. See also, "Comparing and Optimizing Co—Cr Tubing for Stent Applications," Poncin, P, Millet, C., Chevy, J, and Profit, J. L., Materials & Processes for Medical Devices Conference, August 2004, ASM International.

Suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used.

Suitable polymeric materials include, but are not limited to, polystyrene and substituted polystyrenes, polyethylene, polypropylene, polyacetylene, TEFLON®, poly(vinyl chloride) (PVC), polyolefin copolymers, poly(urethane)s, polyacrylates and polymethacrylates, polyacrylamides and polymethacrylamides, poly(methyl methacrylate), poly(2-hydroxyethyl methacrylate), polyesters, polysiloxanes, polydimethylsiloxane (PDMS), polyethers, poly(orthoester), poly(carbonates), poly(hydroxyalkanoate)s, polyfluorocarbons, PEEK®, Teflon® (polytetrafluoroethylene, PTFE), PEEK, silicones, epoxy resins, Kevlar®, Dacron® (a condensation polymer obtained from ethylene glycol and terephthalic acid), polyethylene glycol, nylon, polyalkenes, phenolic resins, natural and synthetic elastomers, adhesives and sealants, polyolefins, polysulfones, polyacrylonitrile, biopolymers such as polysaccharides and natural latex, collagen, cellulosic polymers (e.g., alkyl celluloses, etc.), polyethylene glycol and 2-hydroxyethyl methacrylate (HEMA), polysaccharides, poly(glycolic acid), poly(L-lactic acid) (PLLA), poly(lactic glycolic acid) (PLGA), a polydioxanone (PDA), or racemic poly(lactic acid), polycarbonates, (e.g., polyamides (nylon); fluoroplastics, carbon fiber, agarose, alginate, chitsan, and blends or copolymers thereof.

In some embodiments, the polymer is alginate, e.g., a polysaccharides made up of β-D-mannuronic acid (M) and α-L-guluronic acid (G) linked together. In some embodiments, alginate is a high guluronic acid (G) alginate. In some embodiments, the alginate is a high mannuronic acid (M) alginate. In some embodiments, the ratio of M:G is about 1. In some embodiments, the ratio of M:G is less than 1. In some embodiments, the ratio of M:G is greater than 1.

The polymer can be covalently or non-covalently associated with the surface; however, in particular embodiments, the polymer is non-covalently associated with the surface. The polymer can be applied by a variety of techniques in the art including, but not limited to, spraying, wetting, immersing, dipping, such as dip coating (e.g., intraoperative dip coating), painting, or otherwise applying a hydrophobic, polycationic polymer to a surface of the implant.

B. Product Forms

A product can have any form, composition, use, and purpose that can be used to treat a subject. For example, useful products include devices, prostheses, and other components for implantation or incorporation into a subject. Products useful for surface modification include any types of medical devices used, at least in part, for implantation in the body, or in long term contact with biomaterial, of a patient or subject in need thereof. Examples include, but are not limited to, implants, implantable medical products, implantable devices, catheters and other tubes (including urological and biliary tubes, endotracheal tubes, wound drain tubes, needle injection catheters, peripherably insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), vascular catheter ports, blood clot filters, urinary devices (including long term urinary devices, tissue bonding urinary devices, artificial urinary sphincters, urinary dilators), shunts (including ventricular or arterio-venous shunts, stent transplants, biliary stents, intestinal stents, bronchial stents, esophageal stents, ureteral stents, and hydrocephalus shunts), cannulas, (including intravenous cannulas and nasal cannulas), balloons, pacemakers, implantable defibrillators, orthopedic products (including pins, plates, screws, and implants), transplants (including organs, vascular transplants, vessels, aortas, heart valves, and organ replacement parts), prostheses (including breast implants, penile prostheses, vascular grafting prostheses, heart valves, artificial joints, artificial larynxes, otological implants, artificial hearts, artificial blood vessels, and artificial kidneys), aneurysm-filling coils and other coil devices, transmyocardial revascularization devices, percutaneous myocardial revascularization devices, tubes, fibers, hollow fibers, membranes, blood containers, titer plates, adsorber media, dialyzers, connecting pieces, sensors, valves, endoscopes, filters, pump chambers, scalpels, needles, scissors (and other devices used in invasive surgical, therapeutic, or diagnostic procedures), and other medical products and devices intended to have anti-fibrotic properties. The expression "medical products" is broad and refers in particular to products that come in contact with blood briefly (e.g., endoscopes) or permanently (e.g., stents).

Useful medical products are balloon catheters and endovascular prostheses, in particular stents. Stents of a conventional design have a filigree support structure composed of metallic struts. The support structure is initially provided in an unexpanded state for insertion into the body, and is then widened into an expanded state at the application site. The stent can be coated before or after it is crimped onto a balloon. A wide variety of medical endoprostheses or medical products or implants for highly diverse applications and are known. They are used, for example, to support vessels, hollow organs, and ductal systems (endovascular implants), to attach and temporarily affix tissue implants and tissue transplants, and for orthopedic purposes such as pins, plates, or screws.

Substrates can be in the form of, or form part of, films, particles (nanoparticles, microparticles, or millimeter diameter beads), fibers (wound dressings, bandages, gauze, tape, pads, sponges, including woven and non-woven sponges and those designed specifically for dental or ophthalmic surgeries), sensors, pacemaker leads, catheters, stents, contact lenses, bone implants (hip replacements, pins, rivets, plates, bone cement, etc.), or tissue regeneration or cell culture devices, or other medical devices used within or in contact with the body.

Implants with surface modifications are described herein. "Implants" are any object intended for placement in the body of a mammal, such as a human, that is not a living tissue. Implants are a form of medical product. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body or that of a mammal, including orthopedic applications, dental applications, ear, nose, and throat ("ENT") applications, and cardiovascular applications.

In some embodiments, "implant" as used herein refers to a macroscopic composition including a device for implantation or a surface of a device for implantation with a covalently modified surface. In some embodiments, the implant a device for implantation or a surface of a device for implantation and a modified alginate polymer coating. In these embodiments, the term "implant" does not encompass nanoparticles and/or microparticles. "Macroscopic" as used herein generally refers to devices, implants, or compositions that can be viewed by the unaided eye. In some embodiments the implant is extravascular. In some embodiments the implant is intravascular.

Examples of implantable medical devices and medical devices and mechanical structures that can use a bio-compatible coating include, but are not limited to, stents, conduits, scaffolds, cardiac valve rings, cardiovascular valves, pacemakers, hip replacement devices, implanted sensor devices, esophageal stents, heart implants, bio-compatible linings for heart valves, dialysis equipment and oxygenator tubing for heart-lung by-pass systems.

In general, a stent is a device, typically tubular in shape, that is inserted into a lumen of the body, such as a blood vessel or duct, to prevent or counteract a localized flow constriction. The purpose of a stent, in some cases, is to mechanically prop open a bodily fluid conduit. Stents are often used to alleviate diminished blood flow to organs and extremities in order to maintain adequate delivery of oxygenated blood. The most common use of stents is in coronary arteries, but they are also widely used in other bodily conduits, such as, for example, central and peripheral arteries and veins, bile ducts, the esophagus, colon, trachea, large bronchi, ureters, and urethra. Frequently, stents inserted into a lumen are capable of being expanded after insertion or are self-expanding. For example, metal stents are deployed into an occluded artery using a balloon catheter and expanded to restore blood flow. For example, stainless steel wire mesh stents are commercially available from Boston Scientific, Natick, Mass.

In some embodiments, the implant is an orthopedic implant. An "orthopedic implant" is defined as an implant which replaces bone or provides fixation to bone, replaces articulating surfaces of a joint, provides abutment for a prosthetic, or combinations thereof or assists in replacing bone or providing fixation to bone, replacing articulating surfaces of a joint, providing abutment for a prosthetic, and combinations thereof.

Orthopedic implants can be used to replace bone or provide fixation to bone, replace articulating surfaces of a joint, provide abutment for a prosthetic, or combinations thereof or assist in replacing bone or providing fixation to bone, replacing articulating surfaces of a joint, providing abutment for a prosthetic, including dental applications, and combinations thereof.

Suitable orthopedic implants include, but are not limited to, wire, Kirschner wire, bone plates, screws, pins, tacs, rods, nails, nuts, bolts, washers, spikes, buttons, wires, fracture plates, reconstruction and stabilizer devices, endo- and exoprostheses (articulating and non-articulating), intraosseous transcutaneous prostheses, spacers, mesh, implant abutments, anchors, barbs, clamps, suture, interbody fusion devices, tubes of any geometry, scaffolds, and combinations thereof.

In other embodiments, the implant is an ear, nose, and/or throat ("ENT") implant. Exemplary ENT implants include, but are not limited to, ear tubes, endotracheal tubes, ventilation tubes, cochlear implants and bone anchored hearing devices.

In other embodiments, the implant is a cardiovascular implant. Exemplary cardiovascular implants are cardiac valves or alloplastic vessel wall supports, total artificial heart implants, ventricular assist devices, vascular grafts, stents, electrical signal carrying devices such as pacemaker and neurological leads, defibrillator leads, and the like.

In some embodiments, products can be surface modified artificial organs and organ-repair implants. For example, surface modified substrate material surfaces that are used in the preparation of scaffolds and/or matrices that are subsequently used to fabricate surgical implants for diseased or impaired organs or used to grow whole, artificial organs. A variety of materials have been used in scaffold applications such as, but not limited to, tubular, fibrous, filamentous, and woven polymers, and natural materials. Other starting material configurations suitable for scaffold fabrication include woven or knitted items, micro- or nano-spheres (i.e., fullerenes), micro- or nano-tubes, cobweb-like configurations or foams/sponge-like forms. Any of these materials may be surface modified as disclosed herein.

In some embodiments, products can be chemically modified cardiovascular, vascular and associated implant devices. For example, surface modified cardiovascular or vascular implants can be used to improve the biocompatibility of medical devices meant to be implanted into the body. In those cases where the implant's surface interfaces with blood, other body fluids and/or tissue, these surfaces can be modified. Such modifications can be combined with other chemical and/or biological coating of cardiovascular implants useful to prevent formation of thrombi, aggregation, and ultimately emboli.

Implants can be prepared from a variety of materials. In some embodiments, the material is biocompatible. In some embodiments, the material is biocompatible and non-biodegradable. Exemplary materials include metallic materials, metal oxides, polymeric materials, including degradable and non-degradable polymeric materials, ceramics, porcelains, glass, allogeneic, xenogenic bone or bone matrix; genetically engineered bone; and combinations thereof.

In some embodiments, the products can have any suitable shape. Useful shapes include spheres, sphere-like shapes, spheroids, spheroid-like shapes, ellipsoids, ellipsoid-like shapes, stadiumoids, stadiumoid-like shapes, disks, disk-like shapes, cylinders, cylinder-like shapes, rods, rod-like shapes, cubes, cube-like shapes, cuboids, cuboid-like shapes, toruses, torus-like shapes, and flat and curved surfaces. Products, devices, and surfaces that have been or will be derivatized can have any of these shapes or any shape suitable for the product, device, or surface.

Spheres, spheroids, and ellipsoids are shapes with curved surfaces that can be defined by rotation of circles, ellipses, or a combination around each of the three perpendicular axes, a, b, and c. For a sphere, the three axes are the same length. For oblate spheroids (also referred to as oblate ellipsoids of rotation), the length of the axes are a=b>c. For prolate spheroids (also referred to as prolate ellipsoids of rotation), the length of the axes are a=b<c. For tri-axial ellipsoids (also referred to as scalene ellipsoids), the length of the axes are a>b>c. Stadiumoids are rotational shapes of stadiums. Cylinders are rotational shapes of rectangles rotated on the long axis. Disks are squashed cylinders where the diameter is greater than the height. Rods are elongated cylinders where the long axis is ten or more times the diameter.

"Sphere-like shape," "spheroid-like shape," "ellipsoid-like shape," "stadiumoid-like shape," "cylinder-like shape," "rod-like shape," "cube-like shape," "cuboid-like shape," and "torus-like shape" refers to an object having a surface that roughly forms a sphere, spheroid, ellipsoid, stadiumoid, cylinder, rod, cube, cuboid, or torus, respectively. Beyond a perfect or classical form of the shape, a sphere-like shape, spheroid-like shape, ellipsoid-like shape, stadiumoid-like shape, cylinder-like shape, rod-like shape, cube-like shape, cuboid-like shape, and torus-like shape can have waves and undulations.

Generally, a sphere-like shape is an ellipsoid (for its averaged surface) with semi-principal axes within 10% of each other. The diameter of a sphere or sphere-like shape is the average diameter, such as the average of the semi-principal axes. Generally, a spheroid-like shape is an ellipsoid (for its averaged surface) with semi-principal axes within 100% of each other. The diameter of a spheroid or spheroid-like shape is the average diameter, such as the average of the semi-principal axes. Generally, an ellipsoid-like shape is an ellipsoid (for its averaged surface) with semi-principal axes within 100% of each other. The diameter of an ellipsoid or ellipsoid-like shape is the average diameter, such as the average of the semi-principal axes. Generally, a stadiumoid-like shape is a stadiumoid (for its averaged surface) with semi-principal axes of the ends within 20% of each other. The diameter of a stadiumoid or stadiumoid-like shape is the average diameter, such as the average of the semi-principal axes. Alternatively, the size of a stadiumoid or stadiumoid-like shape can be given as the average of the long axis. Generally, a cylinder-like shape is a cylinder (for its averaged surface) with semi-principal axes within 20% of each other. The diameter of a cylinder or cylinder-like shape is the average diameter, such as the average of the semi-principal axes. Alternatively, the size of a cylinder or cylinder-like shape can be given as the average of the long axis. Generally, a rod-like shape is a rod (for its averaged surface) with semi-principal axes within 10% of each other. The diameter of a rod or rod-like shape is the average diameter, such as the average of the semi-principal axes. Alternatively, the size of a rod or rod-like shape can be given as the average of the long axis. Generally, a cube-like shape is a cube (for its averaged surface) with sides within 10% of each other. The diameter of a cube or cube-like shape is the average side length. Generally, a cuboid-like shape is a cuboid (for its averaged surface) with matching sides within 10% of each other. The diameter of a cuboid or cuboid-like shape is the average side length. Generally, a torus-like shape is a torus (for its averaged surface) with semi-principal axes within 10% of each other. The diameter of a torus or torus-like shape is the average diameter, such as the average of the semi-principal axes. Alternatively, the size of a torus or torus-like shape can be given as the diameter across the ring.

"Flat side" refers to a contiguous area of more than 5% of a surface that has a curvature of 0.

"Sharp angle" refers to a location on a surface across which the tangent to the surface changes by more than 10% over a distance of 2% or less of the circumference of the surface. Edges, corners, grooves, and ridges in a surface are all forms of sharp angles.

Preferred products can be made of biocompatible materials, have a diameter of at least 1 mm and less than 10 mm, has a spheroid-like shape, and have one or more of the additional characteristics: surface pores of the products greater than 0 nm and less than m; surface of the products neutral or hydrophilic; curvature of the surface or a surface of the products at least 0.2 and is not greater than 2 on all points of the surface; and surface of the products lacking flat sides, sharp angles, grooves, or ridges. Generally, the products elicit less of a fibrotic reaction after implantation than the same products lacking one or more of these characteristics that are present on the products.

In some embodiments, the product is provided as a preparation and at least 30%, 35%, 40%, 45%, 50%, 55%, 60%, 65%, 70%, 75%, 80%, 85%, 90%, 95% or 100% of the products in the preparation have a shape characteristic described herein, e.g., have a spheroid-like shape, or have a curvature of the surface of at least 0.2 to 2.0 on all points of the surface.

In some embodiments, the products have a mean diameter or size that is greater than 1 mm, preferably 1.5 mm or greater. In some embodiments, the products can be as large as 8 mm in diameter or size. For example, the products is in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm. In some embodiments, the product has a mean diameter or size between 1 mm to 8 mm. In some embodiments, the product has a mean diameter or size between 1 mm to 4 mm. In some embodiments, the product has a mean diameter or size between 1 mm to 2 mm.

In some embodiments, the products are provided as a preparation and at least 30%, 35%, 40%, 45%, 50%, 55%, 60%, 65%, 70%, 75%, 80%, 85%, 90%, 95% or 100% of the products in the preparation, have a diameter or size in a size range described herein.

In some embodiments, the products have a mean pore size ranging from 0.1 µm to 10 µm. For example, the pores is in a size range of 0.1 µm to 10 µm, 0.1 µm to 9 µm, 0.1 µm to 8 µm, 0.1 µm to 7 µm, 0.1 µm to 6 µm, 0.1 µm to 5 µm, 0.1 µm to 4 µm, 0.1 µm to 3 µm, 0.1 µm to 2 µm, 0.15 µm to 10 µm, 0.15 µm to 9 µm, 0.15 µm to 8 µm, 0.15 µm to 7 µm, 0.15 µm to 6 µm, 0.15 µm to 5 µm, 0.15 µm to 4 µm, 0.15 µm to 3 µm, 0.15 µm to 2 µm, 0.2 µm to 10 µm, 0.2 µm to 9 µm, 0.2 µm to 8 µm, 0.2 µm to 7 µm, 0.2 µm to 6 µm, 0.2 µm to 5 µm, 0.2 µm to 4 µm, 0.2 µm to 3 µm, 0.25 µm to 10 µm, 0.25 µm to 9 µm, 0.25 µm to 8 µm, 0.25 µm to 7 µm, 0.25 µm to 6 µm, 0.25 µm to 5 µm, 0.25 µm to 4 µm, 0.25 µm to 3 µm, 0.3 µm to 10 µm, 0.3 µm to 9 µm, 0.3 µm to 8 µm, 0.3 µm to 7 µm, 0.3 µm to 6 µm, 0.3 µm to 5 µm, 0.3 µm to 4 µm, 0.35 µm to 10 µm, 0.35 µm to 9 µm, 0.35 µm to 8 µm, 0.35 µm to 7 µm, 0.35 µm to 6 µm, 0.35 µm to 5 µm, 0.35 µm to 4 µm, 0.4 µm to 10 µm, 0.4 µm to 9 µm, 0.4 µm to 8 µm, 0.4 µm to 7 µm, 0.4 µm to 6 µm, 0.4 µm to 5 µm, 0.45 µm to 10 µm, 0.45 µm to 9 µm, 0.45 µm to 8 µm, 0.45 µm to 7 µm, 0.45 µm to 6 µm, 0.45 µm to 5 µm, 0.5 µm to 10 µm, 0.5 µm to 9 µm, 0.5 µm to 8 µm, 0.5 µm to 7 µm, 0.5 µm to 6 µm, 0.55 µm to 10 µm, 0.55 µm to 9 µm, 0.55 µm to 8 µm, 0.55 µm to 7 µm, 0.55 µm to 6 µm, 0.6 µm to 10 µm, 0.6 µm to 9 µm, 0.6 µm to 8 µm, 0.6 µm to 7 µm, 0.65 µm to 10 µm, 0.65 µm to 9 µm, 0.65 µm to 8 µm, 0.65 µm to 7 µm, 0.7 µm to 10 µm, 0.7 µm to 9 µm, 0.7 µm to 8 µm, 0.75 µm to 10 µm, 0.75 µm to 9 µm, 0.75 µm to 8 µm, 0.8 µm to 10 µm, 0.8 µm to 9 µm, 0.85 µm to 10 µm, 0.85 µm to 9 µm, 0.9 µm to 10 µm, 0.95 µm to 10 µm, 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm. In some embodiments, the product has a mean pore size ranging from 0.1 µm to 10 µm. In some embodiments, the product has a mean pore size ranging from 0.1 µm to 5 µm. In some embodiments, the product has a mean pore size ranging from 0.1 µm to 1 µm.

In some embodiments, the products are provided as a preparation and at least 30%, 35%, 40%, 45%, 50%, 55%, 60%, 65%, 70%, 75%, 80%, 85%, 90%, 95% or 100% of the products in the preparation have pores in a size range described herein.

In some embodiments, the chemical derivatizations of the surface or a surface of the products are expressed as a density, i.e., average number of attached compounds per given area. In some embodiments, the density is at least, is less than, or is 0.1, 0.2, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, or 1000 chemical derivatizations per µm$^2$ on the surface or a surface of the products, in the interior of the products, or both. In some embodiments, the density is at least 100 chemical derivatizations per µm$^2$ on the surface or a surface of the products, in the interior of the products, or both. In some embodiments, the density is at least 1000 chemical derivatizations per µm$^2$ on the surface oe a surface of the products, in the interior of the products, or both.

In some embodiments the density is in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.1 to 110, 0.1 to 120, 0.1 to 130, 0.1 to 140, 0.1 to 150, 0.1 to 160, 0.1 to 170, 0.1 to 180, 0.1 to 190, 0.1 to 200, 0.1 to 210, 0.1 to 220, 0.1 to 230, 0.1 to 240, 0.1 to 250, 0.1 to 260, 0.1 to 270, 0.1 to 280, 0.1 to 290, 0.1 to 300, 0.1 to 320, 0.1 to 340, 0.1 to 360, 0.1 to 380, 0.1 to 400, 0.1 to 420, 0.1 to 440, 0.1 to 460, 0.1 to 480, 0.1 to 500, 0.1 to 550, 0.1 to 600, 0.1 to 650, 0.1 to 700, 0.1 to 750, 0.1 to 800, 0.1 to 850, 0.1 to 900, and 0.1 to 1000 chemical derivatizations per µm$^2$ on the surface or a surface of the products, in the interior of the products, or both.

In some embodiments the density is in the range of 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.2 to 110, 0.2 to 120, 0.2 to 130, 0.2 to 140, 0.2 to 150, 0.2 to 160, 0.2 to 170, 0.2 to 180, 0.2 to 190, 0.2 to 200, 0.2 to 210, 0.2 to 220, 0.2 to 230, 0.2 to 240, 0.2 to 250, 0.2 to 260, 0.2 to 270, 0.2 to 280, 0.2 to 290, 0.2 to 300, 0.2 to 320, 0.2 to 340, 0.2 to 360, 0.2 to 380, 0.2 to 400, 0.2 to 420, 0.2 to 440, 0.2 to 460, 0.2 to 480, 0.2 to 500, 0.2 to 550, 0.2 to 600, 0.2 to 650, 0.2 to 700, 0.2 to 750, 0.2 to 800, 0.2 to 850, 0.2 to 900, and 0.2 to 1000 chemical derivatizations per µm$^2$ on the surface or a surface of the products, in the interior of the products, or both.

In some embodiments the density is in the range of 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 0.5 to 110, 0.5 to 120, 0.5 to 130, 0.5 to 140, 0.5 to 150, 0.5 to 160, 0.5 to 170, 0.5 to 180, 0.5 to 190, 0.5 to 200, 0.5 to 210, 0.5 to 220, 0.5 to 230, 0.5 to 240, 0.5 to 250, 0.5 to 260, 0.5 to 270, 0.5 to 280, 0.5 to 290, 0.5 to 300, 0.5 to 320, 0.5 to 340, 0.5 to 360, 0.5 to 380, 0.5 to 400, 0.5 to 420, 0.5 to 440, 0.5 to 460, 0.5 to 480, 0.5 to 500, 0.5 to 550, 0.5 to 600, 0.5 to 650, 0.5 to 700, 0.5 to 750, 0.5 to 800, 0.5 to 850, 0.5 to 900, and 0.5 to 1000 chemical derivatizations per µm$^2$ on the surface or a surface of the products, in the interior of the products, or both.

In some embodiments the density is in the range of 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 110, 1 to 120, 1 to 130, 1 to 140, 1 to 150, 1 to 160, 1 to 170, 1 to 180, 1 to 190, 1 to 200, 1 to 210, 1 to 220, 1 to 230, 1 to 240, 1 to 250, 1 to 260, 1 to 270, 1 to 280, 1 to 290, 1 to 300, 1 to 320, 1 to 340, 1 to 360, 1 to 380, 1 to 400, 1 to 420, 1 to 440, 1 to 460, 1 to 480, 1 to 500, 1 to 550, 1 to 600, 1 to 650, 1 to 700, 1 to 750, 1 to 800, 1 to 850, 1 to 900, and 1 to 1000 chemical derivatizations per µm$^2$ on the surface or a surface of the products, in the interior of the products, or both.

In some embodiments the density is in the range of 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 2 to 110, 2 to 120, 2 to 130, 2 to 140, 2 to 150, 2 to 160, 2 to 170, 2 to 180, 2 to 190, 2 to 200, 2 to 210, 2 to 220, 2 to 230, 2 to 240, 2 to 250, 2 to 260, 2 to 270, 2 to 280, 2 to 290, 2 to 300, 2 to 320, 2 to 340, 2 to 360, 2 to 380, 2 to 400, 2 to 420, 2 to 440, 2 to 460, 2 to 480, 2 to 500, 2 to 550, 2 to 600, 2 to 650, 2 to 700, 2 to 750, 2 to 800, 2 to 850, 2 to 900, and 2 to 1000 chemical derivatizations per µm$^2$ on the surface or a surface of the products, in the interior of the products, or both.

In some embodiments the density is in the range of 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 3 to 110, 3 to 120, 3 to 130, 3 to 140, 3 to 150, 3 to 160, 3 to 170, 3 to 180, 3 to 190, 3 to 200, 3 to 210, 3 to 220, 3 to 230, 3 to 240, 3 to 250, 3 to 260, 3 to 270, 3 to 280, 3 to 290, 3 to 300, 3 to 320, 3 to 340, 3 to 360, 3 to 380, 3 to 400, 3 to 420, 3 to 440, 3 to 460, 3 to 480, 3 to 500, 3 to 550, 3 to 600, 3 to 650, 3 to 700, 3 to 750, 3 to 800, 3 to 850, 3 to 900, and 3 to 1000 chemical derivatizations per µm$^2$ on the surface or a surface of the products, in the interior of the products, or both.

In some embodiments the density is in the range of 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 4 to 110, 4 to 120, 4 to 130, 4 to 140, 4 to 150, 4 to 160, 4 to 170, 4 to 180, 4 to 190, 4 to 200, 4 to 210, 4 to 220, 4 to 230, 4 to 240, 4 to 250, 4 to 260, 4 to 270, 4 to 280, 4 to 290, 4 to 300, 4 to 320, 4 to 340, 4 to 360, 4 to 380, 4 to 400, 4 to 420, 4 to 440, 4 to 460, 4 to 480, 4 to 500, 4 to 550, 4 to 600, 4 to 650, 4 to 700, 4 to 750, 4 to 800, 4 to 850, 4 to 900, and 4 to 1000 chemical derivatizations per µm$^2$ on the surface or a surface of the products, in the interior of the products, or both.

In some embodiments the density is in the range of 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 5 to 110, 5 to 120, 5 to 130, 5 to 140, 5 to 150, 5 to 160, 5 to 170, 5 to 180, 5 to 190, 5 to 200, 5 to 210, 5 to 220, 5 to 230, 5 to 240, 5 to 250, 5 to 260, 5 to 270, 5 to 280, 5 to 290, 5 to 300, 5 to 320, 5 to 340, 5 to 360, 5 to 380, 5 to 400, 5 to 420, 5 to 440, 5 to 460, 5 to 480, 5 to 500, 5 to 550, 5 to 600, 5 to 650, 5 to 700, 5 to 750, 5 to 800, 5 to 850, 5 to 900, and 5 to 1000 chemical derivatizations per µm$^2$ on the surface or a surface of the products, in the interior of the products, or both.

In some embodiments the density is in the range of 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 6 to 110, 6 to 120, 6 to 130, 6 to 140, 6 to 150, 6 to 160, 6 to 170, 6 to 180, 6 to 190, 6 to 200, 6 to 210, 6 to 220, 6 to 230, 6 to 240, 6 to 250, 6 to 260, 6 to 270, 6 to 280, 6 to 290, 6 to 300, 6 to 320, 6 to 340, 6 to 360, 6 to 380, 6 to 400, 6 to 420, 6 to 440, 6 to 460, 6 to 480, 6 to 500, 6 to 550, 6 to 600, 6 to 650, 6 to 700, 6 to 750, 6 to 800, 6 to 850, 6 to 900, and 6 to 1000 chemical derivatizations per $\mu m^2$ on the surface or a surface of the products, in the interior of the products, or both.

In some embodiments the density is in the range of 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 7 to 110, 7 to 120, 7 to 130, 7 to 140, 7 to 150, 7 to 160, 7 to 170, 7 to 180, 7 to 190, 7 to 200, 7 to 210, 7 to 220, 7 to 230, 7 to 240, 7 to 250, 7 to 260, 7 to 270, 7 to 280, 7 to 290, 7 to 300, 7 to 320, 7 to 340, 7 to 360, 7 to 380, 7 to 400, 7 to 420, 7 to 440, 7 to 460, 7 to 480, 7 to 500, 7 to 550, 7 to 600, 7 to 650, 7 to 700, 7 to 750, 7 to 800, 7 to 850, 7 to 900, and 7 to 1000 chemical derivatizations per $\mu m^2$ on the surface or a surface of the products, in the interior of the products, or both.

In some embodiments the density is in the range of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 8 to 110, 8 to 120, 8 to 130, 8 to 140, 8 to 150, 8 to 160, 8 to 170, 8 to 180, 8 to 190, 8 to 200, 8 to 210, 8 to 220, 8 to 230, 8 to 240, 8 to 250, 8 to 260, 8 to 270, 8 to 280, 8 to 290, 8 to 300, 8 to 320, 8 to 340, 8 to 360, 8 to 380, 8 to 400, 8 to 420, 8 to 440, 8 to 460, 8 to 480, 8 to 500, 8 to 550, 8 to 600, 8 to 650, 8 to 700, 8 to 750, 8 to 800, 8 to 850, 8 to 900, and 8 to 1000 chemical derivatizations per $\mu m^2$ on the surface or a surface of the products, in the interior of the products, or both.

In some embodiments the density is in the range of 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 9 to 110, 9 to 120, 9 to 130, 9 to 140, 9 to 150, 9 to 160, 9 to 170, 9 to 180, 9 to 190, 9 to 200, 9 to 210, 9 to 220, 9 to 230, 9 to 240, 9 to 250, 9 to 260, 9 to 270, 9 to 280, 9 to 290, 9 to 300, 9 to 320, 9 to 340, 9 to 360, 9 to 380, 9 to 400, 9 to 420, 9 to 440, 9 to 460, 9 to 480, 9 to 500, 9 to 550, 9 to 600, 9 to 650, 9 to 700, 9 to 750, 9 to 800, 9 to 850, 9 to 900, and 9 to 1000 chemical derivatizations per $\mu m^2$ on the surface or a surface of the products, in the interior of the products, or both.

In some embodiments the density is in the range of 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 10 to 110, 10 to 120, 10 to 130, 10 to 140, 10 to 150, 10 to 160, 10 to 170, 10 to 180, 10 to 190, 10 to 200, 10 to 210, 10 to 220, 10 to 230, 10 to 240, 10 to 250, 10 to 260, 10 to 270, 10 to 280, 10 to 290, 10 to 300, 10 to 320, 10 to 340, 10 to 360, 10 to 380, 10 to 400, 10 to 420, 10 to 440, 10 to 460, 10 to 480, 10 to 500, 10 to 550, 10 to 600, 10 to 650, 10 to 700, 10 to 750, 10 to 800, 10 to 850, 10 to 900, and 10 to 1000 chemical derivatizations per $\mu m^2$ on the surface or a surface of the products, in the interior of the products, or both.

In some embodiments the density is in the range of 20 to 25, 20 to 30, 20 to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 20 to 110, 20 to 120, 20 to 130, 20 to 140, 20 to 150, 20 to 160, 20 to 170, 20 to 180, 20 to 190, 20 to 200, 20 to 210, 20 to 220, 20 to 230, 20 to 240, 20 to 250, 20 to 260, 20 to 270, 20 to 280, 20 to 290, 20 to 300, 20 to 320, 20 to 340, 20 to 360, 20 to 380, 20 to 400, 20 to 420, 20 to 440, 20 to 460, 20 to 480, 20 to 500, 20 to 550, 20 to 600, 20 to 650, 20 to 700, 20 to 750, 20 to 800, 20 to 850, 20 to 900, and 20 to 1000 chemical derivatizations per $\mu m^2$ on the surface or a surface of the products, in the interior of the products, or both.

In some embodiments the density is in the range of 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 30 to 110, 30 to 120, 30 to 130, 30 to 140, 30 to 150, 30 to 160, 30 to 170, 30 to 180, 30 to 190, 30 to 200, 30 to 210, 30 to 220, 30 to 230, 30 to 240, 30 to 250, 30 to 260, 30 to 270, 30 to 280, 30 to 290, 30 to 300, 30 to 320, 30 to 340, 30 to 360, 30 to 380, 30 to 400, 30 to 420, 30 to 440, 30 to 460, 30 to 480, 30 to 500, 30 to 550, 30 to 600, 30 to 650, 30 to 700, 30 to 750, 30 to 800, 30 to 850, 30 to 900, and 30 to 1000 chemical derivatizations per $\mu m^2$ on the surface or a surface of the products, in the interior of the products, or both.

In some embodiments the density is in the range of 40 to 45, 40 to 50, 40 to 55, 40 to 60, 40 to 65, 40 to 70, 40 to 75, 40 to 80, 40 to 85, 40 to 90, 40 to 95, 40 to 100, 40 to 110, 40 to 120, 40 to 130, 40 to 140, 40 to 150, 40 to 160, 40 to 170, 40 to 180, 40 to 190, 40 to 200, 40 to 210, 40 to 220, 40 to 230, 40 to 240, 40 to 250, 40 to 260, 40 to 270, 40 to 280, 40 to 290, 40 to 300, 40 to 320, 40 to 340, 40 to 360, 40 to 380, 40 to 400, 40 to 420, 40 to 440, 40 to 460, 40 to 480, 40 to 500, 40 to 550, 40 to 600, 40 to 650, 40 to 700, 40 to 750, 40 to 800, 40 to 850, 40 to 900, and 40 to 1000 chemical derivatizations per $\mu m^2$ on the surface or a surface of the products, in the interior of the products, or both.

In some embodiments the density is in the range of 50 to 55, 50 to 60, 50 to 65, 50 to 70, 50 to 75, 50 to 80, 50 to 85, 50 to 90, 50 to 95, 50 to 100, 50 to 110, 50 to 120, 50 to 130, 50 to 140, 50 to 150, 50 to 160, 50 to 170, 50 to 180, 50 to 190, 50 to 200, 50 to 210, 50 to 220, 50 to 230, 50 to 240, 50 to 250, 50 to 260, 50 to 270, 50 to 280, 50 to 290, 50 to 300, 50 to 320, 50 to 340, 50 to 360, 50 to 380, 50 to 400, 50 to 420, 50 to 440, 50 to 460, 50 to 480, 50 to 500, 50 to 550, 50 to 600, 50 to 650, 50 to 700, 50 to 750, 50 to 800, 50 to 850, 50 to 900, and 50 to 1000 chemical derivatizations per $\mu m^2$ on the surface or a surface of the products, in the interior of the products, or both.

In some embodiments the density is in the range of 60 to 65, 60 to 70, 60 to 75, 60 to 80, 60 to 85, 60 to 90, 60 to 95, 60 to 100, 60 to 110, 60 to 120, 60 to 130, 60 to 140, 60 to 150, 60 to 160, 60 to 170, 60 to 180, 60 to 190, 60 to 200, 60 to 210, 60 to 220, 60 to 230, 60 to 240, 60 to 250, 60 to 260, 60 to 270, 60 to 280, 60 to 290, 60 to 300, 60 to 320, 60 to 340, 60 to 360, 60 to 380, 60 to 400, 60 to 420, 60 to 440, 60 to 460, 60 to 480, 60 to 500, 60 to 550, 60 to 600, 60 to 650, 60 to 700, 60 to 750, 60 to 800, 60 to 850, 60 to 900, and 60 to 1000 chemical derivatizations per $\mu m^2$ on the surface or a surface of the products, in the interior of the products, or both.

In some embodiments the density is in the range of 70 to 75, 70 to 80, 70 to 85, 70 to 90, 70 to 95, 70 to 100, 70 to 110, 70 to 120, 70 to 130, 70 to 140, 70 to 150, 70 to 160, 70 to 170, 70 to 180, 70 to 190, 70 to 200, 70 to 210, 70 to 220, 70 to 230, 70 to 240, 70 to 250, 70 to 260, 70 to 270, 70 to 280, 70 to 290, 70 to 300, 70 to 320, 70 to 340, 70 to 360, 70 to 380, 70 to 400, 70 to 420, 70 to 440, 70 to 460, 70 to 480, 70 to 500, 70 to 550, 70 to 600, 70 to 650, 70 to 700, 70 to 750, 70 to 800, 70 to 850, 70 to 900, and 70 to 1000 chemical derivatizations per $\mu m^2$ on the surface or a surface of the products, in the interior of the products, or both.

In some embodiments the density is in the range of 80 to 85, 80 to 90, 80 to 95, 80 to 100, 80 to 110, 80 to 120, 80 to 130, 80 to 140, 80 to 150, 80 to 160, 80 to 170, 80 to 180, 80 to 190, 80 to 200, 80 to 210, 80 to 220, 80 to 230, 80 to 240, 80 to 250, 80 to 260, 80 to 270, 80 to 280, 80 to 290, 80 to 300, 80 to 320, 80 to 340, 80 to 360, 80 to 380, 80 to 400, 80 to 420, 80 to 440, 80 to 460, 80 to 480, 80 to 500, 80 to 550, 80 to 600, 80 to 650, 80 to 700, 80 to 750, 80 to 800, 80 to 850, 80 to 900, and 80 to 1000 chemical derivatizations per $\mu m^2$ on the surface or a surface of the products, in the interior of the products, or both.

In some embodiments the density is in the range of 90 to 95, 90 to 100, 90 to 110, 90 to 120, 90 to 130, 90 to 140, 90 to 150, 90 to 160, 90 to 170, 90 to 180, 90 to 190, 90 to 200, 90 to 210, 90 to 220, 90 to 230, 90 to 240, 90 to 250, 90 to 260, 90 to 270, 90 to 280, 90 to 290, 90 to 300, 90 to 320, 90 to 340, 90 to 360, 90 to 380, 90 to 400, 90 to 420, 90 to 440, 90 to 460, 90 to 480, 90 to 500, 90 to 550, 90 to 600, 90 to 650, 90 to 700, 90 to 750, 90 to 800, 90 to 850, 90 to 900, and 90 to 1000 chemical derivatizations per $\mu m^2$ on the surface or a surface of the products, in the interior of the products, or both.

In some embodiments the density is in the range of 100 to 110, 100 to 120, 100 to 130, 100 to 140, 100 to 150, 100 to 160, 100 to 170, 100 to 180, 100 to 190, 100 to 200, 100 to 210, 100 to 220, 100 to 230, 100 to 240, 100 to 250, 100 to 260, 100 to 270, 100 to 280, 100 to 290, 100 to 300, 100 to 320, 100 to 340, 100 to 360, 100 to 380, 100 to 400, 100 to 420, 100 to 440, 100 to 460, 100 to 480, 100 to 500, 100 to 550, 100 to 600, 100 to 650, 100 to 700, 100 to 750, 100 to 800, 100 to 850, 100 to 900, and 100 to 1000 chemical derivatizations per $\mu m^2$ on the surface or a surface of the products, in the interior of the products, or both.

In some embodiments the density is in the range of 200 to 210, 200 to 220, 200 to 230, 200 to 240, 200 to 250, 200 to 260, 200 to 270, 200 to 280, 200 to 290, 200 to 300, 200 to 320, 200 to 340, 200 to 360, 200 to 380, 200 to 400, 200 to 420, 200 to 440, 200 to 460, 200 to 480, 200 to 500, 200 to 550, 200 to 600, 200 to 650, 200 to 700, 200 to 750, 200 to 800, 200 to 850, 200 to 900, and 200 to 1000 chemical derivatizations per $\mu m^2$ on the surface or a surface of the products, in the interior of the products, or both.

In some embodiments the density is in the range of 300 to 320, 300 to 340, 300 to 360, 300 to 380, 300 to 400, 300 to 420, 300 to 440, 300 to 460, 300 to 480, 300 to 500, 300 to 550, 300 to 600, 300 to 650, 300 to 700, 300 to 750, 300 to 800, 300 to 850, 300 to 900, and 300 to 1000 chemical derivatizations per $\mu m^2$ on the surface or a surface of the products, in the interior of the products, or both.

In some embodiments the density is in the range of 400 to 420, 400 to 440, 400 to 460, 400 to 480, 400 to 500, 400 to 550, 400 to 600, 400 to 650, 400 to 700, 400 to 750, 400 to 800, 400 to 850, 400 to 900, and 400 to 1000 chemical derivatizations per $\mu m^2$ on the surface or a surface of the products, in the interior of the products, or both.

In some embodiments the density is in the range of 500 to 550, 500 to 600, 500 to 650, 500 to 700, 500 to 750, 500 to 800, 500 to 850, 500 to 900, and 500 to 1000 chemical derivatizations per $\mu m^2$ on the surface or a surface of the products, in the interior of the products, or both.

In some embodiments the density is in the range of 600 to 650, 600 to 700, 600 to 750, 600 to 800, 600 to 850, 600 to 900, and 600 to 1000 chemical derivatizations per $\mu m^2$ on the surface or a surface of the products, in the interior of the products, or both.

In some embodiments the density is in the range of 700 to 750, 700 to 800, 700 to 850, 700 to 900, and 700 to 1000 chemical derivatizations per $\mu m^2$ on the surface or a surface of the products, in the interior of the products, or both.

In some embodiments the density is in the range of 800 to 850, 800 to 900, and 800 to 1000 chemical derivatizations per $\mu m^2$ on the surface or a surface of the products, in the interior of the products, or both.

In some embodiments the density is in the range of 900 to 1000 chemical derivatizations per $\mu m^2$ on the surface or a surface of the products, in the interior of the products, or both.

In some embodiments, the product is provided as a preparation and at least 30%, 35%, 40%, 45%, 50%, 55%, 60%, 65%, 70%, 75%, 80%, 85%, 90%, 95% or 100% of the products in the preparation have a density of attached compounds described herein.

In some embodiments, density chemical derivatizations of the surface or a surface of the products are expressed as a percent surface modifications or concentration of surface modifications. In some embodiments, the concentration of surface modifications is at least, is less than, or is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent.

In some embodiments the concentration of surface modifications is in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100 percent surface modifications.

In some embodiments the concentration of surface modifications is in the range of 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100 percent surface modifications.

In some embodiments the concentration of surface modifications is in the range of 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100 percent surface modifications.

In some embodiments the concentration of surface modifications is in the range of 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100 percent surface modifications.

In some embodiments the concentration of surface modifications is in the range of 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100 percent surface modifications.

In some embodiments the concentration of surface modifications is in the range of 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100 percent surface modifications.

In some embodiments the concentration of surface modifications is in the range of 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100 percent surface modifications.

In some embodiments the concentration of surface modifications is in the range of 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100 percent surface modifications.

In some embodiments the concentration of surface modifications is in the range of 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100 percent surface modifications.

In some embodiments the concentration of surface modifications is in the range of 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100 percent surface modifications.

In some embodiments the concentration of surface modifications is in the range of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100 percent surface modifications.

In some embodiments the concentration of surface modifications is in the range of 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100 percent surface modifications.

In some embodiments the concentration of surface modifications is in the range of 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100 percent surface modifications. In some embodiments, the concentration of surface modifications is in the range of 10 to 100 percent surface modifications.

In some embodiments the concentration of surface modifications is in the range of 20 to 25, 20 to 30, 20 to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100 percent surface modifications.

In some embodiments the concentration of surface modifications is in the range of 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100 percent surface modifications.

In some embodiments the concentration of surface modifications is in the range of 40 to 45, 40 to 50, 40 to 55, 40 to 60, 40 to 65, 40 to 70, 40 to 75, 40 to 80, 40 to 85, 40 to 90, 40 to 95, 40 to 100 percent surface modifications.

In some embodiments the concentration of surface modifications is in the range of 50 to 55, 50 to 60, 50 to 65, 50 to 70, 50 to 75, 50 to 80, 50 to 85, 50 to 90, 50 to 95, 50 to 100 percent surface modifications.

In some embodiments the concentration of surface modifications is in the range of 60 to 65, 60 to 70, 60 to 75, 60 to 80, 60 to 85, 60 to 90, 60 to 95, 60 to 100 percent surface modifications.

In some embodiments the concentration of surface modifications is in the range of 70 to 75, 70 to 80, 70 to 85, 70 to 90, 70 to 95, 70 to 100 percent surface modifications.

In some embodiments the concentration of surface modifications is in the range of 80 to 85, 80 to 90, 80 to 95, 80 to 100 percent surface modifications.

In some embodiments the concentration of surface modifications is in the range of 90 to 95, 90 to 100 percent surface modifications.

In some embodiments, the product is provided as a preparation and at least 30%, 35%, 40%, 45%, 50%, 55%, 60%, 65%, 70%, 75%, 80%, 85%, 90%, 95% or 100% of the products in the preparation have a concentration of attached compounds described herein.

In some embodiments, the products have a mean diameter or size that is greater than 1 mm and less than 8 mm, greater than 1.5 mm and less than 8 mm, greater than 2 mm and less than 8 mm, greater than 2.5 mm and less than 8 mm, greater than 3 mm and less than 8 mm, greater than 3.5 mm and less than 8 mm, greater than 4 mm and less than 8 mm, greater than 4.5 mm and less than 8 mm, greater than 5 mm and less than 8 mm, greater than 5.5 mm and less than 8 mm, greater than 6 mm and less than 8 mm, greater than 6.5 mm and less than 8 mm, greater than 7 mm and less than 8 mm, or greater than 7.5 mm and less than 8 mm, and, independently, pores in a size range of 0.1 µm to 10 µm, 0.1 µm to 9 µm, 0.1 µm to 8 µm, 0.1 µm to 7 µm, 0.1 µm to 6 µm, 0.1 µm to 5 µm, 0.1 µm to 4 µm, 0.1 µm to 3 µm, 0.1 µm to 2 µm, 0.15 µm to 10 µm, 0.15 µm to 9 µm, 0.15 µm to 8 µm, 0.15 µm to 7 µm, 0.15 µm to 6 µm, 0.15 µm to 5 µm, 0.15 µm to 4 µm, 0.15 µm to 3 µm, 0.15 µm to 2 µm, 0.2 µm to 10 µm, 0.2 µm to 9 µm, 0.2 µm to 8 µm, 0.2 µm to 7 µm, 0.2 µm to 6 µm, 0.2 µm to 5 µm, 0.2 µm to 4 µm, 0.2 µm to 3 µm, 0.25 µm to 10 µm, 0.25 µm to 9 µm, 0.25 µm to 8 µm, 0.25 µm to 7 µm, 0.25 µm to 6 µm, 0.25 µm to 5 µm, 0.25 µm to 4 µm, 0.25 µm to 3 µm, 0.3 µm to 10 µm, 0.3 µm to 9 µm, 0.3 µm to 8 µm, 0.3 µm to 7 µm, 0.3 µm to 6 µm, 0.3 µm to 5 µm, 0.3 µm to 4 µm, 0.35 µm to 10 µm, 0.35 µm to 9 µm, 0.35 µm to 8 µm, 0.35 µm to 7 µm, 0.35 µm to 6 µm, 0.35 µm to 5 µm, 0.35 µm to 4 µm, 0.4 µm to 10 µm, 0.4 µm to 9 µm, 0.4 µm to 8 µm, 0.4 µm to 7 µm, 0.4 µm to 6 µm, 0.4 µm to 5 µm, 0.45 µm to 10 µm, 0.45 µm to 9 µm, 0.45 µm to 8 µm, 0.45 µm to 7 µm, 0.45 µm to 6 µm, 0.45 µm to 5 µm, 0.5 µm to 10 µm, 0.5 µm to 9 µm, 0.5 µm to 8 µm, 0.5 µm to 7 µm, 0.5 µm to 6 µm, 0.55 µm to 10 µm, 0.55 µm to 9 µm, 0.55 µm to 8 µm, 0.55 µm to 7 µm, 0.55 µm to 6 µm, 0.6 µm to 10 µm, 0.6 µm to 9 µm, 0.6 µm to 8 µm, 0.6 µm to 7 µm, 0.65 µm to 10 µm, 0.65 µm to 9 µm, 0.65 µm to 8 µm, 0.65 µm to 7 µm, 0.7 µm to 10 µm, 0.7 µm to 9 µm, 0.7 µm to 8 µm, 0.75 µm to 10 µm, 0.75 µm to 9 µm, 0.75 µm to 8 µm, 0.8 µm to 10 µm, 0.8 µm to 9 µm, 0.85 µm to 10 µm, 0.85 µm to 9 µm, 0.9 µm to 10 µm, 0.95 µm to 10 µm, 1 µm to 10 µm, 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm.

In some embodiments, the product is provided as a preparation and at least 30%, 35%, 40%, 45%, 50%, 55%, 60%, 65%, 70%, 75%, 80%, 85%, 90%, 95% or 100% of the products in the preparation have a combination of diameter and pore size described herein.

In some embodiments, the products have a mean diameter or size that is greater than 1 mm and less than 8 mm, greater than 1.5 mm and less than 8 mm, greater than 2 mm and less than 8 mm, greater than 2.5 mm and less than 8 mm, greater than 3 mm and less than 8 mm, greater than 3.5 mm and less than 8 mm, greater than 4 mm and less than 8 mm, greater than 4.5 mm and less than 8 mm, greater than 5 mm and less than 8 mm, greater than 5.5 mm and less than 8 mm, greater than 6 mm and less than 8 mm, greater than 6.5 mm and less than 8 mm, greater than 7 mm and less than 8 mm, or greater than 7.5 mm and less than 8 mm, and, independently, the density is at least, is less than, or is 0.1, 0.2, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, or 1000 chemical derivatizations per µm² on the surface or a surface of the products, in the interior of the products, or both.

In some embodiments, the products have a mean diameter or size in a range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, and a density in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.1 to 110, 0.1 to 120, 0.1 to 130, 0.1 to 140, 0.1 to 150, 0.1 to 160, 0.1 to 170, 0.1 to 180, 0.1 to 190, 0.1 to 200, 0.1 to 210, 0.1 to 220, 0.1 to 230, 0.1 to 240, 0.1 to 250, 0.1 to 260, 0.1 to 270, 0.1 to 280, 0.1 to 290, 0.1 to 300, 0.1 to 320, 0.1 to 340, 0.1 to 360, 0.1 to 380, 0.1 to 400, 0.1 to 420, 0.1 to 440, 0.1 to 460, 0.1 to 480, 0.1 to 500, 0.1 to 550, 0.1 to 600, 0.1 to 650, 0.1 to 700, 0.1 to 750, 0.1 to 800, 0.1 to 850, 0.1 to 900, 0.1 to 1000, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.2 to 110, 0.2 to 120, 0.2 to 130, 0.2 to 140, 0.2 to 150, 0.2 to 160, 0.2 to 170, 0.2 to 180, 0.2 to 190, 0.2 to 200, 0.2 to 210, 0.2 to 220, 0.2 to 230, 0.2 to 240, 0.2 to 250, 0.2 to 260, 0.2 to 270, 0.2 to 280, 0.2 to 290, 0.2 to 300, 0.2 to 320, 0.2 to 340, 0.2 to 360, 0.2 to 380, 0.2 to 400, 0.2 to 420, 0.2 to 440, 0.2 to 460, 0.2 to 480, 0.2 to 500, 0.2 to 550, 0.2 to 600, 0.2 to 650, 0.2 to 700, 0.2 to 750, 0.2 to 800, 0.2 to 850, 0.2 to 900, 0.2 to 1000, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 0.5 to 110, 0.5 to 120, 0.5 to 130, 0.5 to 140, 0.5 to 150, 0.5 to 160, 0.5 to 170, 0.5 to 180, 0.5 to 190, 0.5 to 200, 0.5 to 210, 0.5 to 220, 0.5 to 230, 0.5 to 240, 0.5 to 250, 0.5 to 260, 0.5 to 270, 0.5 to 280, 0.5 to 290, 0.5 to 300, 0.5 to 320, 0.5 to 340, 0.5 to 360, 0.5 to 380, 0.5 to 400, 0.5 to 420, 0.5 to 440, 0.5 to 460, 0.5 to 480, 0.5 to 500, 0.5 to 550, 0.5 to 600, 0.5 to 650, 0.5 to 700, 0.5 to 750, 0.5 to 800, 0.5 to 850, 0.5 to 900, 0.5 to 1000, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 110, 1 to 120, 1 to 130, 1 to 140, 1 to 150, 1 to 160, 1 to 170, 1 to 180, 1 to 190, 1 to 200, 1 to 210, 1 to 220, 1 to 230, 1 to 240, 1 to 250, 1 to 260, 1 to 270, 1 to 280, 1 to 290, 1 to 300, 1 to 320, 1 to 340, 1 to 360, 1 to 380, 1 to 400, 1 to 420, 1 to 440, 1 to 460, 1 to 480, 1 to 500, 1 to 550, 1 to 600, 1 to 650, 1 to 700, 1 to 750, 1 to 800, 1 to 850, 1 to 900, 1 to 1000, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 2 to 110, 2 to 120, 2 to 130, 2 to 140, 2 to 150, 2 to 160, 2 to 170, 2 to 180, 2 to 190, 2 to 200, 2 to 210, 2 to 220, 2 to 230, 2 to 240, 2 to 250, 2 to 260, 2 to 270, 2 to 280, 2 to 290, 2 to 300, 2 to 320, 2 to 340, 2 to 360, 2 to 380, 2 to 400, 2 to 420, 2 to 440, 2 to 460, 2 to 480, 2 to 500, 2 to 550, 2 to 600, 2 to 650, 2 to 700, 2 to 750, 2 to 800, 2 to 850, 2 to 900, 2 to 1000, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 3 to 110, 3 to 120, 3 to 130, 3 to 140, 3 to 150, 3 to 160, 3 to 170, 3 to 180, 3 to 190, 3 to 200, 3 to 210, 3 to 220, 3 to 230, 3 to 240, 3 to 250, 3 to 260, 3 to 270, 3 to 280, 3 to 290, 3 to 300, 3 to 320, 3 to 340, 3 to 360, 3 to 380, 3 to 400, 3 to 420, 3 to 440, 3 to 460, 3 to 480, 3 to 500, 3 to 550, 3 to 600, 3 to 650, 3 to 700, 3 to 750, 3 to 800, 3 to 850, 3 to 900, 3 to 1000, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 4 to 110, 4 to 120, 4 to 130, 4 to 140, 4 to 150, 4 to 160, 4 to 170, 4 to 180, 4 to 190, 4 to 200, 4 to 210, 4 to 220, 4 to 230, 4 to 240, 4 to 250, 4 to 260, 4 to 270, 4 to 280, 4 to 290, 4 to 300, 4 to 320, 4 to 340, 4 to 360, 4 to 380, 4 to 400, 4 to 420, 4 to 440, 4 to 460, 4 to 480, 4 to 500, 4 to 550, 4 to 600, 4 to 650, 4 to 700, 4 to 750, 4 to 800, 4 to 850, 4 to 900, 4 to 1000, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 5 to 110, 5 to 120, 5 to 130, 5 to 140, 5 to 150, 5 to 160, 5 to 170, 5 to 180, 5 to 190, 5 to 200, 5 to 210, 5 to 220, 5 to 230, 5 to 240, 5 to 250, 5 to 260, 5 to 270, 5 to 280, 5 to 290, 5 to 300, 5 to 320, 5 to 340, 5 to 360, 5 to 380, 5 to 400, 5 to 420, 5 to 440, 5 to 460, 5 to 480, 5 to 500, 5 to 550, 5 to 600, 5 to 650, 5 to 700, 5 to 750, 5 to 800, 5 to 850, 5 to 900, 5 to 1000, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 6 to 110, 6 to 120, 6 to 130, 6 to 140, 6 to 150, 6 to 160, 6 to 170, 6 to 180, 6 to 190, 6 to 200, 6 to 210, 6 to 220, 6 to 230, 6 to 240, 6 to 250, 6 to 260, 6 to 270, 6 to 280, 6 to 290, 6 to 300, 6 to 320, 6 to 340, 6 to 360, 6 to 380, 6 to 400, 6 to 420, 6 to 440, 6 to 460, 6 to 480, 6 to 500, 6 to 550, 6 to 600, 6 to 650, 6 to 700, 6 to 750, 6 to 800, 6 to 850, 6 to 900, 6 to 1000, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 7 to 110, 7 to 120, 7 to 130, 7 to 140, 7 to 150, 7 to 160, 7 to 170, 7 to 180, 7 to 190, 7 to 200, 7 to 210, 7 to 220, 7 to 230, 7 to 240, 7 to 250, 7 to 260, 7 to 270, 7 to 280, 7 to 290, 7 to 300, 7 to 320, 7 to 340, 7 to 360, 7 to 380, 7 to 400, 7 to 420, 7 to 440, 7 to 460, 7 to 480, 7 to 500, 7 to 550, 7 to 600, 7 to 650, 7 to 700, 7 to 750, 7 to 800, 7 to 850, 7 to 900, 7 to 1000, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 8 to 110, 8 to 120, 8 to 130, 8 to 140, 8 to 150, 8 to 160, 8 to 170, 8 to 180, 8 to 190, 8 to 200, 8 to 210, 8 to 220, 8 to 230, 8 to 240, 8 to 250, 8 to 260, 8 to 270, 8 to 280, 8 to 290, 8 to 300, 8 to 320, 8 to 340, 8 to 360, 8 to 380, 8 to 400, 8 to 420, 8 to 440, 8 to 460, 8 to 480, 8 to 500, 8 to 550, 8 to 600, 8 to 650, 8 to 700, 8 to 750, 8 to 800, 8 to 850, 8 to 900, 8 to 1000, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 9 to 110, 9 to 120, 9 to 130, 9 to 140, 9 to 150, 9 to 160, 9 to 170, 9 to 180, 9 to 190, 9 to 200, 9 to 210, 9 to 220, 9 to 230, 9 to 240, 9 to 250, 9 to 260, 9 to 270, 9 to 280, 9 to 290, 9 to 300, 9 to 320, 9 to 340, 9 to 360, 9 to 380, 9 to 400, 9 to 420, 9 to 440, 9 to 460, 9 to 480, 9 to 500, 9 to 550, 9 to 600, 9 to 650, 9 to 700, 9 to 750, 9 to 800, 9 to 850, 9 to 900, 9 to 1000, 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 10 to 110, 10 to 120, 10 to 130, 10 to 140, 10 to 150, 10 to 160, 10 to 170, 10 to 180, 10 to 190, 10 to 200, 10 to 210, 10 to 220, 10 to 230, 10 to 240, 10 to 250, 10 to 260, 10 to 270, 10 to 280, 10 to 290, 10 to 300, 10 to 320, 10 to 340, 10 to 360, 10 to 380, 10 to 400, 10 to 420, 10 to 440, 10 to 460, 10 to 480, 10 to 500, 10 to 550, 10 to 600, 10 to 650, 10 to 700, 10 to 750, 10 to 800, 10 to 850, 10 to 900, 10 to 1000, 20 to 25, 20 to 30, 20 to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 20 to 110, 20 to 120, 20 to 130, 20 to 140, 20 to 150, 20 to 160, 20 to 170, 20 to 180, 20 to 190, 20 to 200, 20 to 210, 20 to 220, 20 to 230, 20 to 240, 20 to 250, 20 to 260, 20 to 270, 20 to 280, 20 to 290, 20 to 300, 20 to 320, 20 to 340, 20 to 360, 20 to 380, 20 to 400, 20 to 420, 20 to 440, 20 to 460, 20 to 480, 20 to 500, 20 to 550, 20 to 600, 20 to 650, 20 to 700, 20 to 750, 20 to 800, 20 to 850, 20 to 900, 20 to 1000, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 30 to 110, 30 to 120, 30 to 130, 30 to 140, 30 to 150, 30 to 160, 30 to 170, 30 to 180, 30 to 190, 30 to 200, 30 to 210, 30 to 220, 30 to 230, 30 to 240, 30 to 250, 30 to 260, 30 to 270, 30 to 280, 30 to 290, 30 to 300, 30 to 320, 30 to 340, 30 to 360, 30 to 380, 30 to 400, 30 to 420, 30 to 440, 30 to 460, 30 to 480, 30 to 500, 30 to 550, 30 to 600, 30 to 650, 30 to 700, 30 to 750, 30 to 800, 30 to 850, 30 to 900, 30 to 1000, 40 to 45, 40 to 50, 40 to 55, 40 to 60, 40 to 65, 40 to 70, 40 to 75, 40 to 80, 40 to 85, 40 to 90, 40 to 95, 40 to 100, 40 to 110, 40 to 120, 40 to 130, 40 to 140, 40 to 150, 40 to 160, 40 to 170, 40 to 180, 40 to 190, 40 to 200, 40 to 210, 40 to 220, 40 to 230, 40 to 240, 40 to 250, 40 to 260, 40 to 270, 40 to 280, 40 to 290, 40 to 300, 40 to 320, 40 to 340, 40 to 360, 40 to 380, 40 to 400, 40 to 420, 40 to 440, 40 to 460, 40 to 480, 40 to 500, 40 to 550, 40 to 600, 40 to 650, 40 to 700, 40 to 750, 40 to 800, 40 to 850, 40 to 900, 40 to 1000, 50 to 55, 50 to 60, 50 to 65, 50 to 70, 50 to 75, 50 to 80, 50 to 85, 50 to 90, 50 to 95, 50 to 100, 50 to 110, 50 to 120, 50 to 130, 50 to 140, 50 to 150, 50 to 160, 50 to 170, 50 to 180, 50 to 190, 50 to 200, 50 to 210, 50 to 220, 50 to 230, 50 to 240, 50 to 250, 50 to 260, 50 to 270, 50 to 280, 50 to 290, 50 to 300, 50 to 320, 50 to 340, 50 to 360, 50 to 380, 50 to 400, 50 to 420, 50 to 440, 50 to 460, 50 to 480, 50 to 500, 50 to 550, 50 to 600, 50 to 650, 50 to 700, 50 to 750, 50 to 800, 50 to 850, 50 to 900, 50 to 1000, 60 to 65, 60 to 70, 60 to 75, 60 to 80, 60 to 85, 60 to 90, 60 to 95, 60 to 100, 60 to 110, 60 to 120, 60 to 130, 60 to 140, 60 to 150, 60 to 160, 60 to 170, 60 to 180, 60 to 190, 60 to 200, 60 to 210, 60 to 220, 60 to 230, 60 to 240, 60 to 250, 60 to 260, 60 to 270, 60 to 280, 60 to 290, 60 to 300, 60 to 320, 60 to 340, 60 to 360, 60 to 380, 60 to 400, 60 to 420, 60 to 440, 60 to 460, 60 to 480, 60 to 500, 60 to 550, 60 to 600, 60 to 650, 60 to 700, 60 to 750, 60 to 800, 60 to 850, 60 to 900, 60 to 1000, 70 to 75, 70 to 80, 70 to 85, 70 to 90, 70 to 95, 70 to 100, 70 to 110, 70 to 120, 70 to 130, 70 to 140, 70 to 150, 70 to 160, 70 to 170, 70 to 180, 70 to 190, 70 to 200, 70 to 210, 70 to 220, 70 to 230, 70 to 240, 70 to 250, 70 to 260, 70 to 270, 70 to 280, 70 to 290, 70 to 300, 70 to 320, 70 to 340, 70 to 360, 70 to 380, 70 to 400, 70 to 420, 70 to 440, 70 to 460, 70 to 480, 70 to 500, 70 to 550, 70 to 600, 70 to 650, 70 to 700, 70 to 750, 70 to 800, 70 to 850, 70 to 900, 70 to 1000, 80 to 85, 80 to 90, 80 to 95, 80 to 100, 80 to 110, 80 to 120, 80 to 130, 80 to 140, 80 to 150, 80 to 160, 80 to 170, 80 to 180, 80 to 190, 80 to 200, 80 to 210, 80 to 220, 80 to 230, 80 to 240, 80 to 250, 80 to 260, 80 to 270, 80 to 280, 80 to 290, 80 to 300, 80 to 320, 80 to 340, 80 to 360, 80 to 380, 80 to 400, 80 to 420, 80 to 440, 80 to 460, 80 to 480, 80 to 500, 80 to 550, 80 to 600, 80 to 650, 80 to 700, 80 to 750, 80 to 800, 80 to 850, 80 to 900, 80 to 1000, 90 to 95, 90 to 100, 90 to 110, 90 to 120, 90 to 130, 90 to 140, 90 to 150, 90 to 160, 90 to 170, 90 to 180, 90 to 190, 90 to 200, 90 to 210, 90 to 220, 90 to 230, 90 to 240, 90 to 250, 90 to 260, 90 to 270, 90 to 280, 90 to 290, 90 to 300, 90 to 320, 90 to 340, 90 to 360, 90 to 380, 90 to 400, 90 to 420, 90 to 440, 90 to 460, 90 to 480, 90 to 500, 90 to 550, 90 to 600, 90 to 650, 90 to 700, 90 to 750, 90 to 800, 90 to 850, 90 to 900, 90 to 1000, 100 to 110, 100 to 120, 100 to 130, 100 to 140, 100 to 150, 100 to 160, 100 to 170, 100 to 180, 100 to 190, 100 to 200, 100 to 210, 100 to 220, 100 to 230, 100 to 240, 100 to 250, 100 to 260, 100 to 270, 100 to 280, 100 to 290, 100 to 300, 100 to 320, 100 to 340, 100 to 360, 100 to 380, 100 to 400, 100 to 420, 100 to 440, 100 to 460, 100 to 480, 100 to 500, 100 to 550, 100 to 600, 100 to 650, 100 to 700, 100 to 750, 100 to 800, 100 to 850, 100 to 900, 100 to 1000, 200 to 210, 200 to 220, 200 to 230, 200 to 240, 200 to 250, 200 to 260, 200 to 270, 200 to 280, 200 to 290, 200 to 300, 200 to 320, 200 to 340, 200 to 360, 200 to 380, 200 to 400, 200 to 420, 200 to 440, 200 to 460, 200 to 480, 200 to 500, 200 to 550, 200 to 600, 200 to 650, 200 to 700, 200 to 750, 200 to 800, 200 to 850, 200 to 900, 200 to 1000, 300 to 320, 300 to 340, 300 to 360, 300 to 380, 300 to 400, 300 to 420, 300 to 440, 300 to 460, 300 to 480, 300 to 500, 300 to 550, 300 to 600, 300 to 650, 300 to 700, 300 to 750, 300 to 800, 300 to 850, 300 to 900, 300 to 1000, 400 to 420, 400 to 440, 400 to 460, 400 to 480, 400 to 500, 400 to 550, 400 to 600, 400 to 650, 400 to 700, 400 to 750, 400 to 800, 400 to 850, 400 to 900, 400 to 1000, 500 to 550, 500 to 600, 500 to 650, 500 to 700, 500 to 750, 500 to 800, 500 to 850, 500 to 900, 500 to 1000, 600 to 650, 600 to 700, 600 to 750, 600 to 800, 600 to 850, 600 to 900, 600 to 1000, 700 to 750, 700 to 800, 700 to 850, 700 to 900, 700 to 1000, 800 to 850, 800 to 900, 800 to 1000, and 900 to 1000 chemical derivatizations per µm$^2$ on the surface or a surface of the products, in the interior of the products, or both In some embodiments, the product is provided as a preparation and at least 30%, 35%, 40%, 45%, 50%, 55%, 60%, 65%, 70%, 75%, 80%, 85%, 90%, 95% or 100% of the products in the preparation have a combination of product size or diameter and derivatization density described herein.

In some embodiments, the products have a mean diameter or size that is greater than 1 mm and less than 8 mm, greater than 1.5 mm and less than 8 mm, greater than 2 mm and less than 8 mm, greater than 2.5 mm and less than 8 mm, greater than 3 mm and less than 8 mm, greater than 3.5 mm and less than 8 mm, greater than 4 mm and less than 8 mm, greater than 4.5 mm and less than 8 mm, greater than 5 mm and less than 8 mm, greater than 5.5 mm and less than 8 mm, greater than 6 mm and less than 8 mm, greater than 6.5 mm and less than 8 mm, greater than 7 mm and less than 8 mm, or greater than 7.5 mm and less than 8 mm, and, independently, the concentration of surface modifications is at least, is less than, or is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent.

In some embodiments, the products have a mean diameter or size in a range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, and a concentration of surface modifications in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 20 to 25, 20 to 30, 20 to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 40 to 45, 40 to 50, 40 to 55, 40 to 60, 40 to 65, 40 to 70, 40 to 75, 40 to 80, 40 to 85, 40 to 90, 40 to 95, 40 to 100, 50 to 55, 50 to 60, 50 to 65, 50 to 70, 50 to 75, 50 to 80, 50 to 85, 50 to 90, 50 to 95, 50 to 100, 60 to 65, 60 to 70, 60 to 75, 60 to 80, 60 to 85, 60 to 90, 60 to 95, 60 to 100, 70 to 75, 70 to 80, 70 to 85, 70 to 90, 70 to 95, 70 to 100, 80 to 85, 80 to 90, 80 to 95, 80 to 100, 90 to 95, 90 to 100 percent.

In some embodiments, the product is provided as a preparation and at least 30%, 35%, 40%, 45%, 50%, 55%, 60%, 65%, 70%, 75%, 80%, 85%, 90%, 95% or 100% of the products in the preparation have a combination of product size or diameter and concentrations of surface modifications described herein.

In some embodiments, the density of the chemical derivatizations is at least, is less than, or is 0.1, 0.2, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, or 1000 chemical derivatizations per µm² on the surface or a surface of the products, in the interior of the products, or both, or the concentration of surface modifications is at least, is less than, or is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 percent, and, independently, the products have pores in a size range of 0.1 µm to 10 µm, 0.1 µm to 9 µm, 0.1 µm to 8 µm, 0.1 µm to 7 µm, 0.1 µm to 6 µm, 0.1 µm to 5 µm, 0.1 µm to 4 µm, 0.1 µm to 3 µm, 0.1 µm to 2 µm, 0.15 µm to 10 µm, 0.15 µm to 9 µm, 0.15 µm to 8 µm, 0.15 µm to 7 µm, 0.15 µm to 6 µm, 0.15 µm to 5 µm, 0.15 µm to 4 µm, 0.15 µm to 3 µm, 0.15 µm to 2 µm, 0.2 µm to 10 µm, 0.2 µm to 9 µm, 0.2 µm to 8 µm, 0.2 µm to 7 µm, 0.2 µm to 6 µm, 0.2 µm to 5 µm, 0.2 µm to 4 µm, 0.2 µm to 3 µm, 0.25 µm to 10 µm, 0.25 µm to 9 µm, 0.25 µm to 8 µm, 0.25 µm to 7 µm, 0.25 µm to 6 µm, 0.25 µm to 5 µm, 0.25 µm to 4 µm, 0.25 µm to 3 µm, 0.3 µm to 10 µm, 0.3 µm to 9 µm, 0.3 µm to 8 µm, 0.3 µm to 7 µm, 0.3 µm to 6 µm, 0.3 µm to 5 µm, 0.3 µm to 4 µm, 0.35 µm to 10 µm, 0.35 µm to 9 µm, 0.35 µm to 8 µm, 0.35 µm to 7 µm, 0.35 µm to 6 µm, 0.35 µm to 5 µm, 0.35 µm to 4 µm, 0.4 µm to 10 µm, 0.4 µm to 9 µm, 0.4 µm to 8 µm, 0.4 µm to 7 µm, 0.4 µm to 6 µm, 0.4 µm to 5 µm, 0.45 µm to 10 µm, 0.45 µm to 9 µm, 0.45 µm to 8 µm, 0.45 µm to 7 µm, 0.45 µm to 6 µm, 0.45 µm to 5 µm, 0.5 µm to 10 µm, 0.5 µm to 9 µm, 0.5 µm to 8 µm, 0.5 µm to 7 µm, 0.5 µm to 6 µm, 0.55 µm to 10 µm, 0.55 µm to 9 µm, 0.55 µm to 8 µm, 0.55 µm to 7 µm, 0.55 µm to 6 µm, 0.6 µm to 10 µm, 0.6 µm to 9 µm, 0.6 µm to 8 µm, 0.6 µm to 7 µm, 0.65 µm to 10 µm, 0.65 µm to 9 µm, 0.65 µm to 8 µm, 0.65 µm to 7 µm, 0.7 µm to 10 µm, 0.7 µm to 9 µm, 0.7 µm to 8 µm, 0.75 µm to 10 µm, 0.75 µm to 9 µm, 0.75 µm to 8 µm, 0.8 µm to 10 µm, 0.8 µm to 9 µm, 0.85 µm to 10 µm, 0.85 µm to 9 µm, 0.9 µm to 10 µm, 0.95 µm to 10 µm, 1 µm to 10 µm, 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm.

In some embodiments, the density of the chemical derivatizations is in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.1 to 110, 0.1 to 120, 0.1 to 130, 0.1 to 140, 0.1 to 150, 0.1 to 160, 0.1 to 170, 0.1 to 180, 0.1 to 190, 0.1 to 200, 0.1 to 210, 0.1 to 220, 0.1 to 230, 0.1 to 240, 0.1 to 250, 0.1 to 260, 0.1 to 270, 0.1 to 280, 0.1 to 290, 0.1 to 300, 0.1 to 320, 0.1 to 340, 0.1 to 360, 0.1 to 380, 0.1 to 400, 0.1 to 420, 0.1 to 440, 0.1 to 460, 0.1 to 480, 0.1 to 500, 0.1 to 550, 0.1 to 600, 0.1 to 650, 0.1 to 700, 0.1 to 750, 0.1 to 800, 0.1 to 850, 0.1 to 900, 0.1 to 1000, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.2 to 110, 0.2 to 120, 0.2 to 130, 0.2 to 140, 0.2 to 150, 0.2 to 160, 0.2 to 170, 0.2 to 180, 0.2 to 190, 0.2 to 200, 0.2 to 210, 0.2 to 220, 0.2 to 230, 0.2 to 240, 0.2 to 250, 0.2 to 260, 0.2 to 270, 0.2 to 280, 0.2 to 290, 0.2 to 300, 0.2 to 320, 0.2 to 340, 0.2 to 360, 0.2 to 380, 0.2 to 400, 0.2 to 420, 0.2 to 440, 0.2 to 460, 0.2 to 480, 0.2 to 500, 0.2 to 550, 0.2 to 600, 0.2 to 650, 0.2 to 700, 0.2 to 750, 0.2 to 800, 0.2 to 850, 0.2 to 900, 0.2 to 1000, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 0.5 to 110, 0.5 to 120, 0.5 to 130, 0.5 to 140, 0.5 to 150, 0.5 to 160, 0.5 to 170, 0.5 to 180, 0.5 to 190, 0.5 to 200, 0.5 to 210, 0.5 to 220, 0.5 to 230, 0.5 to 240, 0.5 to 250, 0.5 to 260, 0.5 to 270, 0.5 to 280, 0.5 to 290, 0.5 to 300, 0.5 to 320, 0.5 to 340, 0.5 to 360, 0.5 to 380, 0.5 to 400, 0.5 to 420, 0.5 to 440, 0.5 to 460, 0.5 to 480, 0.5 to 500, 0.5 to 550, 0.5 to 600, 0.5 to 650, 0.5 to 700, 0.5 to 750, 0.5 to 800, 0.5 to 850, 0.5 to 900, 0.5 to 1000, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 110, 1 to 120, 1 to 130, 1 to 140, 1 to 150, 1 to 160, 1 to 170, 1 to 180, 1 to 190, 1 to 200, 1 to 210, 1 to 220, 1 to 230, 1 to 240, 1 to 250, 1 to 260, 1 to 270, 1 to 280, 1 to 290, 1 to 300, 1 to 320, 1 to 340, 1 to 360, 1 to 380, 1 to 400, 1 to 420, 1 to 440, 1 to 460, 1 to 480, 1 to 500, 1 to 550, 1 to 600, 1 to 650, 1 to 700, 1 to 750, 1 to 800, 1 to 850, 1 to 900, 1 to 1000, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 2 to 110, 2 to 120, 2 to 130, 2 to 140, 2 to 150, 2 to 160, 2 to 170, 2 to 180, 2 to 190, 2 to 200, 2 to 210, 2 to 220, 2 to 230, 2 to 240, 2 to 250, 2 to 260, 2 to 270, 2 to 280, 2 to 290, 2 to 300, 2 to 320, 2 to 340, 2 to 360, 2 to 380, 2 to 400, 2 to 420, 2 to 440, 2 to 460, 2 to 480, 2 to 500, 2 to 550, 2 to 600, 2 to 650, 2 to 700, 2 to 750, 2 to 800, 2 to 850, 2 to 900, 2 to 1000, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 3 to 110, 3 to 120, 3 to 130, 3 to 140, 3 to 150, 3 to 160, 3 to 170, 3 to 180, 3 to 190, 3 to 200, 3 to 210, 3 to 220, 3 to 230, 3 to 240, 3 to 250, 3 to 260, 3 to 270, 3 to 280, 3 to 290, 3 to 300, 3 to 320, 3 to 340, 3 to 360, 3 to 380, 3 to 400, 3 to 420, 3 to 440, 3 to 460, 3 to 480, 3 to 500, 3 to 550, 3 to 600, 3 to 650, 3 to 700, 3 to 750, 3 to 800, 3 to 850, 3 to 900, 3 to 1000, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 4 to 110, 4 to 120, 4 to 130, 4 to 140, 4 to 150, 4 to 160, 4 to 170, 4 to 180, 4 to 190, 4 to 200, 4 to 210, 4 to 220, 4 to 230, 4 to 240, 4 to 250, 4 to 260, 4 to 270, 4 to 280, 4 to 290, 4 to 300, 4 to 320, 4 to 340, 4 to 360, 4 to 380, 4 to 400, 4 to 420, 4 to 440, 4 to 460, 4 to 480, 4 to 500, 4 to 550, 4 to 600, 4 to 650, 4 to 700, 4 to 750, 4 to 800, 4 to 850, 4 to 900, 4 to 1000, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 5 to 110, 5 to 120, 5 to 130, 5 to 140, 5 to 150, 5 to 160, 5 to 170, 5 to 180, 5 to 190, 5 to 200, 5 to 210, 5 to 220, 5 to 230, 5 to 240, 5 to 250, 5 to 260, 5 to 270, 5 to 280, 5 to 290, 5 to 300, 5 to 320, 5 to 340, 5 to 360, 5 to 380, 5 to 400, 5 to 420, 5 to 440, 5 to 460, 5 to 480, 5 to 500, 5 to 550, 5 to 600, 5 to 650, 5 to 700, 5 to 750, 5 to 800, 5 to 850, 5 to 900, 5 to 1000, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 6 to 110, 6 to 120, 6 to 130, 6 to 140, 6 to 150, 6 to 160, 6 to 170, 6 to 180, 6 to 190, 6 to 200, 6 to 210, 6 to 220, 6 to 230, 6 to 240, 6 to 250, 6 to 260, 6 to 270, 6 to 280, 6 to 290, 6 to 300, 6 to 320, 6 to 340, 6 to 360, 6 to 380, 6 to 400, 6 to 420, 6 to 440, 6 to 460, 6 to 480, 6 to 500, 6 to 550, 6 to 600, 6 to 650, 6 to 700, 6 to 750, 6 to 800, 6 to 850, 6 to 900, 6 to 1000, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 7 to 110, 7 to 120, 7 to 130, 7 to 140, 7 to 150, 7 to 160, 7 to 170, 7 to 180, 7 to 190, 7 to 200, 7 to 210, 7 to 220, 7 to 230, 7 to 240, 7 to 250, 7 to 260, 7 to 270, 7 to 280, 7 to 290, 7 to 300, 7 to 320, 7 to 340, 7 to 360, 7 to 380, 7 to 400, 7 to 420, 7 to 440, 7 to 460, 7 to 480, 7 to 500, 7 to 550, 7 to 600, 7 to 650, 7 to 700, 7 to 750, 7 to 800, 7 to 850, 7 to 900, 7 to 1000, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 8 to 110, 8 to 120, 8 to 130, 8 to 140, 8 to 150, 8 to 160, 8 to 170, 8 to 180, 8 to 190, 8 to 200, 8 to 210, 8 to 220, 8 to 230, 8 to 240, 8 to 250, 8 to 260, 8 to 270, 8 to 280, 8 to 290, 8 to 300, 8 to 320, 8 to 340, 8 to 360, 8 to 380, 8 to 400, 8 to 420, 8 to 440, 8 to 460, 8 to 480, 8 to 500, 8 to 550, 8 to 600, 8 to 650, 8 to 700, 8 to 750, 8 to 800, 8 to 850, 8 to 900, 8 to 1000, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 9 to 110, 9 to 120, 9 to 130, 9 to 140, 9 to 150, 9 to 160, 9 to 170, 9 to 180, 9 to 190, 9 to 200, 9 to 210, 9 to 220, 9 to 230, 9 to 240, 9 to 250, 9 to 260, 9 to 270, 9 to 280, 9 to 290, 9 to 300, 9 to 320, 9 to 340, 9 to 360, 9 to 380, 9 to 400, 9 to 420, 9 to 440, 9 to 460, 9 to 480, 9 to 500, 9 to 550, 9 to 600, 9 to 650, 9 to 700, 9 to 750, 9 to 800, 9 to 850, 9 to 900, 9 to 1000, 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 10 to 110, 10 to 120, 10 to 130, 10 to 140, 10 to 150, 10 to 160, 10 to 170, 10 to 180, 10 to 190, 10 to 200, 10 to 210, 10 to 220, 10 to 230, 10 to 240, 10 to 250, 10 to 260, 10 to 270, 10 to 280, 10 to 290, 10 to 300, 10 to 320, 10 to 340, 10 to 360, 10 to 380, 10 to 400, 10 to 420, 10 to 440, 10 to 460, 10 to 480, 10 to 500, 10 to 550, 10 to 600, 10 to 650, 10 to 700, 10 to 750, 10 to 800, 10 to 850, 10 to 900, 10 to 1000, 20 to 25, 20 to 30, 20 to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 20 to 110, 20 to 120, 20 to 130, 20 to 140, 20 to 150, 20 to 160, 20 to 170, 20 to 180, 20 to 190, 20 to 200, 20 to 210, 20 to 220, 20 to 230, 20 to 240, 20 to 250, 20 to 260, 20 to 270, 20 to 280, 20 to 290, 20 to 300, 20 to 320, 20 to 340, 20 to 360, 20 to 380, 20 to 400, 20 to 420, 20 to 440, 20 to 460, 20 to 480, 20 to 500, 20 to 550, 20 to 600, 20 to 650, 20 to 700, 20 to 750, 20 to 800, 20 to 850, 20 to 900, 20 to 1000, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 30 to 110, 30 to 120, 30 to 130, 30 to 140, 30 to 150, 30 to 160, 30 to 170, 30 to 180, 30 to 190, 30 to 200, 30 to 210, 30 to 220, 30 to 230, 30 to 240, 30 to 250, 30 to 260, 30 to 270, 30 to 280, 30 to 290, 30 to 300, 30 to 320, 30 to 340, 30 to 360, 30 to 380, 30 to 400, 30 to 420, 30 to 440, 30 to 460, 30 to 480, 30 to 500, 30 to 550, 30 to 600, 30 to 650, 30 to 700, 30 to 750, 30 to 800, 30 to 850, 30 to 900, 30 to 1000, 40 to 45, 40 to 50, 40 to 55, 40 to 60, 40 to 65, 40 to 70, 40 to 75, 40 to 80, 40 to 85, 40 to 90, 40 to 95, 40 to 100, 40 to 110, 40 to 120, 40 to 130, 40 to 140, 40 to 150, 40 to 160, 40 to 170, 40 to 180, 40 to 190, 40 to 200, 40 to 210, 40 to 220, 40 to 230, 40 to 240, 40 to 250, 40 to 260, 40 to 270, 40 to 280, 40 to 290, 40 to 300, 40 to 320, 40 to 340, 40 to 360, 40 to 380, 40 to 400, 40 to 420, 40 to 440, 40 to 460, 40 to 480, 40 to 500, 40 to 550, 40 to 600, 40 to 650, 40 to 700, 40 to 750, 40 to 800, 40 to 850, 40 to 900, 40 to 1000, 50 to 55, 50 to 60, 50 to 65, 50 to 70, 50 to 75, 50 to 80, 50 to 85, 50 to 90, 50 to 95, 50 to 100, 50 to 110, 50 to 120, 50 to 130, 50 to 140, 50 to 150, 50 to 160, 50 to 170, 50 to 180, 50 to 190, 50 to 200, 50 to 210, 50 to 220, 50 to 230, 50 to 240, 50 to 250, 50 to 260, 50 to 270, 50 to 280, 50 to 290, 50 to 300, 50 to 320, 50 to 340, 50 to 360, 50 to 380, 50 to 400, 50 to 420, 50 to 440, 50 to 460, 50 to 480, 50 to 500, 50 to 550, 50 to 600, 50 to 650, 50 to 700, 50 to 750, 50 to 800, 50 to 850, 50 to 900, 50 to 1000, 60 to 65, 60 to 70, 60 to 75, 60 to 80, 60 to 85, 60 to 90, 60 to 95, 60 to 100, 60 to 110, 60 to 120, 60 to 130, 60 to 140, 60 to 150, 60 to 160, 60 to 170, 60 to 180, 60 to 190, 60 to 200, 60 to 210, 60 to 220, 60 to 230, 60 to 240, 60 to 250, 60 to 260, 60 to 270, 60 to 280, 60 to 290, 60 to 300, 60 to 320, 60 to 340, 60 to 360, 60 to 380, 60 to 400, 60 to 420, 60 to 440, 60 to 460, 60 to 480, 60 to 500, 60 to 550, 60 to 600, 60 to 650, 60 to 700, 60 to 750, 60 to 800, 60 to 850, 60 to 900, 60 to 1000, 70 to 75, 70 to 80, 70 to 85, 70 to 90, 70 to 95, 70 to 100, 70 to 110, 70 to 120, 70 to 130, 70 to 140, 70 to 150, 70 to 160, 70 to 170, 70 to 180, 70 to 190, 70 to 200, 70 to 210, 70 to 220, 70 to 230, 70 to 240, 70 to 250, 70 to 260, 70 to 270, 70 to 280, 70 to 290, 70 to 300, 70 to 320, 70 to 340, 70 to 360, 70 to 380, 70 to 400, 70 to 420, 70 to 440, 70 to 460, 70 to 480, 70 to 500, 70 to 550, 70 to 600, 70 to 650, 70 to 700, 70 to 750, 70 to 800, 70 to 850, 70 to 900, 70 to 1000, 80 to 85, 80 to 90, 80 to 95, 80 to 100, 80 to 110, 80 to 120, 80 to 130, 80 to 140, 80 to 150, 80 to 160, 80 to 170, 80 to 180, 80 to 190, 80 to 200, 80 to 210, 80 to 220, 80 to 230, 80 to 240, 80 to 250, 80 to 260, 80 to 270, 80 to 280, 80 to 290, 80 to 300, 80 to 320, 80 to 340, 80 to 360, 80 to 380, 80 to 400, 80 to 420, 80 to 440, 80 to 460, 80 to 480, 80 to 500, 80 to 550, 80 to 600, 80 to 650, 80 to 700, 80 to 750, 80 to 800, 80 to 850, 80 to 900, 80 to 1000, 90 to 95, 90 to 100, 90 to 110, 90 to 120, 90 to 130, 90 to 140, 90 to 150, 90 to 160, 90 to 170, 90 to 180, 90 to 190, 90 to 200, 90 to 210, 90 to 220, 90 to 230, 90 to 240, 90 to 250, 90 to 260, 90 to 270, 90 to 280, 90 to 290, 90 to 300, 90 to 320, 90 to 340, 90 to 360, 90 to 380, 90 to 400, 90 to 420, 90 to 440, 90 to 460, 90 to 480, 90 to 500, 90 to 550, 90 to 600, 90 to 650, 90 to 700, 90 to 750, 90 to 800, 90 to 850, 90 to 900, 90 to 1000, 100 to 110, 100 to 120, 100 to 130, 100 to 140, 100 to 150, 100 to 160, 100 to 170, 100 to 180, 100 to 190, 100 to 200, 100 to 210, 100 to 220, 100 to 230, 100 to 240, 100 to 250, 100 to 260, 100 to 270, 100 to 280, 100 to 290, 100 to 300, 100 to 320, 100 to 340, 100 to 360, 100 to 380, 100 to 400, 100 to 420, 100 to 440, 100 to 460, 100 to 480, 100 to 500, 100 to 550, 100 to 600, 100 to 650, 100 to 700, 100 to 750, 100 to 800, 100 to 850, 100 to 900, 100 to 1000, 200 to 210, 200 to 220, 200 to 230, 200 to 240, 200 to 250, 200 to 260, 200 to 270, 200 to 280, 200 to 290, 200 to 300, 200 to 320, 200 to 340, 200 to 360, 200 to 380, 200 to 400, 200 to 420, 200 to 440, 200 to 460, 200 to 480, 200 to 500, 200 to 550, 200 to 600, 200 to 650, 200 to 700, 200 to 750, 200 to 800, 200 to 850, 200 to 900, 200 to 1000, 300 to 320, 300 to 340, 300 to 360, 300 to 380, 300 to 400, 300 to 420, 300 to 440, 300 to 460, 300 to 480, 300 to 500, 300 to 550, 300 to 600, 300 to 650, 300 to 700, 300 to 750, 300 to 800, 300 to 850, 300 to 900, 300 to 1000, 400 to 420, 400 to 440, 400 to 460, 400 to 480, 400 to 500, 400 to 550, 400 to 600, 400 to 650, 400 to 700, 400 to 750, 400 to 800, 400 to 850, 400 to 900, 400 to 1000, 500 to 550, 500 to 600, 500 to 650, 500 to 700, 500 to 750, 500 to 800, 500 to 850, 500 to 900, 500 to 1000, 600 to 650, 600 to 700, 600 to 750, 600 to 800, 600 to 850, 600 to 900, 600 to 1000, 700 to 750, 700 to 800, 700 to 850, 700 to 900, 700 to 1000, 800 to 850, 800 to 900, 800 to 1000, and 900 to 1000 chemical derivatizations per $\mu m^2$ on the surface or a surface of the products, in the interior of the products, or both, and the products have pores in a size range of 1 μm to 10 μm, 1 μm to 9 μm, 1 μm to 8 μm, 1 μm to 7 μm, 1 μm to 6 μm, 1 μm to 5 μm, 1 μm to 4 μm, 1 μm to 3 μm, 1 μm to 2 μm, 1.5 μm to 10 μm, 1.5 μm to 9 μm, 1.5 μm to 8 μm, 1.5 μm to 7 μm, 1.5 μm to 6 μm, 1.5 μm to 5 μm, 1.5 μm to 4 μm, 1.5 μm to 3 μm, 1.5 μm to 2 μm, 2 μm to 10 μm, 2 μm to 9 μm, 2 μm to 8 μm, 2 μm to 7 μm, 2 μm to 6 μm, 2 μm to 5 μm, 2 μm to 4 μm, 2 μm to 3 μm, 2.5 μm to 10 μm, 2.5 μm to 9 μm, 2.5 μm to 8 μm, 2.5 μm to 7 μm, 2.5 μm to 6 μm, 2.5 μm to 5 μm, 2.5 μm to 4 μm, 2.5 μm to 3 μm, 3 μm to 10 μm, 3 μm to 9 μm, 3 μm to 8 μm, 3 μm to 7 μm, 3 μm to 6 μm, 3 μm to 5 μm, 3 μm to 4 μm, 3.5 μm to 10 μm, 3.5 μm to 9 μm, 3.5 μm to 8 μm, 3.5 μm to 7 μm, 3.5 μm to 6 μm, 3.5 μm to 5 μm, 3.5 μm to 4 μm, 4 μm to 10 μm, 4 μm to 9 μm, 4 μm to 8 μm, 4 μm to 7 μm, 4 μm to 6 μm, 4 μm to 5 μm, 4.5 μm to 10 μm, 4.5 μm to 9 μm, 4.5 μm to 8 μm, 4.5 μm to 7 μm, 4.5 μm to 6 μm, 4.5 μm to 5 μm, 5 μm to 10 μm, 5 μm to 9 μm, 5 μm to 8 μm, 5 μm to 7 μm, 5 μm to 6 μm, 5.5 μm to 10 μm, 5.5 μm to 9 μm, 5.5 μm to 8 μm, 5.5 μm to 7 μm, 5.5 μm to 6 μm, 6 μm to 10 μm, 6 μm to 9 μm, 6 μm to 8 μm, 6 μm to 7 μm, 6.5 μm to 10 μm, 6.5 μm to 9 μm, 6.5 μm to 8 μm, 6.5 μm to 7 μm, 7 μm to 10 μm, 7 μm to 9 μm, 7 μm to 8 μm, 7.5 μm to 10 μm, 7.5 μm to 9 μm, 7.5 μm to 8 μm, 8 μm to 10 μm, 8 μm to 9 μm, 8.5 μm to 10 μm, 8.5 μm to 9 μm, 9 μm to 10 μm, or 9.5 μm to 10 μm.

In some embodiments, the concentration of surface modifications in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 20 to 25, 20 to 30, 20 to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 40 to 45, 40 to 50, 40 to 55, 40 to 60, 40 to 65, 40 to 70, 40 to 75, 40 to 80, 40 to 85, 40 to 90, 40 to 95, 40 to 100, 50 to 55, 50 to 60, 50 to 65, 50 to 70, 50 to 75, 50 to 80, 50 to 85, 50 to 90, 50 to 95, 50 to 100, 60 to 65, 60 to 70, 60 to 75, 60 to 80, 60 to 85, 60 to 90, 60 to 95, 60 to 100, 70 to 75, 70 to 80, 70 to 85, 70 to 90, 70 to 95, 70 to 100, 80 to 85, 80 to 90, 80 to 95, 80 to 100, 90 to 95, 90 to 100 percent, and the products have pores in a size range of 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 m to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm.

In some embodiments, the product is provided as a preparation and at least 30%, 35%, 40%, 45%, 50%, 55%, 60%, 65%, 70%, 75%, 80%, 85%, 90%, 95% or 100% of the products in the preparation have a combination of pore size and derivatization density or concentration of surface modifications described herein.

In some embodiments, the products are in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, have pores in a size range of 0.1 µm to 10 µm, 0.1 µm to 9 µm, 0.1 µm to 8 µm, 0.1 µm to 7 µm, 0.1 µm to 6 µm, 0.1 µm to 5 µm, 0.1 µm to 4 µm, 0.1 µm to 3 µm, 0.1 µm to 2 µm, 0.15 µm to 10 µm, 0.15 µm to 9 µm, 0.15 µm to 8 µm, 0.15 µm to 7 µm, 0.15 µm to 6 µm, 0.15 µm to 5 µm, 0.15 µm to 4 µm, 0.15 µm to 3 µm, 0.15 µm to 2 µm, 0.2 µm to 10 µm, 0.2 µm to 9 µm, 0.2 µm to 8 µm, 0.2 µm to 7 µm, 0.2 µm to 6 µm, 0.2 µm to 5 µm, 0.2 µm to 4 µm, 0.2 µm to 3 µm, 0.25 µm to 10 µm, 0.25 µm to 9 µm, 0.25 µm to 8 µm, 0.25 µm to 7 µm, 0.25 µm to 6 µm, 0.25 µm to 5 m, 0.25 µm to 4 µm, 0.25 µm to 3 µm, 0.3 µm to 10 µm, 0.3 µm to 9 µm, 0.3 µm to 8 µm, 0.3 µm to 7 µm, 0.3 µm to 6 µm, 0.3 µm to 5 µm, 0.3 µm to 4 µm, 0.35 µm to 10 µm, 0.35 µm to 9 µm, 0.35 µm to 8 µm, 0.35 µm to 7 µm, 0.35 µm to 6 µm, 0.35 µm to 5 µm, 0.35 m to 4 µm, 0.4 m to 10 µm, 0.4 m to 9 µm, 0.4 m to 8 µm, 0.4 m to 7 µm, 0.4 µm to 6 µm, 0.4 µm to 5 µm, 0.45 µm to 10 µm, 0.45 µm to 9 µm, 0.45 µm to 8 µm, 0.45 µm to 7 µm, 0.45 µm to 6 µm, 0.45 µm to 5 µm, 0.5 µm to 10 µm, 0.5 µm to 9 µm, 0.5 µm to 8 µm, 0.5 µm to 7 µm, 0.5 µm to 6 µm, 0.55 µm to 10 µm, 0.55 µm to 9 µm, 0.55 µm to 8 µm, 0.55 µm to 7 µm, 0.55 µm to 6 µm, 0.6 µm to 10 µm, 0.6 µm to 9 µm, 0.6 µm to 8 µm, 0.6 µm to 7 µm, 0.65 µm to 10 µm, 0.65 µm to 9 µm, 0.65 µm to 8 µm, 0.65 µm to 7 µm, 0.7 µm to 10 µm, 0.7 µm to 9 µm, 0.7 µm to 8 µm, 0.75 µm to 10 µm, 0.75 µm to 9 µm, 0.75 µm to 8 µm, 0.8 µm to 10 µm, 0.8 µm to 9 µm, 0.85 µm to 10 µm, 0.85 µm to 9 µm, 0.9 µm to 10 µm, 0.95 µm to 10 µm, 1 µm to 10 µm, 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm, and have a density of at least, of less than, or of 0.1, 0.2, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, or 1000 chemical derivatizations per µm² on its surface, interior or both, or have a concentration of surface modifications is at least, is less than, or is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 percent.

In some embodiments, the products are in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, have pores in a size range of 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm, and have a density in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.1 to 110, 0.1 to 120, 0.1 to 130, 0.1 to 140, 0.1 to 150, 0.1 to 160, 0.1 to 170, 0.1 to 180, 0.1 to 190, 0.1 to 200, 0.1 to 210, 0.1 to 220, 0.1 to 230, 0.1 to 240, 0.1 to 250, 0.1 to 260, 0.1 to 270, 0.1 to 280, 0.1 to 290, 0.1 to 300, 0.1 to 320, 0.1 to 340, 0.1 to 360, 0.1 to 380, 0.1 to 400, 0.1 to 420, 0.1 to 440, 0.1 to 460, 0.1 to 480, 0.1 to 500, 0.1 to 550, 0.1 to 600, 0.1 to 650, 0.1 to 700, 0.1 to 750, 0.1 to 800, 0.1 to 850, 0.1 to 900, 0.1 to 1000, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.2 to 110, 0.2 to 120, 0.2 to 130, 0.2 to 140, 0.2 to 150, 0.2 to 160, 0.2 to 170, 0.2 to 180, 0.2 to 190, 0.2 to 200, 0.2 to 210, 0.2 to 220, 0.2 to 230, 0.2 to 240, 0.2 to 250, 0.2 to 260, 0.2 to 270, 0.2 to 280, 0.2 to 290, 0.2 to 300, 0.2 to 320, 0.2 to 340, 0.2 to 360, 0.2 to 380, 0.2 to 400, 0.2 to 420, 0.2 to 440, 0.2 to 460, 0.2 to 480, 0.2 to 500, 0.2 to 550, 0.2 to 600, 0.2 to 650, 0.2 to 700, 0.2 to 750, 0.2 to 800, 0.2 to 850, 0.2 to 900, 0.2 to 1000, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 0.5 to 110, 0.5 to 120, 0.5 to 130, 0.5 to 140, 0.5 to 150, 0.5 to 160, 0.5 to 170, 0.5 to 180, 0.5 to 190, 0.5 to 200, 0.5 to 210, 0.5 to 220, 0.5 to 230, 0.5 to 240, 0.5 to 250, 0.5 to 260, 0.5 to 270, 0.5 to 280, 0.5 to 290, 0.5 to 300, 0.5 to 320, 0.5 to 340, 0.5 to 360, 0.5 to 380, 0.5 to 400, 0.5 to 420, 0.5 to 440, 0.5 to 460, 0.5 to 480, 0.5 to 500, 0.5 to 550, 0.5 to 600, 0.5 to 650, 0.5 to 700, 0.5 to 750, 0.5 to 800, 0.5 to 850, 0.5 to 900, 0.5 to 1000, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 110, 1 to 120, 1 to 130, 1 to 140, 1 to 150, 1 to 160, 1 to 170, 1 to 180, 1 to 190, 1 to 200, 1 to 210, 1 to 220, 1 to 230, 1 to 240, 1 to 250, 1 to 260, 1 to 270, 1 to 280, 1 to 290, 1 to 300, 1 to 320, 1 to 340, 1 to 360, 1 to 380, 1 to 400, 1 to 420, 1 to 440, 1 to 460, 1 to 480, 1 to 500, 1 to 550, 1 to 600, 1 to 650, 1 to 700, 1 to 750, 1 to 800, 1 to 850, 1 to 900, 1 to 1000, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 2 to 110, 2 to 120, 2 to 130, 2 to 140, 2 to 150, 2 to 160, 2 to 170, 2 to 180, 2 to 190, 2 to 200, 2 to 210, 2 to 220, 2 to 230, 2 to 240, 2 to 250, 2 to 260, 2 to 270, 2 to 280, 2 to 290, 2 to 300, 2 to 320, 2 to 340, 2 to 360, 2 to 380, 2 to 400, 2 to 420, 2 to 440, 2 to 460, 2 to 480, 2 to 500, 2 to 550, 2 to 600, 2 to 650, 2 to 700, 2 to 750, 2 to 800, 2 to 850, 2 to 900, 2 to 1000, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 3 to 110, 3 to 120, 3 to 130, 3 to 140, 3 to 150, 3 to 160, 3 to 170, 3 to 180, 3 to 190, 3 to 200, 3 to 210, 3 to 220, 3 to 230, 3 to 240, 3 to 250, 3 to 260, 3 to 270, 3 to 280, 3 to 290, 3 to 300, 3 to 320, 3 to 340, 3 to 360, 3 to 380, 3 to 400, 3 to 420, 3 to 440, 3 to 460, 3 to 480, 3 to 500, 3 to 550, 3 to 600, 3 to 650, 3 to 700, 3 to 750, 3 to 800, 3 to 850, 3 to 900, 3 to 1000, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 4 to 110, 4 to 120, 4 to 130, 4 to 140, 4 to 150, 4 to 160, 4 to 170, 4 to 180, 4 to 190, 4 to 200, 4 to 210, 4 to 220, 4 to 230, 4 to 240, 4 to 250, 4 to 260, 4 to 270, 4 to 280, 4 to 290, 4 to 300, 4 to 320, 4 to 340, 4 to 360, 4 to 380, 4 to 400, 4 to 420, 4 to 440, 4 to 460, 4 to 480, 4 to 500, 4 to 550, 4 to 600, 4 to 650, 4 to 700, 4 to 750, 4 to 800, 4 to 850, 4 to 900, 4 to 1000, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 5 to 110, 5 to 120, 5 to 130, 5 to 140, 5 to 150, 5 to 160, 5 to 170, 5 to 180, 5 to 190, 5 to 200, 5 to 210, 5 to 220, 5 to 230, 5 to 240, 5 to 250, 5 to 260, 5 to 270, 5 to 280, 5 to 290, 5 to 300, 5 to 320, 5 to 340, 5 to 360, 5 to 380, 5 to 400, 5 to 420, 5 to 440, 5 to 460, 5 to 480, 5 to 500, 5 to 550, 5 to 600, 5 to 650, 5 to 700, 5 to 750, 5 to 800, 5 to 850, 5 to 900, 5 to 1000, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 6 to 110, 6 to 120, 6 to 130, 6 to 140, 6 to 150, 6 to 160, 6 to 170, 6 to 180, 6 to 190, 6 to 200, 6 to 210, 6 to 220, 6 to 230, 6 to 240, 6 to 250, 6 to 260, 6 to 270, 6 to 280, 6 to 290, 6 to 300, 6 to 320, 6 to 340, 6 to 360, 6 to 380, 6 to 400, 6 to 420, 6 to 440, 6 to 460, 6 to 480, 6 to 500, 6 to 550, 6 to 600, 6 to 650, 6 to 700, 6 to 750, 6 to 800, 6 to 850, 6 to 900, 6 to 1000, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 7 to 110, 7 to 120, 7 to 130, 7 to 140, 7 to 150, 7 to 160, 7 to 170, 7 to 180, 7 to 190, 7 to 200, 7 to 210, 7 to 220, 7 to 230, 7 to 240, 7 to 250, 7 to 260, 7 to 270, 7 to 280, 7 to 290, 7 to 300, 7 to 320, 7 to 340, 7 to 360, 7 to 380, 7 to 400, 7 to 420, 7 to 440, 7 to 460, 7 to 480, 7 to 500, 7 to 550, 7 to 600, 7 to 650, 7 to 700, 7 to 750, 7 to 800, 7 to 850, 7 to 900, 7 to 1000, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 8 to 110, 8 to 120, 8 to 130, 8 to 140, 8 to 150, 8 to 160, 8 to 170, 8 to 180, 8 to 190, 8 to 200, 8 to 210, 8 to 220, 8 to 230, 8 to 240, 8 to 250, 8 to 260, 8 to 270, 8 to 280, 8 to 290, 8 to 300, 8 to 320, 8 to 340, 8 to 360, 8 to 380, 8 to 400, 8 to 420, 8 to 440, 8 to 460, 8 to 480, 8 to 500, 8 to 550, 8 to 600, 8 to 650, 8 to 700, 8 to 750, 8 to 800, 8 to 850, 8 to 900, 8 to 1000, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 9 to 110, 9 to 120, 9 to 130, 9 to 140, 9 to 150, 9 to 160, 9 to 170, 9 to 180, 9 to 190, 9 to 200, 9 to 210, 9 to 220, 9 to 230, 9 to 240, 9 to 250, 9 to 260, 9 to 270, 9 to 280, 9 to 290, 9 to 300, 9 to 320, 9 to 340, 9 to 360, 9 to 380, 9 to 400, 9 to 420, 9 to 440, 9 to 460, 9 to 480, 9 to 500, 9 to 550, 9 to 600, 9 to 650, 9 to 700, 9 to 750, 9 to 800, 9 to 850, 9 to 900, 9 to 1000, 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 10 to 110, 10 to 120, 10 to 130, 10 to 140, 10 to 150, 10 to 160, 10 to 170, 10 to 180, 10 to 190, 10 to 200, 10 to 210, 10 to 220, 10 to 230, 10 to 240, 10 to 250, 10 to 260, 10 to 270, 10 to 280, 10 to 290, 10 to 300, 10 to 320, 10 to 340, 10 to 360, 10 to 380, 10 to 400, 10 to 420, 10 to 440, 10 to 460, 10 to 480, 10 to 500, 10 to 550, 10 to 600, 10 to 650, 10 to 700, 10 to 750, 10 to 800, 10 to 850, 10 to 900, 10 to 1000, 20 to 25, 20 to 30, 20 to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 20 to 110, 20 to 120, 20 to 130, 20 to 140, 20 to 150, 20 to 160, 20 to 170, 20 to 180, 20 to 190, 20 to 200, 20 to 210, 20 to 220, 20 to 230, 20 to 240, 20 to 250, 20 to 260, 20 to 270, 20 to 280, 20 to 290, 20 to 300, 20 to 320, 20 to 340, 20 to 360, 20 to 380, 20 to 400, 20 to 420, 20 to 440, 20 to 460, 20 to 480, 20 to 500, 20 to 550, 20 to 600, 20 to 650, 20 to 700, 20 to 750, 20 to 800, 20 to 850, 20 to 900, 20 to 1000, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 30 to 110, 30 to 120, 30 to 130, 30 to 140, 30 to 150, 30 to 160, 30 to 170, 30 to 180, 30 to 190, 30 to 200, 30 to 210, 30 to 220, 30 to 230, 30 to 240, 30 to 250, 30 to 260, 30 to 270, 30 to 280, 30 to 290, 30 to 300, 30 to 320, 30 to 340, 30 to 360, 30 to 380, 30 to 400, 30 to 420, 30 to 440, 30 to 460, 30 to 480, 30 to 500, 30 to 550, 30 to 600, 30 to 650, 30 to 700, 30 to 750, 30 to 800, 30 to 850, 30 to 900, 30 to 1000, 40 to 45, 40 to 50, 40 to 55, 40 to 60, 40 to 65, 40 to 70, 40 to 75, 40 to 80, 40 to 85, 40 to 90, 40 to 95, 40 to 100, 40 to 110, 40 to 120, 40 to 130, 40 to 140, 40 to 150, 40 to 160, 40 to 170, 40 to 180, 40 to 190, 40 to 200, 40 to 210, 40 to 220, 40 to 230, 40 to 240, 40 to 250, 40 to 260, 40 to 270, 40 to 280, 40 to 290, 40 to 300, 40 to 320, 40 to 340, 40 to 360, 40 to 380, 40 to 400, 40 to 420, 40 to 440, 40 to 460, 40 to 480, 40 to 500, 40 to 550, 40 to 600, 40 to 650, 40 to 700, 40 to 750, 40 to 800, 40 to 850, 40 to 900, 40 to 1000, 50 to 55, 50 to 60, 50 to 65, 50 to 70, 50 to 75, 50 to 80, 50 to 85, 50 to 90, 50 to 95, 50 to 100, 50 to 110, 50 to 120, 50 to 130, 50 to 140, 50 to 150, 50 to 160, 50 to 170, 50 to 180, 50 to 190, 50 to 200, 50 to 210, 50 to 220, 50 to 230, 50 to 240, 50 to 250, 50 to 260, 50 to 270, 50 to 280, 50 to 290, 50 to 300, 50 to 320, 50 to 340, 50 to 360, 50 to 380, 50 to 400, 50 to 420, 50 to 440, 50 to 460, 50 to 480, 50 to 500, 50 to 550, 50 to 600, 50 to 650, 50 to 700, 50 to 750, 50 to 800, 50 to 850, 50 to 900, 50 to 1000, 60 to 65, 60 to 70, 60 to 75, 60 to 80, 60 to 85, 60 to 90, 60 to 95, 60 to 100, 60 to 110, 60 to 120, 60 to 130, 60 to 140, 60 to 150, 60 to 160, 60 to 170, 60 to 180, 60 to 190, 60 to 200, 60 to 210, 60 to 220, 60 to 230, 60 to 240, 60 to 250, 60 to 260, 60 to 270, 60 to 280, 60 to 290, 60 to 300, 60 to 320, 60 to 340, 60 to 360, 60 to 380, 60 to 400, 60 to 420, 60 to 440, 60 to 460, 60 to 480, 60 to 500, 60 to 550, 60 to 600, 60 to 650, 60 to 700, 60 to 750, 60 to 800, 60 to 850, 60 to 900, 60 to 1000, 70 to 75, 70 to 80, 70 to 85, 70 to 90, 70 to 95, 70 to 100, 70 to 110, 70 to 120, 70 to 130, 70 to 140, 70 to 150, 70 to 160, 70 to 170, 70 to 180, 70 to 190, 70 to 200, 70 to 210, 70 to 220, 70 to 230, 70 to 240, 70 to 250, 70 to 260, 70 to 270, 70 to 280, 70 to 290, 70 to 300, 70 to 320, 70 to 340, 70 to 360, 70 to 380, 70 to 400, 70 to 420, 70 to 440, 70 to 460, 70 to 480, 70 to 500, 70 to 550, 70 to 600, 70 to 650, 70 to 700, 70 to 750, 70 to 800, 70 to 850, 70 to 900, 70 to 1000, 80 to 85, 80 to 90, 80 to 95, 80 to 100, 80 to 110, 80 to 120, 80 to 130, 80 to 140, 80 to 150, 80 to 160, 80 to 170, 80 to 180, 80 to 190, 80 to 200, 80 to 210, 80 to 220, 80 to 230, 80 to 240, 80 to 250, 80 to 260, 80 to 270, 80 to 280, 80 to 290, 80 to 300, 80 to 320, 80 to 340, 80 to 360, 80 to 380, 80 to 400, 80 to 420, 80 to 440, 80 to 460, 80 to 480, 80 to 500, 80 to 550, 80 to 600, 80 to 650, 80 to 700, 80 to 750, 80 to 800, 80 to 850, 80 to 900, 80 to 1000, 90 to 95, 90 to 100, 90 to 110, 90 to 120, 90 to 130, 90 to 140, 90 to 150, 90 to 160, 90 to 170, 90 to 180, 90 to 190, 90 to 200, 90 to 210, 90 to 220, 90 to 230, 90 to 240, 90 to 250, 90 to 260, 90 to 270, 90 to 280, 90 to 290, 90 to 300, 90 to 320, 90 to 340, 90 to 360, 90 to 380, 90 to 400, 90 to 420, 90 to 440, 90 to 460, 90 to 480, 90 to 500, 90 to 550, 90 to 600, 90 to 650, 90 to 700, 90 to 750, 90 to 800, 90 to 850, 90 to 900, 90 to 1000, 100 to 110, 100 to 120, 100 to 130, 100 to 140, 100 to 150, 100 to 160, 100 to 170, 100 to 180, 100 to 190, 100 to 200, 100 to 210, 100 to 220, 100 to 230, 100 to 240, 100 to 250, 100 to 260, 100 to 270, 100 to 280, 100 to 290, 100 to 300, 100 to 320, 100 to 340, 100 to 360, 100 to 380, 100 to 400, 100 to 420, 100 to 440, 100 to 460, 100 to 480, 100 to 500, 100 to 550, 100 to 600, 100 to 650, 100 to 700, 100 to 750, 100 to 800, 100 to 850, 100 to 900, 100 to 1000, 200 to 210, 200 to 220, 200 to 230, 200 to 240, 200 to 250, 200 to 260, 200 to 270, 200 to 280, 200 to 290, 200 to 300, 200 to 320, 200 to 340, 200 to 360, 200 to 380, 200 to 400, 200 to 420, 200 to 440, 200 to 460, 200 to 480, 200 to 500, 200 to 550, 200 to 600, 200 to 650, 200 to 700, 200 to 750, 200 to 800, 200 to 850, 200 to 900, 200 to 1000, 300 to 320, 300 to 340, 300 to 360, 300 to 380, 300 to 400, 300 to 420, 300 to 440, 300 to 460, 300 to 480, 300 to 500, 300 to 550, 300 to 600, 300 to 650, 300 to 700, 300 to 750, 300 to 800, 300 to 850, 300 to 900, 300 to 1000, 400 to 420, 400 to 440, 400 to 460, 400 to 480, 400 to 500, 400 to 550, 400 to 600, 400 to 650, 400 to 700, 400 to 750, 400 to 800, 400 to 850, 400 to 900, 400 to 1000, 500 to 550, 500 to 600, 500 to 650, 500 to 700, 500 to 750, 500 to 800, 500 to 850, 500 to 900, 500 to 1000, 600 to 650, 600 to 700, 600 to 750, 600 to 800, 600 to 850, 600 to 900, 600 to 1000, 700 to 750, 700 to 800, 700 to 850, 700 to 900, 700 to 1000, 800 to 850, 800 to 900, 800 to 1000, and 900 to 1000 chemical derivatizations per µm² on the surface or a surface of the products, in the interior of the products, or both.

In some embodiments, the products are in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, have pores in a size range of 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm, and have a concentration of surface modifications in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 20 to 25, 20 to 30, 20 to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 40 to 45, 40 to 50, 40 to 55, 40 to 60, 40 to 65, 40 to 70, 40 to 75, 40 to 80, 40 to 85, 40 to 90, 40 to 95, 40 to 100, 50 to 55, 50 to 60, 50 to 65, 50 to 70, 50 to 75, 50 to 80, 50 to 85, 50 to 90, 50 to 95, 50 to 100, 60 to 65, 60 to 70, 60 to 75, 60 to 80, 60 to 85, 60 to 90, 60 to 95, 60 to 100, 70 to 75, 70 to 80, 70 to 85, 70 to 90, 70 to 95, 70 to 100, 80 to 85, 80 to 90, 80 to 95, 80 to 100, 90 to 95, 90 to 100 percent.

In some embodiments, the product is provided as a preparation and at least 30%, 35%, 40%, 45%, 50%, 55%, 60%, 65%, 70%, 75%, 80%, 85%, 90%, 95% or 100% of the products in the preparation have a combination of product size or diameter, pore size, and derivatization density or concentration of surface modifications described herein.

C. Properties of Surface-Modified Products

In preferred embodiments, the surface modified product shows an improved beneficial effect. In further embodiments, the improved beneficial effect involves enhanced biocompatibility such that the fluorescence response normalized to a corresponding unmodified product measured using the in vivo biocompatibility assay described herein is less than 100%, 95%, 90%, 85%, 80%, 75%, 70%, 65%, 60%, 55%, 50%, 45%, or 40%. In preferred embodiments, the surface modified product induces a lower foreign body response than the corresponding unmodified product. This is indicated by fluorescence response normalized to unmodified surface of less than 100%. In some embodiments, the surface modified product is biocompatible such that the fluorescence response normalized a corresponding unmodified product measured using the in vivo biocompatibility assay described herein is less than 75%, more preferably less than 65%, and most preferably less than 50%.

A surface of a product adapted for use in a medical environment can be capable of sterilization using autoclaving, biocide exposure, irradiation, or gassing techniques, like ethylene oxide exposure. Surfaces found in medical environments include the inner and outer aspects of various instruments and devices, whether disposable or intended for repeated uses.

D. Therapeutic Agents Included in Products

The disclosed surface modified products can include one or more therapeutic agents. Therapeutic agents are any compound, composition, conjugate, or construct that can be used to treat a disease, disorder, condition, symptom, etc. Examples of therapeutic agents include cells, tissues, cell products, tissue products, proteins, antibodies, vaccines, vaccine components, antigens, epitopes, drugs, salts, nutrients, buffers, acids, and bases. In some embodiments, the therapeutic agent can be a biological material.

In some embodiments, the product can include a cell or tissue, e.g., a living cell or tissue, which in some embodiments is encapsulated in, or coated with, a polymer. In such embodiments, the surface or a surface of the polymer encapsulation or coating is modified with moieties or compounds disclosed herein. In some embodiments, the cell can include an exogenous nucleic acid that encodes a therapeutic or diagnostic polypeptide. In some embodiments the cell or engineered cell is autologous, allogenic, or zenogeneic.

In some embodiments, the cell is a genetically engineered cell that secretes a therapeutic agent, such as a protein or hormone for treating a disease or other condition. In some embodiments, the cell is a genetically engineered cell that secretes a diagnostic agent. In some embodiments, the cell is a stem cell, e.g., an embryonic stem cell, mesenchymal stem cell, hepatic stem cell, or bone marrow stem cell.

1. Biological Materials

Biological material for inclusion in the disclosed products can be any biological substance. For example, the biological material can be tissue, cells, biological micromolecules, or biological macromolecules. Examples of biological macromolecules include nucleotides, amino acids, cofactors, and hormones. Examples of biological macromolecules include nucleic acids, polypeptides, proteins, and polysaccharides. Examples of proteins include enzymes, receptors, secretory proteins, structural proteins, signaling proteins, hormones, and ligands. Any class, type, form, or particular biological material can be used together with any other classes, types, forms, or particular biological materials.

a. Cells

The cell type chosen for inclusion in the disclosed products depends on the desired therapeutic effect. The cells may be from the patient (autologous cells), from another donor of the same species (allogeneic cells), or from another species (xenogeneic). Xenogeneic cells are easily accessible, but the potential for rejection and the danger of possible transmission of viruses to the patient restricts their clinical application. Any of these types of cells can be from natural sources, stem cells, derived cells, or genetically engineered cell.

In some embodiments, the cells secrete a therapeutically effective substance, such as a protein or nucleic acid. In some embodiments, the cells produce a metabolic product. In some embodiments, the cells metabolize toxic substances. In some embodiments, the cells form structural tissues, such as skin, bone, cartilage, blood vessels, or muscle. In some embodiments, the cells are natural, such as islet cells that naturally secrete insulin, or hepatocytes that naturally detoxify. In some embodiments, the cells are genetically engineered to express a heterologous protein or nucleic acid and/or overexpress an endogenous protein or nucleic acid. In some embodiments, the cells are genetically engineered to produce a new or different product, which can be an expression product of the engineered gene(s) or another product, such as a metabolite, produced because of the engineered gene(s).

Types of cells for inclusion in the disclosed products include cells from natural sources, such as cells from xeno-tissue, cells from a cadaver, and primary cells; stem cells, such as embryonic stem cells, mesenchymal stem cells, and induced pluripotent stem cells; derived cells, such as cells derived from stem cells, cells from a cell line, reprogrammed cells, reprogrammed stem cells, and cells derived from reprogrammed stem cells; and genetically engineered cells, such as cells genetically engineered to express a protein or nucleic acid, cells genetically engineered to produce a metabolic product, and cells genetically engineered to metabolize toxic substances.

Types of cells for inclusion in the disclosed products include liver cells (e.g., hepatoblasts liver stellate cells, biliary cells, or hepatocytes), insulin producing cells (e.g., pancreatic islet cells, isolated pancreatic beta cells, or insulinoma cells), kidney cells, epidermal cells, epithelial cells, neural cells, including neurons and glial cells (e.g., astrocytes), ganglion cells, retinal epithelial cells, adrenal medulla cells, lung cells, cardiac muscle cells, osteoblast cells, osteoclast cells, bone marrow cells, spleen cells, thymus cells, glandular cells, blood cells (e.g., T cells, B cells, macrophage lineage cells, lymphocytes, or monocytes), endocrine hormone-producing cells (e.g., parathyroid, thyroid, or adrenal cells), cells of intestinal origin and other cells acting primarily to synthesize and secret or to metabolize materials, endothelial cells (e.g., capillary endothelial cells), fibroblasts (e.g., dermal fibroblasts), myogenic cells, keratinocytes, smooth muscle cells, progenitor cells (e.g., bone marrow progenitor cells, adipose progenitor cells, hepatic precursor cells, endothelia progenitor cells, peripheral blood progenitor cells, or progenitor cells from muscle, skin) marrow stromal cells cell lines (e.g., CHO cells, MDCK cells and PC12 cells).

A preferred cell type is a pancreatic islet cell or other insulin-producing cell. Hormone-producing cells can produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. Genetically engineered cells are also suitable for inclusion in the disclosed products. In some embodiments, the cells are engineered to produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. In some embodiments, the cells are engineered to secrete blood clotting factors (e.g., for hemophilia treatment) or to secrete growth hormones. In some embodiments, the cells are contained in natural or bioengineered tissue. For example, the cells for inclusion in the disclosed products are in some embodiments a bioartificial renal glomerulus. In some embodiments, the cells are suitable for transplantation into the central nervous system for treatment of neurodegenerative disease.

Cells can be obtained directly from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell viability can be assessed using standard techniques, such as histology and fluorescent microscopy. The function of the implanted cells can be determined using a combination of these techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, pancreatic islet cells and other insulin-producing cells can be implanted to achieve glucose regulation by appropriate secretion of insulin. Other endocrine tissues and cells can also be implanted.

The site, or sites, where cells are to be implanted is determined based on individual need, as is the requisite number of cells. For cells replacing or supplementing organ or gland function (for example, hepatocytes or islet cells), the mixture can be injected into the mesentery, subcutaneous tissue, retroperitoneum, properitoneal space, and intramuscular space.

The amount and density of cells included in the disclosed products will vary depending on the choice of cell and site of implantation. In some embodiments, the single cells are present in the product at a concentration of $0.1 \times 10^6$ to $4 \times 10^6$ cells/ml, preferred $0.5 \times 10^6$ to $2 \times 10^6$ cells/ml. In other embodiments, the cells are present as cell aggregates. For example, islet cell aggregates (or whole islets) preferably contain about 1500-2000 cells for each aggregate of 150 μm diameter, which is defined as one islet equivalent (IE). Therefore, in some embodiments, islet cells are present at a concentration of 100-10000 IE/ml, preferably 200-3,000 IE/ml, more preferably 500-1500 IE/ml.

i. Islet Cells and Other Insulin-Producing Cells

In preferred embodiments, the disclosed compositions contain islet cells or other insulin-producing cells. Methods of isolating pancreatic islet cells are known in the art. Field et al., *Transplantation* 61:1554 (1996); Linetsky et al., *Diabetes* 46:1120 (1997). Fresh pancreatic tissue can be divided by mincing, teasing, comminution and/or collagenase digestion. The islets can then be isolated from contaminating cells and materials by washing, filtering, centrifuging or picking procedures. Methods and apparatus for isolating and purifying islet cells are described in U.S. Pat. No. 5,447,863 to Langley, U.S. Pat. No. 5,322,790 to Scharp et al., U.S. Pat. No. 5,273,904 to Langley, and U.S. Pat. No. 4,868,121 to Scharp et al. The isolated pancreatic cells may optionally be cultured prior to inclusion in the product using any suitable method of culturing islet cells as is known in the art. See e.g., U.S. Pat. No. 5,821,121 to Brothers. Isolated cells may be cultured in a medium under conditions that helps to eliminate antigenic components. Insulin-producing cells can also be derived from stem cells and cell lines and can be cells genetically engineered to produce insulin.

2. Genetically Engineered Cells

In some embodiments, the disclosed compositions contain cells genetically engineered to produce a protein or nucleic acid (e.g., a therapeutic protein or nucleic acid). In these embodiments, the cell can be, for example, a stem cell (e.g., pluripotent), a progenitor cell (e.g., multipotent or oligopotent), or a terminally differentiated cell (i.e., unipotent). Any of the disclosed cell types can be genetically engineered. The cell can be engineered, for example, to contain a nucleic acid encoding, for example, a polynucleotide such miRNA or RNAi or a polynucleotide encoding a protein. The nucleic acid can be, for example, integrated into the cells genomic DNA for stable expression or can be, for example, in an expression vector (e.g., plasmid DNA). The polynucleotide or protein can be selected based on the disease to be treated (or effect to be achieved) and the site of transplantation or implantation. In some embodiments, the polynucleotide or protein is anti-neoplastic. In other embodiments, the polynucleotide or protein is a hormone, growth factor, or enzyme.

Therapeutic agents for secretion by genetically engineered cells include, for example, thyroid stimulating hormone; beneficial lipoproteins such as Apo1; prostacyclin and other vasoactive substances, anti-oxidants and free radical scavengers; soluble cytokine receptors, for example soluble transforming growth factor (TGF) receptor, or cytokine receptor antagonists, for example IL1ra; soluble adhesion molecules, for example ICAM-1; soluble receptors for viruses, e.g. CD4, CXCR4, CCR5 for HIV; cytokines; elastase inhibitors; bone morphogenetic proteins (BMP) and BMP receptors 1 and 2; endoglin; serotonin receptors; tissue inhibiting metaloproteinases; potassium channels or potassium channel modulators; anti-inflammatory factors; angiogenic factors including vascular endothelial growth factor (VEGF), transforming growth factor (TGF), hepatic growth factor, and hypoxia inducible factor (HIF); polypeptides with neurotrophic and/or anti-angiogenic activity including ciliary neurotrophic factor (CNTF), glial-derived neurotrophic factor (GDNF), nerve growth factor (NGF), brain-derived neurotrophic factor (BDNF), neurotrophin-3, nurturin, fibroblast growth factors (FGFs), endostatin, ATF, fragments of thrombospondin, variants thereof and the like. More preferred polypeptides are FGFs, such as acidic FGF (aFGF), basic FGF (bFGF), FGF-1 and FGF-2 and endostatin.

In some embodiments, the active agent is a protein or peptide. Examples of protein active agents include, but are not limited to, cytokines and their receptors, as well as chimeric proteins including cytokines or their receptors, including, for example tumor necrosis factor alpha and beta, their receptors and their derivatives; renin; lipoproteins; colchicine; prolactin; corticotrophin; vasopressin; somatostatin; lypressin; pancreozymin; leuprolide; alpha-1-antitrypsin; clotting factors such as factor VIIIC, factor IX, tissue factor, and von Willebrands factor; anti-clotting factors such as Protein C; atrial natriuretic factor; lung surfactant; a plasminogen activator other than a tissue-type plasminogen activator (t-PA), for example a urokinase; bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; a microbial protein, such as beta-lactamase; DNase; inhibin; activin; receptors for hormones or growth factors; integrin; protein A or D; rheumatoid factors; platelet-derived growth factor (PDGF); epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; an interferon such as interferon-alpha (e.g., interferon.alpha.2A), -beta, -gamma, -lambda and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; transport proteins; homing receptors; addressins; fertility inhibitors such as the prostaglandins; fertility promoters; regulatory proteins; antibodies (including fragments thereof) and chimeric proteins, such as immunoadhesins; precursors, derivatives, prodrugs and analogues of these compounds, and pharmaceutically acceptable salts of these compounds, or their precursors, derivatives, prodrugs and analogues. Suitable proteins or peptides may be native or recombinant and include, e.g., fusion proteins.

Examples of protein active agents also include CCL1, CCL2 (MCP-1), CCL3 (MIP-1α), CCL4 (MIP-13), CCL5 (RANTES), CCL6, CCL7, CCL8, CCL9 (CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1 (KC), CXCL2 (SDF1a), CXCL3, CXCL4, CXCL5, CXCL6, CXCL7, CXCL8 (IL8), CXCL9, CXCL10, CXCL11, CXCL12, CXCL13, CXCL14, CXCL15, CXCL16, CXCL17, CX3CL1, XCL1, XCL2, TNFA, TNFB (LTA), TNFC (LTB), TNFSF4, TNFSF5 (CD40LG), TNFSF6, TNFSF7, TNFSF8, TNFSF9, TNFSF10, TNFSF11, TNFSF13B, EDA, IL2, IL15, IL4, IL13, IL7, IL9, IL21, IL3, IL5, IL6, IL11, IL27, IL30, IL31, OSM, LIF, CNTF, CTF1, IL12a, IL12b, IL23, IL27, IL35, IL14, IL16, IL32, IL34, IL10, IL22, IL19, IL20, IL24, IL26, IL29, IFNL1, IFNL2, IFNL3, IL28, IFNA1, IFNA2, IFNA4, IFNA5, IFNA6, IFNA7, IFNA8, IFNA10, IFNA13, IFNA14, IFNA16, IFNA17, IFNA21, IFNB1, IFNK, IFNW1, IFNG, IL1A (IL1F1), IL1B (IL1F2), IL1Ra (IL1F3), IL1F5 (IL36RN), IL1F6 (IL36A), IL1F7 (IL37), IL1F8 (IL36B), IL1F9 (IL36G), IL1F10 (IL38), IL33 (IL1F11), IL18 (IL1G), IL17, KITLG, IL25 (IL17E), CSF1 (M-CSF), CSF2 (GM-CSF), CSF3 (G-CSF), SPP1, TGFB1, TGFB2, TGFB3, CCL3L1, CCL3L2, CCL3L3, CCL4L1, CCL4L2, IL17B, IL17C, IL17D, IL17F, AIMP1 (SCYE1), MIF, Areg, BC096441, Bmp1, Bmp10, Bmp15, Bmp2, Bmp3, Bmp4, Bmp5, Bmp6, Bmp7, Bmp8a, Bmp8b, C1qtnf4, Ccl21a, Ccl27a, Cd70, Cer1, Cklf, Clcfl, Cmtm2a, Cmtm2b, Cmtm3, Cmtm4, Cmtm5, Cmtm6, Cmtm7, Cmtm8, Crlfl, Ctf2, Ebi3, Edn1, Fam3b, Fasl, Fgf2, Flt31, Gdf10, Gdf11, Gdf15, Gdf2, Gdf3, Gdf5, Gdf6, Gdf7, Gdf9, Gm12597, Gm13271, Gm13275, Gm13276, Gm13280, Gm13283, Gm2564, Gpi1, Grem1, Grem2, Grn, Hmgb1, Ifna11, Ifna12, Ifna9, Ifnab, Ifne, Il17a, Il23a, Il25, Il31, Iltifb, Inhba, Lefty1, Lefty2, Mstn, Nampt, Ndp, Nodal, Pf4, Pglyrp1, Prl7d1, Scg2, Scgb3a1, Slurp1, Spp1, Thpo, Tnfsf10, Tnfsf11, Tnfsf12, Tnfsf13, Tnfsf13b, Tnfsf14, Tnfsf15, Tnfsf18, Tnfsf4, Tnfsf8, Tnfsf9, Tslp, Vegfa, Wnt1, Wnt2, Wnt5a, Wnt7a, Xcl1, Epinephrine, Melatonin, Triiodothyronine, Thyroxine, Prostaglandins, Leukotrienes, Prostacyclin, Thromboxane, Islet Amyloid Polypeptide, Muillerian inhibiting factor or hormone, Adiponectin, Corticotropin, Angiotensin, vasopressin, arginine vasopressin, atriopeptin, Brain natriuretic peptide, Calcitonin, Cholecystokinin, Cortistatin, Enkephalin, Endothelin, Erythropoietin, Follicle-stimulating hormone, Galanin, Gastric inhibitory polypeptide, Gastrin, Ghrelin, Glucagon, Glucagon-like peptide-1, Gonadotropin-releasing hormone, Growth hormone-releasing hormone, Hepcidin, Human chorionic gonadotropin, Human placental lactogen, Growth hormone, Inhibin, Insulin, Somatomedin, Leptin, Lipotropin, Luteinizing hormone, Melanocyte stimulating hormone, Motilin, Orexin, Oxytocin, Pancreatic polypeptide, Parathyroid hormone, Pituitary adenylate cyclase-activating peptide, Prolactin, Prolactin releasing hormone, Relaxin, Renin, Secretin, Somatostatin, Thrombopoietin, Thyrotropin, Thyrotropin-releasing hormone, Vasoactive intestinal peptide, Androgen, Androgen, acid maltase (alpha-glucosidase), glycogen phosphorylase, glycogen debrancher enzyme, Phosphofructokinase, Phosphoglycerate kinase, Phosphoglycerate mutase, Lactate dehydrogenase, Camitine palymityl transferase, Camitine, and Myoadenylate deaminase.

b. Hormones

Hormones to be included in the disclosed products or, most preferably, produced from cells included in the disclosed products can be any hormone of interest.

Examples of endocrine hormones include Anti-diuretic Hormone (ADH), which is produced by the posterior pituitary, targets the kidneys, and affects water balance and blood pressure; Oxytocin, which is produced by the posterior pituitary, targets the uterus, breasts, and stimulates uterine contractions and milk secretion; Growth Hormone (GH), which is produced by the anterior pituitary, targets the body cells, bones, muscles, and affects growth and development; Prolactin, which is produced by the anterior pituitary, targets the breasts, and maintains milk secretions;

Growth Hormone-Releasing Hormone (GHRH), which is a releasing hormone of GH and is produced in the arcuate nucleas of the hypothalamus; Thyroid Stimulating Hormone (TSH), which is produced by the anterior pituitary, targets the thyroid, and regulates thyroid hormones; Thyrotropin-Release Hormone (TRH), which is produced by the hypothalamus and stimulates the release of TSH and prolactin from the anterior pituitary; Adrenocorticotropic Hormone (ACTH), which is produced by the anterior pituitary, targets the adrenal cortex, and regulates adrenal cortex hormones; Follicle-Stimulating Hormone (FSH), which is produced by the anterior pituitary, targets the ovaries/testes, and stimulates egg and sperm production; Lutenizing Hormone (LH), which is produced by the anterior pituitary, targets the ovaries/testes, and stimulates ovulation and sex hormone release; Luteinizing Hormone-Releasing Hormone (LHRH), also known as Gonadotropin-Releasing Hormone (GnRH), which is synthesized and released from GnRH neurons within the hypothalamus and is a trophic peptide hormone responsible for the release of FSH and LH; Thyroxine, which is produced by the thyroid, targets the body cells, and regulates metabolism; Calcitonin, which is produced by the thyroid, targets the adrenal cortex, and lowers blood calcium; Parathyroid Hormone, which is produced by the parathyroid, targets the bone matrix, and raises blood calcium; Aldosterone, which is produced by the adrenal cortex, targets the kidney, and regulates water balance; Cortisol, which is produced by the adrenal cortex, targets the body cells, and weakens immune system and stress responses; Epinephrine, which is produced by the adrenal medulla, targets the heart, lungs, liver, and body cells, and affects primary "fight or flight" responses; Glucagon, which is produced by the pancreas, targets the liver body, and raises blood glucose level; Insulin, which is produced by the pancreas, targets body cells, and lowers blood glucose level; Estrogen, which is produced by the ovaries, targets the reproductive system, and affects puberty, menstrual, and development of gonads; Progesterone, which is produced by the ovaries, targets the reproductive system, and affects puberty, menstrual cycle, and development of gonads; and Testosterone, which is produced by the adrenal gland, testes, targets the reproductive system, and affects puberty, development of gonads, and sperm.

In some embodiments, the protein is a growth hormone, such as human growth hormone (hGH), recombinant human growth hormone (rhGH), bovine growth hormone, methione-human growth hormone, des-phenylalanine human growth hormone, and porcine growth hormone; insulin, insulin A-chain, insulin B-chain, and proinsulin; or a growth factor, such as vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

c. Vaccines

The disclosed products and materials can also be used to provide vaccine components. For example, cells expressing vaccine antigens can be included in the product or material. A vaccine is a biological preparation that provides active acquired immunity to a particular disease. A vaccine typically contains the same antigens (or parts of antigens) from a microorganism that causes disease. For example, measles vaccine contains measles virus. However, the antigens in vaccines are either killed, or weakened to the point that the do not cause disease but they are strong enough to stimulate the body's immune system so that the immune system can readily recognize and kill any of microorganisms that it later encounters (immunity).

An antigen can include any protein or peptide that is foreign to the subject organism. Preferred antigens can be presented at the surface of antigen presenting cells (APC) of a subject for surveillance by immune effector cells, such as leucocytes expressing the CD4 receptor (CD4 T cells) and Natural Killer (NK) cells. Typically, the antigen is of viral, bacterial, protozoan, fungal, or animal origin. In some embodiments the antigen is a cancer antigen. Cancer antigens can be antigens expressed only on tumor cells and/or required for tumor cell survival.

Certain antigens are recognized by those skilled in the art as immuno-stimulatory (i.e., stimulate effective immune recognition) and provide effective immunity to the organism or molecule from which they derive. Antigens can be peptides, proteins, polysaccharides, saccharides, lipids, nucleic acids, or combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof. Suitable antigens are known in the art and are available from commercial government and scientific sources. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. Antigens may be provided as single antigens or may be provided in combination. Antigens may also be provided as complex mixtures of polypeptides or nucleic acids.

Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3. Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria,* Meningococcus A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.*

Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.* These include Sporozoan antigens, Plasmodian antigens, such as all or part of a Circumsporozoite protein, a Sporozoite surface protein, a liver stage antigen, an apical membrane associated protein, or a Merozoite surface protein.

Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale,* and *Sorghum,* the orders of Asterales and Urticales including i.a. herbs of the genera *Ambrosia, Artemisia,* and *Parietaria.* Other allergen antigens that may be used include allergens from house dust mites of the genus *Dermatophagoides* and *Euroglyphus,* storage mite e.g. *Lepidoglyphys, Glycyphagus* and *Tyrophagus,* those from cockroaches, midges and fleas e.g. *Blatella, Periplaneta, Chironomus* and *Ctenocepphalides,* those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium.*

Tumor Antigens

The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARa fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, b-Catenin, CDK4, Mum-1, p16, TAGE, PSMA, PSCA, CT7, telomerase, 43-9F, 5T4, 791Tgp72, a-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

d. Antibodies

The disclosed products and materials can also be used to provide antibodies. For example, cells expressing antibodies can be included in the product or material. Antibodies that function by binding directly to one or more epitopes, other ligands or accessory molecules at the surface of eukaryote cells, are described. Typically, the antibody or antigen binding fragment thereof has affinity for a receptor at the surface of a specific cell type, such as a receptor expressed at the surface of macrophage cells.

In some embodiments, the antibody or antigen binding fragment binds specifically to an epitope. The epitope can be a linear epitope. The epitope can be specific to one cell type or can be expressed by multiple different cell types. In other embodiments, the antibody or antigen binding fragment thereof can bind a conformational epitope that includes a 3-D surface feature, shape, or tertiary structure at the surface of the target cell.

In some embodiments, the antibody or antigen binding fragment that binds specifically to an epitope on the target cell can only bind if the protein epitope is not bound by a ligand or small molecule.

Various types of antibodies and antibody fragments can be used in the described compositions and methods, including whole immunoglobulin of any class, fragments thereof, and synthetic proteins containing at least the antigen binding variable domain of an antibody. The antibody can be an IgG antibody, such as $IgG_1$, $IgG_2$, $IgG_3$, or $IgG_4$. An antibody can be in the form of an antigen binding fragment including a Fab fragment, F(ab')2 fragment, a single chain variable region, and the like. Antibodies can be polyclonal or monoclonal (mAb). Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison, et al., *Proc. Natl. Acad. Sci. USA*, 81: 6851-6855 (1984)). The described antibodies can also be modified by recombinant means, for example by deletions, additions or substitutions of amino acids, to increase efficacy of the antibody in mediating the desired function. Substitutions can be conservative substitutions. For example, at least one amino acid in the constant region of the antibody can be replaced with a different residue (see, e.g., U.S. Pat. Nos. 5,624,821; 6,194,551; WO 9958572; and Angal, et al., Mol. Immunol. 30:105-08 (1993)). In some cases changes are made to reduce undesired activities, e.g., complement-dependent cytotoxicity. The antibody can be a bi-specific antibody having binding specificities for at least two different antigenic epitopes. In one embodiment, the epitopes are from the same antigen. In another embodiment, the epitopes are from two different antigens. Bi-specific antibodies can include bi-specific antibody fragments (see, e.g., Hollinger, et al., *Proc. Natl. Acad. Sci. U.S.A.*, 90:6444-48 (1993); Gruber, et al., *J. Immunol.*, 152:5368 (1994)).

Antibodies can be generated by any means known in the art. Exemplary descriptions means for antibody generation and production include Delves, Antibody Production: Essential Techniques (Wiley, 1997); Shephard, et al., Monoclonal Antibodies (Oxford University Press, 2000); Goding, Monoclonal Antibodies: Principles And Practice (Academic Press, 1993); and Current Protocols In Immunology (John Wiley & Sons, most recent edition). Fragments of intact Ig molecules can be generated using methods well known in the art, including enzymatic digestion and recombinant means.

V. Methods of Making

The surfaces of the products described herein, can be modified using procedures known in the art.

For example, stainless steel and glass can be derivatized using the following procedure. Material to be derivatized is stirred in piranha solution for 1 h at room temperature. The material is washed by ultra-sonication in water, then ethanol, then acetone for 10 min each and then dried by blowing nitrogen over them. Immediate after drying the material is stirred in a 10% (v/v) silane/toluene solution for 48 h at 55° C. The material is cleaned by ultra-sonication in Toluene and Dichloromethane for 5 min each. The material is dried under Argon and cured in an oven at 70° C. for 3 h to prevent air oxidation.

The material is stirred in water and succinic acid, 2-chloro-4,6-dimethoxy-1,3,5-triazine (CDMT) and N-methylmorpholine (NMM) were added. The suspension was stirred at 55° C. overnight. The material is washed with water, methanol, and acetone to remove unreacted components.

The material is stirred in a water/acetonitrile solution and E9, CDMT, and NMM was added. The material is stirred overnight at 55° C. The material is washed with water, methanol, and acetone.

Polystyrene-COOH, PMMA-COOH and other similar materials can be derivatized by the following procedure. To PS/PMMA material in water/acetonitrile (3:2), E9 NMM and a spatula tip of CDMT is added. The solution is overhead stirred at 50° C. overnight. The material is washed three times with methanol and then three times with ethanol. The material is dried under reduced pressure.

Plastics, ceramics, and metals can be derivatized by treating with plasma. Materials are plasma treated for 1 min on each side and immediately dropped into a 0.2 mol solution of E9 in 5% DMSO in toluene. The reaction is stirred for 90 min and the materials are washed three times in methanol and three times in ethanol. The materials are dried under high vacuum overnight.

A. Compounds Used to Modify Surfaces

Compounds that can be used to modify the surfaces of the products include all of the compounds disclosed herein. Useful compounds include, but are not limited to, alcohols, thiols, amines, and combinations thereof.

a. Alcohols

Preferred alcohols for use as reagents in esterification include those shown below.

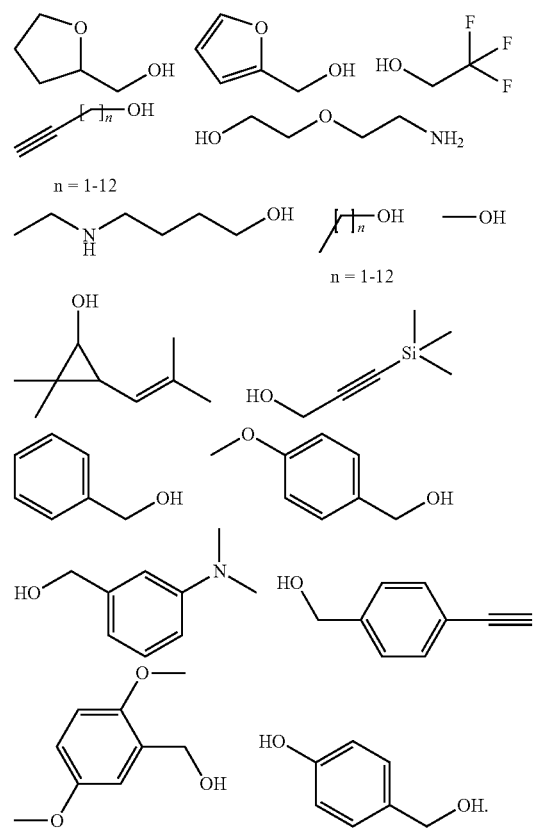

b. Amines

Preferred amines that can be used to modify the surfaces of the products include, but are not limited to,

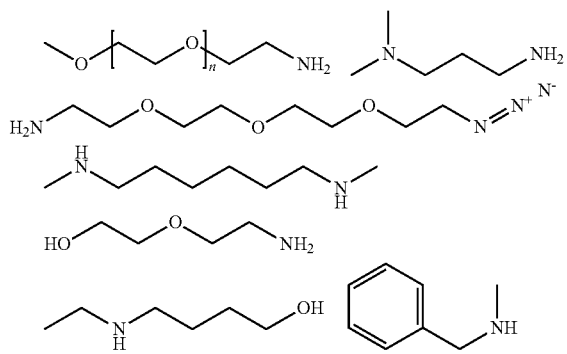

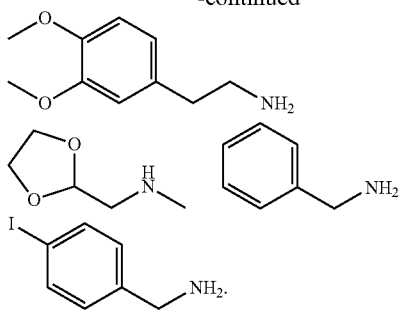

c. Thiols

Preferred thiols that can be used to modify the surfaces of the products include, but are not limited to, d. Derivatization Via Click Chemistry In some embodiments, the surfaces of the products are covalently modified initially to introduce a functional group which can be further reacted via click chemistry.

In preferred embodiments, the alcohols, amines or thiols are used to introduce a functional group which can further reacted using a 1,3-dipolar cycloaddition reaction (i.e., a Huisgen cycloaddition reaction). In a 1,3-dipolar cycloaddition reaction, a first molecule containing an azide moiety is reacted with a second molecule containing a terminal or internal alkyne. As shown below, the azide and the alkyne groups undergo an intramolecular 1,3-dipolar cycloaddition reaction, coupling the two molecules together and forming a 1,2,3-triazole ring.

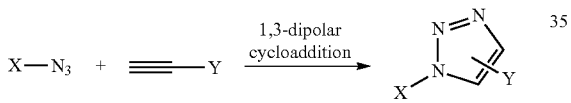

The regiochemistry of 1,3-dipolar cycloadditions reaction can be controlled by addition of a copper(I) catalyst (formed in situ by the reduction of $CuSO_4$ with sodium ascorbate) or a ruthenium catalyst (such as $Cp^*RuCl(PPh_3)_2$, $Cp^*Ru$ (COD), or $Cp^*[RuCl_4]$). For example, using a copper catalyst, azides and terminal alkynes can be reacted to exclusively afford the 1,4-regioisomers of 1,2,3-triazoles. Similarly, in the presence of a suitable ruthenium catalyst, azides can be reacted with internal or terminal alkynes to form exclusively the 1,5-regioisomers of 1,2,3-triazoles.

In some embodiments, the alcohol, amine or thiol containing an alkyne moiety is used to modify the surface initially. In these embodiments, the alkyne moiety present on the surface can be further reacted with a second molecule containing an azide functional group. Upon reaction, the azide and the alkyne groups undergo an intramolecular 1,3-dipolar cycloaddition reaction forming a 1,2,3-triazole ring, coupling the second molecule to the covalently modified surface.

Examples of the alkyne-containing alcohol, amine or thiol reactant include $X_a$—$R_z$—C≡C—$R_x$; wherein $X_a$ is —OH, —SH or —$NH_2$; wherein $R_z$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$); and wherein $R_x$ is hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments,
(1) $R_z$ is (A)

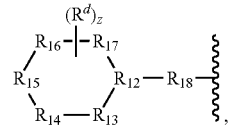

Formula VI wherein z is an integer from 1-11; wherein $R^d$ is independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring; wherein one instance of $R^d$ is or contains $X_a$; wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ is independently —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$);
wherein $R_6$, $R_9$, $R_{10}$, and $R_{11}$ are independently present or absent according to valency, and wherein the ring bonds are double or single according to valency;

(B) —(CH$_2$)$_s$—R$_{34}$, wherein s is an integer from 0 to 20; wherein $R_{34}$ is —$X_a$, —O—R$_{35}$, —S—R$_{35}$, —(CH$_2$)$_r$—R$_{35}$, —CO—R$_{35}$, or —CHR$_{36}$R$_{37}$, wherein r is an integer from 0 to 19; wherein $R_{35}$ is —$X_a$, —(CH$_2$)$_u$—R$_{38}$, wherein u is an integer from 0 to 18; wherein $R_{36}$ is —(CH$_2$)$_t$—R$_{38}$, $R_{37}$ is —(CH$_2$)$_v$—R$_{38}$, and t and v are integers from 0 to 18, wherein t and v together total 0 to 18; wherein $R_{38}$ is —$X_a$, methyl, —OH, —SH, or —COOH; $R_x$ is hydrogen or —(CH$_2$)$_s$—R$_{34}$, wherein s is an integer from 0 to 20; wherein $R_{26}$ is —O—R$_{35}$, —S—R$_{35}$, —(CH$_2$)$_r$—R$_{35}$, —CO—R$_{35}$, or —CHR$_{35}$R$_{36}$, wherein r is an integer from 0 to 19; wherein $R_{35}$ is —(CH$_2$)$_u$—R$_{38}$, wherein u is an integer from 0 to 18; wherein $R_{36}$ is —(CH$_2$)$_t$—R$_{38}$, $R_{37}$ is —(CH$_2$)$_v$—R$_{38}$, and t and v are integers from 0 to 18, wherein t and v together total 0 to 18; wherein $R_{38}$ is methyl, —OH, —SH, or —COOH; wherein $R_z$ and $R_x$ are not both hydrogen; and wherein $R_x$ can be hydrogen.

In some embodiments, $R_z$ and $R_x$ are independently (C)

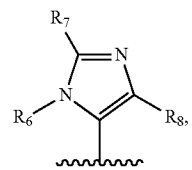

Formula IV

-continued

Formula V

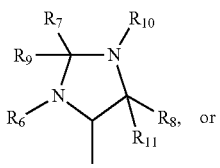

wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein one instance of $R_6$, $R_7$, $R_8$, $R_9$, $R_{10}$, or $R_{11}$ is or contains $X_a$;
(2) and $R_x$ is hydrogen, (A)

Formula VI

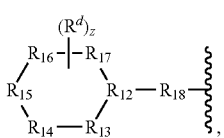

wherein z is an integer from 0-11; wherein $R^d$ is independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring; wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ is independently —(CR$_{19}$R$_{19}$)$_p$— or —(CR$_{19}$R$_{19}$)$_p$—X$_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$);
wherein $R_6$, $R_9$, $R_{10}$, and $R_{11}$ are independently present or absent according to valency, and wherein the ring bonds are double or single according to valency;
(B) —(CH$_2$)$_s$—R$_{34}$, wherein s is an integer from 0 to 20; wherein $R_{34}$ is —O—R$_{35}$, —S—R$_{35}$, —(CH$_2$)$_r$—R$_{35}$, —CO—R$_{35}$, or —CHR$_{36}$R$_{37}$, wherein r is an integer from 0 to 19; wherein $R_{35}$ is —(CH$_2$)$_u$—R$_{38}$, wherein u is an integer from 0 to 18; wherein $R_{28}$ is —(CH$_2$)$_t$—R$_{38}$, $R_{37}$ is —(CH$_2$)$_v$—R$_{38}$, and t and v are integers from 0 to 18, wherein t and v together total 0 to 18; wherein $R_{38}$ is methyl, —OH, —SH, or —COOH; wherein $R_z$ and $R_x$ are not both hydrogen; and wherein $R_x$ can be hydrogen; and $R_x$ is hydrogen or —(CH$_2$)$_s$—R$_{34}$, wherein s is an integer from 0 to 20; wherein $R_{34}$ is —O—R$_{35}$, —S—R$_{35}$, —(CH$_2$)$_r$—R$_{35}$, —CO—R$_{35}$, or —CHR$_{36}$R$_{37}$, wherein r is an integer from 0 to 19; wherein $R_{35}$ is —(CH$_2$)$_u$—R$_{38}$, wherein u is an integer from 0 to 18; wherein $R_{36}$ is —(CH$_2$)$_t$—R$_{38}$, $R_{37}$ is —(CH$_2$)$_v$—R$_{38}$, and t and v are integers from 0 to 18, wherein t and v together total 0 to 18; wherein $R_{38}$ is methyl, —OH, —SH, or —COOH; wherein $R_z$ and $R_x$ are not both hydrogen; and wherein $R_x$ can be hydrogen;

(C)

Formula IV

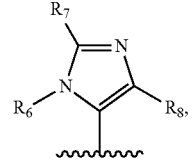

Formula V

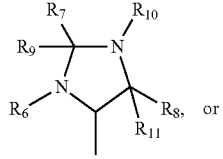

wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

Examples of the azide-containing second molecule include $R_w$—N$_3$, wherein $R_w$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, $R_w$ is (A)

Formula VII

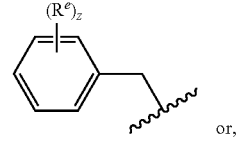

or,

Formula XI

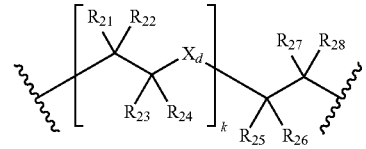

wherein n are independently an integer from 1 to 30; wherein z is an integer from 0-4; wherein $X_d$ are independently O or S; wherein $R^e$ is independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic, or heterocyclic ring; and wherein $R_{21}$, $R_{22}$, $R_{23}$, $R_{24}$, $R_{25}$, $R_{26}$, $R_{27}$, $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$);

(B)

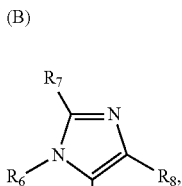

Formula IV

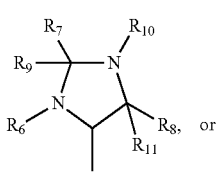

Formula V wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In alternative embodiments, an alcohol, amine or thiol, containing an azide moiety is used to modify the surface. In these embodiments, the azide moiety present on the covalently modified surface can be further reacted with a second molecule containing a terminal or internal alkyne. Upon reaction, the azide and the alkyne groups undergo an intramolecular 1,3-dipolar cycloaddition reaction forming a 1,2,3-triazole ring, coupling the second molecule to the covalent modification.

Examples of the azide-containing amidation/esterification reactant include $X_c$—$R_w$—$N_3$, where $X_c$ is —OH, —SH or —$NH_2$ and $R_w$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, $X_c$ is not —$NH_2$ and $R_w$ is not —$CH_2$—Ar— or —$CH_2$—$CH_2$—(O—$CH_2$—$CH_2$)$_3$—.

In some embodiments, $R_w$ is (A)

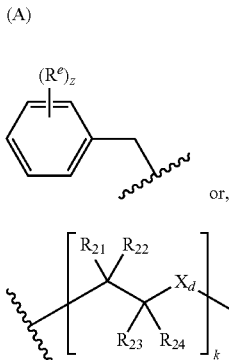

Formula VII or,

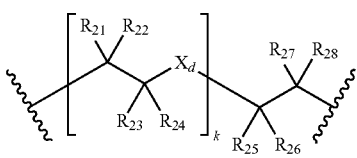

Formula XI wherein n are independently an integer from 1 to 30; wherein z is an integer from 0-4; wherein $X_d$ are independently O or S; wherein $R^e$ is independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring; and wherein $R_{21}$, $R_{22}$, $R_{23}$, $R_{24}$, $R_{25}$, $R_{26}$, $R_{27}$, $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$); and wherein one instance of $R_{21}$, $R_{22}$, $R_{23}$, $R_{24}$, $R_{25}$, $R_{26}$, $R_{27}$, or $R_{28}$ is or contains $X_c$;

(B)

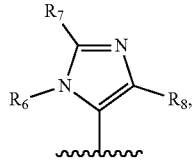

Formula IV

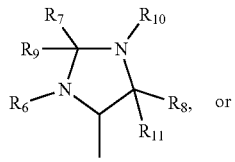

Formula V wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein one instance of $R_6$, $R_7$, $R_8$, $R_9$, $R_{10}$, or $R_{11}$ is or contains $X_c$.

Examples of the alkyne-containing second molecule include $R_z$—C≡C—$R_x$, wherein $R_z$ and $R_x$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, $R_z$ and $R_x$ are independently (A)

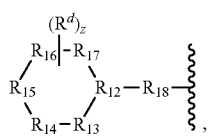

Formula VI wherein z is an integer from 1-11; wherein $R^d$ is independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic or heterocyclic ring; wherein one instance of $R^d$ is or contains $X_a$; wherein $R_{12}$, $R_{13}$, $R_{14}$, $R_{15}$, $R_{16}$, and $R_{17}$ are independently C, O, N, S, S(O), or S(O)$_2$, wherein the bonds between adjacent $R_{12}$ to $R_{17}$ are double or single according to valency, and wherein $R_{12}$ to $R_{17}$ are bound to none, one, or two hydrogens according to valency; and wherein $R_{18}$ is independently —(CR$_{19}$R$_{19}$)$_p$— or —(CR$_{19}$R$_{19}$)$_p$—$X_b$—(CR$_{19}$R$_{19}$)$_q$—, wherein p and q are independently integers from 0 to 5, wherein $X_b$ is absent, —O—, —S—, —S(O)—, —S(O)$_2$—, or NR$_{20}$, wherein each $R_{19}$ is, as valency permits, independently absent, hydrogen, =O, =S, —OH, —SH, or —NR$_{20}$, wherein $R_{20}$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$);

wherein $R_6$, $R_9$, $R_{10}$, and $R_{11}$ are independently present or absent according to valency, and wherein the ring bonds are double or single according to valency;

(B) —$(CH_2)_s$—$R_{34}$, wherein s is an integer from 0 to 20; wherein $R_{34}$ is —O—$R_{35}$, —S—$R_{35}$, —$(CH_2)_r$—$R_{35}$, —CO—$R_{35}$, or —$CHR_{36}R_{37}$, wherein r is an integer from 0 to 19; wherein $R_{35}$ is —$(CH_2)_u$—$R_{38}$, wherein u is an integer from 0 to 18; wherein $R_{28}$ is —$(CH_2)_t$—$R_{38}$, $R_{37}$ is —$(CH_2)_v$—$R_{38}$, and t and v are integers from 0 to 18, wherein t and v together total 0 to 18; wherein $R_{38}$ is methyl, —OH, —SH, or —COOH; wherein $R_z$ and $R_x$ are not both hydrogen; and wherein $R_x$ can be hydrogen; and $R_x$ is hydrogen or —$(CH_2)_s$—$R_{34}$, wherein s is an integer from 0 to 20; wherein $R_{34}$ is —O—$R_{35}$, —S—$R_{35}$, —$(CH_2)_r$—$R_{35}$, —CO—$R_{35}$, or —$CHR_{36}R_{37}$, wherein r is an integer from 0 to 19; wherein $R_{35}$ is —$(CH_2)_u$—$R_{38}$, wherein u is an integer from 0 to 18; wherein $R_{36}$ is —$(CH_2)_t$—$R_{38}$, $R_{37}$ is —$(CH_2)_v$—$R_{38}$, and t and v are integers from 0 to 18, wherein t and v together total 0 to 18; wherein $R_{38}$ is methyl, —OH, —SH, or —COOH; wherein $R_z$ and $R_x$ are not both hydrogen; and wherein $R_x$ can be hydrogen;

(C)

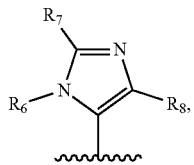

Formula IV

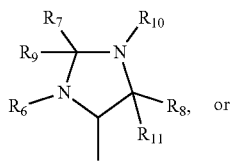

Formula V wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$).

In some embodiments, the azide moiety can be added to a covalently modified surface that has a compound containing a leaving group, such as I, Br, OTs, OMs. In some embodiments, the alcohol, amine or thiol containing the leaving group used to covalently modify the surface. Examples of the leaving group-containing alcohol, amine or thiol reactant include $X_c$—$R_w$-L, where $X_c$ is —OH or —$NH_2$, L is the leaving group, and $R_w$ is $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$).

In some embodiments, $X_c$ is not —$NH_2$ and $R_w$ is not —$CH_2$—Ar— or —$CH_2$—$CH_2$—(O—$CH_2$—$CH_2$)_3—.

In some embodiments, $R_w$ is (A)

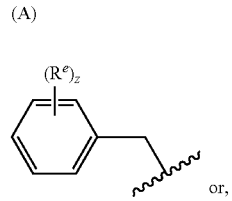

Formula VII or,

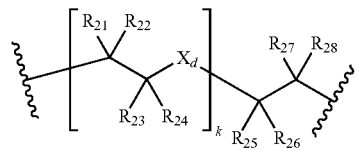

Formula XI wherein n are independently an integer from 1 to 30; wherein z is an integer from 0-4; wherein $X_d$ are independently O or S; wherein $R^e$ is independently $U_2$, $U_2+Q_1$, $U_2+Q_2$, $U_2+Q_3$, $U_2+Q_1+Q_2$, $U_2+Q_1+Q_3$, $U_2+Q_2+Q_3$, $U_2+Q_1+Q_2+Q_3$, $U_3$, $U_3+Q_1$, $U_3+Q_2$, $U_3+Q_3$, $U_3+Q_1+Q_2$, $U_3+Q_1+Q_3$, $U_3+Q_2+Q_3$, or $U_3+Q_1+Q_2+Q_3$ (preferably, in these embodiments, $U_3+Q_1+Q_3$); or together with the carbon atom to which they are attached, form a 3- to 8-membered unsubstituted or substituted carbocyclic, or heterocyclic ring; and wherein $R_{21}$, $R_{22}$, $R_{23}$, $R_{24}$, $R_{25}$, $R_{26}$, $R_{27}$, $R_{28}$ are independently hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_2+Q_3$); and wherein one instance of $R_{21}$, $R_{22}$, $R_{23}$, $R_{24}$, $R_{25}$, $R_{26}$, $R_{27}$, or $R_{28}$ is or contains $X_c$;

(B)

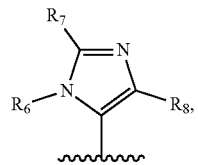

Formula IV

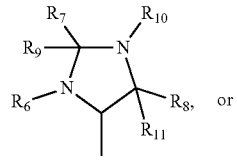

Formula V wherein $R_6$, $R_7$, $R_8$, $R_9$, $R_{10}$, and $R_{11}$ are, independently, hydrogen, $U_1$, $U_1+Q_1$, $U_1+Q_2$, $U_1+Q_3$, $U_1+Q_1+Q_2$, $U_1+Q_1+Q_3$, $U_1+Q_2+Q_3$, or $U_1+Q_1+Q_2+Q_3$ (preferably, in these embodiments, $U_1+Q_1+Q_3$); and wherein one instance of $R_6$, $R_7$, $R_8$, $R_9$, $R_{10}$, or $R_{11}$ is or contains $X_c$.

In some embodiments, $X_c$ is not —$NH_2$ and $R_w$ is not —$CH_2$—Ar— or —$CH_2$—$CH_2$—(O—$CH_2$—$CH_2$)_3—.

In preferred embodiments, an amine containing an azide moiety is used to covalently modify the surface initially. Subsequently, the azide moiety present on the covalently modified surface is reacted with a second molecule containing a terminal or internal alkyne, forming a 1,2,3-triazole ring and coupling the second molecule to the covalent modification.

Different strategies can be employed to prepare covalently modified surfaces containing an azide moiety. For example, the surface can be modified by reaction with an amine substituted with an azide moiety (for example, 11-Azido-3,6,9-trioxaundecan-1-amine) in a single synthetic step. Alternatively, the surface can be amidated by reaction with an amine substituted with any moiety which can be readily transformed into an azide. For example, the surface can be amidated by reaction with 4-iodobenzylamine. The iodine moiety can then be readily converted to the azide, for example by treatment with sodium azide.

Subsequently, the azide-functionalized surfaces can be reacted with a molecule containing an alkyne functionality in the presence of a copper(I) catalyst (formed in situ by the reduction of $CuSO_4$ with sodium ascorbate).

Preferred alkynes for use as reagents in 1,3-dipolarcycloaddition reactions include those shown below.

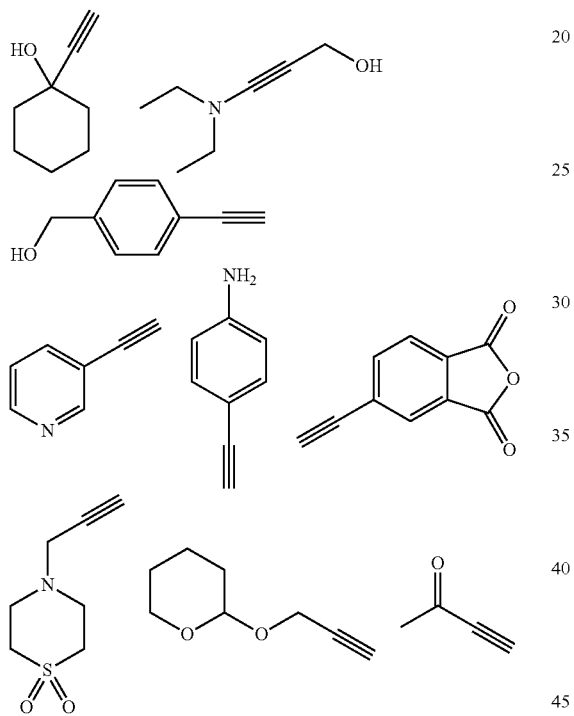

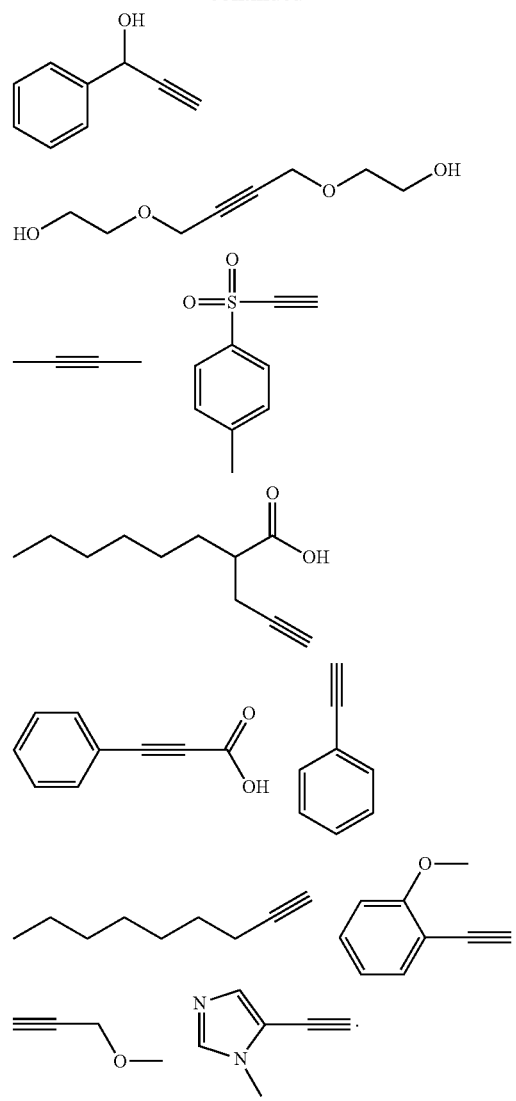

Preferred compounds for modifying products include compounds having the structure:

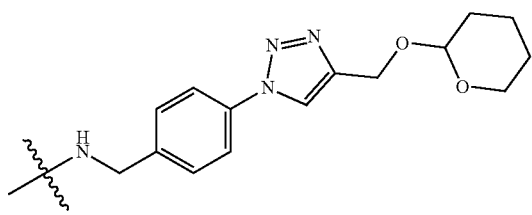

Z2-Y12

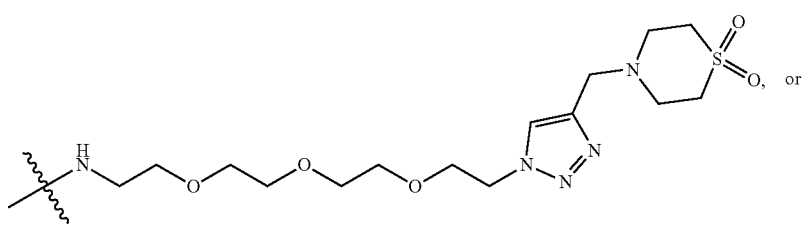

Z1-Y15

, or

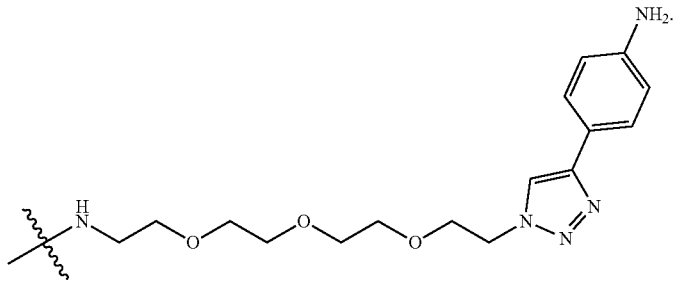

Z1-Y19

The terminal amine can differ in other preferred compounds depending on the attachment chemistry that is used.

B. Chemical Modification of Products and Surfaces

Methods for attaching compounds to materials and surfaces are well established. For example, compounds can be attached to aminated surfaces, carboxylated surfaces or hydroxylated surfaces using standard immobilization chemistries. As another example, products and surfaces can be modified via a variety of methods to possess functional groups designed to covalently attach compounds. Examples of attachment groups include thiol, silane, carboxylate, methyl acrylate, phosphonate, nitrile, isonitrile, hydroxamate, acid chloride, anhydride, sulfonyl, phosphoryl, hydroxyl, amino acid, cyanogen bromide, succinimide, aldehydes (such as glutaraldehyde), tosyl chloride, photocrosslinkable agents, epoxides and maleimides. In some preferred embodiments, the attachment group is a thiol. In some embodiments, the attachment group contains a single functionality therein that can attach to the surface, for example, an amine or dimethyl-methoxysilane moiety. Any art recognized attachment group can be used to anchor a compound can be used to chemically modify products. For example, organosilanes, carboxylic acids, sulfur-containing anchor groups, may be used as attachments. Products and surfaces of products formed from metals such as gold, silver, copper, cadmium, zinc, palladium, platinum, mercury, lead, iron, chromium, manganese, tungsten, and alloys of these can be patterned, for example, by forming thiol, sulfide, and disulfide bonds with compounds having sulfur-containing attachment groups. In addition, compounds can be attached to aluminum via a phosphonic acid ($PO_3^{2-}$) anchor group. Nitriles and isonitriles, for example, can be used to attach compounds to platinum and palladium, and copper and aluminum can be chemically modified via a hydroxamic acid or hydroxamic acid-containing attachment group. Other functional groups suitable for attachment include, but are not limited to, acid chlorides, anhydrides, sulfonyl groups, phosphoryl and phosphonic groups, hydroxyl groups, and amino acid groups.

Free amine groups of compounds can also be attached to products and surfaces containing reactive amine groups via homobifunctional linkers. Linkers such as dithiobis(succinimidylpropionate) (DSP, 8-atom spacer), disuccinimidyl suberate (DSS, 8-atom spacer), glutaraldehyde (4-atom spacer), Bis[2-(succinimidyloxycarbonyloxy)ethyl]sulfone (BSOCOES, 9-atom spacer), all requiring high pH, can be used for this purpose. Examples of homobifunctional sulfhydryl-reactive linkers include, but are not limited to, 1,4-Di-[3'-2'-pyridyldithio)propion-amido]butane (DPDPB, 16-atom spacer) and Bismaleimidohexane (BMH, 14-atom spacer). For example, these homobifunctional linkers are first reacted with a thiolated surface in aqueous solution (for example PBS, pH 7.4), and then in a second step, the thiolated antibody or protein is joined by the link. Homo- and heteromultifunctional linkers can also be used.

Compounds can be directly attached to thiol, amine, or carboxylic acid functional groups on products or surfaces or, conversely, compounds with thiol, amine, or carboxylic acid functional groups can be attached to products or surfaces via these functional groups.

Amino groups can be added to the products and surfaces to, for example, increase the density of compounds on the products and surfaces.

Compounds can be attached to products and surfaces by several different mechanisms. Products and surfaces can be modified via a variety of methods to possess functional groups designed to covalently attach compounds.

Passive adsorption consists of primarily hydrophobic interactions or hydrophobic/ionic interactions between the biomolecules and the surface. Typical nomenclature for passive binding surfaces includes medium binding for hydrophobic surfaces and high binding for surfaces that are modified to have a small number of ionic carboxyl groups resulting in a slightly ionic, hydrophobic surface.

Covalent immobilization to products and surfaces can be accomplished through several means. On surfaces that are aminated or carboxylated, covalent coupling can be achieved using bifunctional crosslinkers that couple the amine or carboxyl group on the surface to a functional group, such as an amine or sulfhydryl, on the biomolecule. Selection of the crosslinker determines the type of covalent bond that will be formed. Functional and covalently reactive groups, such as N-oxysuccinimide, maleimide and hydrazide groups, can also be grafted onto a product or surface. These reactive groups are coupled to the products and surfaces via a photolinkable spacer arm resulting in a stable, yet reactive surface.

Surfaces that are hydrophilic and neutrally charged are considered low binding. Since some compounds passively adsorb to surfaces through hydrophobic and ionic interactions, a surface lacking these characteristics naturally inhibits nonspecific immobilization via these forces.

Some non-modified products and surfaces, such as plastics, are hydrophobic in nature and can bind compounds through passive interactions. This type of surface is referred to as medium binding and is primarily suitable for the immobilization of large molecules that have large hydrophobic regions that can interact with the surface.

Some products and surfaces, such as plastics having benzene rings, can be modified to be what is considered high binding via the use of radiation. The radiation effectively incorporates carboxylic acid on the accessible carbons of the benzene ring. The resulting surface is primarily hydrophobic with intermittent carboxyl groups capable of ionic interactions with positively charged groups on biomolecules. The mechanism of immobilization is passive adsorption through hydrophobic and ionic interactions. This is considered a general purpose surface capable of binding compounds that possess ionic groups and/or hydrophobic regions.

Products and surfaces can also be modified to possess positively charged amine groups. This type of surface lacks hydrophobic character and is strictly ionic in nature. Using the appropriate buffers and pH, this surface can be used to ionically couple to small negatively charged compounds. Such products and surfaces can be used with bifunctional crosslinkers (i.e., glutaraldehyde, carbodiimide) to covalently couple to functional groups (primary amines, thiols, carboxyls) on biomolecules.

The modifying compounds can also be linked to each other (e.g., oligomerized or polymerized) prior to, as part of, or following attachment to the product or surface. For example, methacrylate attachment of compounds can result in both polymerization of modifying compounds (via a polymethacrylate backbone) and attachment to the product or surface. Many other oligomerizable or polymerizable attachment groups can be used in a similar manner. The modifying compounds can also be oligomerized or polymerized ia a separate reaction from the attachment to the product or surface.

Products and surfaces can also be chemically modified by, for example, employing techniques established for producing microarrays. For example, compounds can be spotted or printed. Positioning and localization can also be achieved by specific location and distribution of attachment groups on the product or surface. If photoactivated crosslinkers are used, different compounds or different patterns could be generated by use of activating wavelengths at different stages of the modification. Alternatively, masks can be used to achieve the same effect with a single type of photoactivatable crosslinker. Etching of the product or surface can also be used to create patterns of attachment. Use of such techniques allows more precision in the location, density, and gradient of chemical modification on the products and surfaces.

Every compound within the description and definitions herein is intended to be and should be considered to be specifically disclosed herein. Further, every subgroup that can be identified within the above definition is intended to be and should be considered to be specifically disclosed herein. As a result, it is specifically contemplated that any compound or subgroup of compounds can be either specifically included for or excluded from use or included in or excluded from a list of compounds. For example, as one option, a group of compounds is contemplated where each compound is as defined herein but where $R_6$ is not substituted alkenyl or alkynyl. As another example, a group of compounds is contemplated where each compound is as defined herein and has a specific beneficial effect.

Any type or form of modified alginate, any type or form of alginate modification, and any type or form of reagent for modifying alginate can be, independently and in any combination, specifically included or excluded in any of the disclosed modified alginates, alginate modifications, reagents for alginate modifications, methods, and kits, and in any context, combination, or use. For example, any type or form of esterification reagent, amidation reagent, click reagent, alkyne-containing reagent, azide-containing reagent, phosphorylating reagent, and ketone reagent, such as those described above and in the examples, can be, independently and in any combination, specifically included or excluded from use to modify alginates, and any alginate modifications and any modified alginates that include or are based on such reagents can be, independently and in any combination, specifically included or excluded in any of the disclosed modified alginates, alginate modifications, reagents for alginate modifications, methods, and kits, and in any context, combination, or use.

VI. Methods of Assessing Biocompatibility

Biocompatibility of the disclosed products and materials can be assessed using any suitable techniques. Examples of useful techniques are described below.

A. Assessing Cytotoxicity

The cytotoxicity of the disclosed surface modified products and materials can be evaluated on HeLa cells. The surface modified products and materials can be loaded into containers, such as wells of 96-well plates. The containers can be coated with an attachment molecule, such as poly-L-lysine, if appropriate. Unmodified product and material and saline can be loaded into containers as controls. HeLa cells can then be seeded into the wells and incubated for 3 days at 37° C. in a humidified chamber.

A cell viability assay using 3-(4,5-Dimethylthiazol-2-yl)-2,5-diphenyltetrazolium bromide (MTT) can then be performed, in which the media is aspirated from all containers and an appropriate volume (such as 100 µl for 96-well plate wells) of DMEM media without phenol red and an appropriate volume (such as 10 µl for 96-well plate wells) of MTT (5 mg/ml) added to all of the containers. The containers can then be incubated for 4 hours at 37° C. in a humidified chamber. After incubation, an appropriate volume (such as 85 µl for 96-well plate wells) of solution is aspirated and an appropriate volume (such as 100 µl for 96-well plate wells) of DMSO is added. Purple formazan crystals form during the assay in proportion to the number of viable HeLa cells present in each container. The contents of each container can be pipetted up and down to solubilize the formazan crystals prior to measurement. The containers can then be incubated at 37° C. for 10 minutes after which the bubbles from agitation are removed. The plate can be read using a UV/Vis reader at 540 nm with a reference at 700 nm. The viability can be normalized to cells seeded in containers with no product or material.

B. Assessing Foreign Body Response/Inflammatory Response

Cathepsin activity, which can be detected by fluorescence, can be used as an indicator of foreign body response (a form of inflammatory response). Mice, such as 8-12 week old male SKH1 mice, can be used to assess foreign body response of the disclosed products and materials. After injection or implantation of the product of material, cathepsin activity can be measured using an in vivo fluorescence assay at various times after injection or implantation. For example, imaging can be taken at 7 days after injection or implantation. 24 hours before in vivo fluorescence imaging, 2 nmol of ProSense-680 (VisEn Medical, Woburn, MA, excitation wavelength 680±10 nm, emission 700±10 nm) can be dissolved in 150 µl sterile PBS and injected into the tail vein of each mouse to image cathepsin activity.

In vivo fluorescence imaging can be performed with an in vivo fluorescence imaging system, such as the IVIS-Spectrum measuremeMAstem (Xenogen, Hopkinton, MA). The can be maintained under inhaled anesthesia during imaging, using, for example, 1-4% isoflurane in 100% oxygen at a flow rate of 2.5 L/min. Images and data can be collected as appropriate for the imaging device being use. As an example, images can be presented in fluorescence efficiency, which is defined as the ratio of the collected fluorescent intensity to an internal standard of incident intensity at the selected imaging configuration. Regions of interest (ROIs) can be designated around the site of each injection.

Relative cathepsin activity at the point of injection or implantation of products and materials can be imaged. The fluorescence intensity can be measured and normalized to the fluorescence response measured using the unmodified form of the product or material in order to quantify the biocompatibility of the surface modified products and materials as compared to unmodified products and materials.

Inflammatory response can also be assessed by detecting and measuring a suite of cytokines. The cytokine levels can indicate a high or low inflammatory response. For example, low protein levels of, for example, TNF-α, IL-13, IL-6, G-CSF, GM-CSF, IL-4, CCL2, and CCL4 which are known mediators of the foreign body response and fibrosis (Rodriguez et al., *J. Biomed. Mater. Res. A* 89:152-159 (2009)), can indicate a lack of or lower foreign body response.

C. Assessing Fibrosis

FACS analysis can be performed on retrieved products and materials and appropriate times after implantation to characterize the different immune populations that are recruited to the products and materials compared to control product or material. For example, the presence of macrophages, neutrophils, myofibroblasts, of a combination thereto, on products and materials or at the location of the products and materials indicate a fibrotic response. Cells were tagged with markers for macrophages (CD11b+, CD68+), neutrophils (CD11b+, Ly6g+), or myofibroblasts (SMA). FACS was used to determine the levels of these fibrosis-associated cell types in proximity to the product or material.

D. qPCR Analysis of Innate Immune and Firbrosis Markers

Total RNA is isolated from a source—such as capsules or products retrieved from an animal after implantation for a period of time (or tissues removed from an animal)—by snap freezing in liquid nitrogen immediately following excision, using, for example,CAl (Invitrogen; Carlsbad, CA) according to the manufacturer's instructions. In addition, to help ensure complete tissue disruption, strong mechanical disruption with a Polytron homogenizer can also be employed. By this process, gene expression signatures are proportional and representative of the entire cell population present on and/or around retrieved materials. Before reverse transcription using, for example, the High Capacity cDNA Reverse Transcription kit (Cat. #4368814; ApCABiosystems, Foster City, CA), all samples are first normalized for comparison by loading the same input total RNA in a set volume (1 μg total RNA in a volume of 20 μl, for example) for each sample. cDNA (4.8 μl; 1:20 dilution in a total volume of 16 μl, for example), including a nucleic acid stain, such as SYBR Green, and PCR primers, is amplified by qPCR with the following appropriate primers (such as the primers shown in Table 1). These primers (Table 1) were designed using Primer Express software (Applied Biosystems, Carlsbad, CA, USA) and evaluated using LaserGene software (DNAStar, Madison, WI, USA) to ensure either mouse or rat (host)-specificity. Other primers can be designed by similar or equivalent analysis. Samples are incubated, for example, at 95° C. for 10 min followed by 40 cycles of 95° C. for 15 sec and 60° C. for 1 min in, for example, an ABI PRISM 7900HT Sequence Detection System (Applied Biosystems). Results are analyzed using a suitable method, such as the comparative $C_T$ ($DDC_T$) method as described by Applied Biosystems. Results are presented, for example, as relative RNA levels compared to the RNA expression in either mock-implanted control cell samples (peripheral intraperitoneal fat tissue, or free floating intraperitoneal lavage cells) after normalization to the β-actin RNA content of each sample.

TABLE 1

Mouse (m) or rat (r)-specific (host) forward and reverse primer sets used for qPCR analysis of RNA levels. Gene names are also shown in parentheses.

| Gene | Primers (5' to 3'): Sense & Antisense |
|---|---|
| Mouse Collagen 1a1 (mCol1a1) | Forward: 5'-CATGTTCAGCTTTGTGGACCT-3' (SEQ ID NO: 1)<br>Reverse: 5'-GCAGCTGACTTCAGGGATGT-3' (SEQ ID NO: 2) |
| Mouse Collagen 1a2 (mCol1a2) | Froward: 5'-GCAGGTTCACCTACTCTGTCCT-3' (SEQ ID NO: 3)<br>Reverse: 5'-CTTGCCCCATTCATTTGTCT-3' (SEQ ID NO: 4) |
| Mouse Alpha Smooth Muscle actin (mActa2) | Forward: 5'-CGCTTCCGCTGCCCAGAGACT-3' (SEQ ID NO: 5)<br>Reverse: 5'-TATAGGTGGTTTCGTGGATGCCCGCT-3' (SEQ ID NO: 6) |
| Mouse Myeloid cell Marker CD11b (mItgam) | Froward: 5'-CCAAGAGAATGCAAAAGGCTTT-3' (SEQ ID NO: 7)<br>Reverse: 5'-GGGGGGCTGCAACAACCACA-3' (SEQ ID NO: 8) |
| Mouse Macrophage Marker CD68 (mCd68) | Forward: 5'-GCCCGAGTACAGTCTACCTGG-3' (SEQ ID NO: 9)<br>Reverse: 5'-AGAGATGAATTCTGCGCCAT-3' (SEQ ID NO: 10) |
| Mouse neutrophil Marker Gr1 (mLy6g) | Forward: 5'-TGCCCCTTCTCTGATGGATT-3' (SEQ ID NO: 11)<br>Reverse: 5'-TGCTCTTGACTTGCTTCTGTGA-3' (SEQ ID NO: 12) |
| Mouse β-actin (mActB) | Forward: 5'-GCTTCTTTGCAGCTCCTTCGTT-3' (SEQ ID NO: 13)<br>Reverse: 5'-CGGAGCCGTTCTCGACGACC-3' (SEQ ID NO: 14) |
| Rat Collagen 1a1 (rCol1a1) | Forward: 5'-CATGTTCAGCTTTGTGGACCT-3' (SEQ ID NO: 15)<br>Reverse: 5'-GCAGCTGACTTCAGGGATGT-3' (SEQ ID NO: 16) |
| Rat Collagen 1a2 (rCol1a2) | Forward: 5'-CCTGGCTCTCGAGGTGAAC-3' (SEQ ID NO: 17)<br>Reverse: 5'-CAATGCCCAGAGGACCAG-3' (SEQ ID NO: 18) |

TABLE 1-continued

Mouse (m) or rat (r)-specific (host) forward and reverse primer sets used for qPCR analysis of RNA levels. Gene names are also shown in parentheses.

| Gene | Primers (5' to 3'): Sense & Antisense |
|---|---|
| Rat Alpha Smooth Muscle actin (rActa2) | Forward: 5'-TGCCATGTATGTGGCTATTCA-3' (SEQ ID NO: 19)<br>Reverse: 5'-ACCAGTTGTACGTCCAGAAGC-3' (SEQ ID NO: 20) |
| Rat Pdx1 (rPdx1) | Forward: 5'-CTCTCGTGCCATGTGAACC-3' (SEQ ID NO: 21)<br>Reverse: 5'-TTCTCTAAATTGGTCCCAGGAA-3' (SEQ ID NO: 22) |
| Rat β-actin (rActB) | Forward: 5'-ACCTTCTTGCAGCTCCTCCGTC-3' (SEQ ID NO: 23)<br>Reverse: 5'-CGGAGCCGTTGTCGACGACG-3' (SEQ ID NO: 24) |

E. FACS Analysis

Single-cell suspensions from capsules or products freshly excised from an animal after implantation for a period of time (or of tissues freshly excised from an animal) are prepared using, for example, a gentleMACS Dissociator (Miltenyi Biotec, Auburn, CA) according to the manufacturer's protocol. Single-cell suspensions are prepared in a passive PEB dissociation buffer (1×PBS, pH 7.2, 0.5% BSA, and 2 mM EDTA) and suspensions are passed through 70 µm filters (for example, Cat. #22363548, Fisher Scientific, Pittsburgh, PA). This process removes the majority of cells adhered to the surface (>90%). The single-cell populations thus derived are then subjected to red blood cell lysis with 5 ml of 1×RBC lysis buffer (Cat. #00-4333, eBioscience, San Diego, CA, USA) for 5 min at 4° C. The reaction is terminated by the addition of 20 ml of sterile 1×PBS. The cells remaining are centrifuged at 300-400 g at 4° C. and resuspended in a minimal volume (~50 µl) of, for example, eBioscience Staining Buffer (Cat. #00-4222) for antibody incubation. All samples are then co-stained in the dark for 25 min at 4° C. with fluorescently tagged monoclonal antibodies specific for the appropriate cell markers, such as for CD68 (for example, CD68-Alexa647, Clone FA-11, Cat. #11-5931, BioLegend at 1 µl (0.5 rig) per sample), Ly-6G (Gr-1) (for example, Ly-6G-Alexa-647, Clone RB6-8C5, Cat. #108418, BioLegend at 1 µl (0.5 rig) per sample), or CD11b (for example, CD11b-Alexa-488, Clone M1/70, Cat. #101217, BioLegend at 1 µl (0.2 rig) per sample). Two ml of, for example, eBioscience Flow Cytometry Staining Buffer (Cat. #00-4222, eBioscience) is then added, and the samples are centrifuged at 400-500 g for 5 min at 4° C. Supernatants are removed by aspiration, and this wash step is repeated two more times with staining buffer. Following the third wash, each sample is resuspended in 500 µp of, for example, FlowCytometry Staining Buffer and run through a 40 µm filter (for example, Cat. #22363547, Fisher Scientific) for eventual FACS analysis using a FACS machine (for example, BD FACSCalibur (cat. #342975), BD Biosciences, San Jose, CA, USA). For proper background and laser intensity settings, unstained, single antibody, and IgG (labeled with, for example, Alexa-488 or Alexa-647, BioLegend) controls can also be run.

F. Fabrication of Alginate Hydrogel Capsules and Cell Encapsulation

All buffers are sterilized by autoclave and alginate solutions are sterilized by filtration through a 0.2 um filter. After solutions are sterilized, aseptic processing is implemented by performing capsule formation in a type II class A2 biosafety cabinet to maintain sterility of manufactured microcapsules/spheres for subsequent implantation. The hydrogel capsules are formed by the following protocol.

To solubilize alginates, SLG20 (NovaMatrix, Sandvika, Norway) is dissolved at 1.4% weight to volume in 0.8% saline. TMTD alginate is initially dissolved at 5% weight to volume in 0.8% saline, and then blended with 3% weight to volume SLG100 (also dissolved in 0.8% saline) at a volume ratio of 80% TMTD alginate to 20% SLG100.

Forming different sized capsules: for 300 µm diameter capsules, a 30 gauge blunt tipped needle (SAI Infusion Technologies) is used with a voltage of 7-8 kV. For 500 µm diameter capsules, a 25 gauge blunt tipped needle (SAI Infusion Technologies) is used with a voltage of 5-7 kV. For 1.5 mm capsules, an 18 gauge blunt tipped needle (SAI Infusion Technologies) is used with a voltage of 5-7 kV.

Cells, such as human islet cells or cultured human cells, are used for encapsulation. Immediately prior to encapsulation, the cultured human cell clusters are centrifuged at 1,400 rpm for 1 minute and washed with Ca-free Krebs-Henseleit (KH) Buffer (4.7 mM KCl, 25 mM HEPES, 1.2 mM $KH_2PO_4$, 1.2 mM $MgSO_4 \times 7H_2O$, 135 mM NaCl, pH≈7.4, ≈290 mOsm). After washing, the human cells are centrifuged again and all supernatant is aspirated. The human cell pellet is then re-suspended in the SLG20 or TMTD alginate solutions at cluster densities of 1,000, 250, and 100 clusters per 0.5 ml alginate solution.

An electrostatic droplet generator is set up as follows: an ES series 0-100 KV, 20 Watt high voltage power generator (Gamma ES series, Gamma High Voltage Research, FL, USA) is connected to the top and bottom of a blunt tipped needle (SAI Infusion Technologies, IL, USA). This needle is attached to a 5 mL lure lock syringe (BD, NJ, USA) which is clipped to a syringe pump (Pump 11 Pico Plus, Harvard Apparatus, MA, USA) that is oriented vertically. The syringe pump pumps alginate out into a glass dish containing a 20 mM barium 5% mannitol solution (Sigma Aldrich, MO, USA). The settings of the PicoPlus syringe pump are 12.06 mm diameter and 0.2 mL/min flow rate. Immediately after crosslinking, the encapsulated human cell clusters are washed 4 times with 50 mL of CMRLM media and cultured overnight in a spinner flask at 37° C. prior to transplantation. Due to an inevitable loss of human cell clusters during the encapsulation process, the total number of encapsulated clusters are recounted post-encapsulation.

G. Analysis of Cell Viability of Encapsulated Cells and/or Protein Secreted from Encapsulated Cells Encapsulated cells are added in 3 ml of fresh medium to each well of a six-well tissue-culture polystyrene plate. Culturing of encapsulated cells is maintained for four days. Afterwards, supernatant samples can be collected and frozen at −20° C. for future analysis, such as by Western blot or ELISA. Encapsulated cells are collected into new plates. Both encapsulated cells are washed in HEPES buffer and subjected to live-dead fluorescent staining (Invitrogen) for viability assessment. The proportion of encapsulated cells that are viable (live) can be calculated. The secretion level of one or more proteins of interest, such as insulin form islet cells or a protein of interest secreted by a recombinant cell, can be assessed by analyzing the supernatant by Western blot or ELISA. The level of secretion can be assessed by, for example, raw level, normalized level (normalized to the level of a housekeeping secreted protein, for example), or either of these compared to the level measured form control cells.

H. Insulin Secretion Analysis

Encapsulated islet cell insulin responses are assessed by loading capsules or product containing encapsulated islet cells into a microfluidic device modified for encapsulated islets (Nourmohammadzadeh et al., Analytical Chem. 85:11240-11249 (2013)). The encapsulated islet cells can be, for example, newly encapsulated or retrieved after implantation into a subject, such as a mouse. Perifusate samples are collected every minute (500 µL/min) by an automated fraction collector (Gilson, model 203B, WI, USA). Insulin concentrations are quantified every other minute using, for example, a chemiluminescent insulin ELISA (Alpco, NH, USA). The following perifusion protocol is used: (1) KRB2 (0-20 min); (2) 20 mM glucose or 30 mM KCl (20-55 min); (3) KRB2 (55-100 min). An appropriate measure of the secreted insulin can be calculated. For example, the area under the curve for each insulin curve can be calculated in order to statistically compare groups using one-way ANOVA ($p<0.05$ as significant).

Biological and temporal characteristics of the disclosed products can be assessed by any suitable analysis. For example, the length of time a product implanted into a subject remains acceptably free of fibrotic effects, produces a desired effect, maintains encapsulated cell viability, or combinations thereof can be assessed. Analogously, the suitability of surface modifications for facilitating desirable biological and temporal characteristics of the disclosed products can be assessed in similar ways. In some embodiments, a product with surface modifications as described herein, if implanted into and retrieved from an immunocompetent animal, such as a C57BL/6J mouse, as described herein, can have one or more of the following properties:

(a) expression of one or more immune and fibrosis markers on the product will be less than 3-fold higher, 2.5-fold higher, 2-fold higher, or 1.5-fold higher than in untreated control tissue at least 14 days, 30 days, 60 days, 120 days, 240 days, or 360 days after implantation into the immunocompetent animal as determined by, for example, Western blot analysis, ELISA, or qPCR analysis as known in the art or as described herein;

(b) expression of one or more immune and fibrosis markers on the product will be less than 3-fold higher, 2.5-fold higher, 2-fold higher, or 1.5-fold higher than in untreated control tissue at least 14 days, 30 days, 60 days, 120 days, 240 days, or 360 days after implantation into the immunocompetent animal as determined by, for example, Western blot analysis, ELISA, or qPCR analysis as known in the art or as described herein;

(c) the cell population of one or more immune- and fibrosis-associated cells on the product will be less than 20%, 18%, 15%, 12%, 10%, of 5% of the cell population observed for a control similar product lacking the surface modification at least 14 days, 30 days, 60 days, 120 days, 240 days, or 360 days after implantation into the immunocompetent animal as determined by, for example, FACS analysis or ELISA as known in the art or as described herein;

(d) expression of a cell viability marker from cells encapsulated in the product will be more than 2-fold higher, 3-fold higher, 3.5-fold higher, 4-fold higher, 5-fold higher, or 10-fold higher observed for similar encapsulated cells comprised in a control similar product lacking the surface modification at least 14 days, 30 days, 60 days, 120 days, 240 days, or 360 days after implantation into the immunocompetent animal as determined by, for example, FACS analysis, Western blot analysis, ELISA, histology, or qPCR analysis as known in the art or as described herein;

(e) secretion of a protein of interest from cells encapsulated in the product will be detectable at least 14 days, 30 days, 60 days, 120 days, 240 days, or 360 days after implantation into the immunocompetent animal as determined by, for example, Western blot analysis or ELISA as known in the art or as described herein;

(f) secretion of insulin from islet cells encapsulated in the product will be detectable at least 14 days, 30 days, 60 days, 120 days, 240 days, or 360 days after implantation into the immunocompetent animal as determined by, for example, Western blot analysis or ELISA as known in the art or as described herein; and (g) at least 50%, 45%, 40%, 35%, 30%, 25%, 20%, 15%, or 10% of the cells encapsulated in the product will be viable for at least 14 days, 30 days, 60 days, 120 days, 240 days, or 360 days after implantation into the immunocompetent animal as determined by, for example, cell viability analysis as known in the art or as described herein.

The compounds used for the surface modification can be assessed for facilitating desirable biological and temporal characteristics on products by, for example, fabricating alginate capsules modified with the compound to encapsulate human islet cells, implanting the alginate capsules into and retrieving the alginate capsules from a C57BL/6J mouse as described herein, and assessing a suitable property of the retrieved alginate capsules. In some embodiments, the retrieved alginate capsules can have one or more of the following properties:

(a) expression of an islet cell viability marker from the alginate capsules will be more than 2-fold higher, 3-fold higher, 3.5-fold higher, 4-fold higher, 5-fold higher, or 10-fold higher observed for a control similar alginate capsule lacking the surface modification at least 14 days, 30 days, 60 days, 120 days, 240 days, or 360 days after implantation into the immunocompetent animal as determined by, for example, FACS analysis, Western blot analysis, ELISA, histology, or qPCR analysis as known in the art or as described herein;

(b) secretion of insulin from the islet cells encapsulated in the alginate capsule will be detectable at least 14 days, 30 days, 60 days, 120 days, 240 days, or 360 days after implantation into the immunocompetent animal as determined by, for example, Western blot analysis or ELISA as known in the art or as described herein;

(c) expression of one or more immune and fibrosis markers on the alginate capsule will be less than 3-fold higher, 2.5-fold higher, 2-fold higher, or 1.5-fold higher than in untreated control tissue at least 14 days, 30 days, 60 days, 120 days, 240 days, or 360 days after implantation into the immunocompetent animal as determined by, for example, Western blot analysis, ELISA, or qPCR analysis as known in the art or as described herein;

(d) expression of one or more immune and fibrosis markers on the alginate capsule will be less than 3-fold higher, 2.5-fold higher, 2-fold higher, or 1.5-fold higher than in untreated control tissue at least 14 days, 30 days, 60 days, 120 days, 240 days, or 360 days after implantation into the immunocompetent animal as determined by, for example, Western blot analysis, ELISA, or qPCR analysis as known in the art or as described herein;

(e) the cell population of one or more immune- and fibrosis-associated cells on the alginate capsule will be less than 20%, 18%, 15%, 12%, 10%, of 5% of the cell population observed for a control similar product lacking the surface modification at least 14 days, 30 days, 60 days, 120 days, 240 days, or 360 days after implantation into the immunocompetent animal as determined by, for example, FACS analysis or ELISA as known in the art or as described herein;

(f) expression of a cell viability marker from the islet cells encapsulated in the alginate capsule will be more than 2-fold higher, 3-fold higher, 3.5-fold higher, 4-fold higher, 5-fold higher, or 10-fold higher observed for similar encapsulated cells comprised in a control similar product lacking the surface modification at least 14 days, 30 days, 60 days, 120 days, 240 days, or 360 days after implantation into the immunocompetent animal as determined by, for example, FACS analysis, Western blot analysis, ELISA, histology, or qPCR analysis as known in the art or as described herein;

(g) secretion of a protein of interest from the islet cells encapsulated in the alginate capsule will be detectable at least 14 days, 30 days, 60 days, 120 days, 240 days, or 360 days after implantation into the immunocompetent animal as determined by, for example, Western blot analysis or ELISA as known in the art or as described herein; and (h) at least 50%, 45%, 40%, 35%, 30%, 25%, 20%, 15%, or 10% of the islet cells encapsulated in the product will be viable for at least 14 days, 30 days, 60 days, 120 days, 240 days, or 360 days after implantation into the immunocompetent animal as determined by, for example, cell viability analysis as known in the art or as described herein.

In some embodiments of the product, a similar product, if implanted into and retrieved from a C57BL/6J mouse as described herein has the following property: expression of one or more immune and fibrosis markers on the product will be less than 3-fold higher than in untreated control tissue at least 30 days after implantation into the C57BL/6J mouse as determined by, for example, Western blot analysis, ELISA, or qPCR analysis as known in the art or as described herein.

In some embodiments of the product, a similar product, if implanted into and retrieved from a C57BL/6J mouse as described herein has the following property: the cell population of one or more immune- and fibrosis-associated cells on the product will be less than 20% of the cell population observed for an identical product lacking the surface modification at least 14 days after implantation into the C57BL/6J mouse as determined by, for example, FACS analysis, Western blot analysis, ELISA, or histology as known in the art or as described herein.

In some embodiments of the product, alginate capsules, (a) fabricated as described herein to encapsulate human islet cells and (b) having the surface modification of the product on the outer surface of alginate capsules at a similar density as on the surface or a surface of the product, provides encapsulated human islet cells that, if implanted into and retrieved from a C57BL/6J mouse as described herein has the following property: expression of an islet cell viability marker from the alginate capsules will be more than 2-fold higher observed for an identical alginate capsule lacking the surface modification at least 30 days after implantation into the C57BL/6J mouse as determined by, for example, FACS analysis, Western blot analysis, ELISA, histology, or qPCR analysis as known in the art or as described herein.

In some embodiments of the product, alginate capsules, (a) fabricated as described herein to encapsulate human islet cells and (b) having the surface modification of the product on the outer surface of alginate capsules at a similar density as on the surface or a surface of the product, provides encapsulated human islet cells that, if implanted into and retrieved from a C57BL/6J mouse as described herein has the following property: the encapsulated islet cells will be able to secrete detectable levels of insulin at least 30 days after implantation into the C57BL/6J mouse as determined by, for example, Western blot analysis or ELISA as known in the art or as described herein.

In some embodiments of the product, the product includes encapsulated cells, where the encapsulated cells, if implanted, via implantation of the product, into and retrieved from a C57BL/6J mouse as described herein has the following property: expression of a cell viability marker from the encapsulated cells will be more than 2-fold higher observed for similar encapsulated cells included in an identical product lacking the surface modification at least 30 days after implantation into the C57BL/6J mouse as determined by, for example, FACS analysis, Western blot analysis, ELISA, histology or qPCR analysis as known in the art or as described herein.

In some embodiments of the product, the product includes encapsulated cells expressing and secreting a protein of interest, where the encapsulated cells, if implanted, via implantation of the product, into and retrieved from a C57BL/6J mouse as described herein has the following property: the encapsulated islet cells will be able to secrete detectable levels of the protein of interest at least 30 days after implantation into the C57BL/6J mouse as determined by, for example, Western blot analysis or ELISA as known in the art or as described herein.

For testing of a product of interest, suitable products can be, for example, a product identical to the product of interest, a corresponding product to the product of interest, a similar product to the product of interest, a product having identical surface modification as the product of interest, a product having a corresponding surface modification as the product of interest, or a product having a similar surface modification as the product of interest. For testing of a compound, chemical modification, or surface modification of interest, suitable products can be, for example, a product surface modified with the compound of interest, a product with the chemical modification of interest, or a product with the surface modification of interest.

VII. Methods of Using

The products described herein, can be used in applications where improved biocompatibility and physical properties (such as being anti-fibrotic), as compared to other commercially available products, are useful or preferred. These include, but are not limited to tissue engineering, invasive sensors, drug delivery, gene transfection systems, medical nanotechnology and biotechnology, implantable medical devices.

The products described herein can be used to treat a broad spectrum of diseases, disorders, and conditions. For example, products that include cells or tissues can be used to treat disorders characterized by a need for a product produced by the cell or tissue or of a reaction mediated by a product of the cell. For example, the cell or cell product can metabolize glucocerebroside or detoxify compounds. For type I and III Gaucher's disease, enzyme replacement treatment with intravenous recombinant glucocerebrosidase is generally used to hydrolyze the beta-glucosidic linkage of, an intermediate in glyclipid metabolism. Toxin-specific antibodies can be used in prophylaxis or treatment of infections caused by bacteria such as *Bacillus anthracis* and *Clostridium difficile*. In some embodiments, the cell or tissue can produce a product useful to treat a disorder. For example, where the cell is an islet cell and the disorder is diabetes. In some embodiments, the product can include a cell that metabolizes or modifies a substrate produced by the subject.

TABLE 2

List of disorders and the cells or cell-produced substance that can be used to treat the disorder.

| Cell or Cell-produced Substance | Disorder |
|---|---|
| Stem cells | Neurodegenerative diseases, diabetes, heart diseases and many other conditions |
| Pancreatic islet cells | Diabetes |
| Autologous haemopoietic stem cell transplantation | Chronic inflammatory autoimmune diseases including severe forms of scleroderma, multiple sclerosis, and lupus |
| Chimeric antigen receptor T cells | Cancers to be treated include non-solid cancers and solid cacers, for examples, carcinoma, blastoma, and sarcoma, and leukemia or lymphoid malignancies, benign and malignant tumors, and malignancies e.g., sarcomas, carcinomas, and melanomas. |
| Hepatocyte cell therapy | Liver diseases such as cirrhosis, liver cancer and hepatitis. |
| Allogeneic differentiated osteoblastic cells | Orthopedic conditions including impaired fracture, a delayed union fracture, osteonecrosis and osteoporosis. |
| Chemically induced neuron cells from pluripotent cells | neurodegenerative disorder selected from the group consisting of Alzheimer's Disease (AD), Huntington's Disease (HD), Parkinson's Disease (PD) Amyotrophic Lateral Sclerosis (ALS), Multiple Sclerosis (MS) and Cerebral Palsy (CP), Dentatorubro-pallidoluysian Atrophy (DRPLA), Neuronal Intranuclear Hyaline Inclusion Disease (NIHID), dementia with Lewy bodies, Down's Syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Hallervorden-Spatz disease, Jakob-Creutzfeldt disease, Niemann-Pick disease type 3, progressive supranuclear palsy, subacute sclerosing panencephalitis, Spinocerebellar Ataxias, Pick's disease, and dentatorubral-pallidoluysian atrophy |
| | Disorders of Amino Acid Metabolism |
| phenylalanine hydroxylase | Phenylketonuria (PKU) |
| biopterin cofactor | Malignant PKU |
| fumarylacetoacetate hydrolase | Type 1 tyrosinemia |
| tyrosine aminotransferase | Type 2 tyrosinemia |
| protein(s) involved in tyrosine breakdown | Alkaptonuria |
| cystathionine-β-synthase or methylenetetrahydrofolate reductase or protein(s) involved in formation of the methylcobalamin form of vitamin $B_{12}$ | Homocystinuria and Hyperhomocysteinemia |
| branched-chain ketoacid dehydrogenase complex | Maple Syrup Urine disease |
| | Disorders of Organic Acid Metabolism |
| propionyl-CoA carboxylase | Propionic Acidemia |
| pyruvate carboxylase and 3-methylcrotonyl-CoA carboxylase | Multiple Carboxylase deficiency |
| methylmalonyl-CoA mutase; protein(s) involved in vitamin $B_{12}$ metabolism | Methylmalonic Acidemia |
| | Disorders of Fatty Acid Metabolism |
| protein(s) involved in regulation or utilization of lipoproteins | Hyperlipidemia and hypercholesterolemia |
| very long chain acyl-CoA dehydrogenase; long chain hydroxyacyl-CoA dehydrogenase; dehydrogenase; medium chain acyl-CoA dehydrogenase; short chain acyl CoA dehydrogenase; short chain hydroxyacyl-CoA dehydrogenase | Fatty Acid Oxidation disorders |
| protein(s) involved in glycogenolysis galactose-1-phosphate uridyl transferase | Glycogen Storage diseases Galactosemia |
| enzyme(s) that build the carbohydrate side-chains on proteins | Congenital Disorders of Glycosylation |
| | Disorders of Purine and Pyrimidine Metabolism |
| protein(s) involved in balance between purine synthesis and disposal | Purine Overproduction |
| hypoxanthine phosphoribosyl-transferase | Lesch-Nyhan syndrome |
| | Lysosomal Storage Disorders |
| cerebrosidase | Gaucher disease Types I and II |
| beta-hexosaminidase A | Tay-Sachs disease |
| α-galactosidase | Fabry disease |
| α-iduronidase (Hurler syndrome); iduronate sultatase (Hunter syndrome); iduronate sultatase (Hunter syndrome) | Hurler syndrome, Hunter syndrome |
| enzyme(s) involved in heparan sulfate degradation | Sanfilippo syndrome |
| arylsulfatase B | Maroteaux-Lamy syndrome |
| galactose 6-sulfatase; β-galactosidase | Morquio syndrome |

TABLE 2-continued

List of disorders and the cells or cell-produced substance that can be used to treat the disorder.

| Cell or Cell-produced Substance | Disorder |
|---|---|
| carbamyl phosphate synthetase; ornithine transcarbamylase; citrullinemia; argininosuccinic aciduria | Disorders of Urea Formation |
|  | Disorders of Peroxisomal Metabolism |
| protein(s) involved in branched-chain fatty acid production and/or breakdown | Refsum disease |
| alanine-glyoxylate transaminase | Alanine-glyoxylate transaminase defect |
| Cellular metabolic enzymes | Enzyme deficiency diseases |
| Muscle cell metabolic enzymes | metabolic disorders of the muscle (e.g. Pompe's disease) |

TABLE 3

List of products and devices that can be used to treat the disorder.

| Product | Disorder |
|---|---|
| Bioartificial liver devices | Liver diseases |
| Heart pacemakers | Any conditions that case abnormal heart rhythms |

TABLE 3-continued

List of products and devices that can be used to treat the disorder.

| Product | Disorder |
|---|---|
| Breast implants | Misshaped breasts |
| Spine screws, rods and artificial discs | Spinal fusion surgeries |
| Intra-uterine devices | |
| Artificial knees | Disability associated with knee cap or joints |
| Coronary stents | Unstable angina or heart attach due to blacked arteries |
| Artificial eye lenses | Cataract |
| Metal screws, pins, plates and rods | Bone fractures |
| Artificial hips | Disability associated with hips |
| Intestinal stents | Bowl obstruction |

EXAMPLES

Example 1

It was discovered that alginates modified with the Z2-Y12, Z1-Y15, or Z1-Y19 moieties exhibit lower foreign body responses. It has now been discovered that carboxy-polystyrene (C-PS) exhibits lower foreign body responses when modified with Z2-Y12, Z1-Y15, or Z1-Y19 moieties. 500 μm carboxy-polystyrene (C-PS) beads were modified with the following moieties:

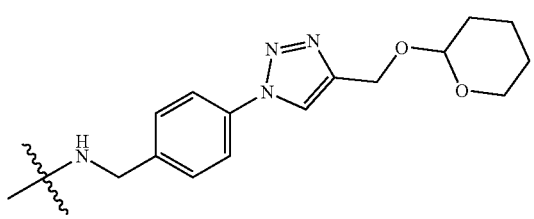

Z2-Y12

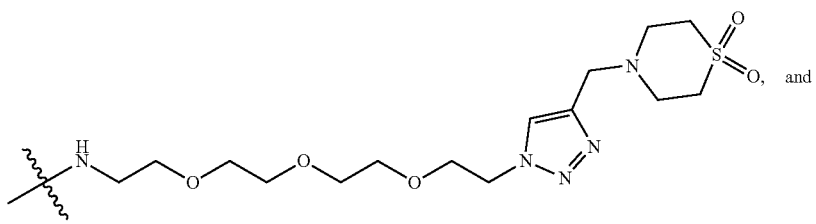

Z1-Y15, and

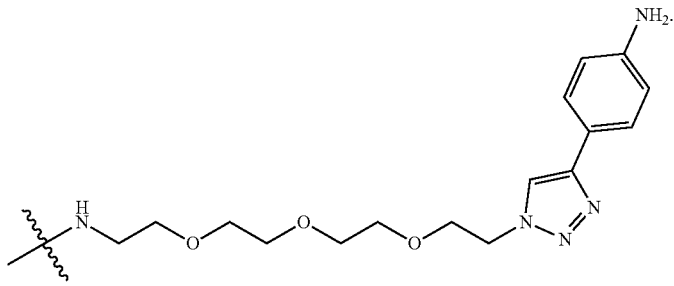

Z1-Y19

After purification, the beads were implanted into the intraperitoneal (IP) space of C57BL/6J mice. After 14 days post-implantation, the beads were retrieved and the amounts of fibrotic or collagenous overgrowth/encapsulation on the implants were analyzed.

Results

Compared to unmodified control C-PS beads, modified C-PS beads showed no clumping or collagenous encapsulation. The control implants showed extreme levels of clumping and fibrotic deposition between beads/capsules. These results mimic similar studies with alginate microcapsules, and show that the chemical derivatizations can successfully mitigate immunological and fibrotic reactions to other biomedical device-relevant materials. These results are surprising, given that the environment on the surface of the beads or device and surface densities of the chemical derivatizations are different from that in the modified alginate polymer.

The materials presented here represent a key advancement in the development of fibrosis-resistant materials. While these compounds have been developed in the context of cell encapsulation and bead surface modification, the compounds are broadly applicable as anti-fibrotic coatings for other biomedical devices.

Example 2

This example shows that various materials, including synthetic materials, exhibit lower foreign body responses when modified with E9 (Z2-Y12). The surfaces of polystyrene, glass, PDMS, and medical-grade silicone have been modified successfully with the E9 molecule, and after 2 weeks implantation into the intraperitoneal space of a C57BL/6 mouse show dramatically reduced foreign body responses. Since many of these very same materials are used for implantable medical devices, such as implanted catheters in the brain, these results have profound implications for medical device composition and manufacture.

Stainless Steel/Glass:

Beads were stirred in piranha solution for 1 h at room temperature. Beads were washed by ultra-sonication in water, then ethanol, then acetone for 10 min each and then dried by blowing nitrogen over them. Immediate after drying the beads were stirred in a 10% (v/v) silane/toluene solution for 48 h at 55° C. Cleaning was done by ultra-sonication in Toluene and Dichloromethane for 5 min each. The beads were dried under Argon and cured in an oven at 70° C. for 3 h to prevent air oxidation.

The beads were stirred in water and succinic acid, 2-chloro-4,6-dimethoxy-1,3,5-triazine (CDMT) and N-methylmorpholine (NMM) were added. The suspension was stirred at 55° C. overnight. The beads were washed with water, methanol, and acetone to remove unreacted material.

The beads were stirred in a water/acetonitrile solution and E9, CDMT, and NMM was added. The beads were stirred overnight at 55° C. Beads were washed with water, methanol, and acetone. The conjugation was analyzed by X-ray photoelectron spectroscopy (XPS).

Polystyrene-COOH/PMMA-COOH:

To PS/PMMA beads in water/acetonitrile (3:2), E9 NMM and a spatula tip of CDMT was added. The solution was overhead stirred at 50° C. overnight. The beads were washed three times with methanol and then three times with ethanol. The beads were dried under reduced pressure. Materials are characterized via XPS.

Plasma treated plastics, ceramics, and metals:

Materials were plasma treated for 1 min on each side and immediately dropped into a 0.2 mol solution of E9 in 5% DMSO in toluene. The reaction was stirred for 90 min and the materials were washed three times in methanol and three times in ethanol. The materials are dried under high vacuum overnight. Materials are characterized via XPS.

XPS analysis of glass shows the ratios of the elements present on the surfaces of the glass. Table 4 shows a quantitative measure of the amount of each element present, the numbers being derived from the corresponding areas under the peaks in the FIGURE. In this case, the data show that the surface of the glass samples have carbon, oxygen, sodium, magnesium and silicon, which is indicative of the presence of surface modifications. From the standard deviations, one can determine that the elemental variations between the three glass samples are small.

TABLE 4

Atomic Concentration Table

| C1s | O1s | Na1s | Mg2p | Si2p | |
|---|---|---|---|---|---|
| 0.314 | 0.733 | 1.102 | 0.167 | 0.368 | RSF |
| 58.791 | 137.408 | 206.930 | 37.158 | 80.087 | Corrected RSF |
| 30.13 | 48.41 | 2.26 | 3.37 | 15.83 | Glass 1 |
| 25.77 | 52.88 | 0.98 | 2.60 | 17.77 | Glass 2 |
| 29.11 | 50.62 | 1.99 | 1.53 | 16.75 | Glass 3 |
| 28.34 | 50.63 | 1.74 | 2.50 | 16.78 | Mean |
| 2.28 | 2.24 | 0.68 | 0.92 | 0.97 | Standard Deviation |

XPS analysis of unmodified polydimethylsiloxane (PDMS) and PDMS modified with compound E9 (Z2-Y12) show that there is a significantly higher amount of elemental nitrogen on the surface of E9-modified PDMS compared to unmodified PDMS (Table 5). For example, (i) the amount of elemental nitrogen in the E9-modified PDMS sample is 7.66, much higher than the value of 1.06 in the unmodified PDMS sample; and (ii) the standard deviation of elemental nitrogen (4.67) is higher than the average amount of nitrogen (4.36) between the samples. Also worth noting is the difference between detected amounts of silicon in the two samples: the values are 10.04 and 18.38 in E9-modified PDMS and in unmodified PDMS, respectively. The lower value in E9-modified PDMS indicates that the surface of the sample has been coated.

TABLE 5

Atomic Concentration Table

| C1s | N1s | O1s | Si2p | |
|---|---|---|---|---|
| 0.314 | 0.499 | 0.733 | 0.368 | RSF |
| 58.791 | 93.486 | 137.408 | 80.087 | Corrected RSF |
| 59.28 | 7.66 | 23.02 | 10.04 | 1. PDMS-E9 |
| 50.88 | 1.06 | 29.69 | 18.38 | 2. PDMS |
| 55.08 | 4.36 | 26.35 | 14.21 | Mean |
| 5.94 | 4.67 | 4.71 | 5.90 | Standard Deviation |

Analysis of the atomic concentration of elemental nitrogen present on the surface of a 1300×1300 µm section of a E9-modified PDMS sample indicates that some areas have a high amount of elemental nitrogen compared to other areas.

XPS analysis of E9-modified silicone show that the surfaces of the silicone samples have been successfully modified with E9 (Table 6). In particular, the averages and standard deviations of elemental nitrogen indicate similar densities of surface E9 in the three samples.

TABLE 6

Atomic Concentration Table

| C1s | N1s | O1s | Si2p | |
|---|---|---|---|---|
| 0.314 | 0.499 | 0.733 | 0.368 | RSF |
| 58.791 | 93.486 | 137.408 | 80.087 | Corrected RSF |
| 57.03 | 4.61 | 24.45 | 13.91 | Silicone1 |
| 54.58 | 5.09 | 25.15 | 15.17 | Silicone2 |
| 53.03 | 4.78 | 26.39 | 15.80 | Silicone3 |
| 54.88 | 4.83 | 25.33 | 14.96 | Mean |
| 2.02 | 0.25 | 0.98 | 0.96 | Standard Deviation |

XPS analysis of glass shows that the surface of the glass samples have carbon, oxygen, sodium, magnesium and silicon (Table 7), which is indicative of the presence of surface modifications. From the standard deviations, one can determine that the elemental variations between the two glass samples are small.

TABLE 7

Atomic Concentration Table

| C1s | N1s | O1s | F1s | Na1s | Si2p | |
|---|---|---|---|---|---|---|
| 0.314 | 0.499 | 0.733 | 1.000 | 1.102 | 0.368 | RSF |
| 58.791 | 93.468 | 137.408 | 187.576 | 206.930 | 80.087 | Corrected RSF |
| 35.22 | 4.98 | 42.95 | 0.44 | 1.01 | 15.40 | 3.Glass-batch 1 |
| 39.82 | 5.87 | 36.80 | 2.02 | 0.80 | 14.69 | 4.Glass-batch2 |
| 37.52 | 5.42 | 39.87 | 1.23 | 0.90 | 15.05 | Mean |
| 3.25 | 0.63 | 4.35 | 1.12 | 0.15 | 0.50 | Standard Deviation |

Grafting E9 to the surface of carboxylic acid terminated polystyrene microspheres (300-500 μm in diameter) reduces fibrosis. Carboxylic acid modified polystyrene or E9 surface modified polystyrene were implanted to the intraperitoneal space of C57BL/6 mice for 14 days. Bright field images of retrieved microspheres revealed extensive clumping and fibrotic coating of the unmodified microspheres and no clumping or coating for the modified microspheres.

Grafting E9 to the surface of PDMS or medical grade silicone cylinders (5 mm diameter×1 mm height) reduces fibrosis. Bright field images obtained from unmodified PDMS cylinders or E9 modified PDMS cylinders after retrieval from the intraperitoneal space of C57BL/6 mice (14-day implantation study) reveal extensive fibrotic coating of unmodified cylinders and no visible coating of modified cylinders. Bright field images obtained from E9 modified or unmodified PDMS cylinders and E9 modified or unmodified medical grade silicone cylinders after retrieval from the intraperitoneal space of C57BL/6 mice (14-day implantation study) reveal extensive fibrotic coating of both unmodified PDMS cylinders and unmodified silicon cylinders and no visible coating of modified PDMS cylinders and modified silicon cylinders. E9 modified or unmodified PDMS cylinders and E9 modified or unmodified medical grade silicone cylinders after retrieval from the intraperitoneal space of C57BL/6 mice (14-day implantation study) were stained for cellular deposition (DAPI, F-actin) and myofibroblasts (α-SMA), the presence of which indicate fibrotic reaction. Confocal immunofluorescence images reveal extensive staining for all three markers on both unmodified PDMS cylinders and unmodified silicon cylinders and minimal staining of modified PDMS cylinders and modified silicon cylinders.

Disclosed are compounds, materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and discussed and a number of modifications that can be made to a number of molecules including the compound are discussed, each and every combination and permutation of compound and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms "a," "an," and "the" include plural reference unless the context clearly dictates otherwise. Thus, for example, reference to "a compound" includes a plurality of such compounds, reference to "the compound" is a reference to one or more compounds and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different compounds does not indicate that the listed compounds are obvious one to the other, nor is it an admission of equivalence or obviousness.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A macroscopic implant comprising a chemical moiety covalently bound to a polymer selected from polytetrafluoroethylene, polyurethane, polydimethylsiloxane, and poly(vinyl) chloride, wherein the polymer is present on a surface of the macroscopic implant, and wherein the chemical moiety is selected from the group consisting of:

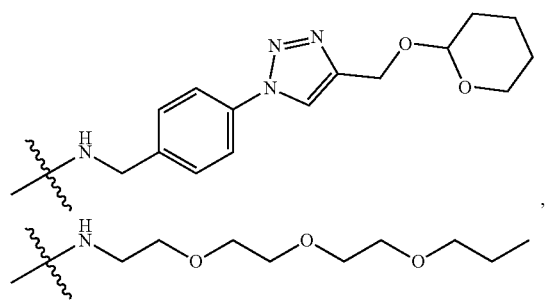

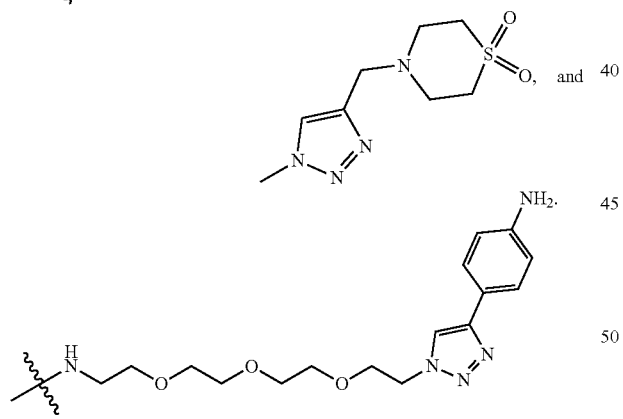

2. The macroscopic implant of claim 1, further comprising a cell that secretes a protein, wherein the macroscopic implant encapsulates the cell.

3. The macroscopic implant of claim 2, wherein the cell is derived from a stem cell.

4. The macroscopic implant of claim 3, wherein the cell is an insulin-producing cell.

5. The macroscopic implant of claim 1, wherein the implant comprises a hollow fiber.

6. The macroscopic implant of claim 1, wherein the implant is cylindrical.

7. The macroscopic implant of claim 1, wherein the implant further comprises a pore having a pore size of between about 0.1 μm and about 1 μm.

8. The macroscopic implant of claim 1, wherein the chemical moiety comprises:

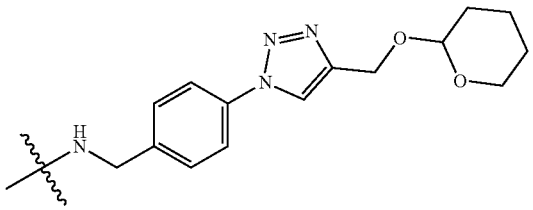

9. The macroscopic implant of claim 1, wherein the chemical moiety comprises:

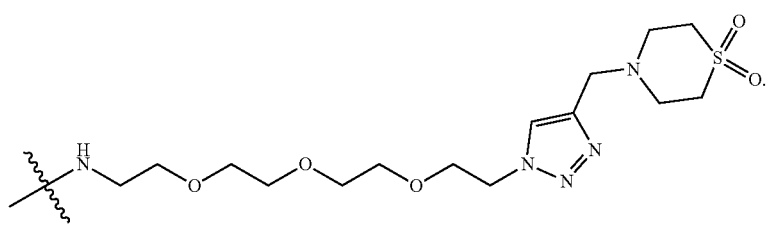 [SMILES: *NCCOCCOCCOCCn1cc(CN2CCS(=O)(=O)CC2)nn1]

10. The macroscopic implant of claim 1, wherein the chemical moiety comprises:

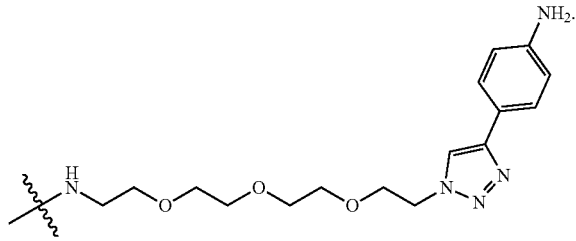 [SMILES: *NCCOCCOCCOCCn1cc(-c2ccc(N)cc2)nn1]

11. The macroscopic implant of claim 1, wherein the surface is an exterior surface.

12. The macroscopic implant of claim 1, wherein the surface is an interior surface.

13. The macroscopic implant of claim 1, wherein the surface is an exterior surface and the chemical moiety comprises

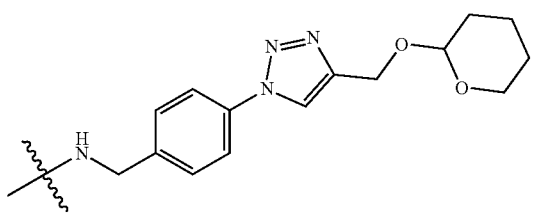

14. The macroscopic implant of claim 1, wherein the surface is an interior surface and the chemical moiety comprises

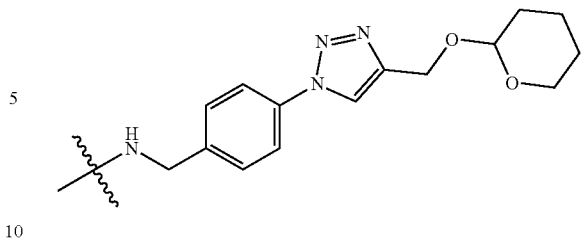

15. The macroscopic implant of claim 4, wherein the insulin producing cell is encapsulated by the polymer.

16. The macroscopic implant of claim 1, wherein the macroscopic implant elicits a lower foreign body response following implantation compared to a corresponding macroscopic implant that lacks the chemical moiety.

17. The macroscopic implant of claim 1, wherein the polymer is polytetrafluoroethylene.

18. The macroscopic implant of claim 1, wherein the polymer is polyurethane.

19. The macroscopic implant of claim 1, wherein the polymer is polydimethylsiloxane.

20. The macroscopic implant of claim 1, wherein the polymer is poly(vinyl) chloride.

21. The macroscopic implant of claim 1, wherein the implant is not a hydrogel.

22. A macroscopic implant comprising a chemical moiety covalently bound to a polymer selected from polyolefin, wherein the polymer is present on a surface of the macroscopic implant, and wherein the chemical moiety is selected from the group consisting of:

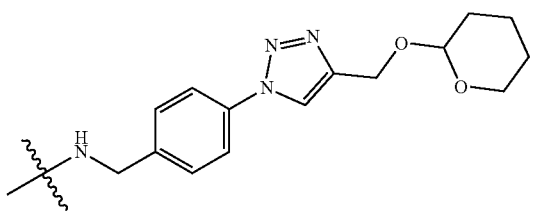

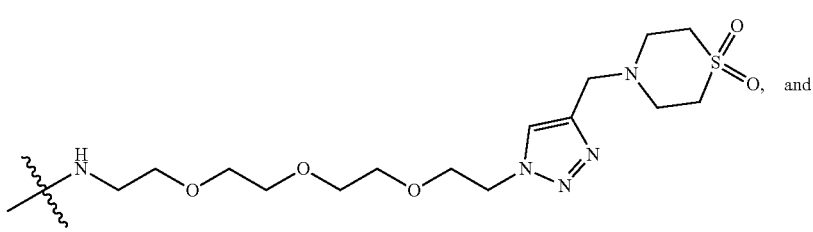

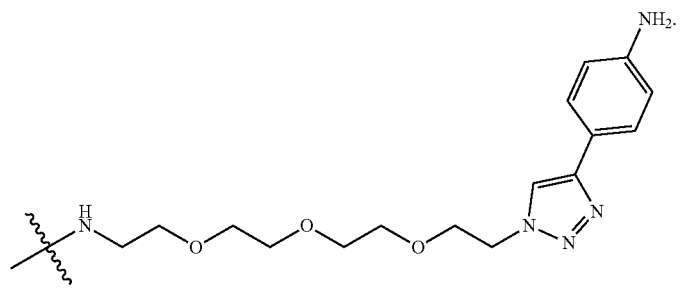
* * * * *

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
catgttcagc tttgtggacc t                                              21

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
gcagctgact tcagggatgt                                                20

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
gcaggttcac ctactctgtc ct                                             22

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

```
<400> SEQUENCE: 4
cttgccccat tcatttgtct                                            20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
cgcttccgct gcccagagac t                                          21

<210> SEQ ID NO 6
<211> LENGTH: 26
<212> TYPE: DNA
<213> ORGANISM: Artificial Sequence
<220> FEATURE:
<223> OTHER INFORMATION: Synthetic Primer

<400> SEQUENCE: 6
tataggtggt ttcgtggatg cccgct                                     26

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
ccaagagaat gcaaaaggct tt                                         22

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8 gggggggctgc aacaaccaca                                           20

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
gcccgagtac agtctacctg g                                          21

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
agagatgaat tctgcgccat                                            20

<210> SEQ ID NO 11
<211> LENGTH: 20
```

```
<212> TYPE: DNA
<213> ORGANISM: Artificial Sequence
<220> FEATURE:
<223> OTHER INFORMATION: Synthetic Primer

<400> SEQUENCE: 11
tgccccttct ctgatggatt                                                  20

<210> SEQ ID NO 12
<211> LENGTH: 22
<212> TYPE: DNA
<213> ORGANISM: Artificial Sequence
<220> FEATURE:
<223> OTHER INFORMATION: Synthetic Primer

<400> SEQUENCE: 12
tgctcttgac ttgcttctgt ga                                               22

<210> SEQ ID NO 13
<211> LENGTH: 22
<212> TYPE: DNA
<213> ORGANISM: Artificial Sequence
<220> FEATURE:
<223> OTHER INFORMATION: Synthetic Primer

<400> SEQUENCE: 13
gcttctttgc agctccttcg tt                                               22

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
cggagccgtt ctcgacgacc                                                  20

<210> SEQ ID NO 15
<211> LENGTH: 21
<212> TYPE: DNA
<213> ORGANISM: Artificial Sequence
<220> FEATURE:
<223> OTHER INFORMATION: Synthetic Primer

<400> SEQUENCE: 15
catgttcagc tttgtggacc t                                                21

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
gcagctgact tcagggatgt                                                  20

<210> SEQ ID NO 17
<211> LENGTH: 19
<212> TYPE: DNA
<213> ORGANISM: Artificial Sequence
<220> FEATURE:
<223> OTHER INFORMATION: Synthetic Primer

<400> SEQUENCE: 17
```
cctggctctc gaggtgaac                                                      19

<210> SEQ ID NO 18
<211> LENGTH: 18
<212> TYPE: DNA
<213> ORGANISM: Artificial Sequence
<220> FEATURE:
<223> OTHER INFORMATION: Synthetic Primer

<400> SEQUENCE: 18
caatgcccag aggaccag                                                       18

<210> SEQ ID NO 19
<211> LENGTH: 21
<212> TYPE: DNA
<213> ORGANISM: Artificial Sequence
<220> FEATURE:
<223> OTHER INFORMATION: Synthetic Primer

<400> SEQUENCE: 19
tgccatgtat gtggctattc a                                                   21

<210> SEQ ID NO 20
<211> LENGTH: 21
<212> TYPE: DNA
<213> ORGANISM: Artificial Sequence
<220> FEATURE:
<223> OTHER INFORMATION: Synthetic Primer

<400> SEQUENCE: 20
accagttgta cgtccagaag c                                                   21

<210> SEQ ID NO 21
<211> LENGTH: 19
<212> TYPE: DNA
<213> ORGANISM: Artificial Sequence
<220> FEATURE:
<223> OTHER INFORMATION: Synthetic Primer

<400> SEQUENCE: 21
ctctcgtgcc atgtgaacc                                                      19

<210> SEQ ID NO 22
<211> LENGTH: 22
<212> TYPE: DNA
<213> ORGANISM: Artificial Sequence
<220> FEATURE:
<223> OTHER INFORMATION: Synthetic Primer

<400> SEQUENCE: 22
ttctctaaat tggtcccagg aa                                                  22

<210> SEQ ID NO 23
<211> LENGTH: 22
<212> TYPE: DNA
<213> ORGANISM: Artificial Sequence
<220> FEATURE:
<223> OTHER INFORMATION: Synthetic Primer

```
<400> SEQUENCE: 23
accttcttgc agctcctccg tc                                        22

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
cggagccgtt gtcgacgacg                                           20
```